US010266465B2

(12) United States Patent
Bonnet et al.

(10) Patent No.: US 10,266,465 B2
(45) Date of Patent: Apr. 23, 2019

(54) COMPOSITION COMPRISING HF AND 1,3,3,3-TETRAFLUOROPROPENE

(71) Applicant: ARKEMA FRANCE, Colombes (FR)

(72) Inventors: Philippe Bonnet, Lyons (FR); Bertrand Collier, Saint-Genis-Laval (FR); Dominque Deur-Bert, Charly (FR); Laurent Wendlinger, Soucieu en Jarrest (FR)

(73) Assignee: ARKEMA FRANCE, Colombes (FR)

(*) Notice: Subject to any disclaimer, the term of this patent is extended or adjusted under 35 U.S.C. 154(b) by 0 days.

(21) Appl. No.: 16/029,078

(22) Filed: Jul. 6, 2018

(65) Prior Publication Data
US 2018/0312453 A1 Nov. 1, 2018

Related U.S. Application Data

(63) Continuation of application No. 14/773,961, filed as application No. PCT/FR2014/050369 on Feb. 24, 2014, now Pat. No. 10,029,963.

(30) Foreign Application Priority Data

Mar. 20, 2013 (FR) .................................... 13 52485

(51) Int. Cl.
C07C 21/18 (2006.01)
C01B 7/19 (2006.01)
C09K 3/30 (2006.01)
C09K 5/04 (2006.01)

(52) U.S. Cl.
CPC .............. C07C 21/18 (2013.01); C01B 7/191 (2013.01); C01B 7/195 (2013.01); C09K 3/30 (2013.01); C09K 5/045 (2013.01)

(58) Field of Classification Search
None
See application file for complete search history.

(56) References Cited

U.S. PATENT DOCUMENTS

| 6,013,846 | A | 1/2000 | Wismer et al. |
| 7,423,188 | B2* | 9/2008 | Miller ..................... C01B 7/191 570/155 |
| 8,450,537 | B2 | 5/2013 | Rao et al. |
| 8,951,432 | B2 | 2/2015 | Boutier et al. |
| 9,005,468 | B2 | 4/2015 | Rached |
| 9,315,706 | B2 | 4/2016 | Boussand |
| 9,512,343 | B2 | 12/2016 | Rached et al. |
| 9,574,124 | B2 | 2/2017 | Rached |
| 9,683,154 | B2 | 6/2017 | Rached |
| 10,029,963 | B2* | 7/2018 | Bonnet ..................... C01B 7/195 |
| 2006/0106263 | A1* | 5/2006 | Miller ..................... C01B 7/196 570/155 |
| 2007/0100173 | A1* | 5/2007 | Miller ..................... C01B 7/191 570/178 |
| 2007/0100175 | A1 | 5/2007 | Miller et al. |
| 2008/0051612 | A1 | 2/2008 | Knapp et al. |
| 2009/0127496 | A1* | 5/2009 | Rao ..................... B01J 27/125 252/67 |
| 2010/0072415 | A1* | 3/2010 | Rao ..................... B01J 23/26 252/67 |
| 2010/0187088 | A1 | 7/2010 | Merkel et al. |
| 2010/0237279 | A1 | 9/2010 | Hulse et al. |
| 2011/0112340 | A1 | 5/2011 | Smith et al. |
| 2011/0218359 | A1 | 9/2011 | Eishekh et al. |
| 2012/0041239 | A1* | 2/2012 | Suzuki ..................... C07C 17/206 570/160 |
| 2012/0053359 | A1 | 3/2012 | Hulse et al. |
| 2012/0056122 | A1 | 3/2012 | Hulse et al. |
| 2012/0068104 | A1 | 3/2012 | Rached et al. |
| 2012/0068105 | A1 | 3/2012 | Rached et al. |
| 2012/0138841 | A1 | 6/2012 | Hulse et al. |
| 2012/0222448 | A1 | 9/2012 | Chaki et al. |
| 2013/0055733 | A1 | 3/2013 | Rached |
| 2013/0055739 | A1 | 3/2013 | Rached |
| 2013/0061613 | A1 | 3/2013 | Rached |
| 2013/0105296 | A1 | 5/2013 | Chaki et al. |
| 2013/0299733 | A1 | 11/2013 | Boussand |
| 2014/0012052 | A1 | 1/2014 | Pham et al. |
| 2014/0110623 | A1 | 4/2014 | Boutier et al. |
| 2015/0184051 | A1 | 7/2015 | Rached |

(Continued)

FOREIGN PATENT DOCUMENTS

EP 2 527 313 A1 11/2012
WO WO 2007/053736 A2 5/2007

(Continued)

OTHER PUBLICATIONS

U.S. Appl. No. 13/232,106, Wissam Rached and Béatrice Boussand, filed Sep. 14, 2011.
U.S. Appl. No. 13/697,027, Wissam Rached, filed Nov. 9, 2012.
U.S. Appl. No. 14/880,605, Béatrice Boussand, filed Oct. 12, 2015.
U.S. Appl. No. 15/297,569, Wissam Rached and Béatrice Boussand, filed Oct. 19, 2016.
U.S. Appl. No. 15/343,664, Wissam Rached, Nov. 4, 2016.
U.S. Appl. No. 16/143,505, Wissam Rached and Béatrice Boussand, Sep. 27, 2018.
U.S. Appl. No. 16/143,505, Rached, et al.
International Search Report (PCT/ISA/210) dated Jun. 4, 2014, by the French Patent Office as the International Searching Authority for International Application No. PCT/FR2014/050369, 4 pages.

(Continued)

Primary Examiner — Joseph D Anthony
(74) Attorney, Agent, or Firm — Buchanan Ingersoll & Rooney P.C.

(57) ABSTRACT

An azeotropic or quasi-azeotropic composition including hydrogen fluoride, 1,3,3,3-tetrafluoropropene and one or more (hydro)halogen-carbon compounds including between 1 and 3 carbon atoms. Also, a preferred azeotropic or quasi-azeotropic composition comprising hydrogen fluoride, 1,3,3,3-tetrafluoropropene, and one or more compounds selected from among 1,1,1,2,2-pentafluoropropane, 2,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,3,3-pentafluoropropane, 1,1,1,3,3-pentafluoropropene, 1,1,1,2,3-pentafluoropropene and 2-chloro, 1,1,1,2-tetrafluoropropane.

13 Claims, No Drawings

(56) References Cited

U.S. PATENT DOCUMENTS

| | | |
|---|---|---|
| 2016/0009555 A1 | 1/2016 | Bonnet et al. |
| 2016/0023176 A1 | 1/2016 | Bonnet et al. |
| 2016/0023974 A1 | 1/2016 | Bonnet et al. |
| 2016/0031773 A1 | 2/2016 | Bonnet et al. |
| 2016/0032165 A1 | 2/2016 | Boussand |
| 2016/0046548 A1 | 2/2016 | Bonnet et al. |
| 2017/0037291 A1 | 2/2017 | Rached et al. |
| 2018/0079943 A1 | 3/2018 | Rached |

FOREIGN PATENT DOCUMENTS

| | | |
|---|---|---|
| WO | WO 2009/105521 A1 * | 8/2009 |
| WO | WO 2010/059493 A1 | 5/2010 |
| WO | WO 2010/088196 A2 | 8/2010 |
| WO | WO 2010/088196 A3 | 8/2010 |
| WO | WO 2012/075283 A2 | 6/2012 |
| WO | WO 2014/147310 A1 | 9/2014 |
| WO | WO 2014/147311 A1 | 9/2014 |
| WO | WO 2014/147312 A1 | 9/2014 |
| WO | WO 2014/147313 A1 | 9/2014 |
| WO | WO2014/147314 A1 | 9/2014 |

OTHER PUBLICATIONS

Rached, Wissam, et al., U.S. Appl. No. 16/143,505 entitled "Composition Based on 1,3,3,3-Tetrafluoropropene," filed in the U.S. Patent and Trademark Office on Sep. 27, 2018.

* cited by examiner

COMPOSITION COMPRISING HF AND 1,3,3,3-TETRAFLUOROPROPENE

CROSS REFERENCE TO RELATED APPLICATIONS

The present application is a continuation of U.S. application Ser. No. 14/773,961, filed on Sep. 9, 2015, which is a U.S. National Stage of International Application No. PCT/FR2014/050369, filed on Feb. 24, 2014, which claims the benefit of French Application No. 13.52485, filed on Mar. 20, 2013. The entire contents of each of U.S. application Ser. No. 14/773,961, International Application No. PCT/FR2014/050369, and French Application No. 13.52485 are hereby incorporated herein by reference in their entirety.

TECHNICAL FIELD

The present invention relates to azeotropic or quasi-azeotropic compositions comprising 1,3,3,3-tetrafluoropropene and hydrogen fluoride. These compositions may originate from intermediate compositions in the production of 1,3,3,3-tetrafluoropropene and are generally useful in processes for recycling hydrogen fluoride.

BACKGROUND

The manufacture of 1,3,3,3-tetrafluoropropene accompanied by a multitude of by-products, having a boiling point close to HFO-1234ze, leads to relatively complex and expensive purification steps. The difficulty encountered during the purification of HFO-1234ze generally implies an appreciable loss of desired product. Furthermore, these by-products may form azeotropic compositions with 1,3,3,3-tetrafluoropropene, making separation by distillation simple, very difficult, or even impossible.

Fluids based on 1,3,3,3-tetrafluoropropene have found numerous applications in varied industrial fields, especially as heat-transfer fluid, propellants, foaming agents, swelling agents, gaseous dielectrics, polymerization medium or monomer, support fluids, abrasive agents, drying agents and fluids for power production units.

Particular importance is given to fluids that have a low impact on the environment.

DETAILED DESCRIPTION

The subject of the present invention is an azeotropic or quasi-azeotropic composition comprising hydrogen fluoride, 1,3,3,3-tetrafluoropropene and one or more (hydro)halocarbon compounds comprising between 1 and 3 carbon atoms.

According to one embodiment of the invention, the composition is heteroazeotropic or quasi-heteroazeotropic.

A heteroazeotropic or quasi-heteroazeotropic mixture is an azeotropic or quasi-azeotropic mixture in which the condensed liquid forms two immiscible solutions that can be readily separated, for example by decantation. This property is a considerable advantage for the recovery of HF.

The term "quasi-azeotropic" or "quasi-heteroazeotropic" has a broad meaning and is intended to include compositions that are strictly azeotropic or strictly heteroazeotropic and those that behave like an azeotropic or heteroazeotropic mixture.

A mixture is azeotropic when the pressure at the dew point is equal to that at the bubble formation point, which means that the vapor composition is equal to that of the condensed liquid.

A mixture is considered as quasi-azeotropic when the pressure at the dew point is substantially equal to that at the bubble formation point, which means that the vapor composition is substantially equal to that of the condensed liquid.

Another way of characterizing a mixture as quasi-azeotropic when the pressure difference between the pressure at the dew point and the pressure at the bubble formation point is low, preferentially less than or equal to 5%, on the basis of the pressure at the bubble formation point.

Compositions according to the invention especially concern the following compounds, the acronyms of which represent:

HF: hydrogen fluoride
HCC-40: chloromethane, or $CH_3Cl$
HCFC-115: chloropentafluoroethane, or $C_2F_5Cl$
HCFC-124: chlorotetrafluoroethane, or $C_2HF_4Cl$
HFC-125: pentafluoroethane, or $C_2HF_5$
HCFC-133a: 1-chloro-2,2,2-trifluoroethane, or $C_2H_2F_3Cl$
HFC-134a: 1,1,1,2-tetrafluoroethane, or $C_2H_2F_4$
HCFC-142b: 1-chloro-1,1-difluoroethane, or $C_2H_3F_2Cl$
HFC-143a: 1,1,1-trifluoroethane, or $C_2H_3F_3$
HFC-152a: 1,1-difluoroethane, or $C_2H_4F_2$
HFO-1132: 1,2-difluoroethylene, or $C_2H_2F_2$
HFO-1141: fluoroethylene, or $C_2H_3F$
HFO-1234yf: 2,3,3,3-tetrafluoropropene or $CH_2=CF-CF_3$
HFC-245cb: 1,1,1,2,2-pentafluoropropane or $CF_3-CF_2-CH_3$
HFO-1234zeE: E-1,3,3,3-tetrafluoropropene or E-$CF_3-CH=CHF$
HFO-1234zeZ: Z-1,3,3,3-tetrafluoropropene or Z-$CF_3-CH=CHF$
HFO-1243zf: 3,3,3-trifluoropropene or $CF_3-CH=CH_2$
HCFO-1233xf: 3,3,3-trifluoro-2-chloropropene or $CF_3-CCl=CH_2$
HCFO-1233zdE: E-3,3,3-trifluoro-1-chloropropene or E-$CF_3-CH=CHCl$
HCFO-1233zdZ: Z-3,3,3-trifluoro-1-chloropropene or Z-$CF_3-CH=CHCl$
HFO-1225yeZ: Z-1,1,1,2,3-pentafluoropropene or Z-$CHF=CF-CF_3$
HFO-1225yeE: E-1,1,1,2,3-pentafluoropropene or E-$CHF=CF-CF_3$
HFO-1225zc: 1,1,3,3,3-pentafluoropropene or $CF_2=CH-CF_3$
HFO-1225yc: 1,1,2,3,3-pentafluoropropene or $CF_2=CF-CF_2$
HCFC-1214: dichlorotetrafluoropropene, or $C_3F_4Cl_2$
HCFO-1215: chloropentafluoropropene, or $C_3F_5Cl$
HFO-1216: hexafluoropropene, or $C_3F_6$
HCFO-1223: dichlorotrifluoropropene, or $C_3HF_3Cl_2$
HCFO-1224: chlorotetrafluoropropene, or $C_3HF_4Cl$
HCFO-1232: dichlorodifluoropropene, or $C_3H_2F_2Cl_2$
HCFO-1233xc: 1,1,3-trifluoro-2-chloropropene or $CH_2F-CCl=CF_2$
HCFO-1233xe: 1,3,3-trifluoro-2-chloropropene or $CHF_2-CCl=CHF$
HCFO-1233yb: 1,2,3-trifluoro-1-chloropropene or $CH_2F-CF=CFCl$
HCFO-1233yc: 1,1,2-trifluoro-3-chloropropene or $CH_2Cl-CF=CF_2$
HCFO-1233yd: 2,3,3-trifluoro-1-chloropropene or $CHF_2-CF=CHCl$
HCFO-1233ye: 1,2,3-trifluoro-3-chloropropene or $CHClF-CF=CHF$ HCFO-1233yf: 2,3,3-trifluoro-3-chloropropene or CClF$_2$—CF=CH$_2$ HCFO-1233zb: 1,3,3-trifluoro-1-chloropropene or CHF$_2$—CH=CFCl HCFO-1233zc: 1,1,3-trifluoro-3-chloropropene or CHClF—CH=CF$_2$ HCFO-1233ze: 1,3,3-trifluoro-3-chloropropene or CClF$_2$—CH=CHF HFO-1234yc: 1,1,2,3-tetrafluoropropene or CF$_2$=CF—CH$_2$F HFO-1234ye: 1,2,3,3-tetrafluoropropene or CHF=CF—CHF$_2$ HFO-1234zc: 1,1,3,3-tetrafluoropropene or CF$_2$=CH—CHF$_2$ HCFO-1242: chlorodifluoropropene, or C$_3$H$_3$F$_2$Cl HFO-1243yc: 1,1,2-trifluoropropene or CH$_3$—CF=CF$_2$ HFO-1243ye: 1,2,3-trifluoropropene or CH$_2$F—CF=CHF HFO-1243yf: 2,3,3-trifluoropropene or CHF$_2$—CF=CH$_2$ HFO-1243zc: 1,1,3-trifluoropropene or CH$_2$F—CH=CF$_2$ HFO-1243ze: 1,3,3-trifluoropropene or CHF$_2$—CH=CHF HCFO-1251: chlorofluoropropene, or C$_3$H$_4$FCl HFO-1252: difluoropropene, or C$_3$H$_4$F$_2$ HFO-216: hexafluoropropene, or C$_3$F$_6$Cl$_2$ HCFO-217: chloroheptafluoropropane, or C$_3$F$_7$Cl HFC-218: octafluoropropane, or C$_3$F$_8$ HCFC-225: dichloropentafluoropropane, or C$_3$HF$_5$Cl$_2$ HCFC-226: chlorohexafluoropropane, or C$_3$HF$_6$Cl HFC-227: heptafluoropropane, or C$_3$HF$_7$ HCFC-234: dichlorotetrafluoropropane, or C$_3$H$_2$F$_4$Cl$_2$ HCFC-235: chloropentafluoropropane, or C$_3$H$_2$F$_5$Cl HFC-236: hexafluoropropane, or C$_3$H$_2$F$_6$ HCFC-243: dichlorotrifluoropropane, or C$_3$H$_3$F$_3$Cl$_2$ HCFC-244: chlorotetrafluoropropane, or C$_3$H$_3$F$_4$Cl HCFC-244bb: 2-chloro-1,1,1,2-tetrafluoropropane or CF$_3$—CFCl—CH$_3$ HFC-245fa: 1,1,1,3,3-pentafluoropropane or CF$_3$—CH$_2$—CHF$_2$ HFC-245ea: 1,1,2,3,3-pentafluoropropane or CHF$_2$—CHF—CHF$_2$ HFC-245eb: 1,1,1,2,3-pentafluoropropane or CF$_3$—CHF—CH$_2$F HFC-245ca: 1,1,2,2,3-pentafluoropropane or CHF$_2$—CF$_2$—CH$_2$F HCFC-253: chlorotrifluoropropane, or C$_3$H$_4$F$_3$Cl HFC-254: tetrafluoropropane, or C$_3$H$_4$F$_4$ HCFC-262: chlorodifluoropropane, or C$_3$H$_5$F$_2$Cl HFC-263: trifluoropropane, or C$_3$H$_5$F$_3$ trifluoropropyne: CF$_3$—C≡CH The composition according to the invention may optionally be a mixture of one or more azeotropes and/or heteroazeotropes of ternary, quaternary, penternary systems, systems with six compounds, systems with seven compounds, systems with eight or more compounds.

The compound 1,3,3,3-tetrafluoropropene comprises either the compound E-1,3,3,3-tetrafluoropropene or the compound Z-1,3,3,3-tetrafluoropropene or a mixture of the compounds E-1,3,3,3-tetrafluoropropene and Z-1,3,3,3-tetrafluoropropene.

According to one embodiment of the invention, the 1,3,3,3-tetrafluoropropene is E-1,3,3,3-tetrafluoropropene.

According to one embodiment of the invention, the 1,3,3,3-tetrafluoropropene is Z-1,3,3,3-tetrafluoropropene.

The compound(s) containing 1 and/or 2 carbon atoms may be chosen especially from chloromethane, chloropentafluoroethane, 1-chloro-1,2,2,2-tetrafluoroethane, 1-chloro-1,1,2,2-tetrafluoroethane, pentafluoroethane, 1-chloro-1,2,2-trifluoroethane, 1-chloro-2,2,2-trifluoroethane, 1,1,2,2-tetrafluoroethane, 1,1,1,2-tetrafluoroethane, 1-chloro-1,2-difluoroethane, 1-chloro-1,1-difluoroethane, 1,1,2-trifluoroethane, 1,1,1-trifluoroethane, 1,1,2-trifluoroethane, 1,1-difluoroethane, 1,2-difluoroethylene and fluoroethylene.

The compound(s) containing 3 carbon atoms may be chosen especially from 1,2-dichloro-1,1,2,3,3,3-hexafluoropropane, 1,3-dichloro-1,1,2,2,3,3-hexafluoropropane, 1,1-dichloro-1,2,2,3,3,3-hexafluoropropane, 2,2-dichloro-1,1,1,3,3,3-hexafluoropropane, 1-chloro-1,1,2,2,3,3,3-heptafluoropropane, 2-chloro-1,1,1,2,3,3,3-heptafluoropropane, octafluoropropane, dichloropentafluoropropane, 2,2-dichloro-1,1,1,3,3-pentafluoropropane, 2,3-dichloro-1,1,1,2,3-pentafluoropropane, 1,2-dichloro-1,1,2,3,3-pentafluoropropane, 3,3-dichloro-1,1,1,2,2-pentafluoropropane, 1,3-dichloro-1,2,2,3-pentafluoropropane, 1,1-dichloro-1,2,2,3,3-pentafluoropropane, 1,2-dichloro-1,1,3,3,3-pentafluoropropane, 1,3-dichloro-1,1,2,3,3-pentafluoropropane, 1,1-dichloro-1,2,3,3,3-pentafluoropropane, chlorohexafluoropropane, 2-chloro-1,1,1,2,3,3-hexafluoropropane, 3-chloro-1,1,1,2,2,3-hexafluoropropane, 1-chloro-1,2,2,3,3,3-hexafluoropropane, 2-chloro-1,1,1,3,3,3-hexafluoropropane, 1-chloro-1,1,2,3,3,3-hexafluoropropane, 1,1,2,2,3,3,3-heptafluoropropane, 1,1,1,2,3,3,3-Heptafluoropropane, dichlorotetrafluoropropane, 2,2-dichloro-1,1,3,3-tetrafluoropropane, 2,2-dichloro-1,1,1,3-tetrafluoropropane, 1,2-dichloro-1,2,3,3-tetrafluoropropane, 2,3-dichloro-1,1,1,2-tetrafluoropropane, 1,2-dichloro-1,1,2,3-tetrafluoropropane, 1,3-dichloro-1,2,2,3-tetrafluoropropane, 1,1-dichloro-2,2,3,3-tetrafluoropropane, 1,3-dichloro-1,1,2,2-tetrafluoropropane, 1,1-dichloro-1,2,2,3-tetrafluoropropane, 2,3-dichloro-1,1,1,3-tetrafluoropropane, 1,3-dichloro-1,1,3,3-tetrafluoropropane, 1,3-dichloro-1,1,3,3-tetrafluoropropane, 1,1-dichloro-1,3,3,3-tetrafluoropropane, 1,1-dichloro-2,3,3,3-tetrafluoropropane, 1,3-dichloro-1,1,2,3-tetrafluoropropane, 1,1-dichloro-1,2,3,3-tetrafluoropropane, chloropentafluoropropane, 1-chloro-1,2,2,3,3-pentafluoropropane, 3-chloro-1,1,1,2,3-pentafluoropropane, 1-chloro-1,1,2,2,3-pentafluoropropane, 2-chloro-1,1,1,3,3-pentafluoropropane, 1-chloro-1,1,3,3,3-pentafluoropropane, 1-chloro-1,1,2,3,3-pentafluoropropane, 1-chloro-1,1,2,3,3-pentafluoropropane, 3-chloro-1,1,1,2,2-pentafluoropropane, 2-chloro-1,1,2,3,3-pentafluoropropane, 2-chloro-1,1,1,2,3-pentafluoropropane, 1,1,1,2,2,3-hexafluoropropane, 1,1,1,2,3,3-hexafluoropropane, 1,1,1,3,3,3-hexafluoropropane, 1,1,2,2,3,3-hexafluoropropane, dichlorotrifluoropropane, 1,1-dichloro-3,3,3-trifluoropropane, 1,3-dichloro-1,1,3-trifluoropropane, 1,1-dichloro-1,3,3-trifluoropropane, 1,3-dichloro-1,2,3-trifluoropropane, 1,1-dichloro-2,3,3-trifluoropropane, 1,3-dichloro-1,1,2-trifluoropropane, 1,1-dichloro-1,2,3-trifluoropropane, 1,2-dichloro-1,3,3-trifluoropropane, 2,3-dichloro-1,1,1-trifluoropropane, 1,2-dichloro-1,1,3-trifluoropropane, 1,3-dichloro-1,2,2-trifluoropropane, 1,1-dichloro-2,2,3-trifluoropropane, 1,1-dichloro-1,2,2-trifluoropropane, 2,3-dichloro-1,1,2-trifluoropropane, 1,2-dichloro-1,2,3-trifluoropropane, 1,2-dichloro-1,1,2-trifluoropropane, 2,2-dichloro-1,1,3-trifluoropropane, 2,2-dichloro-3,3,3-trifluoropropane, chlorotetrafluoropropane, 2-chloro-1,2,3,3-tetrafluoropropane, 2-chloro-1,1,1,2-tetrafluoropropane, 3-chloro-1,1,2,2-tetrafluoropropane, 1-chloro-1,2,2,3-tetrafluoropropane, 1-chloro-1,1,2,2-tetrafluoropropane, 2-chloro-1,1,3,3-tetrafluoropropane, 2-chloro-1,1,1,3-tetrafluoropropane, 3-chloro-1,1,2,3-tetrafluoropropane, 3-chloro-1,1,1,2-tetrafluoropropane, 1-chloro-1,1,2,3-tetrafluoropropane, 3-chloro-1,1,1,3-tetrafluoropropane, 1-chloro-1,1,3,3-tetrafluoropropane, pentafluoropropane, 1,1,1,3,3-pentafluoropropane, 1,1,2,2,3-pentafluoropropane, 1,1,2,3,3-pentafluoropropane, 1,1,1,2,3-pentafluoropropane, chlorotrifluoropropane, 2-chloro-1,2,3-trifluoropropane, 2-chloro-1,1,2-trifluoropropane, 1-chloro-2,2,3-trifluoropropane, 1-chloro-1,2,2-trifluoropropane, 3-chloro-1,1,2-trifluoropropane, 1-chloro-1,2,3-trifluoropropane, 1-chloro-1,1,2-trifluoropropane, 3-chloro-1,3,3-trifluoropropane, 3-chloro-1,1,1-trifluoropropane, 1-chloro-1,1,3-trifluoropropane, 2-chloro-1,1,3-trifluoropropane, 2-chloro-1,1,1-trifluoropropane, 1,1,2,2-tetrafluoropropane, 1,1,1,3-tetrafluoropropane, 1,1,2,3-tetrafluoropropane, 1,1,1,2-tetrafluoropropane, 1,2,2,3-tetrafluoropropane, 1,1,3,3-tetrafluoropropane, chlorodifluoropropane, 1-chloro-2,2-difluoropropane, 3-chloro-1,1-difluoropropane, 1-chloro-1,3-difluoropropane, 1-chloro-1,1-difluoropropane, 1-chloro-2,3-difluoropropane, 1-chloro-1,2-difluoropropane, 2-chloro-1,3-difluoropropane, 2-chloro-1,1-difluoropropane, 2-chloro-1,2-difluoropropane, trifluoropropane, 1,1,1-trifluoropropane, 1,1,3-trifluoropropane, 1,2,3-trifluoropropane, 1,1,2-trifluoropropane, 1,2,2-trifluoropropane, dichlorotetrafluoropropene, 1,2-dichloro-1,3,3,3-tetrafluoropropene, 1,1-dichloro-2,3,3,3-tetrafluoropropene, 1,3-dichloro-1,2,3,3-tetrafluoropropene, 2,3-dichloro-1,1,3,3-tetrafluoropropene, 3,3-dichloro-1,1,2,3-tetrafluoropropene, chloropentafluoropropene, 1-chloropentafluoropropene, 2-chloropentafluoropropene, 3-chloropentafluoropropene, hexafluoropropene, dichlorotrifluoropropene, 1,1-dichloro-3,3,3-trifluoropropene, 1,2-dichloro-3,3,3-trifluoropropene, 2,3-dichloro-1,3,3-trifluoropropene, 1,3-dichloro-2,3,3-trifluoropropene, 1,2-dichloro-1,3,3-trifluoropropene, 2,3-dichloro-1,1,3-trifluoropropene, 1,1-dichloro-2,3,3-trifluoropropene, 1,3-dichloro-1,2,3-trifluoropropene, 3,3-dichloro-1,1,2-trifluoropropene, 3,3-dichloro-1,2,3-trifluoropropene, 1,3-dichloro-1,3,3-trifluoropropene, 3,3-dichloro-1,1,3-trifluoropropene, 1-chloro-2,3,3,3-tetrafluoropropene, 1-chloro-1,3,3,3-tetrafluoropropene, 2-chloro-1,3,3,3-tetrafluoropropene, 3-chloro-1,2,3,3-tetrafluoropropene, 3-chloro-1,1,3,3-tetrafluoropropene, 2-chloro-1,1,3,3-tetrafluoropropene, 1-chloro-1,2,3,3-tetrafluoropropene, 3-chloro-1,1,2,3-tetrafluoropropene, 1,2,3,3,3-pentafluoropropene, 1,1,3,3,3-pentafluoropropene, 1,1,2,3,3-pentafluoropropene, dichlorodifluoropropene, 2,3-dichloro-3,3-difluoropropene, 1,2-dichloro-1,3-difluoropropene, 2,3-dichloro-1,1-difluoropropene, 1,2-dichloro-3,3-difluoropropene, 2,3-dichloro-1,3-difluoropropene, 1,1-dichloro-2,3-difluoropropene, 1,3-dichloro-1,2-difluoropropene, 1,3-dichloro-2,3-difluoropropene, 3,3-dichloro-1,2-difluoropropene, 3,3-dichloro-2,3-difluoropropene, 1,1-dichloro-3,3-difluoropropene, 1,3-dichloro-1,3-difluoropropene, 3,3-dichloro-1,1-difluoropropene, 1,3-dichloro-3,3-difluoropropene, 3,3-dichloro-1,3-difluoropropene, chlorotrifluoropropene, 2-chloro-1,1,3-trifluoropropene, 2-chloro-1,3,3-trifluoropropene, 1-chloro-1,2,3-trifluoropropene, 3-chloro-1,1,2-trifluoropropene, 1-chloro-2,3,3-trifluoropropene, 3-chloro-1,2,3-trifluoropropene, 3-chloro-2,3,3-trifluoropropene, 1-chloro-1,3,3-trifluoropropene, 3-chloro-1,1,3-trifluoropropene, 3-chloro-1,3,3-trifluoropropene, 1,1,2,3-tetrafluoropropene, 1,2,3,3-tetrafluoropropene, 1,1,3,3-tetrafluoropropene, chlorodifluoropropene, 3-chloro-3,3-difluoropropene, 3-chloro-1,3-difluoropropene, 2-chloro-1,1-difluoropropene, 2-chloro-3,3-difluoropropene, 1-chloro-1,2-difluoropropene, 1-chloro-2,3-difluoropropene, 3-chloro-1,2-difluoropro-pene, 3-chloro-2,3-difluoropropene, 1-chloro-1,3-difluoropropene, 3-chloro-1,1-difluoropropene, 1-chloro-3,3-difluoropropene, trifluoropropene, 1,1,2-trifluoropropene, 1,2,3-trifluoropropene, 2,3,3-trifluoropropene, 1,1,3-trifluoropropene, 1,3,3-trifluoropropene, chlorofluoropropene, 1-chloro-3-fluoropropene, 1-chloro-1-fluoropropene, 1-chloro-2-fluoropropene, 2-chloro-1-fluoropropene, 2-chloro-3-fluoropropene, 3-chloro-2-fluoropropene, 3-chloro-1-fluoropropene, 3-chloro-3-fluoropropene, difluoropropene, 1,2-difluoropropene, 2,3-difluoropropene, 1,1-difluoropropene, 1,3-difluoropropene, 3,3-difluoropropene, 1,1,1,2,2-pentafluoropropane, 2,3,3,3-tetrafluoropropene, E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, Z-3,3,3-trifluoro-1-chloropropene and trifluoropropyne.

Preferably, the ternary compositions consisting essentially of HF-HFO-1234ze-HFC-245fa and HF—HFO-1234zeE-HFO-1234zeZ are excluded from the present invention.

A subject of the present invention is also an azeotropic or quasi-azeotropic composition comprising hydrogen fluoride, 1,3,3,3-tetrafluoropropene, and one or more compounds chosen from 1,1,1,2,2-pentafluoropropane, 2,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

A subject of the present invention is also an azeotropic or quasi-azeotropic composition comprising hydrogen fluoride, 1,3,3,3-tetrafluoropropene and at least one or more organic compounds chosen from 3,3,3-trifluoro-2-chloropropene, E-3,3,3-trifluoro-1-chloropropene, 3,3,3-trifluoropropene, 1,1,1,2,2-pentafluoropropane and 2,3,3,3-tetrafluoropropene.

According to one embodiment, the composition according to the invention comprises hydrogen fluoride, 1,3,3,3-tetrafluoropropene, 1,1,1,2,2-pentafluoropropane and optionally one or more compounds chosen from 2,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 1,3,3,3-tetrafluoropropene, 2,3,3,3-tetrafluoropropene and optionally one or more compounds chosen from 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, 1,3,3,3-tetrafluoropropene, 3,3,3-trifluoropropene and optionally one or more compounds chosen from 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 1,3,3,3-tetrafluoropropene, 3,3,3-trifluoro-2-chloropropene and optionally one or more compounds chosen from E-3,3, 3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment, the composition according to the invention comprises hydrogen fluoride, 1,3,3,3-tetrafluoropropene, E-3,3,3-trifluoro-1-chloropropene and optionally one or more compounds chosen from trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 1,3,3,3-tetrafluoropropene, trifluoropropyne and optionally one or more compounds chosen from 1,1,1,3,3-pentafluoropropene, 1,1,1,3,3-pentafluoropropane, 1,1,1,2,3-pentafluoropropene and 2-chloro-1,1,1,2-tetrafluoropropane.

According to one embodiment, the composition according to the invention comprises hydrogen fluoride, 1,3,3,3-tetrafluoropropene, 1,1,1,3,3-pentafluoropropene and optionally one or more compounds chosen from 1,1,1,3,3-pentafluoropropane, 1,1,1,2,3-pentafluoropropene and 2-chloro-1,1,1,2-tetrafluoropropane.

According to another embodiment, the composition according to the invention comprises hydrogen fluoride, 1,3,3,3-tetrafluoropropene, 1,1,1,2,3-pentafluoropropene and optionally one or more compounds chosen from 1,1,1,3,3-pentafluoropropane, 2-chloro-1,1,1,2-tetrafluoropropane.

According to another embodiment, the composition according to the invention comprises hydrogen fluoride, 1,3,3,3-tetrafluoropropene, 3,3,3-trifluoro-2-chloropropene and optionally one or more compounds chosen from E-3,3,3-trifluoro-1-chloropropene, 3,3,3-trifluoropropene, 1,1,1,2,2-pentafluoropropane, 2,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

According to one embodiment according to the invention, the composition comprises hydrogen fluoride, 1,3,3,3-tetrafluoropropene, E-3,3,3-trifluoro-1-chloropropene and optionally one or more compounds chosen from 3,3,3-trifluoropropene, 1,1,1,2,2-pentafluoropropane 2,3,3,3-tetrafluoropropene, trifluoropropyne, 1,1,1,3,3-pentafluoropropene, 1,1,1,2,3-pentafluoropropene and 2-chloro-1,1,1,2-tetrafluoropropane.

According to another embodiment, the composition according to the invention comprises hydrogen fluoride, 1,3,3,3-tetrafluoropropene, 3,3,3-trifluoropropene and optionally one or more compounds chosen from 1,1,1,2,2-pentafluoropropane, 2,3,3,3-tetrafluoropropene, trifluoropropyne, 1,1,1,3,3-pentafluoropropane, 1,1,1,3,3-pentafluoropropane, 1,1,1,2,3-pentafluoropropene and 2-chloro-1,1,1,2-tetrafluoropropane.

According to one embodiment of the invention, the composition comprises hydrogen fluoride, 1,3,3,3-tetrafluoropropene, 1,1,1,2,2-pentafluoropropane and optionally one or more compounds chosen from 2,3,3,3-tetrafluoropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

Irrespective of the embodiment, the composition preferably comprises from 1% to 95% and advantageously from 5% to 80% by weight of hydrogen fluoride and from 99% to 5% and advantageously from 20% to 95% by weight of the sum of the organic compounds; more particularly, the composition comprises from 1% to 85% by weight of hydrogen fluoride and from 99% to 15% by weight of the sum of the organic compounds (HFO-1234ze and the (hydro)halocarbon compounds).

Irrespective of the embodiment, the boiling point of the composition according to the invention is between −20° C. and 80° C. and at a pressure between 0.1 and 44 bar absolute, preferentially between 0° C. and 40° C. and preferentially at a pressure of between 0.7 and 18 bar absolute, advantageously between 0.9 and 12.5 bar absolute.

The Applicant has discovered that the compositions according to the invention have advantageous properties in particular for the recycling of HF in the reaction step. Thus, the condensed phase of these compositions, optionally when they are subjected to a distillation step and/or a liquid/liquid separation step, such as by decantation, form two immiscible liquid phases.

By way of example, for the ternary compounds containing hydrogen fluoride, 1,3,3,3-tetrafluoropropene and a compound chosen from 1,1,1,2,2-pentafluoropropane, 2,3,3,3-tetrafluoropropene, 3,3,3-trifluoropropene, 3,3,3-trifluoro-2-chloropropene and E-3,3,3-trifluoro-1-chloropropene, the appearance of a heteroazeotrope characterized by two liquid phases, one rich in HF and the other depleted in HF, depends on the amount of HF in the composition. These decantation ranges as a function of the HF content in the compositions were characterized for at least isotherms at 0° C., 25° C. and 40° C.

Similarly, the decantation ranges for the ternary compounds containing hydrogen fluoride, 1,3,3,3-tetrafluoropropene and a compound chosen from trifluoropropyne, 1,1,1,3,3-pentafluoropropane, 1,1,1,3,3-pentafluoropropene, Z-1,1,1,2,3-pentafluoropropene and 2-chloro-1,1,1,2-tetrafluoropropane are characterized by a phase depleted in HF and a phase enriched in HF for at least isotherms at 0° C., 25° C. and 40° C.

The Applicant has observed the same phenomenon for compositions of hydrogen fluoride, 1,3,3,3-tetrafluoropropene comprising several compounds chosen from 1,1,1,2,2-pentafluoropropane, 2,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

An azeotropic or quasi-azeotropic composition that is preferred according to the invention comprises from 1% to 80% by weight of hydrogen fluoride, and from 99% to 20% by weight of the sum of HFO-1234zeE and HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE and HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ and HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ and HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE and HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE and HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ and HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ and HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HCFO-1233xf and HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HCFO-1233xf and HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HCFO-1233xf and HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HCFO-1233xf and HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233zdE and HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HCFO-1233zdE and HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ, HCFO-1233zdE and HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ, HCFO-1233zdE and HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233xf and HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HCFO-1233xf and HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFC-1234zeE, HFO-1234zeZ and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HFO-1234zeZ and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HFO-1243zf and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HFO-1243zf and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ, HFO-1243zf and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ, HFO-1243zf and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb and HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb and HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ, HFO-1243zf and HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ, HFO-1243zf and HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb, HCFO-1233xf and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb, HCFO-1233xf and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf and HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf and HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233zdE, HCFO-1233xf and HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HCFO-1233zdE, HCFO-1233xf and HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233xf, HCFO-1233zdE and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HCFO-1233zdE, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeZ, HCFO-1233zdE, HCFO-1233xf and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ, HCFO-1233zdE, HCFO-1233xf and HFO-1243zf, the boiling point of this preferred composition is between 0 and 40'C at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233xf, HFO-1234zeZ and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HCFO-1233xf, HFO-1234zeZ and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 1% to 85% by weight of hydrogen fluoride, and from 99% to 15% by weight of the sum of HFO-1234zeE, HFC-245cb, HFO-1234zeZ and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HFO-1234zeZ and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HFO-1243zf and HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HFO-1243zf and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb, HCFO-1233zdE and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb, HCFO-1233zdE and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HFO-1243zf, HCFO-1233zdE and HFO-1234zeZ, the boiling point of this preferred composition is between 0 and 40'C at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HFO-1243zf, HCFO-1233zdE and HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb, HCFO-1234zeE and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb, HCFO-1234zeE and HFO-1243zf, the boiling point of this preferred composition is between 0 and 40'C at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf, HFO-1234zeZ, and HCFO-1233zdE, the boiling point of this preferred composition is between 0 and 40'C at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf, HFO-1234zeZ, and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf, HFO-1234zeZ, and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf, HFO-1234zeZ, and HFO- 1243zf, the boiling point of this preferred composition is between 0 and 40'C at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf, HCFO-1233zdE, and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf, HCFO-1233zdE, and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb, HCFO-1233xf, HCFO-1233zdE, and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb, HCFO-1233xf, HCFO-1233zdE, and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HCFO-1233xf, HFO-1234zeZ, HCFO-1233zdE, and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HFO-1234zeZ, HCFO-1233xf, HCFO-1233zdE, and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeZ, HFC-245cb, HCFO-1233zdE, HFO-1234zeE and HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeZ, HFC-245cb, HCFO-1233zdE, HFO-1234zeE and HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234zeE, HFC-245cb, HCFO-1233xf, HFO-1234zeZ, HCFO-1233zdE and HFO1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234zeE, HFC-245cb, HCFO-1233xf, HFO-1234zeZ, and HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride, and from 99% to 20% by weight of the sum of HFO-1234zeE, HFC-245fa, HCFC-244bb, trifluoropropyne, HFO-1225yeZ and HFO-1225zc, the boiling point of this preferred composition is between 0 and 40° C. at a pressure of between 0.7 and 18 bar absolute.

An azeotropic or quasi-azeotropic composition that is preferred according to the invention preferably comprises from 5% to 75% by weight of hydrogen fluoride, and from 95% to 25% by weight of the sum of HFO-1234zeE, HFC-245fa, HCFC-244bb, trifluoropropyne, HFO-1225yeZ and HFO-1225zc, the boiling point of this preferred composition is between 0 and 40° C. at a pressure of between 0.7 and 18 bar absolute.

An azeotropic or quasi-azeotropic composition that is preferred according to the invention comprises from 1% to 80% by weight of hydrogen fluoride, and from 99% to 20% by weight of the sum of HFO-1234zeZ, HFC-245fa, HCFC-244bb, trifluoropropyne, HFO-1225yeZ and HFO-1225zc, the boiling point of this preferred composition is between 0 and 40° C. at a pressure of between 0.7 and 18 bar absolute.

An azeotropic or quasi-azeotropic composition that is preferred according to the invention preferably comprises from 5% to 75% by weight of hydrogen fluoride, and from 95% to 25% by weight of the sum of HFO-1234zeZ, HFC-245fa, HCFC-244bb, trifluoropropyne, HFO-1225yeZ and HFO-1225zc, the boiling point of this preferred composition is between 0 and 40° C. at a pressure of between 0.7 and 18 bar absolute.

An azeotropic or quasi-azeotropic composition that is preferred according to the invention comprises from 1% to 85% by weight of hydrogen fluoride, and from 99% to 15% by weight of the sum of HFO-1234yf, HFO-1234zeZ, HFC-245cb, HCFO-1233zdE, HCFO-1233xf, HCFC-244bb and HFO-1234zeE, the boiling point of this preferred composition is between 0 and 40° C. at a pressure of between 0.7 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234yf, HFO-1234zeZ, HFC-245cb, HCFO-1233zdE, HCFO-1233xf, HCFC-244bb and HFO-1234zeE, the boiling point of this preferred composition is between 0 and 40° C. at a pressure of between 0.7 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234yf, HFO-1234zeZ, HFC-245cb, HCFO-1233zdE, HCFO-1233xf, trifluoropropyne and HFO-1234zeE, the boiling point of this preferred composition is between 0 and 40° C. at a pressure of between 0.9 and 18 bar absolute.

An azeotropic or quasi-azeotropic composition that is preferred according to the invention preferably comprises from 5% to 80% by weight of hydrogen fluoride, and from 95% to 20% by weight of the sum of HFO-1234yf, HFO-1234zeZ, HFC-245cb, HCFO-1233zdE, HCFO-1233xf, trifluoropropyne and HFO-1234zeE, the boiling point of this preferred composition is between 0 and 40° C. at a pressure of between 0.9 and 18 bar absolute.

An azeotropic or quasi-azeotropic composition that is preferred according to the invention comprises from 1% to 85% by weight of hydrogen fluoride, and from 99% to 15% by weight of the sum of HFO-1234yf, HFO-1234zeZ, HFC-245cb, HCFO-1233zdE, HCFO-1233xf, HFC-245fa and HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234yf, HFO-1234zeZ, HFC-245cb, HCFO-1233zdE, HCFO-1233xf, HFC-245fa and HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234yf, HFO-1234zeZ, HFC-245cb, HCFO-1233zdE, HCFO-1233xf, HFO-1225yeZ and HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234yf, HFO-1234zeZ, HFC-245cb, HCFO-1233zdE, HCFO-1233xf, HFO-1225yeZ and HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234yf, HFO-1234zeZ, HFC-245cb, HCFO-1233zdE, HCFO-1233xf, HFO-1225zc and HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride, and from 95% to 20% by weight of the sum of HFO-1234yf, HFO-1234zeZ, HFC-245cb, HCFO-1233zdE, HCFO-1233xf, HFO-1225zc and HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride, and from 99% to 15% by weight of the sum of HFO-1234yf, HFO-1234zeZ, HFC-245cb, HCFO-1233zdE, HCFO-1233xf, HFO-1225zc, trifluoropropyne, HCFC-244bb, HFC-245fa, HFO-1225yeZ, HFO-1243zf and HFO-1234zeE, the boiling point of this preferred composition is between 0 and 40° C. at a pressure of between 0.7 and 18.0 bar absolute.

An azeotropic or quasi-azeotropic composition that is preferred according to the invention preferably comprises from 5% to 80% by weight of hydrogen fluoride, and from 95% to 20% by weight of the sum of HFO-1234yf, HFO-1234zeZ, HFC-245cb, HCFO-1233zdE, HCFO-1233xf, HFO-1225zc, trifluoropropyne, HCFC-244bb, HFC-245fa, HFO-1225yeZ, HFO-1243zf and HFO-1234zeE, the boiling point of this preferred composition is between 0 and 40° C. at a pressure of between 0.7 and 18.0 bar absolute.

The pressure characteristics of the mixtures of Examples 1, 4, 7, 10, 13, 16 and 19 were calculated for an isotherm at 25° C.

Examples 2, 5, 8, 11, 14, 17 and 20 represent the boiling points and pressure ranges of the mixtures and Examples 3, 6, 9, 12, 15, 18 and 21 represent the decantation ranges of the mixtures of Examples 1, 4, 7, 10, 13, 16 and 19 as a function of the mass percentage of HF characterized for isotherms at 0° C., 25° C. and 40° C. The decantation ranges of Examples 3, 6, 9, 12, 15, 18 and 21 are calculated for mixtures of organic compounds having equal-mass contents. By way of example, for a ternary mixture, a mixture containing 50% by weight of each of the two organic compounds is considered; for a penternary mixture, a mixture containing 25% by weight of each of the four organic compounds is considered, the mass fraction of HF ranging from 0 to 1. These calculations are performed at the liquid-vapor equilibrium, under azeotropic conditions.

Example 1: Ternary Mixtures, Isotherm at 25° C.

| HF-HFO-1234zeE-HCFO-1233xf | | | | | |
|---|---|---|---|---|---|
| Organics 0.95 F1234zeE + 0.05 F1233xf | | Organics 0.5 F1234zeE + 0.5 F1233xf | | Organics 0.05 F1234zeE + 0.95 F1233xf | |
| MASSFRAC HF | TOTAL PRESSURE bar | MASSFRAC HF | TOTAL PRESSURE bar | MASSFRAC HF | TOTAL PRESSURE bar |
| 0 | 4.7 | 0 | 3.3 | 0 | 1.7 |
| 0.05 | 5.7 | 0.05 | 4.3 | 0.05 | 2.8 |
| 0.1 | 5.7 | 0.1 | 4.3 | 0.1 | 2.8 |
| 0.15 | 5.7 | 0.15 | 4.3 | 0.15 | 2.8 |
| 0.2 | 5.7 | 0.2 | 4.3 | 0.2 | 2.8 |
| 0.25 | 5.7 | 0.25 | 4.3 | 0.25 | 2.8 |
| 0.3 | 5.7 | 0.3 | 4.3 | 0.3 | 2.8 |
| 0.35 | 5.7 | 0.35 | 4.3 | 0.35 | 2.8 |
| 0.4 | 5.7 | 0.4 | 4.3 | 0.4 | 2.8 |
| 0.45 | 5.7 | 0.45 | 4.3 | 0.45 | 2.8 |

HF-HFO-1234zeE-HCFO-1233xf

| Organics 0.95 F1234zeE + 0.05 F1233xf | | Organics 0.5 F1234zeE + 0.5 F1233xf | | Organics 0.05 F1234zeE + 0.95 F1233xf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0.5 | 5.6 | 0.5 | 4.3 | 0.5 | 2.8 |
| 0.55 | 5.6 | 0.55 | 4.2 | 0.55 | 2.8 |
| 0.6 | 5.5 | 0.6 | 4.2 | 0.6 | 2.8 |
| 0.65 | 5.4 | 0.65 | 4.2 | 0.65 | 2.8 |
| 0.7 | 5.2 | 0.7 | 4.1 | 0.7 | 2.8 |
| 0.75 | 5.0 | 0.75 | 3.9 | 0.75 | 2.8 |
| 0.8 | 4.7 | 0.8 | 3.7 | 0.8 | 2.6 |
| 0.85 | 4.2 | 0.85 | 3.3 | 0.85 | 2.4 |
| 0.9 | 3.5 | 0.9 | 2.8 | 0.9 | 2.2 |
| 0.95 | 2.5 | 0.95 | 2.1 | 0.95 | 1.7 |
| 1 | 1.2 | 1 | 1.2 | 1 | 1.2 |

HF-HFO-1234zeZ-HCFO-1233xf

| Organics 0.95 F1234zeZ + 0.05 F1233xf | | Organics 0.5 F1234zeZ + 0.5 F1233xf | | Organics 0.05 F1234zeZ + 0.95 F1233xf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.7 | 0 | 1.6 |
| 0.05 | 2.9 | 0.05 | 2.8 | 0.05 | 2.7 |
| 0.1 | 2.9 | 0.1 | 2.8 | 0.1 | 2.7 |
| 0.15 | 2.9 | 0.15 | 2.8 | 0.15 | 2.7 |
| 0.2 | 2.9 | 0.2 | 2.8 | 0.2 | 2.7 |
| 0.25 | 2.9 | 0.25 | 2.8 | 0.25 | 2.7 |
| 0.3 | 2.9 | 0.3 | 2.8 | 0.3 | 2.7 |
| 0.35 | 2.9 | 0.35 | 2.8 | 0.35 | 2.7 |
| 0.4 | 2.9 | 0.4 | 2.8 | 0.4 | 2.7 |
| 0.45 | 2.9 | 0.45 | 2.8 | 0.45 | 2.7 |
| 0.5 | 2.9 | 0.5 | 2.8 | 0.5 | 2.7 |
| 0.55 | 2.9 | 0.55 | 2.8 | 0.55 | 2.7 |
| 0.6 | 2.9 | 0.6 | 2.8 | 0.6 | 2.7 |
| 0.65 | 2.9 | 0.65 | 2.8 | 0.65 | 2.7 |
| 0.7 | 2.9 | 0.7 | 2.8 | 0.7 | 2.7 |
| 0.75 | 2.9 | 0.75 | 2.8 | 0.75 | 2.7 |
| 0.8 | 2.8 | 0.8 | 2.7 | 0.8 | 2.5 |
| 0.85 | 2.6 | 0.85 | 2.5 | 0.85 | 2.4 |
| 0.9 | 2.3 | 0.9 | 2.2 | 0.9 | 2.1 |
| 0.95 | 1.8 | 0.95 | 1.8 | 0.95 | 1.7 |
| 1 | 1.2 | 1 | 1.2 | 1 | 1.2 |

HF-HFO-1234zeE-HCFO-1233zdE

| Organics 0.95 F1233zdE + 0.05 F1234zeE | | Organics 0.5 F1233zdE + 0.5 F1234zeE | | Organics 0.05 F1233zdE + 0.95 F1234zeE | |
|---|---|---|---|---|---|
| MASSFRAC HF | TOTAL PRES bar | MASSFRAC HF | TOTAL PRES bar | MASSFRAC HF | TOTAL PRES bar |
| 0 | 1.5 | 0 | 3.2 | 0 | 4.7 |
| 0.05 | 2.6 | 0.05 | 4.2 | 0.05 | 5.7 |
| 0.1 | 2.6 | 0.1 | 4.2 | 0.1 | 5.7 |
| 0.15 | 2.6 | 0.15 | 4.2 | 0.15 | 5.7 |
| 0.2 | 2.6 | 0.2 | 4.2 | 0.2 | 5.7 |
| 0.25 | 2.6 | 0.25 | 4.2 | 0.25 | 5.7 |
| 0.3 | 2.6 | 0.3 | 4.2 | 0.3 | 5.7 |
| 0.35 | 2.6 | 0.35 | 4.2 | 0.35 | 5.7 |
| 0.4 | 2.6 | 0.4 | 4.2 | 0.4 | 5.7 |
| 0.45 | 2.6 | 0.45 | 4.2 | 0.45 | 5.7 |
| 0.5 | 2.6 | 0.5 | 4.1 | 0.5 | 5.6 |
| 0.55 | 2.6 | 0.55 | 4.1 | 0.55 | 5.6 |
| 0.6 | 2.6 | 0.6 | 4.1 | 0.6 | 5.5 |

| HF-HFO-1234zeE-HCFO-1233zdE ||||||
| Organics 0.95 F1233zdE + 0.05 F1234zeE || Organics 0.5 F1233zdE + 0.5 F1234zeE || Organics 0.05 F1233zdE + 0.95 F1234zeE ||
| MASSFRAC HF | TOTAL PRES bar | MASSFRAC HF | TOTAL PRES bar | MASSFRAC HF | TOTAL PRES bar |
| --- | --- | --- | --- | --- | --- |
| 0.65 | 2.6 | 0.65 | 4.1 | 0.65 | 5.4 |
| 0.7 | 2.6 | 0.7 | 4.0 | 0.7 | 5.2 |
| 0.75 | 2.6 | 0.75 | 3.8 | 0.75 | 5.0 |
| 0.8 | 2.4 | 0.8 | 3.6 | 0.8 | 4.7 |
| 0.85 | 2.3 | 0.85 | 3.2 | 0.85 | 4.2 |
| 0.9 | 2.0 | 0.9 | 2.8 | 0.9 | 3.5 |
| 0.95 | 1.7 | 0.95 | 2.1 | 0.95 | 2.5 |
| 1 | 1.2 | 1 | 1.2 | 1 | 1.2 |

| HF-HFO-1234zeZ-HCFO-1233zdE ||||||
| Organics 0.95 F1233zdE + 0.05 F1234zeZ || Organics 0.5 F1233zdE + 0.5 F1234zeZ || Organics 0.05 F1233zdE + 0.95 F1234zeZ ||
| MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- |
| 0 | 1.3 | 0 | 1.6 | 0 | 1.8 |
| 0.05 | 2.4 | 0.05 | 2.7 | 0.05 | 2.9 |
| 0.1 | 2.4 | 0.1 | 2.7 | 0.1 | 2.9 |
| 0.15 | 2.4 | 0.15 | 2.7 | 0.15 | 2.9 |
| 0.2 | 2.4 | 0.2 | 2.7 | 0.2 | 2.9 |
| 0.25 | 2.4 | 0.25 | 2.7 | 0.25 | 2.9 |
| 0.3 | 2.4 | 0.3 | 2.7 | 0.3 | 2.9 |
| 0.35 | 2.4 | 0.35 | 2.7 | 0.35 | 2.9 |
| 0.4 | 2.4 | 0.4 | 2.7 | 0.4 | 2.9 |
| 0.45 | 2.4 | 0.45 | 2.7 | 0.45 | 2.9 |
| 0.5 | 2.4 | 0.5 | 2.7 | 0.5 | 2.9 |
| 0.55 | 2.4 | 0.55 | 2.7 | 0.55 | 2.9 |
| 0.6 | 2.4 | 0.6 | 2.7 | 0.6 | 2.9 |
| 0.65 | 2.4 | 0.65 | 2.7 | 0.65 | 2.9 |
| 0.7 | 2.4 | 0.7 | 2.7 | 0.7 | 2.9 |
| 0.75 | 2.4 | 0.75 | 2.7 | 0.75 | 2.9 |
| 0.8 | 2.3 | 0.8 | 2.6 | 0.8 | 2.8 |
| 0.85 | 2.2 | 0.85 | 2.4 | 0.85 | 2.6 |
| 0.9 | 2.0 | 0.9 | 2.1 | 0.9 | 2.3 |
| 0.95 | 1.6 | 0.95 | 1.7 | 0.95 | 1.8 |
| 1 | 1.2 | 1 | 1.2 | 1 | 1.2 |

| HF-HFO-1234zeE-HFO-1234yf ||||||
| Organics 0.95 F1234zeE + 0.05 F1234yf || Organics 0.5 F1234zeE + 0.5 F1234yf || Organics 0.05 F1234zeE + 0.95 F1234yf ||
| MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- |
| 0 | 5.0 | 0 | 5.9 | 0 | 6.7 |
| 0.05 | 5.9 | 0.05 | 6.8 | 0.05 | 7.7 |
| 0.1 | 5.9 | 0.1 | 6.8 | 0.1 | 7.7 |
| 0.15 | 5.9 | 0.15 | 6.8 | 0.15 | 7.7 |
| 0.2 | 5.9 | 0.2 | 6.8 | 0.2 | 7.7 |
| 0.25 | 5.9 | 0.25 | 6.8 | 0.25 | 7.6 |
| 0.3 | 5.9 | 0.3 | 6.8 | 0.3 | 7.7 |
| 0.35 | 5.9 | 0.35 | 6.8 | 0.35 | 7.7 |
| 0.4 | 5.9 | 0.4 | 6.8 | 0.4 | 7.7 |
| 0.45 | 5.9 | 0.45 | 6.8 | 0.45 | 7.7 |
| 0.5 | 5.9 | 0.5 | 6.8 | 0.5 | 7.7 |
| 0.55 | 5.8 | 0.55 | 6.8 | 0.55 | 7.7 |
| 0.6 | 5.8 | 0.6 | 6.8 | 0.6 | 7.7 |
| 0.65 | 5.7 | 0.65 | 6.7 | 0.65 | 7.7 |

HF-HFO-1234zeE-HFO-1234yf

| Organics 0.95 F1234zeE + 0.05 F1234yf | | Organics 0.5 F1234zeE + 0.5 F1234yf | | Organics 0.05 F1234zeE + 0.95 F1234yf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0.7 | 5.5 | 0.7 | 6.6 | 0.7 | 7.6 |
| 0.75 | 5.3 | 0.75 | 6.4 | 0.75 | 7.5 |
| 0.8 | 4.9 | 0.8 | 6.1 | 0.8 | 7.1 |
| 0.85 | 4.4 | 0.85 | 5.5 | 0.85 | 6.5 |
| 0.9 | 3.7 | 0.9 | 4.6 | 0.9 | 5.5 |
| 0.95 | 2.6 | 0.95 | 3.2 | 0.95 | 3.8 |
| 1 | 1.2 | 1 | 1.2 | 1 | 1.2 |

HF-HFO-1234zeZ-HFO-1234yf

| Organics 0.95 F1234zeZ + 0.05 F1234yf | | Organics 0.5 F1234zeZ + 0.5 F1234yf | | Organics 0.05 F1234zeZ + 0.95 F1234yf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 2.1 | 0 | 4.3 | 0 | 6.5 |
| 0.05 | 3.2 | 0.05 | 5.4 | 0.05 | 7.5 |
| 0.1 | 3.2 | 0.1 | 5.4 | 0.1 | 7.5 |
| 0.15 | 3.2 | 0.15 | 5.4 | 0.15 | 7.5 |
| 0.2 | 3.2 | 0.2 | 5.4 | 0.2 | 7.5 |
| 0.25 | 3.2 | 0.25 | 5.4 | 0.25 | 7.5 |
| 0.3 | 3.2 | 0.3 | 5.4 | 0.3 | 7.5 |
| 0.35 | 3.2 | 0.35 | 5.4 | 0.35 | 7.5 |
| 0.4 | 3.2 | 0.4 | 5.4 | 0.4 | 7.5 |
| 0.45 | 3.2 | 0.45 | 5.4 | 0.45 | 7.5 |
| 0.5 | 3.2 | 0.5 | 5.4 | 0.5 | 7.5 |
| 0.55 | 3.2 | 0.55 | 5.4 | 0.55 | 7.5 |
| 0.6 | 3.2 | 0.6 | 5.4 | 0.6 | 7.5 |
| 0.65 | 3.2 | 0.65 | 5.4 | 0.65 | 7.5 |
| 0.7 | 3.2 | 0.7 | 5.4 | 0.7 | 7.5 |
| 0.75 | 3.2 | 0.75 | 5.3 | 0.75 | 7.3 |
| 0.8 | 3.0 | 0.8 | 5.0 | 0.8 | 7.0 |
| 0.85 | 2.8 | 0.85 | 4.6 | 0.85 | 6.5 |
| 0.9 | 2.5 | 0.9 | 3.9 | 0.9 | 5.4 |
| 0.95 | 1.9 | 0.95 | 2.8 | 0.95 | 3.8 |
| 1 | 1.2 | 1 | 1.2 | 1 | 1.2 |

HF-HFO-1234zeE-HFC-245cb

| Organics 0.95 F1234zeE + 0.05 F245cb | | Organics 0.5 F1234zeE + 0.5 F245cb | | Organics 0.05 F1234zeE + 0.95 F245cb | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.9 | 0 | 4.8 | 0 | 4.7 |
| 0.05 | 5.8 | 0.05 | 5.9 | 0.05 | 5.8 |
| 0.1 | 5.9 | 0.1 | 5.9 | 0.1 | 5.8 |
| 0.15 | 5.9 | 0.15 | 5.9 | 0.15 | 5.8 |
| 0.2 | 5.9 | 0.2 | 5.9 | 0.2 | 5.8 |
| 0.25 | 5.9 | 0.25 | 5.9 | 0.25 | 5.8 |
| 0.3 | 5.9 | 0.3 | 5.9 | 0.3 | 5.8 |
| 0.35 | 5.9 | 0.35 | 5.9 | 0.35 | 5.8 |
| 0.4 | 5.8 | 0.4 | 5.9 | 0.4 | 5.8 |

HF-HFO-1234zeE-HFC-245cb

| Organics 0.95 F1234zeE + 0.05 F245cb | | Organics 0.5 F1234zeE + 0.5 F245cb | | Organics 0.05 F1234zeE + 0.95 F245cb | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0.45 | 5.8 | 0.45 | 5.9 | 0.45 | 5.8 |
| 0.5 | 5.8 | 0.5 | 5.9 | 0.5 | 5.8 |
| 0.55 | 5.8 | 0.55 | 5.9 | 0.55 | 5.8 |
| 0.6 | 5.7 | 0.6 | 5.9 | 0.6 | 5.8 |
| 0.65 | 5.6 | 0.65 | 5.9 | 0.65 | 5.8 |
| 0.7 | 5.4 | 0.7 | 5.9 | 0.7 | 5.8 |
| 0.75 | 5.2 | 0.75 | 5.8 | 0.75 | 5.8 |
| 0.8 | 4.9 | 0.8 | 5.6 | 0.8 | 5.8 |
| 0.85 | 4.4 | 0.85 | 5.1 | 0.85 | 5.8 |
| 0.9 | 3.7 | 0.9 | 4.3 | 0.9 | 5.0 |
| 0.95 | 2.6 | 0.95 | 3.1 | 0.95 | 3.5 |
| 1 | 1.2 | 1 | 1.2 | 1 | 1.2 |

HF-HFO-1234zeZ-HFC-245cb

| Organics 0.95 F1234zeZ + 0.05 F245cb | | Organics 0.5 F1234zeZ + 0.5 F245cb | | Organics 0.05 F1234zeZ + 0.95 F245cb | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 1.9 | 0 | 3.2 | 0 | 4.5 |
| 0.05 | 3.1 | 0.05 | 4.3 | 0.05 | 5.7 |
| 0.1 | 3.1 | 0.1 | 4.3 | 0.1 | 5.7 |
| 0.15 | 3.1 | 0.15 | 4.3 | 0.15 | 5.7 |
| 0.2 | 3.1 | 0.2 | 4.3 | 0.2 | 5.7 |
| 0.25 | 3.1 | 0.25 | 4.3 | 0.25 | 5.7 |
| 0.3 | 3.1 | 0.3 | 4.3 | 0.3 | 5.7 |
| 0.35 | 3.1 | 0.35 | 4.3 | 0.35 | 5.7 |
| 0.4 | 3.1 | 0.4 | 4.3 | 0.4 | 5.7 |
| 0.45 | 3.1 | 0.45 | 4.4 | 0.45 | 5.7 |
| 0.5 | 3.1 | 0.5 | 4.4 | 0.5 | 5.7 |
| 0.55 | 3.1 | 0.55 | 4.4 | 0.55 | 5.7 |
| 0.6 | 3.1 | 0.6 | 4.4 | 0.6 | 5.7 |
| 0.65 | 3.1 | 0.65 | 4.4 | 0.65 | 5.7 |
| 0.7 | 3.1 | 0.7 | 4.5 | 0.7 | 5.7 |
| 0.75 | 3.1 | 0.75 | 4.5 | 0.75 | 5.7 |
| 0.8 | 3.0 | 0.8 | 4.5 | 0.8 | 5.7 |
| 0.85 | 2.8 | 0.85 | 4.2 | 0.85 | 5.7 |
| 0.9 | 2.4 | 0.9 | 3.6 | 0.9 | 4.9 |
| 0.95 | 1.9 | 0.95 | 2.7 | 0.95 | 3.5 |
| 1 | 1.2 | 1 | 1.2 | 1 | 1.2 |

HF-HFO-1234zeE-HFO-1243zf

| Organics 0.95 F1243zf + 0.05 F1234zeE | | Organics 0.5 F1243zf + 0.5 F1234zeE | | Organics 0.05 F1243zf + 0.95 F1234zeE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 5.8 | 0 | 5.4 | 0 | 4.9 |
| 0.05 | 6.7 | 0.05 | 6.3 | 0.05 | 5.9 |
| 0.1 | 6.8 | 0.1 | 6.4 | 0.1 | 5.9 |
| 0.15 | 6.8 | 0.15 | 6.4 | 0.15 | 5.9 |

| HF-HFO-1234zeE-HFO-1243zf ||||||
|---|---|---|---|---|---|
| Organics 0.95 F1243zf + 0.05 F1234zeE || Organics 0.5 F1243zf + 0.5 F1234zeE || Organics 0.05 F1243zf + 0.95 F1234zeE ||
| MASSFRAC HF | TOTAL PRESSURE bar | MASSFRAC HF | TOTAL PRESSURE bar | MASSFRAC HF | TOTAL PRESSURE bar |
| 0.2 | 6.8 | 0.2 | 6.4 | 0.2 | 5.9 |
| 0.25 | 6.8 | 0.25 | 6.4 | 0.25 | 5.9 |
| 0.3 | 6.8 | 0.3 | 6.4 | 0.3 | 5.9 |
| 0.35 | 6.8 | 0.35 | 6.4 | 0.35 | 5.9 |
| 0.4 | 6.7 | 0.4 | 6.4 | 0.4 | 5.9 |
| 0.45 | 6.7 | 0.45 | 6.4 | 0.45 | 5.9 |
| 0.5 | 6.7 | 0.5 | 6.3 | 0.5 | 5.8 |
| 0.55 | 6.7 | 0.55 | 6.3 | 0.55 | 5.8 |
| 0.6 | 6.7 | 0.6 | 6.3 | 0.6 | 5.7 |
| 0.65 | 6.6 | 0.65 | 6.2 | 0.65 | 5.6 |
| 0.7 | 6.5 | 0.7 | 6.1 | 0.7 | 5.5 |
| 0.75 | 6.4 | 0.75 | 5.8 | 0.75 | 5.2 |
| 0.8 | 6.1 | 0.8 | 5.5 | 0.8 | 4.9 |
| 0.85 | 5.6 | 0.85 | 5.0 | 0.85 | 4.4 |
| 0.9 | 4.7 | 0.9 | 4.2 | 0.9 | 3.6 |
| 0.95 | 3.4 | 0.95 | 3.0 | 0.95 | 2.6 |
| 1 | 1.2 | 1 | 1.2 | 1 | 1.2 |

| HF-HFO-1234zeZ-HFO-1243zf ||||||
|---|---|---|---|---|---|
| Organics 0.95 F1243zf + 0.05 F1234zeZ || Organics 0.5 F1243zf + 0.5 F1234zeZ || Organics 0.05 F1243zf + 0.95 F1234zeZ ||
| MASSFRAC HF | TOTAL PRESSURE bar | MASSFRAC HF | TOTAL PRESSURE bar | MASSFRAC HF | TOTAL PRESSURE bar |
| 0 | 5.7 | 0 | 4.0 | 0 | 2.0 |
| 0.05 | 6.6 | 0.05 | 5.0 | 0.05 | 3.1 |
| 0.1 | 6.6 | 0.1 | 5.0 | 0.1 | 3.1 |
| 0.15 | 6.6 | 0.15 | 5.0 | 0.15 | 3.1 |
| 0.2 | 6.6 | 0.2 | 5.0 | 0.2 | 3.1 |
| 0.25 | 6.6 | 0.25 | 5.0 | 0.25 | 3.1 |
| 0.3 | 6.6 | 0.3 | 5.0 | 0.3 | 3.1 |
| 0.35 | 6.6 | 0.35 | 5.0 | 0.35 | 3.1 |
| 0.4 | 6.6 | 0.4 | 5.0 | 0.4 | 3.1 |
| 0.45 | 6.6 | 0.45 | 5.0 | 0.45 | 3.1 |
| 0.5 | 6.6 | 0.5 | 5.0 | 0.5 | 3.1 |
| 0.55 | 6.6 | 0.55 | 5.0 | 0.55 | 3.1 |
| 0.6 | 6.6 | 0.6 | 5.0 | 0.6 | 3.1 |
| 0.65 | 6.5 | 0.65 | 5.0 | 0.65 | 3.1 |
| 0.7 | 6.4 | 0.7 | 4.9 | 0.7 | 3.1 |
| 0.75 | 6.3 | 0.75 | 4.8 | 0.75 | 3.1 |
| 0.8 | 6.0 | 0.8 | 4.5 | 0.8 | 3.0 |
| 0.85 | 5.5 | 0.85 | 4.2 | 0.85 | 2.8 |
| 0.9 | 4.7 | 0.9 | 3.6 | 0.9 | 2.4 |
| 0.95 | 3.3 | 0.95 | 2.6 | 0.95 | 1.9 |
| 1 | 1.2 | 1 | 1.2 | 1 | 1.2 |

Example 2: Temperature and Pressure Range of Ternary Mixtures

| Ternary | Boiling point range ||
|---|---|---|
| | Temperature °C. | Pressure bar abs |
| HF-HFO-1234zeE-HFC-245cb | 0 to 40 | ~2.5 to ~9.1 |
| HF-HFO-1234zeZ-HFC-245cb | 0 to 40 | ~1.2 to ~8.9 |
| HF-HFO-1234yf-HFO-1234zeE | 0 to 40 | ~2.6 to ~11.6 |
| HF-HFO-1234yf-HFO-1234zeZ | 0 to 40 | ~1.3 to ~11.4 |
| HF-HCFO-1233xf-HFO-1234zeE | 0 to 40 | ~1.1 to ~8.8 |
| HF-HCFO-1233xf-HFO-1234zeZ | 0 to 40 | ~1.0 to ~4.8 |

-continued

| Ternary | Boiling point range | |
|---|---|---|
| | Temperature °C | Pressure bar abs |
| HF-HFO-1234zeE-HCFO-1233zdE | 0 to 40 | ~1.0 to ~8.8 |
| HF-HFO-1234zeE-HFO-1243zf | 0 to 40 | ~2.5 to ~10.4 |
| HF-HFO-1234zeZ-HCFO-1233zdE | 0 to 40 | ~0.9 to ~4.8 |
| HF-HFO-1234zeZ-HFO-1243zf | 0 to 40 | ~1.2 to ~10.2 |

Example 3: Decantation Range of Ternary Mixtures

| Ternary | Decantation ranges Mass percentage of HF | | |
|---|---|---|---|
| | Isotherm 0° C. | Isotherm 25° C. | Isotherm 40° C. |
| HF-HFO-1234zeE-HFC-245cb | 5-75 | 10-70 | 40-65 |
| HF-HFO-1234zeZ-HFC-245cb | 5-80 | 5-75 | 10-75 |
| HF-HFO-1234yf-HFO-1234zeE | 5-65 | * | * |
| HF-HFO-1234yf-HFO-1234zeZ | 5-75 | 10-70 | 15-30 |
| HF-HCFO-1233xf-HFO-1234zeE | 5-70 | 5-60 | 10-45 |
| HF-HCFO-1233xf-HFO-1234zeZ | 5-80 | 5-70 | 5-65 |
| HF-HFO-1234zeE-HCFO-1233zdE | 5-70 | 5-65 | 10-50 |
| HF-HFO-1234zeE-HFO-1243zf | 5-65 | * | * |
| HF-HFO-1234zeZ-HCFO-1233zdE | 5-80 | 5-75 | 5-65 |
| HF-HFO-1234zeZ-HFO-1243zf | 5-75 | 10-65 | * |

Example 4: Quaternary Mixtures, Isotherm at 25° C.

| HF - HCFO-1233xf - HFO-1234zeE - HFC-245cb | | | | | | | |
|---|---|---|---|---|---|---|---|
| Organics 0.9 F1233xf + 0.05 F1234zeE + 0.05 F245cb | | Organics 0.4 F1233xf + 0.3 F1234zeE + 0.3 F245cb | | Organics 0.05 F1233xf + 0.9 F1234zeE + 0.05 F245cb | | Organics 0.05 F1233xf + 0.05 F1234zeE + 0.9 F245cb | |
| MASSFRAC HF | TOTAL PRES bar | MASSFRAC HF | TOTAL PRES bar | MASSFRAC HF | TOTAL PRES bar | MASSFRAC HF | TOTAL PRES bar |
| 0 | 3.2 | 0 | 3.5 | 0 | 4.7 | 0 | 4.5 |
| 0.05 | 4.3 | 0.05 | 4.6 | 0.05 | 5.7 | 0.05 | 5.7 |
| 0.1 | 4.3 | 0.1 | 4.6 | 0.1 | 5.7 | 0.1 | 5.7 |
| 0.15 | 4.3 | 0.15 | 4.6 | 0.15 | 5.7 | 0.15 | 5.7 |
| 0.2 | 4.3 | 0.2 | 4.6 | 0.2 | 5.7 | 0.2 | 5.7 |
| 0.25 | 4.3 | 0.25 | 4.6 | 0.25 | 5.7 | 0.25 | 5.7 |
| 0.3 | 4.3 | 0.3 | 4.6 | 0.3 | 5.7 | 0.3 | 5.7 |
| 0.35 | 4.3 | 0.35 | 4.6 | 0.35 | 5.7 | 0.35 | 5.7 |
| 0.4 | 4.4 | 0.4 | 4.6 | 0.4 | 5.7 | 0.4 | 5.7 |
| 0.45 | 4.4 | 0.45 | 4.6 | 0.45 | 5.7 | 0.45 | 5.7 |
| 0.5 | 4.4 | 0.5 | 4.6 | 0.5 | 5.7 | 0.5 | 5.7 |
| 0.55 | 4.4 | 0.55 | 4.6 | 0.55 | 5.6 | 0.55 | 5.7 |
| 0.6 | 4.4 | 0.6 | 4.6 | 0.6 | 5.6 | 0.6 | 5.7 |
| 0.65 | 4.4 | 0.65 | 4.7 | 0.65 | 5.5 | 0.65 | 5.7 |
| 0.7 | 4.5 | 0.7 | 4.7 | 0.7 | 5.3 | 0.7 | 5.7 |
| 0.75 | 4.5 | 0.75 | 4.6 | 0.75 | 5.1 | 0.75 | 5.7 |
| 0.8 | 4.5 | 0.8 | 4.4 | 0.8 | 4.8 | 0.8 | 5.7 |
| 0.85 | 4.2 | 0.85 | 4.0 | 0.85 | 4.3 | 0.85 | 5.6 |
| 0.9 | 3.6 | 0.9 | 3.4 | 0.9 | 3.6 | 0.9 | 4.8 |
| 0.95 | 2.6 | 0.95 | 2.5 | 0.95 | 2.6 | 0.95 | 3.4 |
| 1 | 1.2 | 1 | 1.2 | 1 | 1.2 | 1 | 1.2 |

| HF - HCFO-1233xf - HFO-1234zeZ - HFC-245cb | | | | | | | |
|---|---|---|---|---|---|---|---|
| Organics 0.9 F1233xf + 0.05 F1234zeZ + 0.05 F245cb | | Organics 0.4 F1233xf + 0.3 F1234zeZ + 0.3 F245cb | | Organics 0.05 F1233xf + 0.9 F1234zeZ + 0.05 F245cb | | Organics 0.05 F1233xf + 0.05 F1234zeZ + 0.9 F245cb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 2.6 | 0 | 1.9 | 0 | 4.3 |
| 0.05 | 2.8 | 0.05 | 3.7 | 0.05 | 3.0 | 0.05 | 5.5 |
| 0.1 | 2.8 | 0.1 | 3.7 | 0.1 | 3.0 | 0.1 | 5.5 |
| 0.15 | 2.8 | 0.15 | 3.7 | 0.15 | 3.0 | 0.15 | 5.5 |
| 0.2 | 2.8 | 0.2 | 3.7 | 0.2 | 3.0 | 0.2 | 5.5 |

HF - HCFO-1233xf - HFO-1234zeZ - HFC-245cb

| Organics 0.9 F1233xf + 0.05 F1234zeZ + 0.05 F245cb | | Organics 0.4 F1233xf + 0.3 F1234zeZ + 0.3 F245cb | | Organics 0.05 F1233xf + 0.9 F1234zeZ + 0.05 F245cb | | Organics 0.05 F1233xf + 0.05 F1234zeZ + 0.9 F245cb | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0.25 | 2.8 | 0.25 | 3.7 | 0.25 | 3.0 | 0.25 | 5.5 |
| 0.3 | 2.8 | 0.3 | 3.7 | 0.3 | 3.0 | 0.3 | 5.5 |
| 0.35 | 2.8 | 0.35 | 3.7 | 0.35 | 3.0 | 0.35 | 5.5 |
| 0.4 | 2.8 | 0.4 | 3.7 | 0.4 | 3.0 | 0.4 | 5.5 |
| 0.45 | 2.8 | 0.45 | 3.7 | 0.45 | 3.1 | 0.45 | 5.5 |
| 0.5 | 2.8 | 0.5 | 3.7 | 0.5 | 3.1 | 0.5 | 5.5 |
| 0.55 | 2.9 | 0.55 | 3.7 | 0.55 | 3.1 | 0.55 | 5.5 |
| 0.6 | 2.9 | 0.6 | 3.8 | 0.6 | 3.1 | 0.6 | 5.5 |
| 0.65 | 2.9 | 0.65 | 3.8 | 0.65 | 3.1 | 0.65 | 5.6 |
| 0.7 | 2.9 | 0.7 | 3.8 | 0.7 | 3.1 | 0.7 | 5.6 |
| 0.75 | 2.9 | 0.75 | 3.8 | 0.75 | 3.1 | 0.75 | 5.6 |
| 0.8 | 2.7 | 0.8 | 3.8 | 0.8 | 2.9 | 0.8 | 5.6 |
| 0.85 | 2.5 | 0.85 | 3.5 | 0.85 | 2.7 | 0.85 | 5.5 |
| 0.9 | 2.2 | 0.9 | 3.0 | 0.9 | 2.4 | 0.9 | 4.8 |
| 0.95 | 1.8 | 0.95 | 2.3 | 0.95 | 1.9 | 0.95 | 3.4 |
| 1 | 1.2 | 1 | 1.2 | 1 | 1.2 | 1 | 1.2 |

HF - HCFO-1233xf - HCFO-1233zdE - HFO-1234zeE

| Organics 0.9 F1233xf + 0.05 F1233zdE + 0.05 F1234zeE | | Organics 0.05 F1233xf + 0.9 F1233zdE + 0.05 F1234zeE | | Organics 0.05 F1233xf + 0.05 F1233zdE + 0.9 F1234zeE | | Organics 0.4 F1233xf + 0.3 F1233zdE + 0.3 F1234zeE | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.5 | 0 | 4.6 | 0 | 2.5 |
| 0.05 | 2.8 | 0.05 | 2.6 | 0.05 | 5.5 | 0.05 | 3.6 |
| 0.1 | 2.8 | 0.1 | 2.6 | 0.1 | 5.5 | 0.1 | 3.6 |
| 0.15 | 2.8 | 0.15 | 2.6 | 0.15 | 5.5 | 0.15 | 3.6 |
| 0.2 | 2.8 | 0.2 | 2.6 | 0.2 | 5.5 | 0.2 | 3.6 |
| 0.25 | 2.8 | 0.25 | 2.6 | 0.25 | 5.5 | 0.25 | 3.6 |
| 0.3 | 2.8 | 0.3 | 2.6 | 0.3 | 5.5 | 0.3 | 3.6 |
| 0.35 | 2.8 | 0.35 | 2.6 | 0.35 | 5.5 | 0.35 | 3.6 |
| 0.4 | 2.8 | 0.4 | 2.6 | 0.4 | 5.5 | 0.4 | 3.6 |
| 0.45 | 2.8 | 0.45 | 2.6 | 0.45 | 5.5 | 0.45 | 3.6 |
| 0.5 | 2.8 | 0.5 | 2.6 | 0.5 | 5.5 | 0.5 | 3.6 |
| 0.55 | 2.8 | 0.55 | 2.6 | 0.55 | 5.4 | 0.55 | 3.5 |
| 0.6 | 2.8 | 0.6 | 2.6 | 0.6 | 5.4 | 0.6 | 3.5 |
| 0.65 | 2.8 | 0.65 | 2.6 | 0.65 | 5.3 | 0.65 | 3.5 |
| 0.7 | 2.8 | 0.7 | 2.6 | 0.7 | 5.1 | 0.7 | 3.5 |
| 0.75 | 2.8 | 0.75 | 2.6 | 0.75 | 4.9 | 0.75 | 3.3 |
| 0.8 | 2.6 | 0.8 | 2.5 | 0.8 | 4.6 | 0.8 | 3.2 |
| 0.85 | 2.4 | 0.85 | 2.3 | 0.85 | 4.1 | 0.85 | 2.9 |
| 0.9 | 2.2 | 0.9 | 2.0 | 0.9 | 3.4 | 0.9 | 2.5 |
| 0.95 | 1.7 | 0.95 | 1.7 | 0.95 | 2.5 | 0.95 | 1.9 |
| 1 | 1.2 | 1 | 1.2 | 1 | 1.2 | 1 | 1.2 |

HF - HCFO-1233xf - HCFO-1233zdE - HFO-1234zeZ

| Organics 0.9 F1233xf + 0.05 F1233zdE + 0.05 F1234zeZ | | Organics 0.05 F1233xf + 0.9 F1233zdE + 0.05 F1234zeZ | | Organics 0.05 F1233xf + 0.05 F1233zdE + 0.9 F1234zeZ | | Organics 0.4 F1233xf + 0.3 F1233zdE + 0.3 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.5 | 0 | 1.4 | 0 | 1.8 | 0 | 1.6 |
| 0.05 | 2.7 | 0.05 | 2.5 | 0.05 | 2.9 | 0.05 | 2.7 |
| 0.1 | 2.7 | 0.1 | 2.5 | 0.1 | 2.9 | 0.1 | 2.7 |
| 0.15 | 2.7 | 0.15 | 2.5 | 0.15 | 2.9 | 0.15 | 2.7 |

| HF - HCFO-1233xf - HCFO-1233zdE - HFO-1234zeZ ||||||||
|---|---|---|---|---|---|---|---|
| Organics 0.9 F1233xf + 0.05 F1233zdE + 0.05 F1234zeZ || Organics 0.05 F1233xf + 0.9 F1233zdE + 0.05 F1234zeZ || Organics 0.05 F1233xf + 0.05 F1233zdE + 0.9 F1234zeZ || Organics 0.4 F1233xf + 0.3 F1233zdE + 0.3 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0.2 | 2.7 | 0.2 | 2.5 | 0.2 | 2.9 | 0.2 | 2.7 |
| 0.25 | 2.7 | 0.25 | 2.5 | 6.25 | 2.9 | 0.25 | 2.7 |
| 0.3 | 2.7 | 0.3 | 2.5 | 0.3 | 2.9 | 0.3 | 2.7 |
| 0.35 | 2.7 | 0.35 | 2.5 | 0.35 | 2.9 | 0.35 | 2.7 |
| 0.4 | 2.7 | 0.4 | 2.5 | 0.4 | 2.9 | 0.4 | 2.7 |
| 0.45 | 2.7 | 0.45 | 2.5 | 0.45 | 2.9 | 0.45 | 2.7 |
| 0.5 | 2.7 | 0.5 | 2.5 | 0.5 | 2.9 | 0.5 | 2.7 |
| 0.55 | 2.7 | 0.55 | 2.5 | 0.55 | 2.9 | 0.55 | 2.7 |
| 0.6 | 2.7 | 0.6 | 2.5 | 0.6 | 2.9 | 0.6 | 2.7 |
| 0.65 | 2.7 | 0.65 | 2.5 | 0.65 | 2.9 | 0.65 | 2.7 |
| 0.7 | 2.7 | 0.7 | 2.5 | 0.7 | 2.9 | 0.7 | 2.7 |
| 0.75 | 2.7 | 0.75 | 2.5 | 0.75 | 2.9 | 0.75 | 2.7 |
| 0.8 | 2.5 | 0.8 | 2.4 | 0.8 | 2.8 | 0.8 | 2.6 |
| 0.85 | 2.4 | 0.85 | 2.2 | 0.85 | 2.6 | 0.85 | 2.4 |
| 0.9 | 2.1 | 0.9 | 2.0 | 0.9 | 2.3 | 0.9 | 2.1 |
| 0.95 | 1.7 | 0.95 | 1.6 | 0.95 | 1.8 | 0.95 | 1.7 |
| 1 | 1.2 | 1 | 1.2 | 1 | 1.2 | 1 | 1.2 |

| HF - HCFO-1233xf - HFO-1234zeE - HFO-1234zeZ ||||||||
|---|---|---|---|---|---|---|---|
| Organics 0.9 F1233xf + 0.05 F1234zeE + 0.05 F1234zeZ || Organics 0.05 F1233xf + 0.9 F1234zeE + 0.05 F1234zeZ || Organics 0.05 F1233xf + 0.05 F1234zeE + 0.9 F1234zeZ || Organics 0.4 F1233xf + 0.3 F1234zeE + 0.3 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 4.6 | 0 | 1.9 | 0 | 2.7 |
| 0.05 | 2.8 | 0.05 | 5.5 | 0.05 | 3.1 | 0.05 | 3.7 |
| 0.1 | 2.8 | 0.1 | 5.5 | 0.1 | 3.6 | 0.1 | 3.7 |
| 0.15 | 2.8 | 0.15 | 5.5 | 0.15 | 3.0 | 0.15 | 3.7 |
| 0.2 | 2.8 | 0.2 | 5.5 | 0.2 | 3.0 | 0.2 | 3.7 |
| 0.25 | 2.8 | 0.25 | 5.5 | 0.25 | 3.0 | 0.25 | 3.7 |
| 0.3 | 2.8 | 0.3 | 5.5 | 0.3 | 3.0 | 0.3 | 3.7 |
| 0.35 | 2.8 | 0.35 | 5.5 | 0.35 | 3.6 | 0.35 | 3.7 |
| 0.4 | 2.8 | 0.4 | 5.5 | 0.4 | 3.0 | 0.4 | 3.7 |
| 0.45 | 2.8 | 0.45 | 5.5 | 0.45 | 3.0 | 0.45 | 3.7 |
| 0.5 | 2.8 | 0.5 | 5.5 | 0.5 | 3.0 | 0.5 | 3.7 |
| 0.55 | 2.8 | 0.55 | 5.4 | 0.55 | 3.0 | 0.55 | 3.7 |
| 0.6 | 2.8 | 0.6 | 5.4 | 0.6 | 3.0 | 0.6 | 3.6 |
| 0.65 | 2.8 | 0.65 | 5.3 | 0.65 | 3.0 | 0.65 | 3.6 |
| 0.7 | 2.8 | 0.7 | 5.1 | 0.7 | 3.0 | 0.7 | 3.6 |
| 0.75 | 2.8 | 0.75 | 4.9 | 0.75 | 3.0 | 0.75 | 3.5 |
| 0.8 | 2.7 | 0.8 | 4.6 | 0.8 | 2.9 | 0.8 | 3.3 |
| 0.85 | 2.5 | 0.85 | 4.1 | 0.85 | 2.7 | 0.85 | 3.0 |
| 0.9 | 2.2 | 0.9 | 3.4 | 0.9 | 2.3 | 0.9 | 2.6 |
| 0.95 | 1.8 | 0.95 | 2.5 | 0.95 | 1.9 | 0.95 | 2.0 |
| 1 | 1.2 | 1 | 1.2 | 1 | 1.2 | 1 | 1.2 |

| HF-HCFO-1233xf-HFO-1234zeE-HFO-1243zf ||||||||
|---|---|---|---|---|---|---|---|
| Organics 0.9 F1233xf + 0.05 F1234zeE + 0.05 F1243zf || Organics 0.05 F1233xf + 0.9 F1234zeE + 0.05 F1243zf || Organics 0.05 F1233xf + 0.05 F1234zeE + 0.9 F1243zf || Organics 0.4 F1233xf + 0.3 F1234zeE + 0.3 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.8 | 0 | 5.6 | 0 | 4.0 |
| 0.05 | 3.1 | 0.05 | 5.7 | 0.05 | 6.6 | 0.05 | 5.1 |

-continued

HF-HCFO-1233xf-HFO-1234zeE-HFO-1243zf

| Organics 0.9 F1233xf + 0.05 F1234zeE + 0.05 F1243zf | | Organics 0.05 F1233xf + 0.9 F1234zeE + 0.05 F1243zf | | Organics 0.05 F1233xf + 0.05 F1234zeE + 0.9 F1243zf | | Organics 0.4 F1233xf + 0.3 F1234zeE + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0.1 | 3.1 | 0.1 | 5.8 | 0.1 | 6.6 | 0.1 | 5.1 |
| 0.15 | 3.1 | 0.15 | 5.8 | 0.15 | 6.6 | 0.15 | 5.1 |
| 0.2 | 3.1 | 0.2 | 5.8 | 0.2 | 6.6 | 0.2 | 5.1 |
| 0.25 | 3.1 | 0.25 | 5.8 | 0.25 | 6.6 | 0.25 | 5.1 |
| 0.3 | 3.1 | 0.3 | 5.8 | 0.3 | 6.6 | 0.3 | 5.0 |
| 0.35 | 3.1 | 0.35 | 5.7 | 0.35 | 6.6 | 0.35 | 5.0 |
| 0.4 | 3.1 | 0.4 | 5.7 | 0.4 | 6.6 | 0.4 | 5.0 |
| 0.45 | 3.1 | 0.45 | 5.7 | 0.45 | 6.6 | 0.45 | 5.0 |
| 0.5 | 3.1 | 0.5 | 5.7 | 0.5 | 6.6 | 0.5 | 5.0 |
| 0.55 | 3.1 | 0.55 | 5.7 | 0.55 | 6.6 | 0.55 | 5.0 |
| 0.6 | 3.1 | 0.6 | 5.6 | 0.6 | 6.5 | 0.6 | 5.0 |
| 0.65 | 3.1 | 0.65 | 5.5 | 0.65 | 6.5 | 0.65 | 4.9 |
| 0.7 | 3.0 | 0.7 | 5.3 | 0.7 | 6.4 | 0.7 | 4.8 |
| 0.75 | 3.0 | 0.75 | 5.1 | 0.75 | 6.2 | 0.75 | 4.7 |
| 0.8 | 2.9 | 0.8 | 4.8 | 0.8 | 5.9 | 0.8 | 4.4 |
| 0.85 | 2.6 | 0.85 | 4.3 | 0.85 | 5.4 | 0.85 | 4.0 |
| 0.9 | 2.3 | 0.9 | 3.6 | 0.9 | 4.6 | 0.9 | 3.4 |
| 0.95 | 1.8 | 0.95 | 2.6 | 0.95 | 3.3 | 0.95 | 2.5 |
| 1 | 1.2 | 1 | 1.2 | 1 | 1.2 | 1 | 1.2 |

HF-HCFO-1233xf-HFO-1234zeZ-HFO-1243zf

| Organics 0.9 F1233xf + 0.05 F1234zeZ + 0.05 F1243zf | | Organics 0.05 F1233xf + 0.9 F1234zeZ + 0.05 F1243zf | | Organics 0.05 F1233xf + 0.05 F1234zeZ + 0.9 F1243zf | | Organics 0.4 F1233xf + 0.3 F1234zeZ + 0.3 F1243zf | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 2.0 | 0 | 5.5 | 0 | 3.1 |
| 0.05 | 2.9 | 0.05 | 3.1 | 0.05 | 6.4 | 0.05 | 4.2 |
| 0.1 | 2.9 | 0.1 | 3.1 | 0.1 | 6.5 | 0.1 | 4.2 |
| 0.15 | 2.9 | 0.15 | 3.1 | 0.15 | 6.5 | 0.15 | 4.2 |
| 0.2 | 2.9 | 0.2 | 3.1 | 0.2 | 6.5 | 0.2 | 4.2 |
| 0.25 | 2.9 | 0.25 | 3.1 | 0.25 | 6.5 | 0.25 | 4.2 |
| 0.3 | 2.9 | 0.3 | 3.1 | 0.3 | 6.5 | 0.3 | 4.2 |
| 0.35 | 2.9 | 0.35 | 3.1 | 0.35 | 6.5 | 0.35 | 4.2 |
| 0.4 | 2.9 | 0.4 | 3.1 | 0.4 | 6.5 | 0.4 | 4.2 |
| 0.45 | 2.9 | 0.45 | 3.1 | 0.45 | 6.5 | 0.45 | 4.2 |
| 0.5 | 2.9 | 0.5 | 3.1 | 0.5 | 6.4 | 0.5 | 4.2 |
| 0.55 | 2.9 | 0.55 | 3.1 | 0.55 | 6.4 | 0.55 | 4.2 |
| 0.6 | 2.9 | 0.6 | 3.1 | 0.6 | 6.4 | 0.6 | 4.1 |
| 0.65 | 2.9 | 0.65 | 3.1 | 0.65 | 6.4 | 0.65 | 4.1 |
| 0.7 | 2.9 | 0.7 | 3.1 | 0.7 | 6.3 | 0.7 | 4.1 |
| 0.75 | 2.9 | 0.75 | 3.1 | 0.75 | 6.1 | 0.75 | 4.0 |
| 0.8 | 2.8 | 0.8 | 3.0 | 0.8 | 5.8 | 0.8 | 3.8 |
| 0.85 | 2.5 | 0.85 | 2.7 | 0.85 | 5.3 | 0.85 | 3.5 |
| 0.9 | 2.2 | 0.9 | 2.4 | 0.9 | 4.5 | 0.9 | 3.0 |
| 0.95 | 1.8 | 0.95 | 1.9 | 0.95 | 3.2 | 0.95 | 2.3 |
| 1 | 1.2 | 1 | 1.2 | 1 | 1.2 | 1 | 1.2 |

| HF-HCFO-1233xf-HFO-1234yf-HFO-1234zeE | | | | | | | |
|---|---|---|---|---|---|---|---|
| Organics 0.9 F1233xf + 0.05 F1234yf + 0.05 F1234zeE | | Organics 0.05 F1233xf + 0.9 F1234yf + 0.05 F1234zeE | | Organics 0.05 F1233xf + 0.05 F1234yf + 0.9 F1234zeE | | Organics 0.4 F1233xf + 0.3 F1234yf + 0.3 F1234zeE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 6.5 | 0 | 4.8 | 0 | 4.2 |
| 0.05 | 3.1 | 0.05 | 7.4 | 0.05 | 5.8 | 0.05 | 5.3 |
| 0.1 | 3.1 | 0.1 | 7.4 | 0.1 | 5.8 | 0.1 | 5.3 |
| 0.15 | 3.1 | 0.15 | 7.4 | 0.15 | 5.8 | 0.15 | 5.3 |
| 0.2 | 3.1 | 0.2 | 7.4 | 0.2 | 5.8 | 0.2 | 5.3 |
| 0.25 | 3.1 | 0.25 | 7.4 | 0.25 | 5.8 | 0.25 | 5.3 |
| 0.3 | 3.1 | 0.3 | 7.4 | 0.3 | 5.8 | 0.3 | 5.3 |
| 0.35 | 3.1 | 0.35 | 7.4 | 0.35 | 5.8 | 0.35 | 5.3 |
| 0.4 | 3.1 | 0.4 | 7.4 | 0.4 | 5.8 | 0.4 | 5.3 |
| 0.45 | 3.1 | 0.45 | 7.4 | 0.45 | 5.8 | 0.45 | 5.3 |
| 0.5 | 3.1 | 0.5 | 7.4 | 0.5 | 5.8 | 0.5 | 5.3 |
| 0.55 | 3.1 | 0.55 | 7.4 | 0.55 | 5.7 | 0.55 | 5.3 |
| 0.6 | 3.1 | 0.6 | 7.4 | 0.6 | 5.6 | 0.6 | 5.3 |
| 0.65 | 3.1 | 0.65 | 7.5 | 0.65 | 5.5 | 0.65 | 5.3 |
| 0.7 | 3.1 | 0.7 | 7.4 | 0.7 | 5.4 | 0.7 | 5.2 |
| 0.75 | 3.1 | 0.75 | 7.2 | 0.75 | 5.2 | 0.75 | 5.0 |
| 0.8 | 2.9 | 0.8 | 6.9 | 0.8 | 4.8 | 0.8 | 4.7 |
| 0.85 | 2.7 | 0.85 | 6.3 | 0.85 | 4.3 | 0.85 | 4.3 |
| 0.9 | 2.3 | 0.9 | 5.3 | 0.9 | 3.6 | 0.9 | 3.6 |
| 0.95 | 1.9 | 0.95 | 3.7 | 0.95 | 2.6 | 0.95 | 2.6 |
| 1 | 1.2 | 1 | 1.2 | 1 | 1.2 | 1 | 1.2 |

| HF-HCFO-1233xf-HFO-1234yf-HFO-1234zeZ | | | | | | | |
|---|---|---|---|---|---|---|---|
| Organics 0.9 F1233xf + 0.05 F1234yf + 0.05 F1234zeZ | | Organics 0.05 F1233xf + 0.9 F1234yf + 0.05 F1234zeZ | | Organics 0.05 F1233xf + 0.05 F1234yf + 0.9 F1234zeZ | | Organics 0.4 F1233xf + 0.3 F1234yf + 0.3 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 6.3 | 0 | 2.1 | 0 | 3.3 |
| 0.05 | 3.0 | 0.05 | 7.3 | 0.05 | 3.2 | 0.05 | 4.4 |
| 0.1 | 3.0 | 0.1 | 7.3 | 0.1 | 3.2 | 0.1 | 4.4 |
| 0.15 | 3.0 | 0.15 | 7.3 | 0.15 | 3.2 | 0.15 | 4.4 |
| 0.2 | 3.0 | 0.2 | 7.3 | 0.2 | 3.2 | 0.2 | 4.4 |
| 0.25 | 3.0 | 0.25 | 7.3 | 0.25 | 3.2 | 0.25 | 4.4 |
| 0.3 | 3.0 | 0.3 | 7.3 | 0.3 | 3.2 | 0.3 | 4.4 |
| 0.35 | 3.0 | 0.35 | 7.3 | 0.35 | 3.2 | 0.35 | 4.4 |
| 0.4 | 3.0 | 0.4 | 7.3 | 0.4 | 3.2 | 0.4 | 4.4 |
| 0.45 | 3.0 | 0.45 | 7.3 | 0.45 | 3.2 | 0.45 | 4.4 |
| 0.5 | 3.0 | 0.5 | 7.3 | 0.5 | 3.2 | 0.5 | 4.4 |
| 0.55 | 3.0 | 0.55 | 7.3 | 0.55 | 3.2 | 0.55 | 4.4 |
| 0.6 | 3.0 | 0.6 | 7.3 | 0.6 | 3.2 | 0.6 | 4.4 |
| 0.65 | 3.0 | 0.65 | 7.3 | 0.65 | 3.2 | 0.65 | 4.4 |
| 0.7 | 3.0 | 0.7 | 7.3 | 0.7 | 3.2 | 0.7 | 4.4 |
| 0.75 | 2.9 | 0.75 | 7.1 | 0.75 | 3.1 | 0.75 | 4.3 |
| 0.8 | 2.8 | 0.8 | 6.8 | 0.8 | 3.0 | 0.8 | 4.1 |
| 0.85 | 2.6 | 0.85 | 6.3 | 0.85 | 2.8 | 0.85 | 3.7 |
| 0.9 | 2.3 | 0.9 | 5.3 | 0.9 | 2.4 | 0.9 | 3.2 |
| 0.95 | 1.8 | 0.95 | 3.7 | 0.95 | 1.9 | 0.95 | 2.4 |
| 1 | 1.2 | 1 | 1.2 | 1 | 1.2 | 1 | 1.2 |

| HF-HFO-1234yf-HFO-1234zeE-HFC-245cb ||||||||
|---|---|---|---|---|---|---|---|
| Organics 0.9 F1234yf + 0.05 F1234zeE + 0.05 F245cb || Organics 0.4 F1234yf + 0.3 F1234zeE + 0.3 F245cb || Organics 0.05 F1234yf + 0.9 F1234zeE + 0.05 F245cb || Organics 0.05 F1234yf + 0.05 F1234zeE + 0.9 F245cb ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.6 | 0 | 5.6 | 0 | 5.0 | 0 | 4.8 |
| 0.05 | 7.6 | 0.05 | 6.7 | 0.05 | 5.9 | 0.05 | 6.0 |
| 0.1 | 7.6 | 0.1 | 6.7 | 0.1 | 6.0 | 0.1 | 6.0 |
| 0.15 | 7.6 | 0.15 | 6.7 | 0.15 | 6.0 | 0.15 | 6.0 |
| 0.2 | 7.6 | 0.2 | 6.7 | 0.2 | 6.0 | 0.2 | 6.0 |
| 0.25 | 7.6 | 0.25 | 6.7 | 0.25 | 6.0 | 0.25 | 6.0 |
| 0.3 | 7.6 | 0.3 | 6.7 | 0.3 | 6.0 | 0.3 | 6.0 |
| 0.35 | 7.6 | 0.35 | 6.7 | 0.35 | 6.0 | 0.35 | 6.0 |
| 0.4 | 7.6 | 0.4 | 6.7 | 0.4 | 6.0 | 0.4 | 6.0 |
| 0.45 | 7.6 | 0.45 | 6.7 | 0.45 | 5.9 | 0.45 | 6.0 |
| 0.5 | 7.6 | 0.5 | 6.7 | 0.5 | 5.9 | 0.5 | 6.0 |
| 0.55 | 7.6 | 0.55 | 6.7 | 0.55 | 5.9 | 0.55 | 5.9 |
| 0.6 | 7.6 | 0.6 | 6.7 | 0.6 | 5.8 | 0.6 | 5.9 |
| 0.65 | 7.6 | 0.65 | 6.7 | 0.65 | 5.7 | 0.65 | 5.9 |
| 0.7 | 7.6 | 0.7 | 6.7 | 0.7 | 5.6 | 0.7 | 5.9 |
| 0.75 | 7.4 | 0.75 | 6.6 | 0.75 | 5.3 | 0.75 | 5.9 |
| 0.8 | 7.1 | 0.8 | 6.3 | 0.8 | 5.0 | 0.8 | 5.9 |
| 0.85 | 6.5 | 0.85 | 5.7 | 0.85 | 4.5 | 0.85 | 5.8 |
| 0.9 | 5.5 | 0.9 | 4.8 | 0.9 | 3.8 | 0.9 | 5.0 |
| 0.95 | 3.8 | 0.95 | 3.4 | 0.95 | 2.7 | 0.95 | 3.5 |
| 1 | 1.2 | 1 | 1.2 | 1 | 1.2 | 1 | 1.2 |

| HF-HFO-1234yf-HFO-1234zeZ-HFC-245cb ||||||||
|---|---|---|---|---|---|---|---|
| Organics 0.9 F1234yf + 0.05 F1234zeZ + 0.05 F245cb || Organics 0.4 F1234yf + 0.3 F1234zeZ + 0.3 F245cb || Organics 0.05 F1234yf + 0.9 F1234zeZ + 0.05 F245cb || Organics 0.05 F1234yf + 0.05 F1234zeZ + 0.9 F245cb ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 4.6 | 0 | 2.2 | 0 | 4.6 |
| 0.05 | 7.4 | 0.05 | 5.7 | 0.05 | 3.3 | 0.05 | 5.8 |
| 0.1 | 7.4 | 0.1 | 5.7 | 0.1 | 3.3 | 0.1 | 5.8 |
| 0.15 | 7.4 | 0.15 | 5.7 | 0.15 | 3.3 | 0.15 | 5.8 |
| 0.2 | 7.4 | 0.2 | 5.7 | 0.2 | 3.3 | 0.2 | 5.8 |
| 0.25 | 7.4 | 0.25 | 5.7 | 0.25 | 3.3 | 0.25 | 5.8 |
| 0.3 | 7.4 | 0.3 | 5.7 | 0.3 | 3.3 | 0.3 | 5.8 |
| 0.35 | 7.4 | 0.35 | 5.7 | 0.35 | 3.3 | 0.35 | 5.8 |
| 0.4 | 7.4 | 0.4 | 5.8 | 0.4 | 3.3 | 0.4 | 5.8 |
| 0.45 | 7.4 | 0.45 | 5.8 | 0.45 | 3.3 | 0.45 | 5.8 |
| 0.5 | 7.4 | 0.5 | 5.8 | 0.5 | 3.3 | 0.5 | 5.8 |
| 0.55 | 7.4 | 0.55 | 5.8 | 0.55 | 3.3 | 0.55 | 5.8 |
| 0.6 | 7.4 | 0.6 | 5.8 | 0.6 | 3.3 | 0.6 | 5.8 |
| 0.65 | 7.4 | 0.65 | 5.8 | 0.65 | 3.3 | 0.65 | 5.8 |
| 0.7 | 7.4 | 0.7 | 5.8 | 0.7 | 3.3 | 0.7 | 5.8 |
| 0.75 | 7.3 | 0.75 | 5.8 | 0.75 | 3.3 | 0.75 | 5.8 |
| 0.8 | 7.0 | 0.8 | 5.6 | 0.8 | 3.2 | 0.8 | 5.8 |
| 0.85 | 6.4 | 0.85 | 5.2 | 0.85 | 3.0 | 0.85 | 5.7 |
| 0.9 | 5.4 | 0.9 | 4.4 | 0.9 | 2.6 | 0.9 | 4.9 |
| 0.95 | 3.8 | 0.95 | 3.2 | 0.95 | 2.0 | 0.95 | 3.5 |
| 1 | 1.2 | 1 | 1.2 | 1 | 1.2 | 1 | 1.2 |

| HF-HFO-1234yf-HFO-1234zeE-HFO-1234zeZ ||||||||
| --- | --- | --- | --- | --- | --- | --- | --- |
| Organics 0.9 F1234yf + 0.05 F1234zeE + 0.05 F1234zeZ || Organics 0.05 F1234yf + 0.9 F1234zeE + 0.05 F1234zeZ || Organics 0.05 F1234yf + 0.05 F1234zeE + 0.9 F1234zeZ || Organics 0.4 F1234yf + 0.3 F1234zeE + 0.3 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 4.8 | 0 | 2.2 | 0 | 4.7 |
| 0.05 | 7.4 | 0.05 | 5.8 | 0.05 | 3.3 | 0.05 | 5.7 |
| 0.1 | 7.4 | 0.1 | 5.8 | 0.1 | 3.3 | 0.1 | 5.7 |
| 0.15 | 7.4 | 0.15 | 5.8 | 0.15 | 3.3 | 0.15 | 5.7 |
| 0.2 | 7.4 | 0.2 | 5.8 | 0.2 | 3.3 | 0.2 | 5.7 |
| 0.25 | 7.4 | 0.25 | 5.8 | 0.25 | 3.3 | 0.25 | 5.8 |
| 0.3 | 7.4 | 0.3 | 5.8 | 0.3 | 3.3 | 0.3 | 5.8 |
| 0.35 | 7.4 | 0.35 | 5.8 | 0.35 | 3.3 | 0.35 | 5.8 |
| 0.4 | 7.4 | 0.4 | 5.8 | 0.4 | 3.3 | 0.4 | 5.8 |
| 0.45 | 7.4 | 0.45 | 5.8 | 0.45 | 3.3 | 0.45 | 5.8 |
| 0.5 | 7.4 | 0.5 | 5.7 | 0.5 | 3.3 | 0.5 | 5.8 |
| 0.55 | 7.4 | 0.55 | 5.7 | 0.55 | 3.3 | 0.55 | 5.8 |
| 0.6 | 7.4 | 0.6 | 5.6 | 0.6 | 3.3 | 0.6 | 5.8 |
| 0.65 | 7.4 | 0.65 | 5.5 | 0.65 | 3.3 | 0.65 | 5.7 |
| 0.7 | 7.4 | 0.7 | 5.4 | 0.7 | 3.3 | 0.7 | 5.6 |
| 0.75 | 7.2 | 0.75 | 5.2 | 0.75 | 3.3 | 0.75 | 5.5 |
| 0.8 | 6.9 | 0.8 | 4.8 | 0.8 | 3.1 | 0.8 | 5.2 |
| 0.85 | 6.3 | 0.85 | 4.3 | 0.85 | 2.9 | 0.85 | 4.7 |
| 0.9 | 5.3 | 0.9 | 3.6 | 0.9 | 2.5 | 0.9 | 4.0 |
| 0.95 | 3.7 | 0.95 | 2.6 | 0.95 | 2.0 | 0.95 | 2.9 |
| 1 | 1.2 | 1 | 1.2 | 1 | 1.2 | 1 | 1.2 |

| HF-HFO-1234yf-HFO-1234zeE-HCFO-1233zdE ||||||||
| --- | --- | --- | --- | --- | --- | --- | --- |
| Organics 0.9 F1234yf + 0.05 F1234zeE + 0.05 F1233zdE || Organics 0.05 F1234yf + 0.9 F1234zeE + 0.05 F1233zdE || Organics 0.05 F1234yf + 0.05 F1234zeE + 0.9 F1233zdE || Organics 0.4 F1234yf + 0.3 F1234zeE + 0.3 F1233zdE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 4.8 | 0 | 1.8 | 0 | 4.7 |
| 0.05 | 7.4 | 0.05 | 5.8 | 0.05 | 2.9 | 0.05 | 5.7 |
| 0.1 | 7.4 | 0.1 | 5.8 | 0.1 | 2.9 | 0.1 | 5.7 |
| 0.15 | 7.4 | 0.15 | 5.8 | 0.15 | 2.9 | 0.15 | 5.7 |
| 0.2 | 7.4 | 0.2 | 5.8 | 0.2 | 2.9 | 0.2 | 5.7 |
| 0.25 | 7.4 | 0.25 | 5.8 | 0.25 | 2.9 | 0.25 | 5.7 |
| 0.3 | 7.4 | 0.3 | 5.8 | 0.3 | 2.9 | 0.3 | 5.7 |
| 0.35 | 7.4 | 0.35 | 5.8 | 0.35 | 2.9 | 0.35 | 5.7 |
| 0.4 | 7.4 | 0.4 | 5.8 | 0.4 | 2.9 | 0.4 | 5.7 |
| 0.45 | 7.4 | 0.45 | 5.8 | 0.45 | 2.9 | 0.45 | 5.7 |
| 0.5 | 7.4 | 0.5 | 5.7 | 0.5 | 2.9 | 0.5 | 5.7 |
| 0.55 | 7.4 | 0.55 | 5.7 | 0.55 | 2.9 | 0.55 | 5.7 |
| 0.6 | 7.4 | 0.6 | 5.6 | 0.6 | 2.9 | 0.6 | 5.7 |
| 0.65 | 7.4 | 0.65 | 5.5 | 0.65 | 2.9 | 0.65 | 5.7 |
| 0.7 | 7.4 | 0.7 | 5.4 | 0.7 | 2.9 | 0.7 | 5.6 |
| 0.75 | 7.2 | 0.75 | 5.1 | 0.75 | 2.9 | 0.75 | 5.4 |
| 0.8 | 6.9 | 0.8 | 4.8 | 0.8 | 2.7 | 0.8 | 5.1 |
| 0.85 | 6.3 | 0.85 | 4.3 | 0.85 | 2.5 | 0.85 | 4.7 |
| 0.9 | 5.3 | 0.9 | 3.6 | 0.9 | 2.2 | 0.9 | 3.9 |
| 0.95 | 3.7 | 0.95 | 2.6 | 0.95 | 1.8 | 0.95 | 2.8 |
| 1 | 1.2 | 1 | 1.2 | 1 | 1.2 | 1 | 1.2 |

| HF-HFO-1234yf-HFO-1234zeE-HFO-1243zf ||||||||
| --- | --- | --- | --- | --- | --- | --- | --- |
| Organics 0.9 F1234yf + 0.05 F1234zeE + 0.05 F1243zf || Organics 0.05 F1234yf + 0.9 F1234zeE + 0.05 F1243zf || Organics 0.05 F1234yf + 0.05 F1234zeE + 0.9 F1243zf || Organics 0.4 F1234yf + 0.3 F1234zeE + 0.3 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.7 | 0 | 5.0 | 0 | 5.8 | 0 | 5.9 |
| 0.05 | 7.6 | 0.05 | 6.0 | 0.05 | 6.8 | 0.05 | 6.9 |
| 0.1 | 7.6 | 0.1 | 6.0 | 0.1 | 6.8 | 0.1 | 6.9 |
| 0.15 | 7.6 | 0.15 | 6.0 | 0.15 | 6.8 | 0.15 | 6.9 |
| 0.2 | 7.6 | 0.2 | 6.0 | 0.2 | 6.8 | 0.2 | 6.9 |
| 0.25 | 7.6 | 0.25 | 6.0 | 0.25 | 6.8 | 0.25 | 6.9 |
| 0.3 | 7.6 | 0.3 | 6.0 | 0.3 | 6.8 | 0.3 | 6.9 |
| 0.35 | 7.6 | 0.35 | 6.0 | 0.35 | 6.8 | 0.35 | 6.9 |
| 0.4 | 7.6 | 0.4 | 6.0 | 0.4 | 6.8 | 0.4 | 6.9 |
| 0.45 | 7.6 | 0.45 | 6.0 | 0.45 | 6.8 | 0.45 | 6.9 |
| 0.5 | 7.6 | 0.5 | 6.0 | 0.5 | 6.8 | 0.5 | 6.9 |
| 0.55 | 7.6 | 0.55 | 5.9 | 0.55 | 6.8 | 0.55 | 6.9 |
| 0.6 | 7.6 | 0.6 | 5.8 | 0.6 | 6.7 | 0.6 | 6.9 |
| 0.65 | 7.6 | 0.65 | 5.7 | 0.65 | 6.7 | 0.65 | 6.8 |
| 0.7 | 7.6 | 0.7 | 5.6 | 0.7 | 6.6 | 0.7 | 6.7 |
| 0.75 | 7.4 | 0.75 | 5.4 | 0.75 | 6.4 | 0.75 | 6.5 |
| 0.8 | 7.1 | 0.8 | 5.0 | 0.8 | 6.1 | 0.8 | 6.2 |
| 0.85 | 6.5 | 0.85 | 4.5 | 0.85 | 5.6 | 0.85 | 5.7 |
| 0.9 | 5.5 | 0.9 | 3.8 | 0.9 | 4.8 | 0.9 | 4.8 |
| 0.95 | 3.8 | 0.95 | 2.7 | 0.95 | 3.4 | 0.95 | 3.3 |
| 1 | 1.2 | 1 | 1.2 | 1 | 1.2 | 1 | 1.2 |

| HF-HFO-1234yf-HFO-1234zeZ-HCFO-1233zdE ||||||||
| --- | --- | --- | --- | --- | --- | --- | --- |
| Organics 0.9 F1234yf + 0.05 F1234zeZ + 0.05 F1233zdE || Organics 0.05 F1234yf + 0.9 F1234zeZ + 0.05 F1233zdE || Organics 0.05 F1234yf + 0.05 F1234zeZ + 0.9 F1233zdE || Organics 0.4 F1234yf + 0.3 F1234zeZ + 0.3 F1233zdE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.3 | 0 | 2.0 | 0 | 1.7 | 0 | 3.8 |
| 0.05 | 7.3 | 0.05 | 3.2 | 0.05 | 2.8 | 0.05 | 4.8 |
| 0.1 | 7.3 | 0.1 | 3.2 | 0.1 | 2.8 | 0.1 | 4.8 |
| 0.15 | 7.3 | 0.15 | 3.2 | 0.15 | 2.8 | 0.15 | 4.8 |
| 0.2 | 7.3 | 0.2 | 3.2 | 0.2 | 2.8 | 0.2 | 4.8 |
| 0.25 | 7.3 | 0.25 | 3.2 | 0.25 | 2.8 | 0.25 | 4.8 |
| 0.3 | 7.3 | 0.3 | 3.2 | 0.3 | 2.8 | 0.3 | 4.8 |
| 0.35 | 7.3 | 0.35 | 3.1 | 0.35 | 2.8 | 0.35 | 4.8 |
| 0.4 | 7.3 | 0.4 | 3.1 | 0.4 | 2.8 | 0.4 | 4.8 |
| 0.45 | 7.3 | 0.45 | 3.1 | 0.45 | 2.8 | 0.45 | 4.8 |
| 0.5 | 7.3 | 0.5 | 3.1 | 0.5 | 2.8 | 0.5 | 4.8 |
| 0.55 | 7.3 | 0.55 | 3.1 | 0.55 | 2.8 | 0.55 | 4.8 |
| 0.6 | 7.3 | 0.6 | 3.1 | 0.6 | 2.8 | 0.6 | 4.8 |
| 0.65 | 7.3 | 0.65 | 3.1 | 0.65 | 2.8 | 0.65 | 4.8 |
| 0.7 | 7.3 | 0.7 | 3.1 | 0.7 | 2.7 | 0.7 | 4.8 |
| 0.75 | 7.1 | 0.75 | 3.1 | 0.75 | 2.7 | 0.75 | 4.7 |
| 0.8 | 6.8 | 0.8 | 3.0 | 0.8 | 2.6 | 0.8 | 4.5 |
| 0.85 | 6.2 | 0.85 | 2.8 | 0.85 | 2.4 | 0.85 | 4.1 |
| 0.9 | 5.3 | 0.9 | 2.4 | 0.9 | 2.2 | 0.9 | 3.5 |
| 0.95 | 3.7 | 0.95 | 1.9 | 0.95 | 1.7 | 0.95 | 2.6 |
| 1 | 1.2 | 1 | 1.2 | 1 | 1.2 | 1 | 1.2 |

| HF-HFO-1234yf-HFO-1234zeZ-HFO-1243zf ||||||||
| Organics 0.9 F1234yf + 0.05 F1234zeZ + 0.05 F1243zf || Organics 0.05 F1234yf + 0.9 F1234zeZ + 0.05 F1243zf || Organics 0.05 F1234yf + 0.05 F1234zeZ + 0.9 F1243zf || Organics 0.4 F1234yf + 0.3 F1234zeZ + 0.3 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- | --- | --- |
| 0 | 6.5 | 0 | 2.3 | 0 | 5.7 | 0 | 5.0 |
| 0.05 | 7.5 | 0.05 | 3.4 | 0.05 | 6.7 | 0.05 | 6.0 |
| 0.1 | 7.5 | 0.1 | 3.4 | 0.1 | 6.7 | 0.1 | 6.1 |
| 0.15 | 7.5 | 0.15 | 3.4 | 0.15 | 6.7 | 0.15 | 6.1 |
| 0.2 | 7.4 | 0.2 | 3.4 | 0.2 | 6.7 | 0.2 | 6.1 |
| 0.25 | 7.4 | 0.25 | 3.4 | 0.25 | 6.7 | 0.25 | 6.1 |
| 0.3 | 7.4 | 0.3 | 3.4 | 0.3 | 6.7 | 0.3 | 6.1 |
| 0.35 | 7.5 | 0.35 | 3.4 | 0.35 | 6.7 | 0.35 | 6.1 |
| 0.4 | 7.5 | 0.4 | 3.4 | 0.4 | 6.7 | 0.4 | 6.1 |
| 0.45 | 7.5 | 0.45 | 3.4 | 0.45 | 6.7 | 0.45 | 6.1 |
| 0.5 | 7.5 | 0.5 | 3.4 | 0.5 | 6.7 | 0.5 | 6.1 |
| 0.55 | 7.5 | 0.55 | 3.4 | 0.55 | 6.6 | 0.55 | 6.1 |
| 0.6 | 7.5 | 0.6 | 3.4 | 0.6 | 6.6 | 0.6 | 6.1 |
| 0.65 | 7.5 | 0.65 | 3.4 | 0.65 | 6.6 | 0.65 | 6.1 |
| 0.7 | 7.4 | 0.7 | 3.4 | 0.7 | 6.5 | 0.7 | 6.0 |
| 0.75 | 7.3 | 0.75 | 3.3 | 0.75 | 6.3 | 0.75 | 5.9 |
| 0.8 | 7.0 | 0.8 | 3.2 | 0.8 | 6.0 | 0.8 | 5.6 |
| 0.85 | 6.4 | 0.85 | 3.0 | 0.85 | 5.5 | 0.85 | 5.1 |
| 0.9 | 5.4 | 0.9 | 2.6 | 0.9 | 4.7 | 0.9 | 4.4 |
| 0.95 | 3.7 | 0.95 | 2.0 | 0.95 | 3.3 | 0.95 | 3.1 |
| 1 | 1.2 | 1 | 1.2 | 1 | 1.2 | 1 | 1.2 |

| HF-HFC-245cb-HCFO-1233zdE-HFO-1234zeE ||||||||
| Organics 0.9 F245cb + 0.05 F1233zdE + 0.05 F1234zeE || Organics 0.05 F245cb + 0.9 F1233zdE + 0.05 F1234zeE || Organics 0.05 F245cb + 0.05 F1233zdE + 0.9 F1234zeE || Organics 0.4 F245cb + 0.3 F1233zdE + 0.3 F1234zeE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- | --- | --- |
| 0 | 4.5 | 0 | 1.7 | 0 | 4.7 | 0 | 3.8 |
| 0.05 | 5.7 | 0.05 | 2.8 | 0.05 | 5.7 | 0.05 | 4.9 |
| 0.1 | 5.7 | 0.1 | 2.8 | 0.1 | 5.7 | 0.1 | 4.9 |
| 0.15 | 5.7 | 0.15 | 2.8 | 0.15 | 5.7 | 0.15 | 4.9 |
| 0.2 | 5.7 | 0.2 | 2.8 | 0.2 | 5.7 | 0.2 | 4.9 |
| 0.25 | 5.7 | 0.25 | 2.8 | 0.25 | 5.7 | 0.25 | 4.9 |
| 0.3 | 5.7 | 0.3 | 2.8 | 0.3 | 5.7 | 0.3 | 4.9 |
| 0.35 | 5.7 | 0.35 | 2.8 | 0.35 | 5.7 | 0.35 | 4.9 |
| 0.4 | 5.7 | 0.4 | 2.8 | 0.4 | 5.7 | 0.4 | 4.9 |
| 0.45 | 5.7 | 0.45 | 2.8 | 0.45 | 5.7 | 0.45 | 4.9 |
| 0.5 | 5.7 | 0.5 | 2.8 | 0.5 | 5.7 | 0.5 | 4.9 |
| 0.55 | 5.7 | 0.55 | 2.8 | 0.55 | 5.6 | 0.55 | 4.9 |
| 0.6 | 5.7 | 0.6 | 2.8 | 0.6 | 5.5 | 0.6 | 4.9 |
| 0.65 | 5.7 | 0.65 | 2.8 | 0.65 | 5.5 | 0.65 | 4.9 |
| 0.7 | 5.7 | 0.7 | 2.8 | 0.7 | 5.3 | 0.7 | 4.9 |
| 0.75 | 5.7 | 0.75 | 2.8 | 0.75 | 5.1 | 0.75 | 4.9 |
| 0.8 | 5.7 | 0.8 | 2.7 | 0.8 | 4.8 | 0.8 | 4.7 |
| 0.85 | 5.6 | 0.85 | 2.5 | 0.85 | 4.3 | 0.85 | 4.3 |
| 0.9 | 4.8 | 0.9 | 2.2 | 0.9 | 3.6 | 0.9 | 3.7 |
| 0.95 | 3.4 | 0.95 | 1.8 | 0.95 | 2.6 | 0.95 | 2.7 |
| 1 | 1.2 | 1 | 1.2 | 1 | 1.2 | 1 | 1.2 |

| HF-HFC-245cb-HCFO-1233zdE-HFO-1234zeZ ||||||||
|---|---|---|---|---|---|---|---|
| Organics 0.9 F245cb + 0.05 F1233zdE + 0.05 F1234zeZ || Organics 0.05 F245cb + 0.9 F1233zdE + 0.05 F1234zeZ || Organics 0.05 F245cb + 0.05 F1233zdE + 0.9 F1234zeZ || Organics 0.4 F245cb + 0.3 F1233zdE + 0.3 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.3 | 0 | 1.5 | 0 | 1.9 | 0 | 2.8 |
| 0.05 | 5.5 | 0.05 | 2.6 | 0.05 | 3.0 | 0.05 | 3.9 |
| 0.1 | 5.5 | 0.1 | 2.6 | 0.1 | 3.0 | 0.1 | 3.9 |
| 0.15 | 5.5 | 0.15 | 2.6 | 0.15 | 3.0 | 0.15 | 3.9 |
| 0.2 | 5.5 | 0.2 | 2.6 | 0.2 | 3.0 | 0.2 | 3.9 |
| 0.25 | 5.5 | 0.25 | 2.6 | 0.25 | 3.0 | 0.25 | 3.9 |
| 0.3 | 5.5 | 0.3 | 2.6 | 0.3 | 3.0 | 0.3 | 4.0 |
| 0.35 | 5.5 | 0.35 | 2.6 | 0.35 | 3.0 | 0.35 | 4.0 |
| 0.4 | 5.5 | 0.4 | 2.6 | 0.4 | 3.0 | 0.4 | 4.0 |
| 0.45 | 5.5 | 0.45 | 2.6 | 0.45 | 3.0 | 0.45 | 4.0 |
| 0.5 | 5.5 | 0.5 | 2.6 | 0.5 | 3.0 | 0.5 | 4.0 |
| 0.55 | 5.5 | 0.55 | 2.6 | 0.55 | 3.0 | 0.55 | 4.0 |
| 0.6 | 5.5 | 0.6 | 2.6 | 0.6 | 3.0 | 0.6 | 4.0 |
| 0.65 | 5.5 | 0.65 | 2.7 | 0.65 | 3.1 | 0.65 | 4.0 |
| 0.7 | 5.6 | 0.7 | 2.7 | 0.7 | 3.1 | 0.7 | 4.1 |
| 0.75 | 5.6 | 0.75 | 2.7 | 0.75 | 3.1 | 0.75 | 4.1 |
| 0.8 | 5.6 | 0.8 | 2.6 | 0.8 | 2.9 | 0.8 | 4.1 |
| 0.85 | 5.5 | 0.85 | 2.4 | 0.85 | 2.7 | 0.85 | 3.8 |
| 0.9 | 4.8 | 0.9 | 2.1 | 0.9 | 2.4 | 0.9 | 3.3 |
| 0.95 | 3.4 | 0.95 | 1.7 | 0.95 | 1.9 | 0.95 | 2.5 |
| 1 | 1.2 | 1 | 1.2 | 1 | 1.2 | 1 | 1.2 |

| HF-HCFO-1233zdE-HFO-1234zeE-HFO-1234zeZ ||||||||
|---|---|---|---|---|---|---|---|
| Organics 0.9 1233zdE + 0.05 1234zeE + 0.05 1234zeZ || Organics 0.05 1233zdE + 0.9 1234zeE + 0.05 1234zeZ || Organics 0.05 1233zdE + 0.05 1234zeE + 0.9 1234zeZ || Organics 0.4 1233zdE + 0.3 1234zeE + 0.3 1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.5 | 0 | 4.5 | 0 | 1.9 | 0 | 2.6 |
| 0.05 | 2.6 | 0.05 | 5.5 | 0.05 | 3.0 | 0.05 | 3.7 |
| 0.1 | 2.6 | 0.1 | 5.5 | 0.1 | 3.0 | 0.1 | 3.6 |
| 0.15 | 2.6 | 0.15 | 5.5 | 0.15 | 3.0 | 0.15 | 3.6 |
| 0.2 | 2.6 | 0.2 | 5.5 | 0.2 | 3.0 | 0.2 | 3.6 |
| 0.25 | 2.6 | 0.25 | 5.5 | 0.25 | 3.0 | 0.25 | 3.6 |
| 0.3 | 2.6 | 0.3 | 5.5 | 0.3 | 3.0 | 0.3 | 3.6 |
| 0.35 | 2.6 | 0.35 | 5.5 | 0.35 | 3.0 | 0.35 | 3.6 |
| 0.4 | 2.6 | 0.4 | 5.5 | 0.4 | 3.0 | 0.4 | 3.6 |
| 0.45 | 2.6 | 0.45 | 5.5 | 0.45 | 3.0 | 0.45 | 3.6 |
| 0.5 | 2.6 | 0.5 | 5.5 | 0.5 | 3.0 | 0.5 | 3.6 |
| 0.55 | 2.6 | 0.55 | 5.4 | 0.55 | 3.0 | 0.55 | 3.6 |
| 0.6 | 2.6 | 0.6 | 5.4 | 0.6 | 3.0 | 0.6 | 3.6 |
| 0.65 | 2.6 | 0.65 | 5.3 | 0.65 | 3.0 | 0.65 | 3.5 |
| 0.7 | 2.6 | 0.7 | 5.1 | 0.7 | 3.0 | 0.7 | 3.5 |
| 0.75 | 2.6 | 0.75 | 4.9 | 0.75 | 3.0 | 0.75 | 3.4 |
| 0.8 | 2.5 | 0.8 | 4.6 | 0.8 | 2.9 | 0.8 | 3.2 |
| 0.85 | 2.3 | 0.85 | 4.1 | 0.85 | 2.7 | 0.85 | 2.9 |
| 0.9 | 2.0 | 0.9 | 3.4 | 0.9 | 2.3 | 0.9 | 2.5 |
| 0.95 | 1.7 | 0.95 | 2.5 | 0.95 | 1.9 | 0.95 | 2.0 |
| 1 | 1.2 | 1 | 1.2 | 1 | 1.2 | 1 | 1.2 |

| HF-HCFO-1233zdE-HFO-1234zeE-HFO-1243zf | | | | | | | |
|---|---|---|---|---|---|---|---|
| Organics 0.9 F1233zdE + 0.05 F1234zeE + 0.05 F1243zf | | Organics 0.05 F1233zdE + 0.9 F1234zeE + 0.05 F1243zf | | Organics 0.05 F1233zdE + 0.05 F1234zeE + 0.9 F1243zf | | Organics 0.4 F1233zdE + 0.3 F1234zeE + 0.3 F1243zf | |
| HF HF | PRESSURE PRES bar | HF HF | PRESSURE PRES bar | HF HF | PRESSURE PRES bar | HF HF | PRESSURE PRES bar |
| 0 | 1.8 | 0 | 4.8 | 0 | 5.6 | 0 | 3.9 |
| 0.05 | 2.9 | 0.05 | 5.7 | 0.05 | 6.6 | 0.05 | 5.0 |
| 0.1 | 2.9 | 0.1 | 5.7 | 0.1 | 6.6 | 0.1 | 5.0 |
| 0.15 | 2.9 | 0.15 | 5.7 | 0.15 | 6.6 | 0.15 | 5.0 |
| 0.2 | 2.9 | 0.2 | 5.7 | 0.2 | 6.6 | 0.2 | 5.0 |
| 0.25 | 2.9 | 0.25 | 5.7 | 0.25 | 6.6 | 0.25 | 5.0 |
| 0.3 | 2.9 | 0.3 | 5.7 | 0.3 | 6.6 | 0.3 | 5.0 |
| 0.35 | 2.9 | 0.35 | 5.7 | 0.35 | 6.6 | 0.35 | 5.0 |
| 0.4 | 2.9 | 0.4 | 5.7 | 0.4 | 6.6 | 0.4 | 4.9 |
| 0.45 | 2.9 | 0.45 | 5.7 | 0.45 | 6.6 | 0.45 | 4.9 |
| 0.5 | 2.9 | 0.5 | 5.7 | 0.5 | 6.6 | 0.5 | 4.9 |
| 0.55 | 2.9 | 0.55 | 5.6 | 0.55 | 6.5 | 0.55 | 4.9 |
| 0.6 | 2.9 | 0.6 | 5.6 | 0.6 | 6.5 | 0.6 | 4.9 |
| 0.65 | 2.9 | 0.65 | 5.5 | 0.65 | 6.5 | 0.65 | 4.9 |
| 0.7 | 2.8 | 0.7 | 5.3 | 0.7 | 6.4 | 0.7 | 4.8 |
| 0.75 | 2.8 | 0.75 | 5.1 | 0.75 | 6.2 | 0.75 | 4.6 |
| 0.8 | 2.7 | 0.8 | 4.8 | 0.8 | 5.9 | 0.8 | 4.3 |
| 0.85 | 2.5 | 0.85 | 4.3 | 0.85 | 5.4 | 0.85 | 3.9 |
| 0.9 | 2.2 | 0.9 | 3.6 | 0.9 | 4.6 | 0.9 | 3.3 |
| 0.95 | 1.8 | 0.95 | 2.6 | 0.95 | 3.3 | 0.95 | 2.5 |
| 1 | 1.2 | 1 | 1.2 | 1 | 1.2 | 1 | 1.2 |

| HF - HCFO-1233zdE - HFO-1234zeZ - HFO-1243zf | | | | | | | |
|---|---|---|---|---|---|---|---|
| Organics 0.9 F1233zdE + 0.05 F1234zeZ + 0.05 F1243zf | | Organics 0.05 F1233zdE + 0.9 F1234zeZ + 0.05 F1243zf | | Organics 0.05 F1233zdE + 0.05 F1234zeZ + 0.9 F1243zf | | Organics 0.4 F1233zdE + 0.3 F1234zeZ + 0.3 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.6 | 0 | 2.0 | 0 | 5.5 | 0 | 3.0 |
| 0.05 | 2.7 | 0.05 | 3.1 | 0.05 | 6.4 | 0.05 | 4.1 |
| 0.1 | 2.7 | 0.1 | 3.1 | 0.1 | 6.5 | 0.1 | 4.1 |
| 0.15 | 2.7 | 0.15 | 3.1 | 0.15 | 6.5 | 0.15 | 4.1 |
| 0.2 | 2.7 | 0.2 | 3.1 | 0.2 | 6.5 | 0.2 | 4.1 |
| 0.25 | 2.7 | 0.25 | 3.1 | 0.25 | 6.5 | 0.25 | 4.1 |
| 0.3 | 2.7 | 0.3 | 3.1 | 0.3 | 6.4 | 0.3 | 4.1 |
| 0.35 | 2.7 | 0.35 | 3.1 | 0.35 | 6.4 | 0.35 | 4.1 |
| 0.4 | 2.7 | 0.4 | 3.1 | 0.4 | 6.4 | 0.4 | 4.1 |
| 0.45 | 2.7 | 0.45 | 3.1 | 0.45 | 6.4 | 0.45 | 4.1 |
| 0.5 | 2.7 | 0.5 | 3.1 | 0.5 | 6.4 | 0.5 | 4.1 |
| 0.55 | 2.7 | 0.55 | 3.1 | 0.55 | 6.4 | 0.55 | 4.1 |
| 0.6 | 2.7 | 0.6 | 3.1 | 0.6 | 6.4 | 0.6 | 4.1 |
| 0.65 | 2.7 | 0.65 | 3.1 | 0.65 | 6.3 | 0.65 | 4.0 |
| 0.7 | 2.7 | 0.7 | 3.1 | 0.7 | 6.3 | 0.7 | 4.0 |
| 0.75 | 2.7 | 0.75 | 3.1 | 0.75 | 6.1 | 0.75 | 3.9 |
| 0.8 | 2.6 | 0.8 | 3.0 | 0.8 | 5.8 | 0.8 | 3.7 |
| 0.85 | 2.4 | 0.85 | 2.7 | 0.85 | 5.3 | 0.85 | 3.4 |
| 0.9 | 2.1 | 0.9 | 2.4 | 0.9 | 4.5 | 0.9 | 2.9 |
| 0.95 | 1.7 | 0.95 | 1.9 | 0.95 | 3.2 | 0.95 | 2.2 |
| 1 | 1.2 | 1 | 1.2 | 1 | 1.2 | 1 | 1.2 |

| HF - HFC-245cb - HFO-1234zeE - HFO-1234zeZ ||||||||
|---|---|---|---|---|---|---|---|
| Organics 0.9 F245cb + 0.05 F1234zeE + 0.05 F1234zeZ || Organics 0.05 F245cb + 0.9 F1234zeE + 0.05 F1234zeZ || Organics 0.05 F245cb + 0.05 F1234zeE + 0.9 F1234zeZ || Organics 0.4 F245cb + 0.3 F1234zeE + 0.3 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.5 | 0 | 4.7 | 0 | 2.1 | 0 | 3.8 |
| 0.05 | 5.7 | 0.05 | 5.7 | 0.05 | 3.2 | 0.05 | 4.9 |
| 0.1 | 5.7 | 0.1 | 5.7 | 0.1 | 3.2 | 0.1 | 4.9 |
| 0.15 | 5.7 | 0.15 | 5.7 | 0.15 | 3.2 | 0.15 | 4.9 |
| 0.2 | 5.7 | 0.2 | 5.7 | 0.2 | 3.2 | 0.2 | 4.9 |
| 0.25 | 5.7 | 0.25 | 5.7 | 0.25 | 3.2 | 0.25 | 4.9 |
| 0.3 | 5.7 | 0.3 | 5.7 | 0.3 | 3.2 | 0.3 | 4.9 |
| 0.35 | 5.7 | 0.35 | 5.7 | 0.35 | 3.2 | 0.35 | 5.0 |
| 0.4 | 5.7 | 0.4 | 5.7 | 0.4 | 3.2 | 0.4 | 5.0 |
| 0.45 | 5.7 | 0.45 | 5.7 | 0.45 | 3.2 | 0.45 | 5.0 |
| 0.5 | 5.7 | 0.5 | 5.7 | 0.5 | 3.2 | 0.5 | 5.0 |
| 0.55 | 5.7 | 0.55 | 5.6 | 0.55 | 3.2 | 0.55 | 5.0 |
| 0.6 | 5.7 | 0.6 | 5.6 | 0.6 | 3.2 | 0.6 | 5.0 |
| 0.65 | 5.7 | 0.65 | 5.5 | 0.65 | 3.2 | 0.65 | 5.0 |
| 0.7 | 5.7 | 0.7 | 5.3 | 0.7 | 3.2 | 0.7 | 5.0 |
| 0.75 | 5.7 | 0.75 | 5.1 | 0.75 | 3.2 | 0.75 | 5.0 |
| 0.8 | 5.7 | 0.8 | 4.8 | 0.8 | 3.1 | 0.8 | 4.8 |
| 0.85 | 5.6 | 0.85 | 4.3 | 0.85 | 2.8 | 0.85 | 4.4 |
| 0.9 | 4.8 | 0.9 | 3.6 | 0.9 | 2.5 | 0.9 | 3.8 |
| 0.95 | 3.4 | 0.95 | 2.6 | 0.95 | 2.0 | 0.95 | 2.7 |
| 1 | 1.2 | 1 | 1.2 | 1 | 1.2 | 1 | 1.2 |

| HF - HFC-245cb - HFO-1234zeE - HFO-1243zf ||||||||
|---|---|---|---|---|---|---|---|
| Organics 0.9 F245cb + 0.05 F1234zeE + 0.05 F1243zf || Organics 0.05 F245cb + 0.9 F1234zeE + 0.05 F1243zf || Organics 0.05 F245cb + 0.05 F1234zeE + 0.9 F1243zf || Organics 0.4 F245cb + 0.3 F1234zeE + 0.3 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.8 | 0 | 4.9 | 0 | 5.8 | 0 | 5.2 |
| 0.05 | 5.9 | 0.05 | 5.9 | 0.05 | 6.7 | 0.05 | 6.2 |
| 0.1 | 5.9 | 0.1 | 5.9 | 0.1 | 6.7 | 0.1 | 6.2 |
| 0.15 | 5.9 | 0.15 | 5.9 | 0.15 | 6.7 | 0.15 | 6.2 |
| 0.2 | 5.9 | 0.2 | 5.9 | 0.2 | 6.7 | 0.2 | 6.2 |
| 0.25 | 5.9 | 0.25 | 5.9 | 0.25 | 6.7 | 0.25 | 6.2 |
| 0.3 | 5.9 | 0.3 | 5.9 | 0.3 | 6.7 | 0.3 | 6.2 |
| 0.35 | 5.9 | 0.35 | 5.9 | 0.35 | 6.7 | 0.35 | 6.2 |
| 0.4 | 5.9 | 0.4 | 5.9 | 0.4 | 6.7 | 0.4 | 6.2 |
| 0.45 | 5.9 | 0.45 | 5.9 | 0.45 | 6.7 | 0.45 | 6.2 |
| 0.5 | 5.9 | 0.5 | 5.9 | 0.5 | 6.7 | 0.5 | 6.2 |
| 0.55 | 5.9 | 0.55 | 5.8 | 0.55 | 6.7 | 0.55 | 6.2 |
| 0.6 | 5.9 | 0.6 | 5.8 | 0.6 | 6.7 | 0.6 | 6.2 |
| 0.65 | 5.9 | 0.65 | 5.7 | 0.65 | 6.6 | 0.65 | 6.2 |
| 0.7 | 5.9 | 0.7 | 5.5 | 0.7 | 6.5 | 0.7 | 6.2 |
| 0.75 | 5.9 | 0.75 | 5.3 | 0.75 | 6.4 | 0.75 | 6.1 |
| 0.8 | 5.9 | 0.8 | 5.0 | 0.8 | 6.1 | 0.8 | 5.8 |
| 0.85 | 5.8 | 0.85 | 4.5 | 0.85 | 5.6 | 0.85 | 5.3 |
| 0.9 | 5.0 | 0.9 | 3.7 | 0.9 | 4.7 | 0.9 | 4.5 |
| 0.95 | 3.5 | 0.95 | 2.7 | 0.95 | 3.4 | 0.95 | 3.2 |
| 1 | 1.2 | 1 | 1.2 | 1 | 1.2 | 1 | 1.2 |

| HF - HFC-245cb - HFO-1234zeZ - HFO-1243zf | | | | | | | |
|---|---|---|---|---|---|---|---|
| Organics 0.9 F245cb + 0.05 F1234zeZ + 0.05 F1243zf | | Organics 0.05 F245cb + 0.9 F1234zeZ + 0.05 F1243zf | | Organics 0.05 F245cb + 0.05 F1234zeZ + 0.9 F1243zf | | Organics 0.4 F245cb + 0.3 F1234zeZ + 0.3 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.6 | 0 | 2.2 | 0 | 5.6 | 0 | 4.2 |
| 0.05 | 5.7 | 0.05 | 3.3 | 0.05 | 6.6 | 0.05 | 5.3 |
| 0.1 | 5.7 | 0.1 | 3.3 | 0.1 | 6.6 | 0.1 | 5.3 |
| 0.15 | 5.7 | 0.15 | 3.3 | 0.15 | 6.6 | 0.15 | 5.3 |
| 0.2 | 5.7 | 0.2 | 3.3 | 0.2 | 6.6 | 0.2 | 5.3 |
| 0.25 | 5.7 | 0.25 | 3.3 | 0.25 | 6.6 | 0.25 | 5.3 |
| 0.3 | 5.7 | 0.3 | 3.3 | 0.3 | 6.6 | 0.3 | 5.3 |
| 0.35 | 5.7 | 0.35 | 3.3 | 0.35 | 6.6 | 0.35 | 5.3 |
| 0.4 | 5.7 | 0.4 | 3.3 | 0.4 | 6.6 | 0.4 | 5.3 |
| 0.45 | 5.7 | 0.45 | 3.3 | 0.45 | 6.6 | 0.45 | 5.3 |
| 0.5 | 5.7 | 0.5 | 3.3 | 0.5 | 6.6 | 0.5 | 5.3 |
| 0.55 | 5.8 | 0.55 | 3.3 | 0.55 | 6.6 | 0.55 | 5.3 |
| 0.6 | 5.8 | 0.6 | 3.3 | 0.6 | 6.5 | 0.6 | 5.3 |
| 0.65 | 5.8 | 0.65 | 3.3 | 0.65 | 6.5 | 0.65 | 5.3 |
| 0.7 | 5.8 | 0.7 | 3.3 | 0.7 | 6.4 | 0.7 | 5.4 |
| 0.75 | 5.8 | 0.75 | 3.3 | 0.75 | 6.3 | 0.75 | 5.4 |
| 0.8 | 5.8 | 0.8 | 3.1 | 0.8 | 6.0 | 0.8 | 5.2 |
| 0.85 | 5.7 | 0.85 | 2.9 | 0.85 | 5.5 | 0.85 | 4.8 |
| 0.9 | 4.9 | 0.9 | 2.6 | 0.9 | 4.7 | 0.9 | 4.1 |
| 0.95 | 3.5 | 0.95 | 2.0 | 0.95 | 3.3 | 0.95 | 3.0 |
| 1 | 1.2 | 1 | 1.2 | 1 | 1.2 | 1 | 1.2 |

| HF - HFO-1234zeE - HFO-1234zeZ - HFO-1243zf | | | | | | | |
|---|---|---|---|---|---|---|---|
| Organics 0.9 F1234zeE + 0.05 F1234zeZ + 0.05 F1243zf | | Organics 0.05 F1234zeE + 0.9 F1234zeZ + 0.05 F1243zf | | Organics 0.05 F1234zeE + 0.05 F1234zeZ + 0.9 F1243zf | | Organics 0.4 F1234zeE + 0.3 F1234zeZ + 0.3 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.8 | 0 | 2.2 | 0 | 5.6 | 0 | 4.3 |
| 0.05 | 5.7 | 0.05 | 3.3 | 0.05 | 6.6 | 0.05 | 5.3 |
| 0.1 | 5.8 | 0.1 | 3.3 | 0.1 | 6.6 | 0.1 | 5.3 |
| 0.15 | 5.8 | 0.15 | 3.3 | 0.15 | 6.6 | 0.15 | 5.3 |
| 0.2 | 5.7 | 0.2 | 3.3 | 0.2 | 6.6 | 0.2 | 5.3 |
| 0.25 | 5.7 | 0.25 | 3.3 | 0.25 | 6.6 | 0.25 | 5.3 |
| 0.3 | 5.7 | 0.3 | 3.3 | 0.3 | 6.6 | 0.3 | 5.3 |
| 0.35 | 5.7 | 0.35 | 3.3 | 0.35 | 6.6 | 0.35 | 5.3 |
| 0.4 | 5.7 | 0.4 | 3.3 | 0.4 | 6.6 | 0.4 | 5.3 |
| 0.45 | 5.7 | 0.45 | 3.3 | 0.45 | 6.6 | 0.45 | 5.3 |
| 0.5 | 5.7 | 0.5 | 3.3 | 0.5 | 6.6 | 0.5 | 5.3 |
| 0.55 | 5.7 | 0.55 | 3.3 | 0.55 | 6.5 | 0.55 | 5.3 |
| 0.6 | 5.6 | 0.6 | 3.3 | 0.6 | 6.5 | 0.6 | 5.3 |
| 0.65 | 5.5 | 0.65 | 3.3 | 0.65 | 6.5 | 0.65 | 5.2 |
| 0.7 | 5.3 | 0.7 | 3.3 | 0.7 | 6.4 | 0.7 | 5.1 |
| 0.75 | 5.1 | 0.75 | 3.2 | 0.75 | 6.2 | 0.75 | 4.9 |
| 0.8 | 4.8 | 0.8 | 3.1 | 0.8 | 5.9 | 0.8 | 4.6 |
| 0.85 | 4.3 | 0.85 | 2.8 | 0.85 | 5.4 | 0.85 | 4.2 |
| 0.9 | 3.6 | 0.9 | 2.5 | 0.9 | 4.6 | 0.9 | 3.6 |
| 0.95 | 2.6 | 0.95 | 2.0 | 0.95 | 3.3 | 0.95 | 2.6 |
| 1 | 1.2 | 1 | 1.2 | 1 | 1.2 | 1 | 1.2 |

HF - HFO-1234yf - HFO-1234zeE - Trifluoropropyne

| Organics 0.34 F1234yf + 0.33 F1234zeE + 0.33 TFP | | Organics 0.99 F1234yf + 0.005 F1234zeE + 0.005 TFP | | Organics 0.005 F1234yf + 0.99 F1234zeE + 0.005 TFP | | Organics 0.005 F1234yf + 0.005 F1234zeE + 0.99 TFP | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 8.0 | 0 | 6.8 | 0 | 4.9 | 0 | 11.6 |
| 0.05 | 8.8 | 0.05 | 7.8 | 0.05 | 5.9 | 0.05 | 12.4 |
| 0.1 | 8.8 | 0.1 | 7.8 | 0.1 | 5.9 | 0.1 | 12.3 |
| 0.15 | 8.8 | 0.15 | 7.8 | 0.15 | 5.9 | 0.15 | 12.2 |
| 0.2 | 8.8 | 0.2 | 7.8 | 0.2 | 5.9 | 0.2 | 12.1 |
| 0.25 | 8.7 | 0.25 | 7.8 | 0.25 | 5.9 | 0.25 | 12.0 |
| 0.3 | 8.7 | 0.3 | 7.7 | 0.3 | 5.9 | 0.3 | 11.9 |
| 0.35 | 8.7 | 0.35 | 7.8 | 0.35 | 5.9 | 0.35 | 11.8 |
| 0.4 | 8.7 | 0.4 | 7.8 | 0.4 | 5.9 | 0.4 | 11.8 |
| 0.45 | 8.7 | 0.45 | 7.8 | 0.45 | 5.9 | 0.45 | 11.8 |
| 0.5 | 8.7 | 0.5 | 7.8 | 0.5 | 5.8 | 0.5 | 11.8 |
| 0.55 | 8.7 | 0.55 | 7.8 | 0.55 | 5.8 | 0.55 | 11.8 |
| 0.6 | 8.7 | 0.6 | 7.8 | 0.6 | 5.7 | 0.6 | 11.8 |
| 0.65 | 8.7 | 0.65 | 7.8 | 0.65 | 5.6 | 0.65 | 11.8 |
| 0.7 | 8.6 | 0.7 | 7.7 | 0.7 | 5.4 | 0.7 | 11.8 |
| 0.75 | 8.5 | 0.75 | 7.6 | 0.75 | 5.2 | 0.75 | 11.8 |
| 0.8 | 8.1 | 0.8 | 7.3 | 0.8 | 4.8 | 0.8 | 11.6 |
| 0.85 | 7.4 | 0.85 | 6.7 | 0.85 | 4.3 | 0.85 | 10.8 |
| 0.9 | 6.2 | 0.9 | 5.6 | 0.9 | 3.6 | 0.9 | 9.1 |
| 0.95 | 4.2 | 0.95 | 3.9 | 0.95 | 2.6 | 0.95 | 6.1 |
| 1 | 1.2 | 1 | 1.2 | 1 | 1.2 | 1 | 1.2 |

HF - HFO-1234yf - HFO-1234zeE - HCFC-244bb

| Organics 0.34 F1234yf + 0.33 F1234zeE + 0.33 F244bb | | Organics 0.99 F1234yf + 0.005 F1234zeE + 0.005 F244bb | | Organics 0.005 F1234yf + 0.99 F1234zeE + 0.005 F244bb | | Organics 0.005 F1234yf + 0.005 F1234zeE + 0.99 F244bb | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 6.8 | 0 | 4.9 | 0 | 0.7 |
| 0.05 | 5.4 | 0.05 | 7.7 | 0.05 | 5.8 | 0.05 | 1.8 |
| 0.1 | 5.4 | 0.1 | 7.7 | 0.1 | 5.8 | 0.1 | 1.8 |
| 0.15 | 5.4 | 0.15 | 7.7 | 0.15 | 5.8 | 0.15 | 1.8 |
| 0.2 | 5.4 | 0.2 | 7.7 | 0.2 | 5.8 | 0.2 | 1.8 |
| 0.25 | 5.4 | 0.25 | 7.7 | 0.25 | 5.8 | 0.25 | 1.8 |
| 0.3 | 5.4 | 0.3 | 7.7 | 0.3 | 5.8 | 0.3 | 1.8 |
| 0.35 | 5.4 | 0.35 | 7.7 | 0.35 | 5.8 | 0.35 | 1.8 |
| 0.4 | 5.4 | 0.4 | 7.7 | 0.4 | 5.8 | 0.4 | 1.8 |
| 0.45 | 5.3 | 0.45 | 7.7 | 0.45 | 5.8 | 0.45 | 1.8 |
| 0.5 | 5.3 | 0.5 | 7.7 | 0.5 | 5.8 | 0.5 | 1.8 |
| 0.55 | 5.3 | 0.55 | 7.7 | 0.55 | 5.7 | 0.55 | 1.8 |
| 0.6 | 5.2 | 0.6 | 7.7 | 0.6 | 5.6 | 0.6 | 1.8 |
| 0.65 | 5.2 | 0.65 | 7.7 | 0.65 | 5.5 | 0.65 | 1.8 |
| 0.7 | 5.1 | 0.7 | 7.7 | 0.7 | 5.4 | 0.7 | 1.8 |
| 0.75 | 5.0 | 0.75 | 7.5 | 0.75 | 5.1 | 0.75 | 1.8 |
| 0.8 | 4.8 | 0.8 | 7.2 | 0.8 | 4.8 | 0.8 | 1.8 |
| 0.85 | 4.3 | 0.85 | 6.6 | 0.85 | 4.3 | 0.85 | 1.8 |
| 0.9 | 3.7 | 0.9 | 5.6 | 0.9 | 3.6 | 0.9 | 1.7 |
| 0.95 | 2.7 | 0.95 | 3.8 | 0.95 | 2.6 | 0.95 | 1.5 |
| 1 | 1.2 | 1 | 1.2 | 1 | 1.2 | 1 | 1.2 |

| HF - HFO-1234yf - HFO-1234zeE - HFC-245fa ||||||||
|---|---|---|---|---|---|---|---|
| Organics 0.34 F1234yf + 0.33 F1234zeE + 0.33 F245fa || Organics 0.99 F1234yf + 0.005 F1234zeE + 0.005 F245fa || Organics 0.005 F1234yf + 0.99 F1234zeE + 0.005 F245fa || Organics 0.005 F1234yf + 0.005 F1234zeE + 0.99 F245fa ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.5 | 0 | 6.8 | 0 | 4.9 | 0 | 1.6 |
| 0.05 | 5.6 | 0.05 | 7.7 | 0.05 | 5.8 | 0.05 | 2.7 |
| 0.1 | 5.6 | 0.1 | 7.7 | 0.1 | 5.8 | 0.1 | 2.7 |
| 0.15 | 5.6 | 0.15 | 7.7 | 0.15 | 5.8 | 0.15 | 2.7 |
| 0.2 | 5.6 | 0.2 | 7.7 | 0.2 | 5.8 | 0.2 | 2.7 |
| 0.25 | 5.6 | 0.25 | 7.7 | 0.25 | 5.8 | 0.25 | 2.7 |
| 0.3 | 5.6 | 0.3 | 7.7 | 0.3 | 5.8 | 0.3 | 2.7 |
| 0.35 | 5.6 | 0.35 | 7.7 | 0.35 | 5.8 | 0.35 | 2.7 |
| 0.4 | 5.6 | 0.4 | 7.7 | 0.4 | 5.8 | 0.4 | 2.7 |
| 0.45 | 5.6 | 0.45 | 7.7 | 0.45 | 5.8 | 0.45 | 2.7 |
| 0.5 | 5.6 | 0.5 | 7.7 | 0.5 | 5.8 | 0.5 | 2.7 |
| 0.55 | 5.5 | 0.55 | 7.7 | 0.55 | 5.7 | 0.55 | 2.7 |
| 0.6 | 5.5 | 0.6 | 7.7 | 0.6 | 5.6 | 0.6 | 2.7 |
| 0.65 | 5.5 | 0.65 | 7.7 | 0.65 | 5.5 | 0.65 | 2.7 |
| 0.7 | 5.4 | 0.7 | 7.7 | 0.7 | 5.4 | 0.7 | 2.7 |
| 0.75 | 5.3 | 0.75 | 7.5 | 0.75 | 5.1 | 0.75 | 2.7 |
| 0.8 | 5.0 | 0.8 | 7.2 | 0.8 | 4.8 | 0.8 | 2.6 |
| 0.85 | 4.5 | 0.85 | 6.6 | 0.85 | 4.3 | 0.85 | 2.4 |
| 0.9 | 3.8 | 0.9 | 5.6 | 0.9 | 3.6 | 0.9 | 2.1 |
| 0.95 | 2.7 | 0.95 | 3.9 | 0.95 | 2.6 | 0.95 | 1.7 |
| 1 | 1.2 | 1 | 1.2 | 1 | 1.2 | 1 | 1.2 |

| HF - HFO-1234yf - HFO-1234zeE - HFO-1225yeZ ||||||||
|---|---|---|---|---|---|---|---|
| Organics 0.34 F1234yf + 0.33 F1234zeE + 0.33 || Organics 0.99 F1234yf + 0.005 F1234zeE + 0.005 || Organics 0.005 F1234yf + 0.99 F1234zeE + 0.005 || Organics 0.005 F1234yf + 0.005 F1234zeE + 0.99 ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 5.7 | 0 | 6.8 | 0 | 4.9 | 0 | 5.2 |
| 0.05 | 6.6 | 0.05 | 7.7 | 0.05 | 5.8 | 0.05 | 6.2 |
| 0.1 | 6.7 | 0.1 | 7.8 | 0.1 | 5.9 | 0.1 | 6.2 |
| 0.15 | 6.7 | 0.15 | 7.7 | 0.15 | 5.9 | 0.15 | 6.2 |
| 0.2 | 6.7 | 0.2 | 7.7 | 0.2 | 5.9 | 0.2 | 6.2 |
| 0.25 | 6.7 | 0.25 | 7.7 | 0.25 | 5.9 | 0.25 | 6.2 |
| 0.3 | 6.7 | 0.3 | 7.7 | 0.3 | 5.9 | 0.3 | 6.2 |
| 0.35 | 6.7 | 0.35 | 7.7 | 0.35 | 5.9 | 0.35 | 6.2 |
| 0.4 | 6.7 | 0.4 | 7.7 | 0.4 | 5.8 | 0.4 | 6.2 |
| 0.45 | 6.7 | 0.45 | 7.7 | 0.45 | 5.8 | 0.45 | 6.2 |
| 0.5 | 6.7 | 0.5 | 7.7 | 0.5 | 5.8 | 0.5 | 6.2 |
| 0.55 | 6.7 | 0.55 | 7.7 | 0.55 | 5.7 | 0.55 | 6.2 |
| 0.6 | 6.6 | 0.6 | 7.7 | 0.6 | 5.7 | 0.6 | 6.2 |
| 0.65 | 6.6 | 0.65 | 7.7 | 0.65 | 5.6 | 0.65 | 6.2 |
| 0.7 | 6.5 | 0.7 | 7.7 | 0.7 | 5.4 | 0.7 | 6.1 |
| 0.75 | 6.3 | 0.75 | 7.6 | 0.75 | 5.2 | 0.75 | 5.9 |
| 0.8 | 5.9 | 0.8 | 7.2 | 0.8 | 4.8 | 0.8 | 5.6 |
| 0.85 | 5.4 | 0.85 | 6.6 | 0.85 | 4.3 | 0.85 | 5.1 |
| 0.9 | 4.5 | 0.9 | 5.6 | 0.9 | 3.6 | 0.9 | 4.2 |
| 0.95 | 3.1 | 0.95 | 3.9 | 0.95 | 2.6 | 0.95 | 3.0 |
| 1 | 1.2 | 1 | 1.2 | 1 | 1.2 | 1 | 1.2 |

| HF - HFO-1234yf - HFO-1234zeE - HFO-1225zc ||||||||
| --- | --- | --- | --- | --- | --- | --- | --- |
| Organics 0.34 F1234yf + 0.33 F1234zeE + 0.33 F1225zc || Organics 0.99 F1234yf + 0.005 F1234zeE + 0.005 F1225zc || Organics 0.005 F1234yf + 0.99 F1234zeE + 0.005 F1225zc || Organics 0.005 F1234yf + 0.005 F1234zeE + 0.99 F1225zc ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 5.7 | 0 | 6.8 | 0 | 4.9 | 0 | 5.3 |
| 0.05 | 6.7 | 0.05 | 7.7 | 0.05 | 5.8 | 0.05 | 6.3 |
| 0.1 | 6.7 | 0.1 | 7.8 | 0.1 | 5.9 | 0.1 | 6.3 |
| 0.15 | 6.7 | 0.15 | 7.7 | 0.15 | 5.9 | 0.15 | 6.3 |
| 0.2 | 6.7 | 0.2 | 7.7 | 0.2 | 5.9 | 0.2 | 6.3 |
| 0.25 | 6.7 | 0.25 | 7.7 | 0.25 | 5.9 | 0.25 | 6.3 |
| 0.3 | 6.7 | 0.3 | 7.7 | 0.3 | 5.9 | 0.3 | 6.3 |
| 0.35 | 6.7 | 0.35 | 7.7 | 0.35 | 5.9 | 0.35 | 6.3 |
| 0.4 | 6.7 | 0.4 | 7.7 | 0.4 | 5.8 | 0.4 | 6.3 |
| 0.45 | 6.7 | 0.45 | 7.7 | 0.45 | 5.8 | 0.45 | 6.3 |
| 0.5 | 6.7 | 0.5 | 7.7 | 0.5 | 5.8 | 0.5 | 6.2 |
| 0.55 | 6.7 | 0.55 | 7.7 | 0.55 | 5.7 | 0.55 | 6.2 |
| 0.6 | 6.6 | 0.6 | 7.7 | 0.6 | 5.7 | 0.6 | 6.1 |
| 0.65 | 6.5 | 0.65 | 7.7 | 0.65 | 5.6 | 0.65 | 6.0 |
| 0.7 | 6.4 | 0.7 | 7.7 | 0.7 | 5.4 | 0.7 | 5.9 |
| 0.75 | 6.2 | 0.75 | 7.6 | 0.75 | 5.2 | 0.75 | 5.6 |
| 0.8 | 5.8 | 0.8 | 7.2 | 0.8 | 4.8 | 0.8 | 5.2 |
| 0.85 | 5.3 | 0.85 | 6.6 | 0.85 | 4.3 | 0.85 | 4.6 |
| 0.9 | 4.4 | 0.9 | 5.6 | 0.9 | 3.6 | 0.9 | 3.8 |
| 0.95 | 3.1 | 0.95 | 3.9 | 0.95 | 2.6 | 0.95 | 2.7 |
| 1 | 1.2 | 1 | 1.2 | 1 | 1.2 | 1 | 1.2 |

Example 5: Temperature and Pressure Range of Quaternary Mixtures

| | Boiling point range ||
| --- | --- | --- |
| Quaternary | Temperature ° C. | Pressure bar abs |
| HF - HCFO-1233xf - HFC-245cb - HFO-1234zeE | 0 to 40 | ~1.1 to ~8.8 |
| HF - HCFO-1233xf - HFC-245cb - HFO-1234zeZ | 0 to 40 | ~1.1 to ~8.8 |
| HF - HFO-1234yf - HFC-245cb - HFO-1234zeE | 0 to 40 | ~2.5 to ~11.5 |
| HF - HFO-1234yf - HFC-245cb - HFO-1234zeZ | 0 to 40 | ~1.3 to ~11.3 |
| HF - HCFO-1233xf - HFO-1234yf - HFO-1234zeE | 0 to 40 | ~1.2 to ~11.3 |
| HF - HCFO-1233xf - HFO-1234yf - HFO-1234zeZ | 0 to 40 | ~1.0 to ~11.0 |
| HF - HCFO-1233xf - HCFO-1233zdE - HFO-1234zeE | 0 to 40 | ~1.0 to ~8.6 |
| HF - HCFO-1233xf - HCFO-1233zdE - HFO-1234zeZ | 0 to 40 | ~0.9 to ~4.8 |
| HF - HCFO-1233xf - HFO-1234zeE - HFO-1234zeZ | 0 to 40 | ~1.1 to ~8.6 |
| HF - HCFO-1233xf - HFO-1234zeE - HFO-1243zf | 0 to 40 | ~1.2 to ~10.1 |
| HF - HCFO-1233xf - HFO-1234zeZ - HFO-1243zf | 0 to 40 | ~1.1 to ~9.9 |
| HF - HFO-1234yf - HFO-1234zeE - HFO-1234zeZ | 0 to 40 | ~1.3 to ~11.3 |
| HF - HFO-1234yf - HFO-1234zeE - HCFO-1233zdE | 0 to 40 | ~1.1 to ~11.3 |
| HF - HFO-1234yf - HFO-1234zeE - HFO-1243zf | 0 to 40 | ~3.0 to ~11.6 |
| HF - HFO-1234yf - HFO-1234zeZ - HCFO-1233zdE | 0 to 40 | ~1.0 to ~11.0 |
| HF - HFO-1234yf - HFO-1234zeZ - HFO-1243zf | 0 to 40 | ~1.3 to ~11.3 |
| HF - HFC-245cb - HCFO-1233zdE - HFO-1234zeE | 0 to 40 | ~1.0 to ~8.9 |
| HF - HFC-245cb - HCFO-1233zdE - HFO-1234zeZ | 0 to 40 | ~1.0 to ~8.9 |
| HF - HFC-245cb - HFO-1234zeE - HFO-1234zeZ | 0 to 40 | ~1.2 to ~9.0 |
| HF - HFC-245cb - HFO-1234zeE - HFO-1243zf | 0 to 40 | ~2.5 to ~10.3 |
| HF - HFC-245cb - HFO-1234zeZ - HFO-1243zf | 0 to 40 | ~1.3 to ~10.1 |
| HF - HCFO-1233zdE - F 1234zeE - HFO-1234zeZ | 0 to 40 | ~1.0 to ~8.6 |
| HF - HCFO-1233zdE - F 1234zeE - HFO-1243zf | 0 to 40 | ~1.1 to ~10.1 |
| HF - HCFO-1233zdE - F 1234zeZ - HFO-1243zf | 0 to 40 | ~1.0 to ~9.9 |
| HF - HFO-1234zeE - HFO-1234zeZ - HFO-1243zf | 0 to 40 | ~1.3 to ~10.1 |
| HF - HFO-1234yf - HFO-1234zeE - Trifluoropropyne | 0 to 40 | ~5.9 to ~12.4 |
| HF - HFO-1234yf - HFO-1234zeE - HCFC-244bb | 0 to 40 | ~1.8 to ~7.7 |
| HF - HFO-1234yf - HFO-1234zeE - HFC-245fa | 0 to 40 | ~2.7 to ~7.7 |
| HF - HFO-1234yf - HFO-1234zeE - HFO-1225yeZ | 0 to 40 | ~5.2 to ~7.7 |
| HF - HFO-1234yf - HFO-1234zeE - HFO-1225zc | 0 to 40 | ~5.2 to ~7.7 |

Example 6: Decantation Range of Quaternary Mixtures

|  | Decantation ranges - Mass percentage of HF | | |
|---|---|---|---|
| Quaternary HF-Orga1 Orga2 Orga3 | Isotherm 0° C. | Isotherm 25° C. | Isotherm 40° C. |
| HF - HCFO-1233xf - HFC-245cb - HFO-1234zeE | 5-75 | 5-70 | 15-60 |
| HF - HCFO-1233xf - HFC-245cb - HFO-1234zeZ | 5-80 | 5-75 | 5-70 |
| HF - HFO-1234yf - HFC-245cb - HFO-1234zeE | 5-75 | 10-70 | * |
| HF - HFO-1234yf - HFC-245cb - HFO-1234zeZ | 5-75 | 10-75 | 20-70 |
| HF - HCFO-1233xf - HFO-1234yf - HFO-1234zeE | 5-70 | 10-60 | * |
| HF - HCFO-1233xf - HFO-1234yf - HFO-1234zeZ | 5-75 | 5-70 | 10-60 |
| HF - HCFO-1233xf - HCFO-1233zdE - HFO-1234zeE | 5-75 | 5-65 | 5-55 |
| HF - HCFO-1233xf - HCFO-1233zdE - HFO-1234zeZ | 5-80 | 5-75 | 5-65 |
| HF - HCFO-1233xf - HFO-1234zeE - HFO-1234zeZ | 5-75 | 5-65 | 10-55 |
| HF - HCFO-1233xf - HFO-1234zeE - HFO-1243zf | 5-70 | 10-60 | * |
| HF - HCFO-1233xf - HFO-1234zeZ - HFO-1243zf | 5-75 | 5-70 | 10-55 |
| HF - HFO-1234yf - HFO-1234zeE - HFO-1234zeZ | 5-70 | 10-60 | * |
| HF - HFO-1234yf - HFO-1234zeE - HCFO-1233zdE | 5-70 | 10-60 | * |
| HF - HFO-1234yf - HFO-1234zeE - HFO-1243zf | 5-65 | * | * |
| HF - HFO-1234yf - HFO-1234zeZ - HCFO-1233zdE | 5-75 | 5-70 | 10-60 |
| HF - HFO-1234yf - HFO-1234zeZ - HFO-1243zf | 5-75 | 10-65 | * |
| HF - HFC-245cb - HCFO-1233zdE - HFO-1234zeE | 5-75 | 5-70 | 10-65 |
| HF - HFC-245cb - HCFO-1233zdE - HFO-1234zeZ | 5-80 | 5-75 | 5-70 |
| HF - HFC-245cb - HFO-1234zeE - HFO-1234zeZ | 5-75 | 5-70 | 15-55 |
| HF - HFC-245cb - HFO-1234zeE - HFO-1243zf | 5-75 | 15-65 | * |
| HF - HFC-245cb - HFO-1234zeZ - HFO-1243zf | 5-75 | 10-70 | 20-60 |
| HF - HCFO-1233zdE - F 1234zeE - HFO-1234zeZ | 5-75 | 5-65 | 10-55 |
| HF - HCFO-1233zdE - F 1234zeE - HFO-1243zf | 5-70 | 10-60 | * |
| HF - HCFO-1233zdE - F 1234zeZ - HFO-1243zf | 5-75 | 5-70 | 10-55 |
| HF - HFO-1234zeE - HFO-1234zeZ - HFO-1243zf | 5-70 | 10-60 | * |
| HF - HFO-1234yf - HFO-1234zeE - Trifluoropropyne | 10-65 | * | * |
| HF - HFO-1234yf - HFO-1234zeE - HCFC-244bb | 5-80 | 5-75 | 10-65 |
| HF - HFO-1234yf - HFO-1234zeE - HFC-245fa | 5-70 | 10-65 | * |
| HF - HFO-1234yf - HFO-1234zeE - HFO-1225yeZ | 5-70 | 20-45 | * |
| HF - HFO-1234yf - HFO-1234zeE - HFO-1225zc | 5-65 | * | * |

Example 7: Penternary Mixtures, Isotherm at 25° C.

| HF - HCFO-1233xf - HFC-245cb - HCFO-1233zdE - HFO-1234zeE | | | | | | | | | |
|---|---|---|---|---|---|---|---|---|---|
| Organics 0.9 F1233xf + 0.033 F1233zdE + 0.033 F245cb + 0.034 F1234zeE | | Organics 0.033 F1233xf + 0.9 F1233zdE + 0.033 F245cb + 0.034 F1234zeE | | Organics 0.033 F1233xf + 0.033 F1233zdE + 0.9 245cb + 0.034 F1234zeE | | Organics 0.034 F1233xf + 0.033 F1233zdE + 0.033 F245cb + 0.9 F1234zeE | | Organics 0.25 F1233xf + 0.25 F1233zdE + 0.25 F245cb + 0.25 F1234zeE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 1.6 | 0 | 4.4 | 0 | 4.7 | 0 | 3.2 |
| 0.05 | 2.9 | 0.05 | 2.7 | 0.05 | 5.6 | 0.05 | 5.6 | 0.05 | 4.3 |
| 0.1 | 2.9 | 0.1 | 2.7 | 0.1 | 5.6 | 0.1 | 5.6 | 0.1 | 4.3 |
| 0.15 | 2.9 | 0.15 | 2.7 | 0.15 | 5.6 | 0.15 | 5.6 | 0.15 | 4.3 |
| 0.2 | 2.9 | 0.2 | 2.7 | 0.2 | 5.6 | 0.2 | 5.6 | 0.2 | 4.3 |
| 0.25 | 2.9 | 0.25 | 2.7 | 0.25 | 5.6 | 0.25 | 5.6 | 0.25 | 4.3 |
| 0.3 | 2.9 | 0.3 | 2.7 | 0.3 | 5.6 | 0.3 | 5.6 | 0.3 | 4.3 |
| 0.35 | 2.9 | 0.35 | 2.7 | 0.35 | 5.6 | 0.35 | 5.6 | 0.35 | 4.3 |
| 0.4 | 2.9 | 0.4 | 2.7 | 0.4 | 5.6 | 0.4 | 5.6 | 0.4 | 4.3 |
| 0.45 | 2.9 | 0.45 | 2.7 | 0.45 | 5.6 | 0.45 | 5.6 | 0.45 | 4.3 |
| 0.5 | 2.9 | 0.5 | 2.7 | 0.5 | 5.6 | 0.5 | 5.6 | 0.5 | 4.3 |
| 0.55 | 2.9 | 0.55 | 2.7 | 0.55 | 5.6 | 0.55 | 5.6 | 0.55 | 4.3 |
| 0.6 | 2.9 | 0.6 | 2.7 | 0.6 | 5.6 | 0.6 | 5.5 | 0.6 | 4.3 |
| 0.65 | 2.9 | 0.65 | 2.7 | 0.65 | 5.6 | 0.65 | 5.4 | 0.65 | 4.3 |
| 0.7 | 2.9 | 0.7 | 2.7 | 0.7 | 5.7 | 0.7 | 5.2 | 0.7 | 4.3 |
| 0.75 | 2.9 | 0.75 | 2.7 | 0.75 | 5.7 | 0.75 | 5.6 | 0.75 | 4.2 |
| 0.8 | 2.7 | 0.8 | 2.6 | 0.8 | 5.7 | 0.8 | 4.7 | 0.8 | 4.0 |
| 0.85 | 2.5 | 0.85 | 2.4 | 0.85 | 5.6 | 0.85 | 4.2 | 0.85 | 3.7 |
| 0.9 | 2.2 | 0.9 | 2.1 | 0.9 | 4.8 | 0.9 | 3.5 | 0.9 | 3.2 |
| 0.95 | 1.8 | 0.95 | 1.7 | 0.95 | 3.4 | 0.95 | 2.5 | 0.95 | 2.4 |
| 1 | 1.2 | 1 | 1.2 | 1 | 1.2 | 1 | 1.2 | 1 | 1.2 |

| HF - HCFO-1233xf - HFC-245cb - HCFO-1233zdE - HFO-1234zeZ ||||||||||
|---|---|---|---|---|---|---|---|---|---|
| Organics 0.9 F1233xf + 0.033 F1233zdE + 0.033 F245cb + 0.034 F1234zeZ || Organics 0.033 F1233xf + 0.9 F1233zdE + 0.033 F245cb + 0.034 F1234zeZ || Organics 0.033 F1233xf + 0.033 F1233zdE + 0.9 F245cb + 0.034 F1234zeZ || Organics 0.034 F1233xf + 0.033 F1233zdE + 0.033 F245cb + 0.9 F1234zeZ || Organics 0.25 F1233xf + 0.25 F1233zdE + 0.25 F245cb + 0.25 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 1.5 | 0 | 4.3 | 0 | 1.9 | 0 | 2.3 |
| 0.05 | 2.8 | 0.05 | 2.6 | 0.05 | 5.5 | 0.05 | 3.0 | 0.05 | 3.5 |
| 0.1 | 2.8 | 0.1 | 2.6 | 0.1 | 5.5 | 0.1 | 3.0 | 0.1 | 3.5 |
| 0.15 | 2.8 | 0.15 | 2.6 | 0.15 | 5.5 | 0.15 | 3.0 | 0.15 | 3.5 |
| 0.2 | 2.8 | 0.2 | 2.6 | 0.2 | 5.5 | 0.2 | 3.0 | 0.2 | 3.5 |
| 0.25 | 2.8 | 0.25 | 2.6 | 0.25 | 5.5 | 0.25 | 3.0 | 0.25 | 3.5 |
| 0.3 | 2.8 | 0.3 | 2.6 | 0.3 | 5.5 | 0.3 | 3.0 | 0.3 | 3.5 |
| 0.35 | 2.8 | 0.35 | 2.6 | 0.35 | 5.5 | 0.35 | 3.0 | 0.35 | 3.5 |
| 0.4 | 2.8 | 0.4 | 2.6 | 0.4 | 5.5 | 0.4 | 3.0 | 0.4 | 3.5 |
| 0.45 | 2.8 | 0.45 | 2.6 | 0.45 | 5.5 | 0.45 | 3.0 | 0.45 | 3.5 |
| 0.5 | 2.8 | 0.5 | 2.6 | 0.5 | 5.5 | 0.5 | 3.0 | 0.5 | 3.5 |
| 0.55 | 2.8 | 0.55 | 2.6 | 0.55 | 5.5 | 0.55 | 3.0 | 0.55 | 3.5 |
| 0.6 | 2.8 | 0.6 | 2.6 | 0.6 | 5.5 | 0.6 | 3.0 | 0.6 | 3.5 |
| 0.65 | 2.8 | 0.65 | 2.6 | 0.65 | 5.5 | 0.65 | 3.0 | 0.65 | 3.6 |
| 0.7 | 2.8 | 0.7 | 2.6 | 0.7 | 5.6 | 0.7 | 3.0 | 0.7 | 3.6 |
| 0.75 | 2.8 | 0.75 | 2.6 | 0.75 | 5.6 | 0.75 | 3.0 | 0.75 | 3.6 |
| 0.8 | 2.7 | 0.8 | 2.5 | 0.8 | 5.6 | 0.8 | 2.9 | 0.8 | 3.5 |
| 0.85 | 2.5 | 0.85 | 2.3 | 0.85 | 5.5 | 0.85 | 2.7 | 0.85 | 3.3 |
| 0.9 | 2.2 | 0.9 | 2.1 | 0.9 | 4.8 | 0.9 | 2.4 | 0.9 | 2.8 |
| 0.95 | 1.8 | 0.95 | 1.7 | 0.95 | 3.4 | 0.95 | 1.9 | 0.95 | 2.2 |
| 1 | 1.2 | 1 | 1.2 | 1 | 1.2 | 1 | 1.2 | 1 | 1.2 |

| HF - HCFO-1233xf - HFC-245cb - HFO-1234zeE - HFO-1234zeZ ||||||||||
|---|---|---|---|---|---|---|---|---|---|
| Organics 0.9 F1233xf + 0.033 F1234zeE + 0.033 F245cb + 0.034 F1234zeZ || Organics 0.033 F1233xf + 0.9 1234zeE + 0.033 F245cb + 0.034 F1234zeZ || Organics 0.033 F1233xf + 0.033 F1234zeE + 0.9 F245cb + 0.034 F1234zeZ || Organics 0.034 F1233xf + 0.033 F1234zeE + 0.033 F245cb + 0.9 F1234zeZ || Organics 0.25 F1233xf + 0.25 F1234zeE + 0.25 F245cb + 0.25 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 4.7 | 0 | 4.5 | 0 | 2.0 | 0 | 3.2 |
| 0.05 | 2.9 | 0.05 | 5.6 | 0.05 | 5.6 | 0.05 | 3.1 | 0.05 | 4.3 |
| 0.1 | 2.9 | 0.1 | 5.7 | 0.1 | 5.6 | 0.1 | 3.1 | 0.1 | 4.3 |
| 0.15 | 2.9 | 0.15 | 5.6 | 0.15 | 5.6 | 0.15 | 3.1 | 0.15 | 4.3 |
| 0.2 | 2.9 | 0.2 | 5.6 | 0.2 | 5.6 | 0.2 | 3.1 | 0.2 | 4.3 |
| 0.25 | 2.9 | 0.25 | 5.6 | 0.25 | 5.6 | 0.25 | 3.1 | 0.25 | 4.3 |
| 0.3 | 2.9 | 0.3 | 5.6 | 0.3 | 5.6 | 0.3 | 3.1 | 0.3 | 4.3 |
| 0.35 | 2.9 | 0.35 | 5.6 | 0.35 | 5.6 | 0.35 | 3.1 | 0.35 | 4.3 |
| 0.4 | 2.9 | 0.4 | 5.6 | 0.4 | 5.6 | 0.4 | 3.1 | 0.4 | 4.3 |
| 0.45 | 2.9 | 0.45 | 5.6 | 0.45 | 5.6 | 0.45 | 3.1 | 0.45 | 4.3 |
| 0.5 | 2.9 | 0.5 | 5.6 | 0.5 | 5.6 | 0.5 | 3.1 | 0.5 | 4.3 |
| 0.55 | 2.9 | 0.55 | 5.6 | 0.55 | 5.6 | 0.55 | 3.1 | 0.55 | 4.3 |
| 0.6 | 2.9 | 0.6 | 5.5 | 0.6 | 5.6 | 0.6 | 3.1 | 0.6 | 4.3 |
| 0.65 | 2.9 | 0.65 | 5.4 | 0.65 | 5.7 | 0.65 | 3.1 | 0.65 | 4.4 |
| 0.7 | 2.9 | 0.7 | 5.2 | 0.7 | 5.7 | 0.7 | 3.1 | 0.7 | 4.4 |
| 0.75 | 2.9 | 0.75 | 5.0 | 0.75 | 5.7 | 0.75 | 3.1 | 0.75 | 4.3 |
| 0.8 | 2.7 | 0.8 | 4.7 | 0.8 | 5.7 | 0.8 | 3.0 | 0.8 | 4.1 |
| 0.85 | 2.5 | 0.85 | 4.2 | 0.85 | 5.6 | 0.85 | 2.7 | 0.85 | 3.8 |
| 0.9 | 2.2 | 0.9 | 3.5 | 0.9 | 4.8 | 0.9 | 2.4 | 0.9 | 3.3 |
| 0.95 | 1.8 | 0.95 | 2.6 | 0.95 | 3.4 | 0.95 | 1.9 | 0.95 | 2.4 |
| 1 | 1.2 | 1 | 1.2 | 1 | 1.2 | 1 | 1.2 | 1 | 1.2 |

| HF - HCFO-1233xf - HFC-245cb - HFO-1234zeE - HFO-1243zf |||||||||
| --- | --- | --- | --- | --- | --- | --- | --- | --- | --- |
| Organics 0.9 F1233xf + 0.033 F1234zeE + 0.033 F245cb + 0.034 F1243zf || Organics 0.033 F1233xf + 0.9 F1234zeE + 0.033 F245cb + 0.034 F1243zf || Organics 0.033 F1233xf + 0.033 F1234zeE + 0.9 F245cb + 0.034 F1243zf || Organics 0.034 F1233xf + 0.033 F1234zeE + 0.033 F245cb + 0.9 F1243zf || Organics 0.25 F1233xf + 0.25 F1234zeE + 0.25 F245cb + 0.25 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.8 | 0 | 4.6 | 0 | 5.7 | 0 | 4.4 |
| 0.05 | 3.1 | 0.05 | 5.8 | 0.05 | 5.8 | 0.05 | 6.6 | 0.05 | 5.4 |
| 0.1 | 3.1 | 0.1 | 5.8 | 0.1 | 5.8 | 0.1 | 6.7 | 0.1 | 5.4 |
| 0.15 | 3.1 | 0.15 | 5.8 | 0.15 | 5.8 | 0.15 | 6.6 | 0.15 | 5.4 |
| 0.2 | 3.1 | 0.2 | 5.8 | 0.2 | 5.8 | 0.2 | 6.6 | 0.2 | 5.4 |
| 0.25 | 3.1 | 0.25 | 5.8 | 0.25 | 5.8 | 0.25 | 6.6 | 0.25 | 5.4 |
| 0.3 | 3.1 | 0.3 | 5.8 | 0.3 | 5.8 | 0.3 | 6.6 | 0.3 | 5.4 |
| 0.35 | 3.1 | 0.35 | 5.8 | 0.35 | 5.8 | 0.35 | 6.6 | 0.35 | 5.4 |
| 0.4 | 3.1 | 0.4 | 5.8 | 0.4 | 5.8 | 0.4 | 6.6 | 0.4 | 5.4 |
| 0.45 | 3.1 | 0.45 | 5.8 | 0.45 | 5.8 | 0.45 | 6.6 | 0.45 | 5.4 |
| 0.5 | 3.1 | 0.5 | 5.7 | 0.5 | 5.8 | 0.5 | 6.6 | 0.5 | 5.4 |
| 0.55 | 3.1 | 0.55 | 5.7 | 0.55 | 5.8 | 0.55 | 6.6 | 0.55 | 5.4 |
| 0.6 | 3.1 | 0.6 | 5.6 | 0.6 | 5.8 | 0.6 | 6.6 | 0.6 | 5.4 |
| 0.65 | 3.1 | 0.65 | 5.5 | 0.65 | 5.8 | 0.65 | 6.5 | 0.65 | 5.4 |
| 0.7 | 3.1 | 0.7 | 5.4 | 0.7 | 5.8 | 0.7 | 6.4 | 0.7 | 5.4 |
| 0.75 | 3.0 | 0.75 | 5.2 | 0.75 | 5.8 | 0.75 | 6.3 | 0.75 | 5.3 |
| 0.8 | 2.9 | 0.8 | 4.8 | 0.8 | 5.8 | 0.8 | 6.0 | 0.8 | 5.0 |
| 0.85 | 2.7 | 0.85 | 4.3 | 0.85 | 5.7 | 0.85 | 5.5 | 0.85 | 4.6 |
| 0.9 | 2.3 | 0.9 | 3.6 | 0.9 | 4.9 | 0.9 | 4.7 | 0.9 | 3.9 |
| 0.95 | 1.9 | 0.95 | 2.6 | 0.95 | 3.5 | 0.95 | 3.3 | 0.95 | 2.8 |
| 1 | 1.2 | 1 | 1.2 | 1 | 1.2 | 1 | 1.2 | 1 | 1.2 |

| HF - HCFO-1233xf - HFC-245cb - HFO-1234zeE - HFO-1234yf |||||||||
| --- | --- | --- | --- | --- | --- | --- | --- | --- | --- |
| Organics 0.9 F1233xf + 0.033 F1234zeE + 0.033 F245cb + 0.034 F1234yf || Organics 0.033 F1233xf + 0.9 F1234zeE + 0.033 F245cb + 0.034 F1234yf || Organics 0.033 F1233xf + 0.033 F1234zeE + 0.9 F245cb + 0.034 F1234yf || Organics 0.034 F1233xf + 0.033 F1234zeE + 0.033 F245cb + 0.9 F1234yf || Organics 0.25 F1233xf + 0.25 F1234zeE + 0.25 F245cb + 0.25 F1234yf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.8 | 0 | 4.6 | 0 | 6.5 | 0 | 4.6 |
| 0.05 | 3.1 | 0.05 | 5.8 | 0.05 | 5.8 | 0.05 | 7.5 | 0.05 | 5.6 |
| 0.1 | 3.1 | 0.1 | 5.8 | 0.1 | 5.8 | 0.1 | 7.5 | 0.1 | 5.6 |
| 0.15 | 3.1 | 0.15 | 5.8 | 0.15 | 5.8 | 0.15 | 7.5 | 0.15 | 5.6 |
| 0.2 | 3.1 | 0.2 | 5.8 | 0.2 | 5.8 | 0.2 | 7.5 | 0.2 | 5.6 |
| 0.25 | 3.1 | 0.25 | 5.8 | 0.25 | 5.8 | 0.25 | 7.5 | 0.25 | 5.6 |
| 0.3 | 3.1 | 0.3 | 5.8 | 0.3 | 5.8 | 0.3 | 7.5 | 0.3 | 5.6 |
| 0.35 | 3.1 | 0.35 | 5.8 | 0.35 | 5.8 | 0.35 | 7.5 | 0.35 | 5.6 |
| 0.4 | 3.1 | 0.4 | 5.8 | 0.4 | 5.8 | 0.4 | 7.5 | 0.4 | 5.6 |
| 0.45 | 3.1 | 0.45 | 5.8 | 0.45 | 5.8 | 0.45 | 7.5 | 0.45 | 5.6 |
| 0.5 | 3.1 | 0.5 | 5.8 | 0.5 | 5.8 | 0.5 | 7.5 | 0.5 | 5.6 |
| 0.55 | 3.1 | 0.55 | 5.7 | 0.55 | 5.8 | 0.55 | 7.5 | 0.55 | 5.6 |
| 0.6 | 3.1 | 0.6 | 5.7 | 0.6 | 5.8 | 0.6 | 7.5 | 0.6 | 5.6 |
| 0.65 | 3.1 | 0.65 | 5.6 | 0.65 | 5.8 | 0.65 | 7.5 | 0.65 | 5.7 |
| 0.7 | 3.1 | 0.7 | 5.4 | 0.7 | 5.8 | 0.7 | 7.5 | 0.7 | 5.7 |
| 0.75 | 3.1 | 0.75 | 5.2 | 0.75 | 5.8 | 0.75 | 7.3 | 0.75 | 5.5 |
| 0.8 | 2.9 | 0.8 | 4.9 | 0.8 | 5.8 | 0.8 | 7.0 | 0.8 | 5.3 |
| 0.85 | 2.7 | 0.85 | 4.4 | 0.85 | 5.7 | 0.85 | 6.4 | 0.85 | 4.8 |
| 0.9 | 2.4 | 0.9 | 3.7 | 0.9 | 4.9 | 0.9 | 5.4 | 0.9 | 4.1 |
| 0.95 | 1.9 | 0.95 | 2.6 | 0.95 | 3.5 | 0.95 | 3.7 | 0.95 | 2.9 |
| 1 | 1.2 | 1 | 1.2 | 1 | 1.2 | 1 | 1.2 | 1 | 1.2 |

| HF - HCFO-1233xf - HFC-245cb - HFO-1234zeZ - HFO-1243zf ||||||||||
|---|---|---|---|---|---|---|---|---|---|
| Organics 0.9 F1233xf + 0.033 F1234zeZ + 0.033 F245cb + 0.034 F1243zf || Organics 0.033 F1233xf + 0.9 F1234zeZ + 0.033 F245cb + 0.034 F1243zf || Organics 0.033 F1233xf + 0.033 F1234zeZ + 0.9 F245cb + 0.034 F1243zf || Organics 0.034 F1233xf + 0.033 F1234zeZ + 0.033 F245cb + 0.9 F1243zf || Organics 0.25 F1233xf + 0.25 F1234zeZ + 0.25 F245cb + 0.25 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 2.1 | 0 | 4.5 | 0 | 5.6 | 0 | 3.6 |
| 0.05 | 3.0 | 0.05 | 3.2 | 0.05 | 5.7 | 0.05 | 6.5 | 0.05 | 4.7 |
| 0.1 | 3.0 | 0.1 | 3.2 | 0.1 | 5.7 | 0.1 | 6.6 | 0.1 | 4.7 |
| 0.15 | 3.0 | 0.15 | 3.2 | 0.15 | 5.7 | 0.15 | 6.6 | 0.15 | 4.7 |
| 0.2 | 3.0 | 0.2 | 3.2 | 0.2 | 5.7 | 0.2 | 6.6 | 0.2 | 4.7 |
| 0.25 | 3.0 | 0.25 | 3.2 | 0.25 | 5.7 | 0.25 | 6.5 | 0.25 | 4.7 |
| 0.3 | 3.0 | 0.3 | 3.2 | 0.3 | 5.7 | 0.3 | 6.5 | 0.3 | 4.7 |
| 0.35 | 3.0 | 0.35 | 3.2 | 0.35 | 5.7 | 0.35 | 6.5 | 0.35 | 4.7 |
| 0.4 | 3.0 | 0.4 | 3.2 | 0.4 | 5.7 | 0.4 | 6.5 | 0.4 | 4.7 |
| 0.45 | 3.0 | 0.45 | 3.2 | 0.45 | 5.7 | 0.45 | 6.5 | 0.45 | 4.7 |
| 0.5 | 3.0 | 0.5 | 3.2 | 0.5 | 5.7 | 0.5 | 6.5 | 0.5 | 4.7 |
| 0.55 | 3.0 | 0.55 | 3.2 | 0.55 | 5.7 | 0.55 | 6.5 | 0.55 | 4.7 |
| 0.6 | 3.0 | 0.6 | 3.2 | 0.6 | 5.7 | 0.6 | 6.5 | 0.6 | 4.7 |
| 0.65 | 3.0 | 0.65 | 3.2 | 0.65 | 5.7 | 0.65 | 6.5 | 0.65 | 4.7 |
| 0.7 | 3.0 | 0.7 | 3.2 | 0.7 | 5.7 | 0.7 | 6.4 | 0.7 | 4.7 |
| 0.75 | 3.0 | 0.75 | 3.2 | 0.75 | 5.7 | 0.75 | 6.2 | 0.75 | 4.7 |
| 0.8 | 2.8 | 0.8 | 3.0 | 0.8 | 5.7 | 0.8 | 5.9 | 0.8 | 4.5 |
| 0.85 | 2.6 | 0.85 | 2.8 | 0.85 | 5.6 | 0.85 | 5.4 | 0.85 | 4.2 |
| 0.9 | 2.3 | 0.9 | 2.5 | 0.9 | 4.8 | 0.9 | 4.6 | 0.9 | 3.6 |
| 0.95 | 1.8 | 0.95 | 1.9 | 0.95 | 3.4 | 0.95 | 3.3 | 0.95 | 2.6 |
| 1 | 1.2 | 1 | 1.2 | 1 | 1.2 | 1 | 1.2 | 1 | 1.2 |

| HF - HCFO-1233xf - HFC-245cb - HFO-1234zeZ - HFO-1234yf ||||||||||
|---|---|---|---|---|---|---|---|---|---|
| Organics 0.9 F1233xf + 0.033 F1234zeZ + 0.033 F245cb + 0.034 F1234yf || Organics 0.033 F1233xf + 0.9 F1234zeZ + 0.033 F245cb + 0.034 F1234yf || Organics 0.033 F1233xf + 0.033 F1234zeZ + 0.9 F245cb + 0.034 F1234yf || Organics 0.034 F1233xf + 0.033 F1234zeZ + 0.033 F245cb + 0.9 F1234yf || Organics 0.25 F1233xf + 0.25 F1234zeZ + 0.25 F245cb + 0.25 F1234yf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 2.1 | 0 | 4.5 | 0 | 6.4 | 0 | 3.7 |
| 0.05 | 3.0 | 0.05 | 3.2 | 0.05 | 5.7 | 0.05 | 7.4 | 0.05 | 4.9 |
| 0.1 | 3.0 | 0.1 | 3.2 | 0.1 | 5.7 | 0.1 | 7.4 | 0.1 | 4.9 |
| 0.15 | 3.0 | 0.15 | 3.2 | 0.15 | 5.7 | 0.15 | 7.4 | 0.15 | 4.9 |
| 0.2 | 3.0 | 0.2 | 3.2 | 0.2 | 5.7 | 0.2 | 7.4 | 0.2 | 4.9 |
| 0.25 | 3.0 | 0.25 | 3.2 | 0.25 | 5.7 | 0.25 | 7.4 | 0.25 | 4.9 |
| 0.3 | 3.0 | 0.3 | 3.2 | 0.3 | 5.7 | 0.3 | 7.4 | 0.3 | 4.3 |
| 0.35 | 3.0 | 0.35 | 3.2 | 0.35 | 5.7 | 0.35 | 7.4 | 0.35 | 4.9 |
| 0.4 | 3.0 | 0.4 | 3.2 | 0.4 | 5.7 | 0.4 | 7.4 | 0.4 | 4.3 |
| 0.45 | 3.0 | 0.45 | 3.2 | 0.45 | 5.7 | 0.45 | 7.4 | 0.45 | 4.9 |
| 0.5 | 3.0 | 0.5 | 3.2 | 0.5 | 5.7 | 0.5 | 7.4 | 0.5 | 4.3 |
| 0.55 | 3.0 | 0.55 | 3.2 | 0.55 | 5.7 | 0.55 | 7.4 | 0.55 | 4.9 |
| 0.6 | 3.0 | 0.6 | 3.2 | 0.6 | 5.7 | 0.6 | 7.4 | 0.6 | 4.9 |
| 0.65 | 3.0 | 0.65 | 3.2 | 0.65 | 5.7 | 0.65 | 7.4 | 0.65 | 4.9 |
| 0.7 | 3.0 | 0.7 | 3.2 | 0.7 | 5.7 | 0.7 | 7.4 | 0.7 | 4.9 |
| 0.75 | 3.0 | 0.75 | 3.2 | 0.75 | 5.7 | 0.75 | 7.2 | 0.75 | 5.0 |
| 0.8 | 2.8 | 0.8 | 3.0 | 0.8 | 5.7 | 0.8 | 6.9 | 0.8 | 4.8 |
| 0.85 | 2.6 | 0.85 | 2.8 | 0.85 | 5.7 | 0.85 | 6.4 | 0.85 | 4.4 |
| 0.9 | 2.3 | 0.9 | 2.5 | 0.9 | 4.9 | 0.9 | 5.4 | 0.9 | 3.8 |
| 0.95 | 1.8 | 0.95 | 2.0 | 0.95 | 3.5 | 0.95 | 3.7 | 0.95 | 2.7 |
| 1 | 1.2 | 1 | 1.2 | 1 | 1.2 | 1 | 1.2 | 1 | 1.2 |

| HF - HCFO-1233xf - HCFO-1233zdE - HFO-1234zeE - HFO-1234zeZ ||||||||||
|---|---|---|---|---|---|---|---|---|---|
| Organics<br>0.9 F1233xf +<br>0.033 F1234zeE +<br>0.033 F1233zdE +<br>0.034 F1234zeZ || Organics<br>0.033 F1233xf +<br>0.9 F1234zeE +<br>0.033 F1233zdE +<br>0.034 F1234zeZ || Organics<br>0.033 F1233xf +<br>0.033 F1234zeE +<br>0.9 F1233zdE +<br>0.034 F1234zeZ || Organics<br>0.034 F1233xf +<br>0.033 F1234zeE +<br>0.033 F1233zdE +<br>0.9 F1234zeZ || Organics<br>0.25 F1233xf +<br>0.25 F1234zeE +<br>0.25 F1233zdE +<br>0.25 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.7 | 0 | 4.6 | 0 | 1.5 | 0 | 1.9 | 0 | 2.4 |
| 0.05 | 2.8 | 0.05 | 5.5 | 0.05 | 2.6 | 0.05 | 3.0 | 0.05 | 3.5 |
| 0.1 | 2.8 | 0.1 | 5.5 | 0.1 | 2.6 | 0.1 | 3.0 | 0.1 | 3.5 |
| 0.15 | 2.8 | 0.15 | 5.5 | 0.15 | 2.6 | 0.15 | 3.0 | 0.15 | 3.5 |
| 0.2 | 2.8 | 0.2 | 5.5 | 0.2 | 2.6 | 0.2 | 3.0 | 0.2 | 3.5 |
| 0.25 | 2.8 | 0.25 | 5.5 | 0.25 | 2.6 | 0.25 | 3.0 | 0.25 | 3.5 |
| 0.3 | 2.8 | 0.3 | 5.5 | 0.3 | 2.6 | 0.3 | 3.0 | 0.3 | 3.5 |
| 0.35 | 2.8 | 0.35 | 5.5 | 0.35 | 2.6 | 0.35 | 3.0 | 0.35 | 3.5 |
| 0.4 | 2.8 | 0.4 | 5.5 | 0.4 | 2.6 | 0.4 | 3.0 | 0.4 | 3.5 |
| 0.45 | 2.8 | 0.45 | 5.5 | 0.45 | 2.6 | 0.45 | 3.0 | 0.45 | 3.5 |
| 0.5 | 2.8 | 0.5 | 5.5 | 0.5 | 2.6 | 0.5 | 3.0 | 0.5 | 3.5 |
| 0.55 | 2.8 | 0.55 | 5.4 | 0.55 | 2.6 | 0.55 | 3.0 | 0.55 | 3.4 |
| 0.6 | 2.8 | 0.6 | 5.4 | 0.6 | 2.6 | 0.6 | 3.0 | 0.6 | 3.4 |
| 0.65 | 2.8 | 0.65 | 5.3 | 0.65 | 2.6 | 0.65 | 3.0 | 0.65 | 3.4 |
| 0.7 | 2.8 | 0.7 | 5.1 | 0.7 | 2.5 | 0.7 | 3.0 | 0.7 | 3.4 |
| 0.75 | 2.7 | 0.75 | 4.9 | 0.75 | 2.5 | 0.75 | 3.0 | 0.75 | 3.3 |
| 0.8 | 2.6 | 0.8 | 4.6 | 0.8 | 2.4 | 0.8 | 2.8 | 0.8 | 3.1 |
| 0.85 | 2.4 | 0.85 | 4.1 | 0.85 | 2.3 | 0.85 | 2.6 | 0.85 | 2.9 |
| 0.9 | 2.1 | 0.9 | 3.4 | 0.9 | 2.0 | 0.9 | 2.3 | 0.9 | 2.5 |
| 0.95 | 1.7 | 0.95 | 2.5 | 0.95 | 1.7 | 0.95 | 1.9 | 0.95 | 1.9 |
| 1 | 1.2 | 1 | 1.2 | 1 | 1.2 | 1 | 1.2 | 1 | 1.2 |

| HF-HCFO-1233xf - HCFO-1233zdE - HFO-1234zeE - HFO-1243zf ||||||||||
|---|---|---|---|---|---|---|---|---|---|
| Organics<br>0.9 F1233xf +<br>0.033 F1234zeE +<br>0.033 F1233zdE +<br>0.034 F1243zf || Organics<br>0.033 F1233xf +<br>0.9 F1234zeE +<br>0.033 F1233zdE +<br>0.034 F1243zf || Organics<br>0.033 F1233xf +<br>0.033 F1234zeE +<br>0.9 F1233zdE +<br>0.034 F1243zf || Organics<br>0.034 F1233xf +<br>0.033 F1234zeE +<br>0.033 F1233zdE +<br>0.9 F1243zf || Organics<br>0.25 F1233xf +<br>0.25 1234zeE +<br>0.25 F1233zdE +<br>0.25 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 1.7 | 0 | 5.6 | 0 | 3.6 |
| 0.05 | 3.0 | 0.05 | 5.7 | 0.05 | 2.8 | 0.05 | 6.5 | 0.05 | 4.7 |
| 0.1 | 3.0 | 0.1 | 5.7 | 0.1 | 2.8 | 0.1 | 6.6 | 0.1 | 4.7 |
| 0.15 | 3.0 | 0.15 | 5.7 | 0.15 | 2.8 | 0.15 | 6.6 | 0.15 | 4.7 |
| 0.2 | 3.0 | 0.2 | 5.7 | 0.2 | 2.8 | 0.2 | 6.5 | 0.2 | 4.7 |
| 0.25 | 3.0 | 0.25 | 5.7 | 0.25 | 2.8 | 0.25 | 6.5 | 0.25 | 4.6 |
| 0.3 | 2.9 | 0.3 | 5.7 | 0.3 | 2.7 | 0.3 | 6.5 | 0.3 | 4.6 |
| 0.35 | 2.9 | 0.35 | 5.7 | 0.35 | 2.7 | 0.35 | 6.5 | 0.35 | 4.6 |
| 0.4 | 2.9 | 0.4 | 5.7 | 0.4 | 2.7 | 0.4 | 6.5 | 0.4 | 4.6 |
| 0.45 | 2.9 | 0.45 | 5.7 | 0.45 | 2.7 | 0.45 | 6.5 | 0.45 | 4.6 |
| 0.5 | 2.9 | 0.5 | 5.6 | 0.5 | 2.7 | 0.5 | 6.5 | 0.5 | 4.6 |
| 0.55 | 2.9 | 0.55 | 5.6 | 0.55 | 2.7 | 0.55 | 6.5 | 0.55 | 4.6 |
| 0.6 | 2.9 | 0.6 | 5.5 | 0.6 | 2.7 | 0.6 | 6.5 | 0.6 | 4.6 |
| 0.65 | 2.9 | 0.65 | 5.4 | 0.65 | 2.7 | 0.65 | 6.4 | 0.65 | 4.5 |
| 0.7 | 2.9 | 0.7 | 5.3 | 0.7 | 2.7 | 0.7 | 6.3 | 0.7 | 4.5 |
| 0.75 | 2.9 | 0.75 | 5.0 | 0.75 | 2.7 | 0.75 | 6.2 | 0.75 | 4.3 |
| 0.8 | 2.7 | 0.8 | 4.7 | 0.8 | 2.6 | 0.8 | 5.9 | 0.8 | 4.1 |
| 0.85 | 2.5 | 0.85 | 4.2 | 0.85 | 2.4 | 0.85 | 5.4 | 0.85 | 3.7 |
| 0.9 | 2.2 | 0.9 | 3.5 | 0.9 | 2.1 | 0.9 | 4.6 | 0.9 | 3.1 |
| 0.95 | 1.8 | 0.95 | 2.5 | 0.95 | 1.7 | 0.95 | 3.3 | 0.95 | 2.3 |
| 1 | 1.2 | 1 | 1.2 | 1 | 1.2 | 1 | 1.2 | 1 | 1.2 |

| HF - HCFO-1233xf - HCFO-1233zdE - HFO-1234zeZ - HFO-1243zf ||||||||||
| Organics 0.9 F1233xf + 0.033 F1234zeZ + 0.033 F1233zdE + 0.034 F1243zf || Organics 0.033 F1233xf + 0.9 F1234zeZ + 0.033 F1233zdE + 0.034 F1243zf || Organics 0.033 F1233xf + 0.033 F1234zeZ + 0.9 F1233zdE + 0.034 F1243zf || Organics 0.034 F1233xf + 0.033 F1234zeZ + 0.033 F1233zdE + 0.9 F1243zf || Organics 0.25 F1233xf + 0.25 F1234zeZ + 0.25 F1233zdE + 0.25 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- | --- | --- | --- | --- |
| 0 | 1.7 | 0 | 1.9 | 0 | 1.5 | 0 | 5.5 | 0 | 2.8 |
| 0.05 | 2.8 | 0.05 | 3.0 | 0.05 | 2.6 | 0.05 | 6.4 | 0.05 | 3.9 |
| 0.1 | 2.8 | 0.1 | 3.0 | 0.1 | 2.6 | 0.1 | 6.5 | 0.1 | 3.9 |
| 0.15 | 2.8 | 0.15 | 3.0 | 0.15 | 2.6 | 0.15 | 6.5 | 0.15 | 3.9 |
| 0.2 | 2.8 | 0.2 | 3.0 | 0.2 | 2.6 | 0.2 | 6.5 | 0.2 | 3.9 |
| 0.25 | 2.8 | 0.25 | 3.0 | 0.25 | 2.6 | 0.25 | 6.5 | 0.25 | 3.9 |
| 0.3 | 2.8 | 0.3 | 3.0 | 0.3 | 2.6 | 0.3 | 6.5 | 0.3 | 3.9 |
| 0.35 | 2.8 | 0.35 | 3.0 | 0.35 | 2.6 | 0.35 | 6.5 | 0.35 | 3.9 |
| 0.4 | 2.8 | 0.4 | 3.0 | 0.4 | 2.6 | 0.4 | 6.5 | 0.4 | 3.9 |
| 0.45 | 2.8 | 0.45 | 3.0 | 0.45 | 2.6 | 0.45 | 6.4 | 0.45 | 3.9 |
| 0.5 | 2.8 | 0.5 | 3.0 | 0.5 | 2.6 | 0.5 | 6.4 | 0.5 | 3.9 |
| 0.55 | 2.8 | 0.55 | 3.0 | 0.55 | 2.6 | 0.55 | 6.4 | 0.55 | 3.9 |
| 0.6 | 2.8 | 0.6 | 3.0 | 0.6 | 2.6 | 0.6 | 6.4 | 0.6 | 3.9 |
| 0.65 | 2.8 | 0.65 | 3.0 | 0.65 | 2.6 | 0.65 | 6.4 | 0.65 | 3.8 |
| 0.7 | 2.8 | 0.7 | 3.0 | 0.7 | 2.6 | 0.7 | 6.3 | 0.7 | 3.8 |
| 0.75 | 2.8 | 0.75 | 3.0 | 0.75 | 2.6 | 0.75 | 6.1 | 0.75 | 3.7 |
| 0.8 | 2.7 | 0.8 | 2.9 | 0.8 | 2.5 | 0.8 | 5.8 | 0.8 | 3.6 |
| 0.85 | 2.5 | 0.85 | 2.7 | 0.85 | 2.3 | 0.85 | 5.3 | 0.85 | 3.3 |
| 0.9 | 2.2 | 0.9 | 2.4 | 0.9 | 2.1 | 0.9 | 4.5 | 0.9 | 2.8 |
| 0.95 | 1.8 | 0.95 | 1.9 | 0.95 | 1.7 | 0.95 | 3.2 | 0.95 | 2.2 |
| 1 | 1.2 | 1 | 1.2 | 1 | 1.2 | 1 | 1.2 | 1 | 1.2 |

| HF - HCFO-1233xf - HFO-1234zeE - HFO-1234zeZ - HFO-1243zf ||||||||||
| Organics 0.9 F1233xf + 0.033 F1234zeE + 0.033 F1234zeZ + 0.034 F1243zf || Organics 0.033 F1233xf + 0.9 F1234zeE + 0.033 F1234zeZ + 0.034 F1243zf || Organics 0.033 F1233xf + 0.033 F1234zeE + 0.9 F1234zeZ + 0.034 F1243zf || Organics 0.034 F1233xf + 0.033 F1234zeE + 0.033 F1234zeZ + 0.9 F1243zf || Organics 0.25 F1233xf + 0.25 F1234zeE + 0.25 F1234zeZ + 0.25 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- | --- | --- | --- | --- |
| 0 | 1.9 | 0 | 4.7 | 0 | 2.1 | 0 | 5.6 | 0 | 3.7 |
| 0.05 | 3.0 | 0.05 | 5.7 | 0.05 | 3.2 | 0.05 | 6.5 | 0.05 | 4.7 |
| 0.1 | 3.0 | 0.1 | 5.7 | 0.1 | 3.2 | 0.1 | 6.6 | 0.1 | 4.7 |
| 0.15 | 3.0 | 0.15 | 5.7 | 0.15 | 3.2 | 0.15 | 6.6 | 0.15 | 4.7 |
| 0.2 | 3.0 | 0.2 | 5.7 | 0.2 | 3.2 | 0.2 | 6.5 | 0.2 | 4.7 |
| 0.25 | 3.0 | 0.25 | 5.7 | 0.25 | 3.2 | 0.25 | 6.5 | 0.25 | 4.7 |
| 0.3 | 3.0 | 0.3 | 5.7 | 0.3 | 3.2 | 0.3 | 6.5 | 0.3 | 4.7 |
| 0.35 | 3.0 | 0.35 | 5.7 | 0.35 | 3.2 | 0.35 | 6.5 | 0.35 | 4.7 |
| 0.4 | 3.0 | 0.4 | 5.7 | 0.4 | 3.2 | 0.4 | 6.5 | 0.4 | 4.7 |
| 0.45 | 3.0 | 0.45 | 5.7 | 0.45 | 3.2 | 0.45 | 6.5 | 0.45 | 4.7 |
| 0.5 | 3.0 | 0.5 | 5.6 | 0.5 | 3.2 | 0.5 | 6.5 | 0.5 | 4.7 |
| 0.55 | 2.9 | 0.55 | 5.6 | 0.55 | 3.1 | 0.55 | 6.5 | 0.55 | 4.6 |
| 0.6 | 2.9 | 0.6 | 5.5 | 0.6 | 3.1 | 0.6 | 6.5 | 0.6 | 4.6 |
| 0.65 | 2.9 | 0.65 | 5.4 | 0.65 | 3.1 | 0.65 | 6.4 | 0.65 | 4.6 |
| 0.7 | 2.9 | 0.7 | 5.3 | 0.7 | 3.1 | 0.7 | 6.3 | 0.7 | 4.5 |
| 0.75 | 2.9 | 0.75 | 5.0 | 0.75 | 3.1 | 0.75 | 6.2 | 0.75 | 4.4 |
| 0.8 | 2.8 | 0.8 | 4.7 | 0.8 | 3.0 | 0.8 | 5.9 | 0.8 | 4.1 |
| 0.85 | 2.6 | 0.85 | 4.2 | 0.85 | 2.7 | 0.85 | 5.4 | 0.85 | 3.8 |
| 0.9 | 2.2 | 0.9 | 3.5 | 0.9 | 2.4 | 0.9 | 4.6 | 0.9 | 3.2 |
| 0.95 | 1.8 | 0.95 | 2.5 | 0.95 | 1.9 | 0.95 | 3.3 | 0.95 | 2.4 |
| 1 | 1.2 | 1 | 1.2 | 1 | 1.2 | 1 | 1.2 | 1 | 1.2 |

HF - HCFO-1233xf - HFO-1234yf - HFO-1234zeE - HFO-1234zeZ

| Organics 0.9 F1233xf + 0.033 F1234zeE + 0.033 F1234zeZ + 0.034 F1234yf | | Organics 0.033 F1233xf + 0.9 F1234zeE + 0.033 F1234zeZ + 0.034 F1234yf | | Organics 0.033 F1233xf + 0.033 F1234zeE + 0.9 F1234zeZ + 0.034 F1234yf | | Organics 0.034 F1233xf + 0.033 F1234zeE + 0.033 F1234zeZ + 0.9 F1234yf | | Organics 0.25 F1233xf + 0.25 F1234zeE + 0.25 F1234zeZ + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 2.1 | 0 | 6.4 | 0 | 3.8 |
| 0.05 | 3.0 | 0.05 | 5.7 | 0.05 | 3.2 | 0.05 | 7.4 | 0.05 | 4.9 |
| 0.1 | 3.0 | 0.1 | 5.7 | 0.1 | 3.2 | 0.1 | 7.4 | 0.1 | 4.9 |
| 0.15 | 3.0 | 0.15 | 5.7 | 0.15 | 3.2 | 0.15 | 7.4 | 0.15 | 4.9 |
| 0.2 | 3.0 | 0.2 | 5.7 | 0.2 | 3.2 | 0.2 | 7.4 | 0.2 | 4.9 |
| 0.25 | 3.0 | 0.25 | 5.7 | 0.25 | 3.2 | 0.25 | 7.4 | 0.25 | 4.9 |
| 0.3 | 3.0 | 0.3 | 5.7 | 0.3 | 3.2 | 0.3 | 7.4 | 0.3 | 4.9 |
| 0.35 | 3.0 | 0.35 | 5.7 | 0.35 | 3.2 | 0.35 | 7.4 | 0.35 | 4.9 |
| 0.4 | 3.0 | 0.4 | 5.7 | 0.4 | 3.2 | 0.4 | 7.4 | 0.4 | 4.9 |
| 0.45 | 3.0 | 0.45 | 5.7 | 0.45 | 3.2 | 0.45 | 7.4 | 0.45 | 4.9 |
| 0.5 | 3.0 | 0.5 | 5.7 | 0.5 | 3.2 | 0.5 | 7.4 | 0.5 | 4.9 |
| 0.55 | 3.0 | 0.55 | 5.6 | 0.55 | 3.2 | 0.55 | 7.4 | 0.55 | 4.9 |
| 0.6 | 3.0 | 0.6 | 5.6 | 0.6 | 3.2 | 0.6 | 7.4 | 0.6 | 4.8 |
| 0.65 | 3.0 | 0.65 | 5.5 | 0.65 | 3.2 | 0.65 | 7.4 | 0.65 | 4.8 |
| 0.7 | 3.0 | 0.7 | 5.3 | 0.7 | 3.2 | 0.7 | 7.4 | 0.7 | 4.8 |
| 0.75 | 2.9 | 0.75 | 5.1 | 0.75 | 3.1 | 0.75 | 7.2 | 0.75 | 4.6 |
| 0.8 | 2.8 | 0.8 | 4.7 | 0.8 | 3.0 | 0.8 | 6.9 | 0.8 | 4.4 |
| 0.85 | 2.6 | 0.85 | 4.3 | 0.85 | 2.8 | 0.85 | 6.3 | 0.85 | 4.0 |
| 0.9 | 2.3 | 0.9 | 3.6 | 0.9 | 2.4 | 0.9 | 5.3 | 0.9 | 3.4 |
| 0.95 | 1.8 | 0.95 | 2.6 | 0.95 | 1.9 | 0.95 | 3.7 | 0.95 | 2.5 |
| 1 | 1.2 | 1 | 1.2 | 1 | 1.2 | 1 | 1.2 | 1 | 1.2 |

HF - HCFO-1233xf - HFO-1234yf - HFO-1234zeE - HFO-1243zf

| Organics 0.9 F1233xf + 0.033 F1234zeE + 0.033 F1243zf + 0.034 F1234yf | | Organics 0.033 F1233xf + 0.9 F1234zeE + 0.033 F1243zf + 0.034 F1234yf | | Organics 0.033 F1233xf + 0.033 F1234zeE + 0.9 F1243zf + 0.034 F1234yf | | Organics 0.034 F1233xf + 0.033 F1234zeE + 0.033 F1243zf + 0.9 F1234yf | | Organics 0.25 F1233xf + 0.25 F1234zeE + 0.25 F1243zf + 0.25 F1234yf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.1 | 0 | 4.9 | 0 | 5.7 | 0 | 6.5 | 0 | 4.9 |
| 0.05 | 3.2 | 0.05 | 5.8 | 0.05 | 6.7 | 0.05 | 7.5 | 0.05 | 5.9 |
| 0.1 | 3.2 | 0.1 | 5.9 | 0.1 | 6.7 | 0.1 | 7.5 | 0.1 | 5.9 |
| 0.15 | 3.2 | 0.15 | 5.9 | 0.15 | 6.7 | 0.15 | 7.5 | 0.15 | 5.9 |
| 0.2 | 3.2 | 0.2 | 5.9 | 0.2 | 6.7 | 0.2 | 7.5 | 0.2 | 5.9 |
| 0.25 | 3.2 | 0.25 | 5.9 | 0.25 | 6.7 | 0.25 | 7.5 | 0.25 | 5.9 |
| 0.3 | 3.2 | 0.3 | 5.9 | 0.3 | 6.7 | 0.3 | 7.5 | 0.3 | 5.9 |
| 0.35 | 3.2 | 0.35 | 5.9 | 0.35 | 6.7 | 0.35 | 7.5 | 0.35 | 5.9 |
| 0.4 | 3.1 | 0.4 | 5.8 | 0.4 | 6.7 | 0.4 | 7.5 | 0.4 | 5.9 |
| 0.45 | 3.1 | 0.45 | 5.8 | 0.45 | 6.7 | 0.45 | 7.5 | 0.45 | 5.9 |
| 0.5 | 3.1 | 0.5 | 5.8 | 0.5 | 6.7 | 0.5 | 7.5 | 0.5 | 5.9 |
| 0.55 | 3.1 | 0.55 | 5.8 | 0.55 | 6.7 | 0.55 | 7.5 | 0.55 | 5.9 |
| 0.6 | 3.1 | 0.6 | 5.7 | 0.6 | 6.6 | 0.6 | 7.5 | 0.6 | 5.9 |
| 0.65 | 3.1 | 0.65 | 5.6 | 0.65 | 6.6 | 0.65 | 7.5 | 0.65 | 5.8 |
| 0.7 | 3.1 | 0.7 | 5.4 | 0.7 | 6.5 | 0.7 | 7.5 | 0.7 | 5.7 |
| 0.75 | 3.1 | 0.75 | 5.2 | 0.75 | 6.3 | 0.75 | 7.3 | 0.75 | 5.6 |
| 0.8 | 2.9 | 0.8 | 4.9 | 0.8 | 6.0 | 0.8 | 7.0 | 0.8 | 5.3 |
| 0.85 | 2.7 | 0.85 | 4.4 | 0.85 | 5.5 | 0.85 | 6.4 | 0.85 | 4.8 |
| 0.9 | 2.4 | 0.9 | 3.6 | 0.9 | 4.7 | 0.9 | 5.4 | 0.9 | 4.0 |
| 0.95 | 1.9 | 0.95 | 2.6 | 0.95 | 3.3 | 0.95 | 3.7 | 0.95 | 2.9 |
| 1 | 1.2 | 1 | 1.2 | 1 | 1.2 | 1 | 1.2 | 1 | 1.2 |

| HF - HCFO-1233xf - HFO-1234yf - HFO-1234zeE - HCFO-1233zdE ||||||||||
|---|---|---|---|---|---|---|---|---|---|
| Organics 0.9 F1233xf + 0.033 F1234zeE + 0.033 F1233zdE + 0.034 F1234yf || Organics 0.033 F1233xf + 0.9 F1234zeE + 0.033 F1233zdE + 0.034 F1234yf || Organics 0.033 F1233xf + 0.033 F1234zeE + 0.9 F1233zdE + 0.034 F1234yf || Organics 0.034 F1233xf + 0.033 F1234zeE + 0.033 F1233zdE + 0.9 F1234yf || Organics 0.25 F1233xf + 0.25 F1234zeE + 0.25 F1233zdE + 0.25 F1234yf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 1.7 | 0 | 6.4 | 0 | 3.8 |
| 0.05 | 3.0 | 0.05 | 5.7 | 0.05 | 2.8 | 0.05 | 7.4 | 0.05 | 4.8 |
| 0.1 | 3.0 | 0.1 | 5.7 | 0.1 | 2.8 | 0.1 | 7.4 | 0.1 | 4.8 |
| 0.15 | 3.0 | 0.15 | 5.7 | 0.15 | 2.8 | 0.15 | 7.4 | 0.15 | 4.8 |
| 0.2 | 3.0 | 0.2 | 5.7 | 0.2 | 2.8 | 0.2 | 7.4 | 0.2 | 4.8 |
| 0.25 | 3.0 | 0.25 | 5.7 | 0.25 | 2.8 | 0.25 | 7.4 | 0.25 | 4.8 |
| 0.3 | 3.0 | 0.3 | 5.7 | 0.3 | 2.8 | 0.3 | 7.4 | 0.3 | 4.8 |
| 0.35 | 3.0 | 0.35 | 5.7 | 0.35 | 2.8 | 0.35 | 7.4 | 0.35 | 4.8 |
| 0.4 | 3.0 | 0.4 | 5.7 | 0.4 | 2.8 | 0.4 | 7.4 | 0.4 | 4.8 |
| 0.45 | 3.0 | 0.45 | 5.7 | 0.45 | 2.8 | 0.45 | 7.4 | 0.45 | 4.8 |
| 0.5 | 3.0 | 0.5 | 5.7 | 0.5 | 2.8 | 0.5 | 7.4 | 0.5 | 4.8 |
| 0.55 | 3.0 | 0.55 | 5.6 | 0.55 | 2.8 | 0.55 | 7.4 | 0.55 | 4.8 |
| 0.6 | 3.0 | 0.6 | 5.5 | 0.6 | 2.8 | 0.6 | 7.4 | 0.6 | 4.8 |
| 0.65 | 2.9 | 0.65 | 5.4 | 0.65 | 2.7 | 0.65 | 7.4 | 0.65 | 4.8 |
| 0.7 | 2.9 | 0.7 | 5.3 | 0.7 | 2.7 | 0.7 | 7.4 | 0.7 | 4.7 |
| 0.75 | 2.9 | 0.75 | 5.1 | 0.75 | 2.7 | 0.75 | 7.2 | 0.75 | 4.6 |
| 0.8 | 2.8 | 0.8 | 4.7 | 0.8 | 2.6 | 0.8 | 6.9 | 0.8 | 4.3 |
| 0.85 | 2.6 | 0.85 | 4.2 | 0.85 | 2.4 | 0.85 | 6.3 | 0.85 | 3.9 |
| 0.9 | 2.3 | 0.9 | 3.6 | 0.9 | 2.1 | 0.9 | 5.3 | 0.9 | 3.3 |
| 0.95 | 1.8 | 0.95 | 2.6 | 0.95 | 1.7 | 0.95 | 3.7 | 0.95 | 2.4 |
| 1 | 1.2 | 1 | 1.2 | 1 | 1.2 | 1 | 1.2 | 1 | 1.2 |

| HF - HCFO-1233xf - HFO-1234yf - HFO-1234zeZ - HFO-1243zf ||||||||||
|---|---|---|---|---|---|---|---|---|---|
| Organics 0.9 F1233xf + 0.033 F1234zeZ + 0.033 F1243zf + 0.034 F1234yf || Organics 0.033 F1233xf + 0.9 F1234zeZ + 0.033 F1243zf + 0.034 F1234yf || Organics 0.033 F1233xf + 0.033 F1234zeZ + 0.9 F1243zf + 0.034 F1234yf || Organics 0.034 F1233xf + 0.033 F1234zeZ + 0.033 F1243zf + 0.9 F1234yf || Organics 0.25 F1233xf + 0.25 F1234zeZ + 0.25 F1243zf + 0.25 F1234yf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 2.1 | 0 | 5.6 | 0 | 6.4 | 0 | 4.1 |
| 0.05 | 3.1 | 0.05 | 3.2 | 0.05 | 6.6 | 0.05 | 7.4 | 0.05 | 5.2 |
| 0.1 | 3.1 | 0.1 | 3.2 | 0.1 | 6.6 | 0.1 | 7.4 | 0.1 | 5.2 |
| 0.15 | 3.1 | 0.15 | 3.2 | 0.15 | 6.6 | 0.15 | 7.4 | 0.15 | 5.2 |
| 0.2 | 3.1 | 0.2 | 3.2 | 0.2 | 6.6 | 0.2 | 7.4 | 0.2 | 5.2 |
| 0.25 | 3.1 | 0.25 | 3.2 | 0.25 | 6.6 | 0.25 | 7.4 | 0.25 | 5.2 |
| 0.3 | 3.1 | 0.3 | 3.2 | 0.3 | 8.6 | 0.3 | 7.4 | 0.3 | 5.2 |
| 0.35 | 3.0 | 0.35 | 3.2 | 0.35 | 6.6 | 0.35 | 7.4 | 0.35 | 5.2 |
| 0.4 | 3.0 | 0.4 | 3.2 | 0.4 | 6.6 | 0.4 | 7.4 | 0.4 | 5.2 |
| 0.45 | 3.0 | 0.45 | 3.2 | 0.45 | 6.6 | 0.45 | 7.4 | 0.45 | 5.2 |
| 0.5 | 3.0 | 0.5 | 3.2 | 0.5 | 6.6 | 0.5 | 7.4 | 0.5 | 5.2 |
| 0.55 | 3.0 | 0.55 | 3.2 | 0.55 | 6.6 | 0.55 | 7.4 | 0.55 | 5.2 |
| 0.6 | 3.0 | 0.6 | 3.2 | 0.6 | 6.5 | 0.6 | 7.4 | 0.6 | 5.2 |
| 0.65 | 3.0 | 0.65 | 3.2 | 0.65 | 6.5 | 0.65 | 7.4 | 0.85 | 5.2 |
| 0.7 | 3.0 | 0.7 | 3.2 | 0.7 | 6.4 | 0.7 | 7.4 | 0.7 | 5.1 |
| 0.75 | 3.0 | 0.75 | 3.2 | 0.75 | 6.2 | 0.75 | 7.2 | 0.75 | 5.0 |
| 0.8 | 2.9 | 0.8 | 3.1 | 0.8 | 6.0 | 0.8 | 6.9 | 0.8 | 4.8 |
| 0.85 | 2.6 | 0.85 | 2.8 | 0.85 | 5.5 | 0.85 | 6.3 | 0.85 | 4.4 |
| 0.9 | 2.3 | 0.9 | 2.5 | 0.9 | 4.6 | 0.9 | 5.3 | 0.9 | 3.7 |
| 0.95 | 1.8 | 0.95 | 2.0 | 0.95 | 3.3 | 0.95 | 3.7 | 0.95 | 2.7 |
| 1 | 1.2 | 1 | 1.2 | 1 | 1.2 | 1 | 1.2 | 1 | 1.2 |

| HF - HCFO-1233xf - HFO-1234yf - HFO-1234zeZ - HCFO-1233zdE ||||||||||
| Organics 0.9 F1233xf + 0.033 F1234zeZ + 0.033 F1233zdE + 0.034 F1234yf || Organics 0.033 F1233xf + 0.9 F1234zeZ + 0.033 F1233zdE + 0.034 F1234yf || Organics 0.033 F1233xf + 0.033 F1234zeZ + 0.9 F1233zdE + 0.034 F1234yf || Organics 0.034 F1233xf + 0.033 F1234zeZ + 0.033 F1233zdE + 0.9 F1234yf || Organics 0.25 F1233xf + 0.25 F1234zeZ + 0.25 F1233zdE + 0.25 F1234yf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- | --- | --- | --- | --- |
| 0 | 1.8 | 0 | 2.0 | 0 | 1.6 | 0 | 6.3 | 0 | 3.0 |
| 0.05 | 2.9 | 0.05 | 3.1 | 0.05 | 2.7 | 0.05 | 7.3 | 0.05 | 4.1 |
| 0.1 | 2.9 | 0.1 | 3.1 | 0.1 | 2.7 | 0.1 | 7.3 | 0.1 | 4.1 |
| 0.15 | 2.9 | 0.15 | 3.1 | 0.15 | 2.7 | 0.15 | 7.3 | 0.15 | 4.1 |
| 0.2 | 2.9 | 0.2 | 3.1 | 0.2 | 2.7 | 0.2 | 7.3 | 0.2 | 4.1 |
| 0.25 | 2.9 | 0.25 | 3.1 | 0.25 | 2.7 | 0.25 | 7.3 | 0.25 | 4.1 |
| 0.3 | 2.9 | 0.3 | 3.1 | 0.3 | 2.7 | 0.3 | 7.3 | 0.3 | 4.1 |
| 0.35 | 2.9 | 0.35 | 3.1 | 0.35 | 2.7 | 0.35 | 7.3 | 0.35 | 4.1 |
| 0.4 | 2.9 | 0.4 | 3.1 | 0.4 | 2.7 | 0.4 | 7.3 | 0.4 | 4.1 |
| 0.45 | 2.9 | 0.45 | 3.1 | 0.45 | 2.7 | 0.45 | 7.3 | 0.45 | 4.1 |
| 0.5 | 2.9 | 0.5 | 3.1 | 0.5 | 2.7 | 0.5 | 7.3 | 0.5 | 4.1 |
| 0.55 | 2.9 | 0.55 | 3.1 | 0.55 | 2.7 | 0.55 | 7.3 | 0.55 | 4.1 |
| 0.6 | 2.9 | 0.6 | 3.1 | 0.6 | 2.7 | 0.6 | 7.3 | 0.6 | 4.1 |
| 0.65 | 2.9 | 0.65 | 3.1 | 0.65 | 2.7 | 0.65 | 7.3 | 0.65 | 4.1 |
| 0.7 | 2.9 | 0.7 | 3.1 | 0.7 | 2.7 | 0.7 | 7.3 | 0.7 | 4.0 |
| 0.75 | 2.8 | 0.75 | 3.1 | 0.75 | 2.6 | 0.75 | 7.1 | 0.75 | 4.0 |
| 0.8 | 2.7 | 0.8 | 2.9 | 0.8 | 2.5 | 0.8 | 6.8 | 0.8 | 3.8 |
| 0.85 | 2.5 | 0.85 | 2.7 | 0.85 | 2.4 | 0.85 | 6.2 | 0.85 | 3.5 |
| 0.9 | 2.2 | 0.9 | 2.4 | 0.9 | 2.1 | 0.9 | 5.3 | 0.9 | 3.0 |
| 0.95 | 1.8 | 0.95 | 1.9 | 0.95 | 1.7 | 0.95 | 3.7 | 0.95 | 2.3 |
| 1 | 1.2 | 1 | 1.2 | 1 | 1.2 | 1 | 1.2 | 1 | 1.2 |

| HF - HFO-1234yf - HFO-1234zeE - HFO-1234zeZ - HCFO-1233zdE ||||||||||
| Organics 0.9 F1234yf + 0.033 F1233zdE + 0.033 F1234zeE + 0.034 F1234zeZ || Organics 0.033 F1234yf + 0.9 F1233zdE + 0.033 F1234zeE + 0.034 F1234zeZ || Organics 0.033 F1234yf + 0.033 F1233zdE + 0.9 F1234zeE + 0.034 F1234zeZ || Organics 0.034 F1234yf + 0.033 F1233zdE + 0.033 F1234zeE + 0.9 F1234zeZ || Organics 0.25 F1234yf + 0.25 F1233zdE + 0.25 F1234zeE + 0.25 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| --- | --- | --- | --- | --- | --- | --- | --- | --- | --- |
| 0 | 6.4 | 0 | 1.7 | 0 | 4.7 | 0 | 2.1 | 0 | 3.8 |
| 0.05 | 7.4 | 0.05 | 2.8 | 0.05 | 5.7 | 0.05 | 3.2 | 0.05 | 4.8 |
| 0.1 | 7.4 | 0.1 | 2.8 | 0.1 | 5.7 | 0.1 | 3.2 | 0.1 | 4.8 |
| 0.15 | 7.4 | 0.15 | 2.8 | 0.15 | 5.7 | 0.15 | 3.2 | 0.15 | 4.8 |
| 0.2 | 7.4 | 0.2 | 2.8 | 0.2 | 5.7 | 0.2 | 3.2 | 0.2 | 4.8 |
| 0.25 | 7.4 | 0.25 | 2.8 | 0.25 | 5.7 | 0.25 | 3.2 | 0.25 | 4.8 |
| 0.3 | 7.4 | 0.3 | 2.8 | 0.3 | 5.7 | 0.3 | 3.2 | 0.3 | 4.8 |
| 0.35 | 7.4 | 0.35 | 2.8 | 0.35 | 5.7 | 0.35 | 3.2 | 0.35 | 4.8 |
| 0.4 | 7.4 | 0.4 | 2.8 | 0.4 | 5.7 | 0.4 | 3.2 | 0.4 | 4.8 |
| 0.45 | 7.4 | 0.45 | 2.8 | 0.45 | 5.7 | 0.45 | 3.2 | 0.45 | 4.8 |
| 0.5 | 7.4 | 0.5 | 2.8 | 0.5 | 5.7 | 0.5 | 3.2 | 0.5 | 4.8 |
| 0.55 | 7.4 | 0.55 | 2.8 | 0.55 | 5.6 | 0.55 | 3.2 | 0.55 | 4.8 |
| 0.6 | 7.4 | 0.6 | 2.8 | 0.6 | 5.5 | 0.6 | 3.2 | 0.6 | 4.8 |
| 0.65 | 7.4 | 0.65 | 2.7 | 0.65 | 5.4 | 0.65 | 3.2 | 0.65 | 4.8 |
| 0.7 | 7.4 | 0.7 | 2.7 | 0.7 | 5.3 | 0.7 | 3.2 | 0.7 | 4.7 |
| 0.75 | 7.2 | 0.75 | 2.7 | 0.75 | 5.1 | 0.75 | 3.1 | 0.75 | 4.6 |
| 0.8 | 6.9 | 0.8 | 2.6 | 0.8 | 4.7 | 0.8 | 3.0 | 0.8 | 4.3 |
| 0.85 | 6.3 | 0.85 | 2.4 | 0.85 | 4.2 | 0.85 | 2.8 | 0.85 | 4.0 |
| 0.9 | 5.3 | 0.9 | 2.1 | 0.9 | 3.6 | 0.9 | 2.4 | 0.9 | 3.4 |
| 0.95 | 3.7 | 0.95 | 1.7 | 0.95 | 2.6 | 0.95 | 1.9 | 0.95 | 2.5 |
| 1 | 1.2 | 1 | 1.2 | 1 | 1.2 | 1 | 1.2 | 1 | 1.2 |

| HF - HFO-1234yf - HFO-1234zeE - HFO-1234zeZ - HFO-1243zf |||||||||
|---|---|---|---|---|---|---|---|---|
| Organics 0.9 F1234yf + 0.033 F1234zeZ + 0.033 F1234zeE + 0.034 F1243zf | | Organics 0.033 F1234yf + 0.9 F1234zeZ + 0.033 F1234zeE + 0.034 F1243zf | | Organics 0.033 F1234yf + 0.033 F1234zeZ + 0.9 F1234zeE + 0.034 F1243zf | | Organics 0.034 F1234yf + 0.033 F1234zeZ + 0.033 F1234zeE + 0.9 F1243zf | | Organics 0.25 F1234yf + 0.25 F1234zeZ + 0.25 F1234zeE + 0.25 F1243zf |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 2.2 | 0 | 4.9 | 0 | 5.7 | 0 | 4.9 |
| 0.05 | 7.5 | 0.05 | 3.3 | 0.05 | 5.8 | 0.05 | 6.7 | 0.05 | 5.9 |
| 0.1 | 7.5 | 0.1 | 3.3 | 0.1 | 5.9 | 0.1 | 6.7 | 0.1 | 5.9 |
| 0.15 | 7.5 | 0.15 | 3.3 | 0.15 | 5.8 | 0.15 | 6.7 | 0.15 | 5.9 |
| 0.2 | 7.5 | 0.2 | 3.3 | 0.2 | 5.8 | 0.2 | 6.7 | 0.2 | 5.9 |
| 0.25 | 7.5 | 0.25 | 3.3 | 0.25 | 5.8 | 0.25 | 6.7 | 0.25 | 5.9 |
| 0.3 | 7.5 | 0.3 | 3.3 | 0.3 | 5.8 | 0.3 | 6.7 | 0.3 | 5.9 |
| 0.35 | 7.5 | 0.35 | 3.3 | 0.35 | 5.8 | 0.35 | 6.7 | 0.35 | 5.9 |
| 0.4 | 7.5 | 0.4 | 3.3 | 0.4 | 5.8 | 0.4 | 6.7 | 0.4 | 5.9 |
| 0.45 | 7.5 | 0.45 | 3.3 | 0.45 | 5.8 | 0.45 | 6.7 | 0.45 | 5.9 |
| 0.5 | 7.5 | 0.5 | 3.3 | 0.5 | 5.8 | 0.5 | 6.7 | 0.5 | 5.9 |
| 0.55 | 7.5 | 0.55 | 3.3 | 0.55 | 5.8 | 0.55 | 6.7 | 0.55 | 5.9 |
| 0.6 | 7.5 | 0.6 | 3.3 | 0.6 | 5.7 | 0.6 | 6.6 | 0.6 | 5.9 |
| 0.65 | 7.5 | 0.65 | 3.3 | 0.65 | 5.6 | 0.65 | 6.6 | 0.65 | 5.8 |
| 0.7 | 7.5 | 0.7 | 3.3 | 0.7 | 5.4 | 0.7 | 6.5 | 0.7 | 5.7 |
| 0.75 | 7.3 | 0.75 | 3.3 | 0.75 | 5.2 | 0.75 | 6.3 | 0.75 | 5.6 |
| 0.8 | 7.0 | 0.8 | 3.1 | 0.8 | 4.9 | 0.8 | 6.0 | 0.8 | 5.3 |
| 0.85 | 6.4 | 0.85 | 2.9 | 0.85 | 4.4 | 0.85 | 5.5 | 0.85 | 4.8 |
| 0.9 | 5.4 | 0.9 | 2.5 | 0.9 | 3.7 | 0.9 | 4.7 | 0.9 | 4.1 |
| 0.95 | 3.7 | 0.95 | 2.0 | 0.95 | 2.6 | 0.95 | 3.3 | 0.95 | 2.9 |
| 1 | 1.2 | 1 | 1.2 | 1 | 1.2 | 1 | 1.2 | 1 | 1.2 |

| HF - HFO-1234yf - HFO-1234zeE - HCFO-1233zdE - HFO-1243zf |||||||||
|---|---|---|---|---|---|---|---|---|
| Organics 0.9 F1234yf + 0.033 F1233zdE + 0.033 F1234zeE + 0.034 F1243zf | | Organics 0.033 F1234yf + 0.9 F1233zdE + 0.033 F1234zeE + 0.034 F1243zf | | Organics 0.033 F1234yf + 0.033 F1233zdE + 0.9 F1234zeE + 0.034 F1243zf | | Organics 0.034 F1234yf + 0.033 F1233zdE + 0.033 F1234zeE + 0.9 F1243zf | | Organics 0.25 F1234yf + 0.25 F1233zdE + 0.25 F1234zeE + 0.25 F1243zf |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 1.9 | 0 | 4.9 | 0 | 5.7 | 0 | 4.8 |
| 0.05 | 7.5 | 0.05 | 3.6 | 0.05 | 5.8 | 0.05 | 6.7 | 0.05 | 5.8 |
| 0.1 | 7.5 | 0.1 | 3.0 | 0.1 | 5.9 | 0.1 | 6.7 | 0.1 | 5.9 |
| 0.15 | 7.5 | 0.15 | 3.0 | 0.15 | 5.8 | 0.15 | 6.7 | 0.15 | 5.9 |
| 0.2 | 7.5 | 0.2 | 3.0 | 0.2 | 5.8 | 0.2 | 6.7 | 0.2 | 5.9 |
| 0.25 | 7.5 | 0.25 | 3.0 | 0.25 | 5.8 | 0.25 | 6.7 | 0.25 | 5.9 |
| 0.3 | 7.5 | 0.3 | 3.0 | 0.3 | 5.8 | 0.3 | 6.7 | 0.3 | 5.9 |
| 0.35 | 7.5 | 0.35 | 2.9 | 0.35 | 5.8 | 0.35 | 6.7 | 0.35 | 5.9 |
| 0.4 | 7.5 | 0.4 | 2.9 | 0.4 | 5.8 | 0.4 | 6.7 | 0.4 | 5.9 |
| 0.45 | 7.5 | 0.45 | 2.9 | 0.45 | 5.8 | 0.45 | 6.7 | 0.45 | 5.9 |
| 0.5 | 7.5 | 0.5 | 2.9 | 0.5 | 5.8 | 0.5 | 6.7 | 0.5 | 5.8 |
| 0.55 | 7.5 | 0.55 | 2.9 | 0.55 | 5.8 | 0.55 | 6.6 | 0.55 | 5.8 |
| 0.6 | 7.5 | 0.6 | 2.9 | 0.6 | 5.7 | 0.6 | 6.6 | 0.6 | 5.8 |
| 0.65 | 7.5 | 0.65 | 2.9 | 0.65 | 5.6 | 0.65 | 6.6 | 0.65 | 5.8 |
| 0.7 | 7.5 | 0.7 | 2.9 | 0.7 | 5.4 | 0.7 | 6.5 | 0.7 | 5.7 |
| 0.75 | 7.3 | 0.75 | 2.9 | 0.75 | 5.2 | 0.75 | 6.3 | 0.75 | 5.5 |
| 0.8 | 7.0 | 0.8 | 2.7 | 0.8 | 4.9 | 0.8 | 6.0 | 0.8 | 5.2 |
| 0.85 | 6.4 | 0.85 | 2.5 | 0.85 | 4.4 | 0.85 | 5.5 | 0.85 | 4.8 |
| 0.9 | 5.4 | 0.9 | 2.2 | 0.9 | 3.6 | 0.9 | 4.7 | 0.9 | 4.0 |
| 0.95 | 3.7 | 0.95 | 1.8 | 0.95 | 2.6 | 0.95 | 3.3 | 0.95 | 2.9 |
| 1 | 1.2 | 1 | 1.2 | 1 | 1.2 | 1 | 1.2 | 1 | 1.2 |

| HF - HFO-1234yf - HFO-1234zeZ - HCFO-1233zdE - HFO-1243zf ||||||||||
|---|---|---|---|---|---|---|---|---|---|
| Organics 0.9 F1234yf + 0.033 F1233zdE + 0.033 F1234zeZ + 0.034 F1243zf || Organics 0.033 F1234yf + 0.9 F1233zdE + 0.033 F1234zeZ + 0.034 F1243zf || Organics 0.033 F1234yf + 0.033 F1233zdE + 0.9 F1234zeZ + 0.034 F1243zf || Organics 0.034 F1234yf + 0.033 F1233zdE + 0.033 F1234zeZ + 0.9 F1243zf || Organics 0.25 F1234yf + 0.25 F1233zdE + 0.25 F1234zeZ + 0.25 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 1.7 | 0 | 2.1 | 0 | 5.6 | 0 | 4.1 |
| 0.05 | 7.4 | 0.05 | 2.9 | 0.05 | 3.2 | 0.05 | 6.6 | 0.05 | 5.2 |
| 0.1 | 7.4 | 0.1 | 2.9 | 0.1 | 3.2 | 0.1 | 6.6 | 0.1 | 5.2 |
| 0.15 | 7.4 | 0.15 | 2.9 | 0.15 | 3.2 | 0.15 | 6.6 | 0.15 | 5.2 |
| 0.2 | 7.4 | 0.2 | 2.9 | 0.2 | 3.2 | 0.2 | 6.6 | 0.2 | 5.2 |
| 0.25 | 7.4 | 0.25 | 2.8 | 0.25 | 3.2 | 0.25 | 6.6 | 0.25 | 5.2 |
| 0.3 | 7.4 | 0.3 | 2.8 | 0.3 | 3.2 | 0.3 | 6.6 | 0.3 | 5.2 |
| 0.35 | 7.4 | 0.35 | 2.8 | 0.35 | 3.2 | 0.35 | 6.6 | 0.35 | 5.1 |
| 0.4 | 7.4 | 0.4 | 2.8 | 0.4 | 3.2 | 0.4 | 6.6 | 0.4 | 5.1 |
| 0.45 | 7.4 | 0.45 | 2.8 | 0.45 | 3.2 | 0.45 | 6.6 | 0.45 | 5.1 |
| 0.5 | 7.4 | 0.5 | 2.8 | 0.5 | 3.2 | 0.5 | 6.6 | 0.5 | 5.1 |
| 0.55 | 7.4 | 0.55 | 2.8 | 0.55 | 3.2 | 0.55 | 6.6 | 0.55 | 5.1 |
| 0.6 | 7.4 | 0.6 | 2.8 | 0.6 | 3.2 | 0.6 | 6.5 | 0.6 | 5.1 |
| 0.65 | 7.4 | 0.65 | 2.8 | 0.65 | 3.2 | 0.65 | 6.5 | 0.65 | 5.1 |
| 0.7 | 7.4 | 0.7 | 2.8 | 0.7 | 3.2 | 0.7 | 6.4 | 0.7 | 5.1 |
| 0.75 | 7.2 | 0.75 | 2.8 | 0.75 | 3.2 | 0.75 | 6.2 | 0.75 | 5.0 |
| 0.8 | 6.9 | 0.8 | 2.7 | 0.8 | 3.0 | 0.8 | 5.9 | 0.8 | 4.7 |
| 0.85 | 6.3 | 0.85 | 2.5 | 0.85 | 2.8 | 0.85 | 5.5 | 0.85 | 4.3 |
| 0.9 | 5.3 | 0.9 | 2.2 | 0.9 | 2.5 | 0.9 | 4.6 | 0.9 | 3.7 |
| 0.95 | 3.7 | 0.95 | 1.8 | 0.95 | 2.0 | 0.95 | 3.3 | 0.95 | 2.7 |
| 1 | 1.2 | 1 | 1.2 | 1 | 1.2 | 1 | 1.2 | 1 | 1.2 |

| HF-HFO-1234yf-HFC-245cb-HFO-1234zeE-HCFO-1233zdE ||||||||||
|---|---|---|---|---|---|---|---|---|---|
| Organics 0.9 F1234yf + 0.033 F1234zeE + 0.033 F245cb + 0.034 F1233zdE || Organics 0.033 F1234yf + 0.9 F1234zeE + 0.033 F245cb + 0.034 F1233zdE || Organics 0.033 F1234yf + 0.033 F1234zeE + 0.9 F245cb + 0.034 F1233zdE || Organics 0.034 F1234yf + 0.033 F1234zeE + 0.033 F245cb + 0.9 F1233zdE || Organics 0.25 F1234yf + 0.25 F1234zeE + 0.25 F245cb + 0.25 F1233zdE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 4.8 | 0 | 4.6 | 0 | 1.8 | 0 | 4.5 |
| 0.05 | 7.5 | 0.05 | 5.8 | 0.05 | 5.8 | 0.05 | 2.9 | 0.05 | 5.6 |
| 0.1 | 7.5 | 0.1 | 5.8 | 0.1 | 5.8 | 0.1 | 2.9 | 0.1 | 5.6 |
| 0.15 | 7.5 | 0.15 | 5.8 | 0.15 | 5.8 | 0.15 | 2.9 | 0.15 | 5.6 |
| 0.2 | 7.5 | 0.2 | 5.8 | 0.2 | 5.8 | 0.2 | 2.9 | 0.2 | 5.6 |
| 0.25 | 7.5 | 0.25 | 5.8 | 0.25 | 5.8 | 0.25 | 2.9 | 0.25 | 5.6 |
| 0.3 | 7.5 | 0.3 | 5.8 | 0.3 | 5.8 | 0.3 | 2.9 | 0.3 | 5.6 |
| 0.35 | 7.5 | 0.35 | 5.8 | 0.35 | 5.8 | 0.35 | 2.9 | 0.35 | 5.6 |
| 0.4 | 7.5 | 0.4 | 5.8 | 0.4 | 5.8 | 0.4 | 2.9 | 0.4 | 5.6 |
| 0.45 | 7.5 | 0.45 | 5.8 | 0.45 | 5.8 | 0.45 | 2.9 | 0.45 | 5.6 |
| 0.5 | 7.5 | 0.5 | 5.8 | 0.5 | 5.8 | 0.5 | 2.9 | 0.5 | 5.6 |
| 0.55 | 7.5 | 0.55 | 5.7 | 0.55 | 5.8 | 0.55 | 2.9 | 0.55 | 5.6 |
| 0.6 | 7.5 | 0.6 | 5.7 | 0.6 | 5.8 | 0.6 | 2.9 | 0.6 | 5.6 |
| 0.65 | 7.5 | 0.65 | 5.6 | 0.65 | 5.8 | 0.65 | 2.9 | 0.65 | 5.6 |
| 0.7 | 7.5 | 0.7 | 5.4 | 0.7 | 5.8 | 0.7 | 2.9 | 0.7 | 5.6 |
| 0.75 | 7.3 | 0.75 | 5.2 | 0.75 | 5.8 | 0.75 | 2.9 | 0.75 | 5.5 |
| 0.8 | 7.0 | 0.8 | 4.9 | 0.8 | 5.8 | 0.8 | 2.7 | 0.8 | 5.2 |
| 0.85 | 6.4 | 0.85 | 4.4 | 0.85 | 5.7 | 0.85 | 2.5 | 0.85 | 4.8 |
| 0.9 | 5.4 | 0.9 | 3.6 | 0.9 | 4.9 | 0.9 | 2.2 | 0.9 | 4.1 |
| 0.95 | 3.7 | 0.95 | 2.6 | 0.95 | 3.5 | 0.95 | 1.8 | 0.95 | 2.9 |
| 1 | 1.2 | 1 | 1.2 | 1 | 1.2 | 1 | 1.2 | 1 | 1.2 |

HF-HFO-1234yf-HFC-245cb-HFO-1234zeE-HFO-1234zeZ

| Organics 0.9 F1234yf + 0.033 F1234zeE + 0.033 F245cb + 0.034 F1234zeZ | | Organics 0.033 F1234yf + 0.9 F1234zeE + 0.033 F245cb + 0.034 F1234zeZ | | Organics 0.033 F1234yf + 0.033 F1234zeE + 0.9 F245cb + 0.034 F1234zeZ | | Organics 0.034 F1234yf + 0.033 F1234zeE + 0.033 F245cb + 0.9 F1234zeZ | | Organics 0.25 F1234yf + 0.25 F1234zeE + 0.25 F245cb + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 4.8 | 0 | 4.6 | 0 | 2.2 | 0 | 4.5 |
| 0.05 | 7.5 | 0.05 | 5.8 | 0.05 | 5.8 | 0.05 | 3.3 | 0.05 | 5.6 |
| 0.1 | 7.5 | 0.1 | 5.8 | 0.1 | 5.8 | 0.1 | 3.3 | 0.1 | 5.6 |
| 0.15 | 7.5 | 0.15 | 5.8 | 0.15 | 5.8 | 0.15 | 3.3 | 0.15 | 5.6 |
| 0.2 | 7.5 | 0.2 | 5.8 | 0.2 | 5.8 | 0.2 | 3.3 | 0.2 | 5.6 |
| 0.25 | 7.5 | 0.25 | 5.8 | 0.25 | 5.8 | 0.25 | 3.3 | 0.25 | 5.6 |
| 0.3 | 7.5 | 0.3 | 5.8 | 0.3 | 5.8 | 0.3 | 3.3 | 0.3 | 5.6 |
| 0.35 | 7.5 | 0.35 | 5.8 | 0.35 | 5.8 | 0.35 | 3.3 | 0.35 | 5.6 |
| 0.4 | 7.5 | 0.4 | 5.8 | 0.4 | 5.8 | 0.4 | 3.3 | 0.4 | 5.6 |
| 0.45 | 7.5 | 0.45 | 5.8 | 0.45 | 5.8 | 0.45 | 3.3 | 0.45 | 5.6 |
| 0.5 | 7.5 | 0.5 | 5.8 | 0.5 | 5.8 | 0.5 | 3.3 | 0.5 | 5.6 |
| 0.55 | 7.5 | 0.55 | 5.7 | 0.55 | 5.8 | 0.55 | 3.3 | 0.55 | 5.6 |
| 0.6 | 7.5 | 0.6 | 5.7 | 0.6 | 5.8 | 0.6 | 3.3 | 0.6 | 5.6 |
| 0.65 | 7.5 | 0.65 | 5.6 | 0.65 | 5.8 | 0.65 | 3.3 | 0.65 | 5.6 |
| 0.7 | 7.5 | 0.7 | 5.4 | 0.7 | 5.8 | 0.7 | 3.3 | 0.7 | 5.6 |
| 0.75 | 7.3 | 0.75 | 5.2 | 0.75 | 5.8 | 0.75 | 3.3 | 0.75 | 5.5 |
| 0.8 | 7.0 | 0.8 | 4.9 | 0.8 | 5.8 | 0.8 | 3.1 | 0.8 | 5.3 |
| 0.85 | 6.4 | 0.85 | 4.4 | 0.85 | 5.7 | 0.85 | 2.9 | 0.85 | 4.9 |
| 0.9 | 5.4 | 0.9 | 3.7 | 0.9 | 4.9 | 0.9 | 2.5 | 0.9 | 4.1 |
| 0.95 | 3.7 | 0.95 | 2.6 | 0.95 | 3.5 | 0.95 | 2.0 | 0.95 | 3.0 |
| 1 | 1.2 | 1 | 1.2 | 1 | 1.2 | 1 | 1.2 | 1 | 1.2 |

HF-HFO-1234yf-HFC-245cb-HFO-1234zeE-HFO-1243zf

| Organics 0.9 F1234yf + 0.033 F1234zeE + 0.033 F245cb + 0.034 F1243zf | | Organics 0.033 F1234yf + 0.9 F1234zeE + 0.033 F245cb + 0.034 F1243zf | | Organics 0.033 F1234yf + 0.033 F1234zeE + 0.9 F245cb + 0.034 F1243zf | | Organics 0.034 F1234yf + 0.033 F1234zeE + 0.033 F245cb + 0.9 F1243zf | | Organics 0.25 F1234yf + 0.25 F1234zeE + 0.25 F245cb + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.6 | 0 | 5.0 | 0 | 4.8 | 0 | 5.8 | 0 | 5.6 |
| 0.05 | 7.6 | 0.05 | 5.9 | 0.05 | 6.0 | 0.05 | 6.8 | 0.05 | 6.6 |
| 0.1 | 7.6 | 0.1 | 6.0 | 0.1 | 6.0 | 0.1 | 6.8 | 0.1 | 6.6 |
| 0.15 | 7.6 | 0.15 | 6.0 | 0.15 | 6.0 | 0.15 | 6.8 | 0.15 | 6.6 |
| 0.2 | 7.6 | 0.2 | 6.0 | 0.2 | 6.0 | 0.2 | 6.8 | 0.2 | 6.6 |
| 0.25 | 7.6 | 0.25 | 6.0 | 0.25 | 6.0 | 0.25 | 6.8 | 0.25 | 6.6 |
| 0.3 | 7.6 | 0.3 | 6.0 | 0.3 | 6.0 | 0.3 | 6.8 | 0.3 | 6.6 |
| 0.35 | 7.6 | 0.35 | 6.0 | 0.35 | 6.0 | 0.35 | 6.8 | 0.35 | 6.6 |
| 0.4 | 7.6 | 0.4 | 6.0 | 0.4 | 6.0 | 0.4 | 6.8 | 0.4 | 6.6 |
| 0.45 | 7.6 | 0.45 | 5.9 | 0.45 | 6.0 | 0.45 | 6.8 | 0.45 | 6.6 |
| 0.5 | 7.6 | 0.5 | 5.9 | 0.5 | 6.0 | 0.5 | 6.8 | 0.5 | 6.6 |
| 0.55 | 7.6 | 0.55 | 5.9 | 0.55 | 6.0 | 0.55 | 6.7 | 0.55 | 6.6 |
| 0.6 | 7.6 | 0.6 | 5.8 | 0.6 | 6.0 | 0.6 | 6.7 | 0.6 | 6.6 |
| 0.65 | 7.6 | 0.65 | 5.7 | 0.65 | 5.9 | 0.65 | 6.7 | 0.65 | 6.6 |
| 0.7 | 7.6 | 0.7 | 5.6 | 0.7 | 5.9 | 0.7 | 6.6 | 0.7 | 6.6 |
| 0.75 | 7.4 | 0.75 | 5.3 | 0.75 | 5.9 | 0.75 | 6.4 | 0.75 | 6.4 |
| 0.8 | 7.1 | 0.8 | 5.0 | 0.8 | 5.9 | 0.8 | 6.1 | 0.8 | 6.1 |
| 0.85 | 6.5 | 0.85 | 4.5 | 0.85 | 5.8 | 0.85 | 5.6 | 0.85 | 5.6 |
| 0.9 | 5.5 | 0.9 | 3.7 | 0.9 | 5.0 | 0.9 | 4.8 | 0.9 | 4.8 |
| 0.95 | 3.8 | 0.95 | 2.7 | 0.95 | 3.5 | 0.95 | 3.4 | 0.95 | 3.4 |
| 1 | 1.2 | 1 | 1.2 | 1 | 1.2 | 1 | 1.2 | 1 | 1.2 |

| HF-HFO-1234yf-HFC-245cb-HFO-1234zeZ-HCFO-1233zdE ||||||||||
|---|---|---|---|---|---|---|---|---|---|
| Organics 0.9 F1234yf + 0.033 F1234zeZ + 0.033 F245cb + 0.034 F1233zdE || Organics 0.033 F1234yf + 0.9 F1234zeZ + 0.033 F245cb + 0.034 F1233zdE || Organics 0.033 F1234yf + 0.033 F1234zeZ + 0.9 F245cb + 0.034 F1233zdE || Organics 0.034 F1234yf + 0.033 F1234zeZ + 0.033 F245cb + 0.9 F1233zdE || Organics 0.25 F1234yf + 0.25 F1234zeZ + 0.25 F245cb + 0.25 F1233zdE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 2.1 | 0 | 4.5 | 0 | 1.7 | 0 | 3.7 |
| 0.05 | 7.4 | 0.05 | 3.2 | 0.05 | 5.7 | 0.05 | 2.8 | 0.05 | 4.8 |
| 0.1 | 7.4 | 0.1 | 3.2 | 0.1 | 5.7 | 0.1 | 2.8 | 0.1 | 4.8 |
| 0.15 | 7.4 | 0.15 | 3.2 | 0.15 | 5.7 | 0.15 | 2.8 | 0.15 | 4.8 |
| 0.2 | 7.4 | 0.2 | 3.2 | 0.2 | 5.7 | 0.2 | 2.8 | 0.2 | 4.8 |
| 0.25 | 7.4 | 0.25 | 3.2 | 0.25 | 5.7 | 0.25 | 2.8 | 0.25 | 4.8 |
| 0.3 | 7.4 | 0.3 | 3.2 | 0.3 | 5.7 | 0.3 | 2.8 | 0.3 | 4.8 |
| 0.35 | 7.4 | 0.35 | 3.2 | 0.35 | 5.7 | 0.35 | 2.8 | 0.35 | 4.8 |
| 0.4 | 7.4 | 0.4 | 3.2 | 0.4 | 5.7 | 0.4 | 2.8 | 0.4 | 4.8 |
| 0.45 | 7.4 | 0.45 | 3.2 | 0.45 | 5.7 | 0.45 | 2.8 | 0.45 | 4.8 |
| 0.5 | 7.4 | 0.5 | 3.2 | 0.5 | 5.7 | 0.5 | 2.8 | 0.5 | 4.8 |
| 0.55 | 7.4 | 0.55 | 3.2 | 0.55 | 5.7 | 0.55 | 2.8 | 0.55 | 4.8 |
| 0.6 | 7.4 | 0.6 | 3.2 | 0.6 | 5.7 | 0.6 | 2.8 | 0.6 | 4.9 |
| 0.65 | 7.4 | 0.65 | 3.2 | 0.65 | 5.7 | 0.65 | 2.8 | 0.65 | 4.9 |
| 0.7 | 7.4 | 0.7 | 3.2 | 0.7 | 5.7 | 0.7 | 2.8 | 0.7 | 4.9 |
| 0.75 | 7.2 | 0.75 | 3.2 | 0.75 | 5.7 | 0.75 | 2.8 | 0.75 | 4.9 |
| 0.8 | 6.9 | 0.8 | 3.0 | 0.8 | 5.7 | 0.8 | 2.7 | 0.8 | 4.7 |
| 0.85 | 6.4 | 0.85 | 2.8 | 0.85 | 5.7 | 0.85 | 2.5 | 0.85 | 4.3 |
| 0.9 | 5.4 | 0.9 | 2.5 | 0.9 | 4.9 | 0.9 | 2.2 | 0.9 | 3.7 |
| 0.95 | 3.7 | 0.95 | 2.0 | 0.95 | 3.5 | 0.95 | 1.8 | 0.95 | 2.7 |
| 1 | 1.2 | 1 | 1.2 | 1 | 1.2 | 1 | 1.2 | 1 | 1.2 |

| HF-HFO-1234yf-HFC-245cb-HFO-1234zeZ-HFO-1243zf ||||||||||
|---|---|---|---|---|---|---|---|---|---|
| Organics 0.9 F1234yf + 0.033 F1234zeZ + 0.033 F245cb + 0.034 F1243zf || Organics 0.033 F1234yf + 0.9 F1234zeZ + 0.033 F245cb + 0.034 F1243zf || Organics 0.033 F1234yf + 0.033 F1234zeZ + 0.9 F245cb + 0.034 F1243zf || Organics 0.034 F1234yf + 0.033 F1234zeZ + 0.033 F245cb + 0.9 F1243zf || Organics 0.25 F1234yf + 0.25 F1234zeZ + 0.25 F245cb + 0.25 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 2.2 | 0 | 4.7 | 0 | 5.7 | 0 | 4.8 |
| 0.05 | 7.5 | 0.05 | 3.3 | 0.05 | 5.8 | 0.05 | 6.7 | 0.05 | 5.9 |
| 0.1 | 7.5 | 0.1 | 3.3 | 0.1 | 5.8 | 0.1 | 6.7 | 0.1 | 5.9 |
| 0.15 | 7.5 | 0.15 | 3.3 | 0.15 | 5.8 | 0.15 | 6.7 | 0.15 | 5.9 |
| 0.2 | 7.5 | 0.2 | 3.3 | 0.2 | 5.8 | 0.2 | 6.7 | 0.2 | 5.9 |
| 0.25 | 7.5 | 0.25 | 3.3 | 0.25 | 5.8 | 0.25 | 6.7 | 0.25 | 5.9 |
| 0.3 | 7.5 | 0.3 | 3.3 | 0.3 | 5.8 | 0.3 | 6.7 | 0.3 | 5.9 |
| 0.35 | 7.5 | 0.35 | 3.3 | 0.35 | 5.8 | 0.35 | 6.7 | 0.35 | 5.9 |
| 0.4 | 7.5 | 0.4 | 3.3 | 0.4 | 5.8 | 0.4 | 6.7 | 0.4 | 5.9 |
| 0.45 | 7.5 | 0.45 | 3.3 | 0.45 | 5.8 | 0.45 | 6.7 | 0.45 | 5.9 |
| 0.5 | 7.5 | 0.5 | 3.3 | 0.5 | 5.8 | 0.5 | 6.7 | 0.5 | 5.9 |
| 0.55 | 7.5 | 0.55 | 3.3 | 0.55 | 5.8 | 0.55 | 6.7 | 0.55 | 5.9 |
| 0.6 | 7.5 | 0.6 | 3.3 | 0.6 | 5.8 | 0.6 | 6.6 | 0.6 | 5.9 |
| 0.65 | 7.5 | 0.65 | 3.3 | 0.65 | 5.8 | 0.65 | 6.6 | 0.65 | 5.9 |
| 0.7 | 7.5 | 0.7 | 3.3 | 0.7 | 5.9 | 0.7 | 6.5 | 0.7 | 5.9 |
| 0.75 | 7.3 | 0.75 | 3.3 | 0.75 | 5.9 | 0.75 | 6.3 | 0.75 | 5.9 |
| 0.8 | 7.0 | 0.8 | 3.2 | 0.8 | 5.9 | 0.8 | 6.1 | 0.8 | 5.6 |
| 0.85 | 6.5 | 0.85 | 2.9 | 0.85 | 5.8 | 0.85 | 5.6 | 0.85 | 5.2 |
| 0.9 | 5.4 | 0.9 | 2.6 | 0.9 | 5.0 | 0.9 | 4.7 | 0.9 | 4.4 |
| 0.95 | 3.8 | 0.95 | 2.0 | 0.95 | 3.5 | 0.95 | 3.4 | 0.95 | 3.2 |
| 1 | 1.2 | 1 | 1.2 | 1 | 1.2 | 1 | 1.2 | 1 | 1.2 |

HF-HFC-245cb-HCFO-1233zdE-HFO-1234zeE-HFO-1234zeZ

| Organics 0.9 F245cb + 0.033 F1234zeE + 0.033 F1233zdE + 0.034 F1234zeZ | | Organics 0.033 F245cb + 0.9 F1234zeE + 0.033 F1233zdE + 0.034 F1234zeZ | | Organics 0.033 F245cb + 0.033 F1234zeE + 0.9 F1233zdE + 0.034 F1234zeZ | | Organics 0.034 F245cb + 0.033 F1234zeE + 0.033 F1233zdE + 0.9 F1234zeZ | | Organics 0.25 F245cb + 0.25 F1234zeE + F1233zdE + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 4.7 | 0 | 1.6 | 0 | 2.0 | 0 | 3.2 |
| 0.05 | 5.6 | 0.05 | 5.6 | 0.05 | 2.7 | 0.05 | 3.1 | 0.05 | 4.3 |
| 0.1 | 5.6 | 0.1 | 5.6 | 0.1 | 2.7 | 0.1 | 3.1 | 0.1 | 4.3 |
| 0.15 | 5.6 | 0.15 | 5.6 | 0.15 | 2.7 | 0.15 | 3.1 | 0.15 | 4.3 |
| 0.2 | 5.6 | 0.2 | 5.6 | 0.2 | 2.7 | 0.2 | 3.1 | 0.2 | 4.3 |
| 0.25 | 5.6 | 0.25 | 5.6 | 0.25 | 2.7 | 0.25 | 3.1 | 0.25 | 4.3 |
| 0.3 | 5.6 | 0.3 | 5.6 | 0.3 | 2.7 | 0.3 | 3.1 | 0.3 | 4.3 |
| 0.35 | 5.6 | 0.35 | 5.6 | 0.35 | 2.7 | 0.35 | 3.1 | 0.35 | 4.3 |
| 0.4 | 5.6 | 0.4 | 5.6 | 0.4 | 2.7 | 0.4 | 3.1 | 0.4 | 4.3 |
| 0.45 | 5.6 | 0.45 | 5.6 | 0.45 | 2.7 | 0.45 | 3.1 | 0.45 | 4.3 |
| 0.5 | 5.6 | 0.5 | 5.6 | 0.5 | 2.7 | 0.5 | 3.1 | 0.5 | 4.3 |
| 0.55 | 5.6 | 0.55 | 5.6 | 0.55 | 2.7 | 0.55 | 3.1 | 0.55 | 4.3 |
| 0.6 | 5.6 | 0.6 | 5.5 | 0.6 | 2.7 | 0.6 | 3.1 | 0.6 | 4.3 |
| 0.65 | 5.6 | 0.65 | 5.4 | 0.65 | 2.7 | 0.65 | 3.1 | 0.65 | 4.3 |
| 0.7 | 5.7 | 0.7 | 5.2 | 0.7 | 2.7 | 0.7 | 3.1 | 0.7 | 4.3 |
| 0.75 | 5.7 | 0.75 | 5.0 | 0.75 | 2.7 | 0.75 | 3.1 | 0.75 | 4.3 |
| 0.8 | 5.7 | 0.8 | 4.7 | 0.8 | 2.6 | 0.8 | 3.0 | 0.8 | 4.1 |
| 0.85 | 5.6 | 0.85 | 4.2 | 0.85 | 2.4 | 0.85 | 2.7 | 0.85 | 3.7 |
| 0.9 | 4.8 | 0.9 | 3.5 | 0.9 | 2.1 | 0.9 | 2.4 | 0.9 | 3.2 |
| 0.95 | 3.4 | 0.95 | 2.5 | 0.95 | 1.7 | 0.95 | 1.9 | 0.95 | 2.4 |
| 1 | 1.2 | 1 | 1.2 | 1 | 1.2 | 1 | 1.2 | 1 | 1.2 |

HF-HFC-245cb-HCFO-1233zdE-HFO-1234zeE-HFO-1243zf

| Organics 0.9 F245cb + 0.033 F1234zeE + 0.033 F1233zdE + 0.034 F1243zf | | Organics 0.033 F245cb + 0.9 F1234zeE + 0.033 F1233zdE + 0.034 F1243zf | | Organics 0.033 F245cb + 0.033 F1234zeE + 0.9 F1233zdE + 0.034 F1243zf | | Organics 0.034 F245cb + 0.033 F1234zeE + 0.033 F1233zdE + 0.9 F1243zf | | Organics 0.25 F245cb + 0.25 F1234zeE + 0.25 F1233zdE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.6 | 0 | 4.8 | 0 | 1.8 | 0 | 5.7 | 0 | 4.3 |
| 0.05 | 5.8 | 0.05 | 5.8 | 0.05 | 2.9 | 0.05 | 6.6 | 0.05 | 5.4 |
| 0.1 | 5.8 | 0.1 | 5.8 | 0.1 | 2.9 | 0.1 | 6.6 | 0.1 | 5.4 |
| 0.15 | 5.8 | 0.15 | 5.8 | 0.15 | 2.9 | 0.15 | 6.6 | 0.15 | 5.4 |
| 0.2 | 5.8 | 0.2 | 5.8 | 0.2 | 2.9 | 0.2 | 6.6 | 0.2 | 5.4 |
| 0.25 | 5.8 | 0.25 | 5.8 | 0.25 | 2.9 | 0.25 | 6.6 | 0.25 | 5.4 |
| 0.3 | 5.8 | 0.3 | 5.8 | 0.3 | 2.9 | 0.3 | 6.6 | 0.3 | 5.4 |
| 0.35 | 5.8 | 0.35 | 5.8 | 0.35 | 2.9 | 0.35 | 6.6 | 0.35 | 5.4 |
| 0.4 | 5.8 | 0.4 | 5.8 | 0.4 | 2.9 | 0.4 | 6.6 | 0.4 | 5.4 |
| 0.45 | 5.8 | 0.45 | 5.8 | 0.45 | 2.9 | 0.45 | 6.6 | 0.45 | 5.4 |
| 0.5 | 5.8 | 0.5 | 5.7 | 0.5 | 2.9 | 0.5 | 6.6 | 0.5 | 5.4 |
| 0.55 | 5.8 | 0.55 | 5.7 | 0.55 | 2.9 | 0.55 | 6.6 | 0.55 | 5.4 |
| 0.6 | 5.8 | 0.6 | 5.6 | 0.6 | 2.9 | 0.6 | 6.6 | 0.6 | 5.4 |
| 0.65 | 5.8 | 0.65 | 5.5 | 0.65 | 2.8 | 0.65 | 6.5 | 0.65 | 5.4 |
| 0.7 | 5.8 | 0.7 | 5.4 | 0.7 | 2.8 | 0.7 | 6.4 | 0.7 | 5.4 |
| 0.75 | 5.8 | 0.75 | 5.2 | 0.75 | 2.8 | 0.75 | 6.3 | 0.75 | 5.2 |
| 0.8 | 5.8 | 0.8 | 4.8 | 0.8 | 2.7 | 0.8 | 6.0 | 0.8 | 5.0 |
| 0.85 | 5.7 | 0.85 | 4.3 | 0.85 | 2.5 | 0.85 | 5.5 | 0.85 | 4.5 |
| 0.9 | 4.9 | 0.9 | 3.6 | 0.9 | 2.2 | 0.9 | 4.7 | 0.9 | 3.9 |
| 0.95 | 3.5 | 0.95 | 2.6 | 0.95 | 1.8 | 0.95 | 3.3 | 0.95 | 2.8 |
| 1 | 1.2 | 1 | 1.2 | 1 | 1.2 | 1 | 1.2 | 1 | 1.2 |

HF-HFC-245cb-HCFO-1233zdE-HFO-1234zeZ-HFO-1243zf

| Organics 0.9 F245cb + 0.033 F1234zeZ + 0.033 F1233zdE + 0.034 F1243zf | | Organics 0.033 F245cb + 0.9 F1234zeZ + 0.033 F1233zdE + 0.034 F1243zf | | Organics 0.033 F245cb + 0.033 F1234zeZ + 0.9 F1233zdE + 0.034 F1243zf | | Organics 0.034 F245cb + 0.033 F1234zeZ + 0.033 F1233zdE + 0.9 F1243zf | | Organics 0.25 F245cb + 0.25 F1234zeZ + 0.25 F1233zdE + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.5 | 0 | 2.0 | 0 | 1.7 | 0 | 5.6 | 0 | 3.5 |
| 0.05 | 5.7 | 0.05 | 3.2 | 0.05 | 2.8 | 0.05 | 6.5 | 0.05 | 4.6 |
| 0.1 | 5.7 | 0.1 | 3.2 | 0.1 | 2.8 | 0.1 | 6.6 | 0.1 | 4.6 |
| 0.15 | 5.7 | 0.15 | 3.2 | 0.15 | 2.8 | 0.15 | 6.6 | 0.15 | 4.6 |
| 0.2 | 5.7 | 0.2 | 3.2 | 0.2 | 2.8 | 0.2 | 6.5 | 0.2 | 4.6 |
| 0.25 | 5.7 | 0.25 | 3.2 | 0.25 | 2.8 | 0.25 | 6.5 | 0.25 | 4.6 |
| 0.3 | 5.7 | 0.3 | 3.2 | 0.3 | 2.8 | 0.3 | 6.5 | 0.3 | 4.6 |
| 0.35 | 5.7 | 0.35 | 3.2 | 0.35 | 2.8 | 0.35 | 6.5 | 0.35 | 4.6 |
| 0.4 | 5.7 | 0.4 | 3.2 | 0.4 | 2.8 | 0.4 | 6.5 | 0.4 | 4.6 |
| 0.45 | 5.7 | 0.45 | 3.2 | 0.45 | 2.8 | 0.45 | 6.5 | 0.45 | 4.6 |
| 0.5 | 5.7 | 0.5 | 3.2 | 0.5 | 2.8 | 0.5 | 6.5 | 0.5 | 4.7 |
| 0.55 | 5.7 | 0.55 | 3.2 | 0.55 | 2.8 | 0.55 | 6.5 | 0.55 | 4.7 |
| 0.6 | 5.7 | 0.6 | 3.2 | 0.6 | 2.8 | 0.6 | 6.5 | 0.6 | 4.7 |
| 0.65 | 5.7 | 0.65 | 3.2 | 0.65 | 2.8 | 0.65 | 6.4 | 0.65 | 4.7 |
| 0.7 | 5.7 | 0.7 | 3.2 | 0.7 | 2.8 | 0.7 | 6.4 | 0.7 | 4.7 |
| 0.75 | 5.7 | 0.75 | 3.1 | 0.75 | 2.8 | 0.75 | 6.2 | 0.75 | 4.7 |
| 0.8 | 5.7 | 0.8 | 3.0 | 0.8 | 2.6 | 0.8 | 5.9 | 0.8 | 4.5 |
| 0.85 | 5.6 | 0.85 | 2.8 | 0.85 | 2.4 | 0.85 | 5.4 | 0.85 | 4.1 |
| 0.9 | 4.8 | 0.9 | 2.5 | 0.9 | 2.2 | 0.9 | 4.6 | 0.9 | 3.5 |
| 0.95 | 3.4 | 0.95 | 1.9 | 0.95 | 1.8 | 0.95 | 3.3 | 0.95 | 2.6 |
| 1 | 1.2 | 1 | 1.2 | 1 | 1.2 | 1 | 1.2 | 1 | 1.2 |

HF-HCFO-1233zdE-HFO-1234zeE-HFO-1234zeZ-HFO-1243zf

| Organics 0.9 F1234zeE + 0.033 F1234zeZ + 0.033 F1233zdE + 0.034 F1243zf | | Organics 0.033 F1234zeE + 0.9 F1234zeZ + 0.033 F1233zdE + 0.034 F1243zf | | Organics 0.033 F1234zeE + 0.033 F1234zeZ + 0.9 F1233zdE + 0.034 F1243zf | | Organics 0.034 F1234zeE + 0.033 F1234zeZ + 0.033 F1233zdE + 0.9 F1243zf | | Organics 0.25 F1234zeE + 0.25 F1234zeZ + 0.25 F1233zdE + 0.25 F1243zf | |
|---|---|---|---|---|---|---|---|---|---|
| MASSFRAC HF | TOTAL PRES bar | MASSFRAC HF | TOTAL PRES bar | MASSFRAC HF | TOTAL PRES bar | MASSFRAC HF | TOTAL PRES bar | MASSFRAC HF | TOTAL PRES bar |
| 0 | 4.7 | 0 | 2.1 | 0 | 1.7 | 0 | 5.6 | 0 | 3.6 |
| 0.05 | 5.7 | 0.05 | 3.2 | 0.05 | 2.8 | 0.05 | 6.5 | 0.05 | 4.7 |
| 0.1 | 5.7 | 0.1 | 3.2 | 0.1 | 2.8 | 0.1 | 6.6 | 0.1 | 4.7 |
| 0.15 | 5.7 | 0.15 | 3.2 | 0.15 | 2.8 | 0.15 | 6.5 | 0.15 | 4.7 |
| 0.2 | 5.7 | 0.2 | 3.2 | 0.2 | 2.8 | 0.2 | 6.5 | 0.2 | 4.7 |
| 0.25 | 5.7 | 0.25 | 3.2 | 0.25 | 2.8 | 0.25 | 6.5 | 0.25 | 4.7 |
| 0.3 | 5.7 | 0.3 | 3.2 | 0.3 | 2.8 | 0.3 | 6.5 | 0.3 | 4.6 |
| 0.35 | 5.7 | 0.35 | 3.1 | 0.35 | 2.8 | 0.35 | 6.5 | 0.35 | 4.6 |
| 0.4 | 5.7 | 0.4 | 3.1 | 0.4 | 2.8 | 0.4 | 6.5 | 0.4 | 4.6 |
| 0.45 | 5.7 | 0.45 | 3.1 | 0.45 | 2.7 | 0.45 | 6.5 | 0.45 | 4.6 |
| 0.5 | 5.6 | 0.5 | 3.1 | 0.5 | 2.7 | 0.5 | 6.5 | 0.5 | 4.6 |
| 0.55 | 5.6 | 0.55 | 3.1 | 0.55 | 2.7 | 0.55 | 6.5 | 0.55 | 4.6 |
| 0.6 | 5.5 | 0.6 | 3.1 | 0.6 | 2.7 | 0.6 | 6.5 | 0.6 | 4.6 |
| 0.65 | 5.4 | 0.65 | 3.1 | 0.65 | 2.7 | 0.65 | 6.4 | 0.65 | 4.6 |
| 0.7 | 5.3 | 0.7 | 3.1 | 0.7 | 2.7 | 0.7 | 6.3 | 0.7 | 4.5 |
| 0.75 | 5.0 | 0.75 | 3.1 | 0.75 | 2.7 | 0.75 | 6.2 | 0.75 | 4.3 |
| 0.8 | 4.7 | 0.8 | 3.0 | 0.8 | 2.6 | 0.8 | 5.9 | 0.8 | 4.1 |
| 0.85 | 4.2 | 0.85 | 2.7 | 0.85 | 2.4 | 0.85 | 5.4 | 0.85 | 3.7 |
| 0.9 | 3.5 | 0.9 | 2.4 | 0.9 | 2.1 | 0.9 | 4.6 | 0.9 | 3.2 |
| 0.95 | 2.5 | 0.95 | 1.9 | 0.95 | 1.7 | 0.95 | 3.3 | 0.95 | 2.4 |
| 1 | 1.2 | 1 | 1.2 | 1 | 1.2 | 1 | 1.2 | 1 | 1.2 |

HF-HFC-245cb-HFO-1234zeE-HFO-1234zeZ-HFO-1243zf

| Organics 0.9 F245cb + 0.033 F1234zeE + 0.033 F1234zeZ + 0.034 F1243zf | | Organics 0.033 F245cb + 0.9 F1234zeE + 0.033 F1234zeZ + 0.034 F1243zf | | Organics 0.033 F245cb + 0.033 F1234zeE + 0.9 F1234zeZ + 0.034 F1243zf | | Organics 0.034 F245cb + 0.033 F1234zeE + 0.033 F1234zeZ + 0.9 F1243zf | | Organics 0.25 F245cb + 0.25 F1234zeE + 0.25 F1234zeZ + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.6 | 0 | 4.8 | 0 | 2.2 | 0 | 5.7 | 0 | 4.4 |
| 0.05 | 5.8 | 0.05 | 5.8 | 0.05 | 3.3 | 0.05 | 6.6 | 0.05 | 5.4 |
| 0.1 | 5.8 | 0.1 | 5.8 | 0.1 | 3.3 | 0.1 | 6.7 | 0.1 | 5.4 |
| 0.15 | 5.8 | 0.15 | 5.8 | 0.15 | 3.3 | 0.15 | 6.6 | 0.15 | 5.4 |
| 0.2 | 5.8 | 0.2 | 5.8 | 0.2 | 3.3 | 0.2 | 6.6 | 0.2 | 5.4 |
| 0.25 | 5.8 | 0.25 | 5.8 | 0.25 | 3.3 | 0.25 | 6.6 | 0.25 | 5.4 |
| 0.3 | 5.8 | 0.3 | 5.8 | 0.3 | 3.3 | 0.3 | 6.6 | 0.3 | 5.4 |
| 0.35 | 5.8 | 0.35 | 5.8 | 0.35 | 3.3 | 0.35 | 6.6 | 0.35 | 5.4 |
| 0.4 | 5.8 | 0.4 | 5.8 | 0.4 | 3.3 | 0.4 | 6.6 | 0.4 | 5.4 |
| 0.45 | 5.8 | 0.45 | 5.8 | 0.45 | 3.3 | 0.45 | 6.6 | 0.45 | 5.4 |
| 0.5 | 5.8 | 0.5 | 5.7 | 0.5 | 3.3 | 0.5 | 6.6 | 0.5 | 5.4 |
| 0.55 | 5.8 | 0.55 | 5.7 | 0.55 | 3.3 | 0.55 | 6.6 | 0.55 | 5.4 |
| 0.6 | 5.8 | 0.6 | 5.6 | 0.6 | 3.3 | 0.6 | 6.6 | 0.6 | 5.4 |
| 0.65 | 5.8 | 0.65 | 5.5 | 0.65 | 3.3 | 0.65 | 6.5 | 0.65 | 5.4 |
| 0.7 | 5.8 | 0.7 | 5.4 | 0.7 | 3.2 | 0.7 | 6.4 | 0.7 | 5.4 |
| 0.75 | 5.8 | 0.75 | 5.2 | 0.75 | 3.2 | 0.75 | 6.3 | 0.75 | 5.3 |
| 0.8 | 5.8 | 0.8 | 4.8 | 0.8 | 3.1 | 0.8 | 6.0 | 0.8 | 5.0 |
| 0.85 | 5.7 | 0.85 | 4.3 | 0.85 | 2.9 | 0.85 | 5.5 | 0.85 | 4.6 |
| 0.9 | 4.9 | 0.9 | 3.6 | 0.9 | 2.5 | 0.9 | 4.7 | 0.9 | 3.9 |
| 0.95 | 3.5 | 0.95 | 2.6 | 0.95 | 2.0 | 0.95 | 3.3 | 0.95 | 2.8 |
| 1 | 1.2 | 1 | 1.2 | 1 | 1.2 | 1 | 1.2 | 1 | 1.2 |

Example 8: Temperature and Pressure Range of Penternary Mixtures

| System with 5 compounds | Boiling point range | |
|---|---|---|
| | Temperature ° C. | Pressure bar abs |
| HF - HCFO-1233xf - HFC-245cb - HCFO-1233zdE - HFO-1234zeE | 0 to 40 | ~1.0~8.9 |
| HF - HCFO-1233xf - HFC-245cb - HCFO-1233zdE - HFO-1234zeZ | 0 to 40 | ~1.0 to ~8.8 |
| HF - HCFO-1233xf - HFC-245cb - HFO-1234zeE - HFO-1234zeZ | 0 to 40 | ~1.1 to ~8.8 |
| HF - HCFO-1233xf - HFC-245cb - HFO-1234zeE - HFO-1243zf | 0 to 40 | ~1.0 to ~10.2 |
| HF - HCFO-1233xf - HFC-245cb - HFO-1234zeE - HFO-1234yf | 0 to 40 | ~1.0 to ~11.4 |
| HF - HCFO-1233xf - HFC-245cb - HFO-1234zeZ - HFO-1243zf | 0 to 40 | ~1.1 to ~10.1 |
| HF - HCFO-1233xf - HFC-245cb - HFO-1234zeZ - HFO-1234yf | 0 to 40 | ~1.1 to ~11.2 |
| HF - HCFO-1233xf - HFO-1234yf - HFO-1234zeE - HFO-1234zeZ | 0 to 40 | ~1.1 to ~11.2 |
| HF - HCFO-1233xf - HFO-1234yf - HFO-1234zeE - HFO-1243zf | 0 to 40 | ~1.2 to ~11.4 |
| HF - HCFO-1233xf - HFO-1234yf - HFO-1234zeE - HCFO-1233zdE | 0 to 40 | ~1.0 to ~11.2 |
| HF - HCFO-1233xf - HFO-1234yf - HFO-1234zeZ - HFO-1243zf | 0 to 40 | ~1.2 to ~11.2 |
| HF - HCFO-1233xf - HFO-1234yf - HFO-1234zeZ - HCFO-1233zdE | 0 to 40 | ~1.0~11.1 |
| HF - HCFO-1233xf - HCFO-1233zdE - HFO-1234zeE - HFO-1234zeZ | 0 to 40 | ~0.9 to ~8.6 |
| HF - HCFO-1233xf - HCFO-1233zdE - HFO-1234zeE - HFO-1243zf | 0 to 40 | ~1.0 to ~10.1 |
| HF - HCFO-1233xf - HCFO-1233zdE - HFO-1234zeZ - HFO-1243zf | 0 to 40 | ~1.0 to ~9.9 |
| HF - HCFO-1233xf - HFO-1234zeE - HFO-1234zeZ - HFO-1243zf | 0 to 40 | ~1.0 to ~10.1 |
| HF - HFO-1234yf - HFO-1234zeE - HFO-1234zeZ - HCFO-1233zdE | 0 to 40 | ~1.0 to ~11.2 |
| HF - HFO-1234yf - HFO-1234zeE - HFO-1234zeZ - HFO-1243zf | 0 to 40 | ~1.3 to ~11.4 |
| HF - HFO-1234yf - HFO-1234zeE - HCFO-1233zdE - HFO-1243zf | 0 to 40 | ~1.0 to ~11.4 |
| HF - HFO-1234yf - HFO-1234zeZ - HCFO-1233zdE - HFO-1243zf | 0 to 40 | ~1.1 to ~11.2 |
| HF - HFO-1234yf - HFC-245cb - HFO-1234zeE - HCFO-1233zdE | 0 to 40 | ~1.1 to ~11.4 |
| HF - HFO-1234yf - HFC-245cb - HFO-1234zeE - HFO-1234zeZ | 0 to 40 | ~1.3 to ~9.1 |
| HF - HFO-1234yf - HFC-245cb - HFO-1234zeE - HFO-1243zf | 0 to 40 | ~2.5 to ~11.6 |
| HF - HFO-1234yf - HFC-245cb - HFO-1234zeZ - HCFO-1233zdE | 0 to 40 | ~1.0 to ~11.2 |
| HF - HFO-1234yf - HFC-245cb - HFO-1234zeZ- HFO-1243zf | 0 to 40 | ~1.3 to ~10.3 |
| HF - HFC-245cb - HCFO-1233zdE - HFO-1234zeE - HFO-1234zeZ | 0 to 40 | ~1.0 to ~8.9 |
| HF - HFC-245cb - HCFO-1233zdE - F 1234zeE - HFO-1243zf | 0 to 40 | ~1.1 to ~10.2 |
| HF - HFC-245cb - HCFO-1233zdE - F 1234zeZ - HFO-1243zf | 0 to 40 | ~1.0 to ~10.1 |
| HF - HFC-245cb - HFO-1234zeE - F 1234zeZ - HFO-1243zf | 0 to 40 | ~1.2 to ~10.2 |
| HF - HCFO-1233zdE - HFO-1234zeE - HFO-1234zeZ - HFO-1243zf | 0 to 40 | ~1.0 to ~10.1 |

Example 9: Decantation Range of Penternary Mixtures

| System with 5 compounds | Decantation ranges - Mass percentage of HF | | |
|---|---|---|---|
| | Isotherm 0° C. | Isotherm 25° C. | Isotherm 40° C. |
| HF - HCFO-1233xf - HFC-245cb - HCFO-1233zdE - HFO-1234zeE | 5-75 | 5-70 | 10-60 |
| HF - HCFO-1233xf - HFC-245cb - HCFO-1233zdE - HFO-1234zeZ | 5-80 | 5-75 | 5-70 |
| HF - HCFO-1233xf - HFC-245cb - HFO-1234zeE - HFO-1234zeZ | 5-75 | 5-70 | 10-60 |
| HF - HCFO-1233xf - HFC-245cb - HFO-1234zeE - HFO-1243zf | 10-75 | 10-65 | * |
| HF - HCFO-1233xf - HFC-245cb - HFO-1234zeE - HFO-1234yf | 5-75 | 10-70 | * |
| HF - HCFO-1233xf - HFC-245cb - HFO-1234zeZ - HFO-1243zf | 5-75 | 5-70 | 10-60 |
| HF - HCFO-1233xf - HFC-245cb - HFO-1234zeZ - HFO-1234yf | 5-75 | 5-75 | 10-65 |
| HF - HCFO-1233xf - HFO-1234yf - HFO-1234zeE - HFO-1234zeZ | 5-75 | 5-65 | 15-45 |
| HF - HCFO-1233xf - HFO-1234yf - HFO-1234zeE - HFO-1243zf | 5-70 | 10-60 | * |
| HF - HCFO-1233xf - HFO-1234yf- HFO-1234zeE - HCFO-1233zdE | 5-75 | 5-65 | 10-50 |
| HF - HCFO-1233xf - HFO-1234yf - HFO-1234zeZ - HFO-1243zf | 5-75 | 10-65 | 20-40 |
| HF - HCFO-1233xf - HFO-1234yf - HFO-1234zeZ - HCFO-1233zdE | 5-75 | 5-70 | 10-60 |
| HF - HCFO-1233xf - HCFO-1233zdE - HFO-1234zeE - HFO-1234zeZ | 5-75 | 5-70 | 5-60 |
| HF - HCFO-1233xf - HCFO-1233zdE - HFO-1234zeE - HFO-1243zf | 5-75 | 5-65 | 15-45 |
| HF - HCFO-1233xf - HCFO-1233zdE - HFO-1234zeZ - HFO-1243zf | 5-75 | 5-70 | 10-60 |
| HF - HCFO-1233xf - HFO-1234zeE - HFO-1234zeZ - HFO-1243zf | 5-75 | 10-65 | 15-40 |
| HF - HFO-1234yf - HFO-1234zeE - HFO-1234zeZ - HCFO-1233zdE | 5-75 | 5-65 | 15-45 |
| HF - HFO-1234yf - HFO-1234zeE - HFO-1234zeZ - HFO-1243zf | 5-70 | 10-60 | * |
| HF - HFO-1234yf - HFO-1234zeE - HCFO-1233zdE - HFO-1243zf | 5-70 | 10-60 | * |
| HF - HFO-1234yf - HFO-1234zeZ - HCFO-1233zdE - HFO-1243zf | 5-75 | 10-65 | 15-45 |
| HF - HFO-1234yf - HFC-245cb - HFO-1234zeE - HCFO-1233zdE | 5-75 | 10-70 | * |
| HF - HFO-1234yf - HFC-245cb - HFO-1234zeE - HFO-1234zeZ | 5-75 | 10-70 | * |
| HF - HFO-1234yf - HFC-245cb - HFO-1234zeE - HFO-1243zf | 5-75 | 15-65 | * |
| HF - HFO-1234yf - HFC-245cb - HFO-1234zeZ - HCFO-1233zdE | 5-75 | 5-75 | 10-65 |
| HF - HFO-1234yf - HFC-245cb - HFO-1234zeZ - HFO-1243zf | 5-75 | 10-70 | * |
| HF - HFC-245cb - HCFO-1233zdE - HFO-1234zeE - HFO-1234zeZ | 5-75 | 5-70 | 10-60 |
| HF - HFC-245cb - HCFO-1233zdE - F 1234zeE - HFO-1243zf | 5-75 | 10-65 | * |
| HF - HFC-245cb - HCFO-1233zdE - F 1234zeZ - HFO-1243zf | 5-75 | 5-70 | 10-60 |
| HF - HFC-245cb - HFO-1234zeE - F 1234zeZ - HFO-1243zf | 5-75 | 10-65 | * |
| HF - HCFO-1233zdE - HFO-1234zeE - HFO-1234zeZ - HFO-1243zf | 5-75 | 5-65 | 15-50 |

Example 10: Systems with Six Compounds, Isotherm at 25° C.

| HF-HCFO-1233xf-HFO-1234yf-HFC-245cb-HFO-1234zeE-HFO-1234zeZ | | | | | |
|---|---|---|---|---|---|
| Organics 0.2 F1233xf + 0.2 F1234yf + 0.2 F245cb 0.2 F1234zeE + 0.2 F1234zeZ | | Organics 0.96 F1233xf + 0.01 F1234yf + 0.01 F245cb + 0.01 F1234zeE + 0.01 F1234zeZ | | Organics 0.01 F1233xf + 0.96 F1234yf + 0.01 F245cb + 0.01 F1234zeE + 0.01 F1234zeZ | |
| MASSFRAC HF | TOTAL PRESSURE bar | MASSFRAC HF | TOTAL PRESSURE bar | MASSFRAC HF | TOTAL PRESSURE bar |
| 0 | 4.0 | 0 | 1.7 | 0 | 6.7 |
| 0.05 | 5.1 | 0.05 | 2.8 | 0.05 | 7.6 |
| 0.1 | 5.1 | 0.1 | 2.8 | 0.1 | 7.6 |
| 0.15 | 5.1 | 0.15 | 2.8 | 0.15 | 7.6 |
| 0.2 | 5.1 | 0.2 | 2.8 | 0.2 | 7.6 |
| 0.25 | 5.1 | 0.25 | 2.8 | 0.25 | 7.6 |
| 0.3 | 5.1 | 0.3 | 2.8 | 0.3 | 7.6 |
| 0.35 | 5.1 | 0.35 | 2.8 | 0.35 | 7.6 |
| 0.4 | 5.1 | 0.4 | 2.8 | 0.4 | 7.6 |
| 0.45 | 5.1 | 0.45 | 2.8 | 0.45 | 7.6 |
| 0.5 | 5.1 | 0.5 | 2.8 | 0.5 | 7.6 |
| 0.55 | 5.1 | 0.55 | 2.8 | 0.55 | 7.6 |
| 0.6 | 5.1 | 0.6 | 2.8 | 0.6 | 7.6 |
| 0.65 | 5.1 | 0.65 | 2.8 | 0.65 | 7.6 |
| 0.7 | 5.1 | 0.7 | 2.8 | 0.7 | 7.6 |
| 0.75 | 5.0 | 0.75 | 2.8 | 0.75 | 7.5 |
| 0.8 | 4.8 | 0.8 | 2.6 | 0.8 | 7.1 |
| 0.85 | 4.4 | 0.85 | 2.5 | 0.85 | 6.5 |
| 0.9 | 3.7 | 0.9 | 2.2 | 0.9 | 5.5 |
| 0.95 | 2.7 | 0.95 | 1.8 | 0.95 | 3.8 |
| 1 | 1.2 | 1 | 1.2 | 1 | 1.2 |

| HF-HCFO-1233xf-HFO-1234yf-HFC-245cb-HFO-1234zeE-HFO-1234zeZ ||||||
|---|---|---|---|---|---|
| Organics 0.01 F1233xf + 0.01 F1234yf + 0.96 F245cb + 0.01 F1234zeE + 0.01 F1234zeZ ||  Organics 0.01 F1233xf + 0.01 F1234yf + 0.01 F245cb + 0.96 F1234zeE + 0.01 F1234zeZ || Organics 0.01 F1233xf + 0.01 F1234yf + 0.01 F245cb + 0.01 F1234zeE + 0.96 F1234zeZ ||
| MASSFRAC HF | TOTAL PRESSURE bar | MASSFRAC HF | TOTAL PRESSURE bar | MASSFRAC HF | TOTAL PRESSURE bar |
| 0 | 4.6 | 0 | 4.8 | 0 | 1.9 |
| 0.05 | 5.8 | 0.05 | 5.8 | 0.05 | 3.0 |
| 0.1 | 5.8 | 0.1 | 5.8 | 0.1 | 3.0 |
| 0.15 | 5.8 | 0.15 | 5.8 | 0.15 | 3.0 |
| 0.2 | 5.8 | 0.2 | 5.8 | 0.2 | 3.0 |
| 0.25 | 5.8 | 0.25 | 5.8 | 0.25 | 3.0 |
| 0.3 | 5.8 | 0.3 | 5.8 | 0.3 | 3.0 |
| 0.35 | 5.8 | 0.35 | 5.8 | 0.35 | 3.0 |
| 0.4 | 5.8 | 0.4 | 5.8 | 0.4 | 3.0 |
| 0.45 | 5.8 | 0.45 | 5.8 | 0.45 | 3.0 |
| 0.5 | 5.8 | 0.5 | 5.7 | 0.5 | 3.0 |
| 0.55 | 5.8 | 0.55 | 5.7 | 0.55 | 3.0 |
| 0.6 | 5.8 | 0.6 | 5.6 | 0.6 | 3.0 |
| 0.65 | 5.8 | 0.65 | 5.5 | 0.65 | 3.0 |
| 0.7 | 5.8 | 0.7 | 5.4 | 0.7 | 3.0 |
| 0.75 | 5.8 | 0.75 | 5.1 | 0.75 | 3.0 |
| 0.8 | 5.8 | 0.8 | 4.8 | 0.8 | 2.9 |
| 0.85 | 5.8 | 0.85 | 4.3 | 0.85 | 2.7 |
| 0.9 | 5.0 | 0.9 | 3.6 | 0.9 | 2.4 |
| 0.95 | 3.5 | 0.95 | 2.6 | 0.95 | 1.9 |
| 1 | 1.2 | 1 | 1.2 | 1 | 1.2 |

| HF-HCFO-1233xf-HFO-1234yf-HFC-245cb-HFO-1234zeE-HCFO-1233zdE ||||||
|---|---|---|---|---|---|
| Organics 0.2 F1233xf + 0.2 F1234yf + 0.2 F245cb 0.2 F1234zeE + 0.2 F1233zdE || Organics 0.96 F1233xf + 0.01 F1234yf + 0.01 F245cb + 0.01 F1234zeE + 0.01 F1233zdE || Organics 0.01 F1233xf + 0.96 F1234yf + 0.01 F245cb + 0.01 F1234zeE + 0.01 F1233zdE ||
| MASSFRAC HF | TOTAL PRESSURE bar | MASSFRAC HF | TOTAL PRESSURE bar | MASSFRAC HF | TOTAL PRESSURE bar |
| 0 | 3.9 | 0 | 1.7 | 0 | 6.7 |
| 0.05 | 5.0 | 0.05 | 2.8 | 0.05 | 7.6 |
| 0.1 | 5.0 | 0.1 | 2.8 | 0.1 | 7.6 |
| 0.15 | 5.0 | 0.15 | 2.8 | 0.15 | 7.6 |
| 0.2 | 5.0 | 0.2 | 2.8 | 0.2 | 7.6 |
| 0.25 | 5.0 | 0.25 | 2.8 | 0.25 | 7.6 |
| 0.3 | 5.0 | 0.3 | 2.8 | 0.3 | 7.6 |
| 0.35 | 5.0 | 0.35 | 2.8 | 0.35 | 7.6 |
| 0.4 | 5.0 | 0.4 | 2.8 | 0.4 | 7.6 |
| 0.45 | 5.0 | 0.45 | 2.8 | 0.45 | 7.6 |
| 0.5 | 5.0 | 0.5 | 2.8 | 0.5 | 7.6 |
| 0.55 | 5.0 | 0.55 | 2.8 | 0.55 | 7.6 |
| 0.6 | 5.0 | 0.8 | 2.8 | 0.6 | 7.6 |
| 0.65 | 5.0 | 0.65 | 2.8 | 0.65 | 7.6 |
| 0.7 | 5.1 | 0.7 | 2.8 | 0.7 | 7.6 |
| 0.75 | 5.0 | 0.75 | 2.8 | 0.75 | 7.5 |
| 0.8 | 4.7 | 0.8 | 2.6 | 0.8 | 7.1 |
| 0.85 | 4.3 | 0.85 | 2.5 | 0.85 | 6.5 |
| 0.9 | 3.7 | 0.9 | 2.2 | 0.9 | 5.5 |
| 0.95 | 2.7 | 0.95 | 1.8 | 0.95 | 3.8 |
| 1 | 1.2 | 1 | 1.2 | 1 | 1.2 |

| HF-HCFO-1233xf-HFO-1234yf-HFC-245cb-HFO-1234zeE-HCFO-1233zdE ||||||
|---|---|---|---|---|---|
| Organics 0.01 F1233xf + 0.01 F1234yf + 0.96 F245cb + 0.01 F1234zeE + 0.01 F1233zdE ||  Organics 0.01 F1233xf + 0.01 F1234yf + 0.01 F245cb + 0.96 F1234zeE + 0.01 F1233zdE || Organics 0.01 F1233xf + 0.01 F1234yf + 0.01 F245cb + 0.01 F1234zeE + 0.96 F1233zdE ||
| MASSFRAC HF | TOTAL PRESSURE bar | MASSFRAC HF | TOTAL PRESSURE bar | MASSFRAC HF | TOTAL PRESSURE bar |
| 0 | 4.6 | 0 | 4.8 | 0 | 1.5 |
| 0.05 | 5.8 | 0.05 | 5.8 | 0.05 | 2.6 |
| 0.1 | 5.8 | 0.1 | 5.8 | 0.1 | 2.6 |
| 0.15 | 5.8 | 0.15 | 5.8 | 0.15 | 2.6 |
| 0.2 | 5.8 | 0.2 | 5.8 | 0.2 | 2.6 |
| 0.25 | 5.8 | 0.25 | 5.8 | 0.25 | 2.6 |
| 0.3 | 5.8 | 0.3 | 5.8 | 0.3 | 2.6 |
| 0.35 | 5.8 | 0.35 | 5.8 | 0.35 | 2.6 |
| 0.4 | 5.8 | 0.4 | 5.8 | 0.4 | 2.6 |
| 0.45 | 5.8 | 0.45 | 5.8 | 0.45 | 2.6 |
| 0.5 | 5.8 | 0.5 | 5.7 | 0.5 | 2.6 |
| 0.55 | 5.8 | 0.55 | 5.7 | 0.55 | 2.6 |
| 0.6 | 5.8 | 0.6 | 5.8 | 0.6 | 2.6 |
| 0.65 | 5.8 | 0.65 | 5.5 | 0.65 | 2.6 |
| 0.7 | 5.8 | 0.7 | 5.4 | 0.7 | 2.6 |
| 0.75 | 5.8 | 0.75 | 5.1 | 0.75 | 2.6 |
| 0.8 | 5.8 | 0.8 | 4.8 | 0.8 | 2.4 |
| 0.85 | 5.8 | 0.85 | 4.3 | 0.85 | 2.3 |
| 0.9 | 5.0 | 0.9 | 3.6 | 0.9 | 2.0 |
| 0.95 | 3.5 | 0.95 | 2.6 | 0.95 | 1.7 |
| 1 | 1.2 | 1 | 1.2 | 1 | 1.2 |

| HF-HCFO-1233xf-HFO-1234yf-HFC-245cb-HFO-1234zeE-HFO-1243zf ||||||
|---|---|---|---|---|---|
| Organics 0.2 F1233xf + 0.2 F1234yf + 0.2 F245cb 0.2 F1234zeE + 0.2 F1243zf || Organics 0.96 F1233xf + 0.01 F1234yf + 0.01 F245cb + 0.01 F1234zeE + 0.01 F1243zf || Organics 0.01 F1233xf + 0.96 F1234yf + 0.01 F245cb + 0.01 F1234zeE + 0.01 F1243zf ||
| MASSFRAC HF | TOTAL PRESSURE bar | MASSFRAC HF | TOTAL PRESSURE bar | MASSFRAC HF | TOTAL PRESSURE bar |
| 0 | 4.9 | 0 | 1.7 | 0 | 6.7 |
| 0.05 | 5.9 | 0.05 | 2.8 | 0.05 | 7.7 |
| 0.1 | 5.9 | 0.1 | 2.8 | 0.1 | 7.7 |
| 0.15 | 5.9 | 0.15 | 2.8 | 0.15 | 7.7 |
| 0.2 | 5.9 | 0.2 | 2.8 | 0.2 | 7.7 |
| 0.25 | 5.9 | 0.25 | 2.8 | 0.25 | 7.7 |
| 0.3 | 5.9 | 0.3 | 2.8 | 0.3 | 7.7 |
| 0.35 | 5.9 | 0.35 | 2.8 | 0.35 | 7.7 |
| 0.4 | 5.9 | 0.4 | 2.8 | 0.4 | 7.7 |
| 0.45 | 5.9 | 0.45 | 2.8 | 0.45 | 7.7 |
| 0.5 | 5.9 | 0.5 | 2.8 | 0.5 | 7.7 |
| 0.55 | 5.9 | 0.55 | 2.8 | 0.55 | 7.7 |
| 0.6 | 5.9 | 0.6 | 2.8 | 0.6 | 7.7 |
| 0.65 | 5.9 | 0.65 | 2.8 | 0.65 | 7.7 |
| 0.7 | 5.9 | 0.7 | 2.8 | 0.7 | 7.6 |
| 0.75 | 5.7 | 0.75 | 2.8 | 0.75 | 7.5 |
| 0.8 | 5.5 | 0.8 | 2.7 | 0.8 | 7.2 |
| 0.85 | 5.0 | 0.85 | 2.5 | 0.85 | 6.6 |
| 0.9 | 4.2 | 0.9 | 2.2 | 0.9 | 5.5 |
| 0.95 | 3.0 | 0.95 | 1.8 | 0.95 | 3.8 |
| 1 | 1.2 | 1 | 1.2 | 1 | 1.2 |

HF-HCFO-1233xf-HFO-1234yf-HFC-245cb-HFO-1234zeE-HFO-1243zf

| Organics 0.01 F1233xf + 0.01 F1234yf + 0.96 F245cb + 0.01 F1234zeE + 0.01 F1243zf | | Organics 0.01 F1233xf + 0.01 F1234yf + 0.01 F245cb + 0.96 F1234zeE + 0.01 F1243zf | | Organics 0.01 F1233xf + 0.01 F1234yf + 0.01 F245cb + 0.01 F1234zeE + 0.96 F1243zf | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.7 | 0 | 4.9 | 0 | 5.8 |
| 0.05 | 5.8 | 0.05 | 5.8 | 0.05 | 6.7 |
| 0.1 | 5.8 | 0.1 | 5.9 | 0.1 | 6.8 |
| 0.15 | 5.8 | 0.15 | 5.8 | 0.15 | 6.8 |
| 0.2 | 5.8 | 0.2 | 5.8 | 0.2 | 6.8 |
| 0.25 | 5.8 | 0.25 | 5.8 | 0.25 | 6.8 |
| 0.3 | 5.8 | 0.3 | 5.8 | 0.3 | 6.8 |
| 0.35 | 5.8 | 0.35 | 5.8 | 0.35 | 6.8 |
| 0.4 | 5.8 | 0.4 | 5.8 | 0.4 | 6.8 |
| 0.45 | 5.8 | 0.45 | 5.8 | 0.45 | 6.7 |
| 0.5 | 5.8 | 0.5 | 5.8 | 0.5 | 6.7 |
| 0.55 | 5.8 | 0.55 | 5.7 | 0.55 | 6.7 |
| 0.6 | 5.8 | 0.6 | 5.7 | 0.6 | 6.7 |
| 0.65 | 5.8 | 0.65 | 5.6 | 0.65 | 6.6 |
| 0.7 | 5.8 | 0.7 | 5.4 | 0.7 | 6.5 |
| 0.75 | 5.8 | 0.75 | 5.2 | 0.75 | 6.4 |
| 0.8 | 5.8 | 0.8 | 4.8 | 0.8 | 6.1 |
| 0.85 | 5.8 | 0.85 | 4.3 | 0.85 | 5.6 |
| 0.9 | 5.0 | 0.9 | 3.6 | 0.9 | 4.8 |
| 0.95 | 3.5 | 0.95 | 2.6 | 0.95 | 3.4 |
| 1 | 1.2 | 1 | 1.2 | 1 | 1.2 |

HF-HCFO-1233xf-HFO-1234yf-HFC-245cb-HFO-1234zeZ-HCFO-1233zdE

| Organics 0.2 F1233xf + 0.2 F1234yf + 0.2 F245cb 0.2 F1234zeZ + 0.2 F1233zdE | | Organics 0.96 F1233xf + 0.01 F1234yf + 0.01 F245cb + 0.01 F1234zeZ + 0.01 F1233zdE | | Organics 0.01 F1233xf + 0.96 F1234yf + 0.01 F245cb + 0.01 F1234zeZ + 0.01 F1233zdE | |
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 3.3 | 0 | 1.6 | 0 | 6.6 |
| 0.05 | 4.4 | 0.05 | 2.8 | 0.05 | 7.6 |
| 0.1 | 4.4 | 0.1 | 2.8 | 0.1 | 7.6 |
| 0.15 | 4.4 | 0.15 | 2.8 | 0.15 | 7.6 |
| 0.2 | 4.4 | 0.2 | 2.8 | 0.2 | 7.6 |
| 0.25 | 4.4 | 0.25 | 2.8 | 0.25 | 7.6 |
| 0.3 | 4.4 | 0.3 | 2.8 | 0.3 | 7.6 |
| 0.35 | 4.4 | 0.35 | 2.8 | 0.35 | 7.6 |
| 0.4 | 4.4 | 0.4 | 2.8 | 0.4 | 7.6 |
| 0.45 | 4.4 | 0.45 | 2.8 | 0.45 | 7.6 |
| 0.5 | 4.4 | 0.5 | 2.8 | 0.5 | 7.6 |
| 0.55 | 4.4 | 0.55 | 2.8 | 0.55 | 7.6 |
| 0.6 | 4.4 | 0.6 | 2.8 | 0.6 | 7.6 |
| 0.65 | 4.5 | 0.65 | 2.8 | 0.65 | 7.6 |
| 0.7 | 4.5 | 0.7 | 2.8 | 0.7 | 7.6 |
| 0.75 | 4.5 | 0.75 | 2.8 | 0.75 | 7.4 |
| 0.8 | 4.3 | 0.8 | 2.6 | 0.8 | 7.1 |
| 0.85 | 4.0 | 0.85 | 2.4 | 0.85 | 6.5 |
| 0.9 | 3.4 | 0.9 | 2.2 | 0.9 | 5.5 |
| 0.95 | 2.5 | 0.95 | 1.7 | 0.95 | 3.8 |
| 1 | 1.2 | 1 | 1.2 | 1 | 1.2 |

| HF-HCFO-1233xf-HFO-1234yf-HFC-245cb-HFO-1234zeZ-HCFO-1233zdE ||||||
|---|---|---|---|---|---|
| Organics 0.01 F1233xf + 0.01 F1234yf + 0.96 F245cb + 0.01 F1234zeZ + 0.01 F1233zdE || Organics 0.01 F1233xf + 0.01 F1234yf + 0.01 F245cb + 0.96 F1234zeZ + 0.01 F1233zdE || Organics 0.01 F1233xf + 0.01 F1234yf + 0.01 F245cb + 0.01 F1234zeZ + 0.96 F1233zdE ||
| MASSFRAC HF | TOTAL PRESSURE bar | MASSFRAC HF | TOTAL PRESSURE bar | MASSFRAC HF | TOTAL PRESSURE bar |
| 0 | 4.6 | 0 | 1.9 | 0 | 1.4 |
| 0.05 | 5.8 | 0.05 | 3.0 | 0.05 | 2.5 |
| 0.1 | 5.8 | 0.1 | 3.0 | 0.1 | 2.5 |
| 0.15 | 5.8 | 0.15 | 3.0 | 0.15 | 2.5 |
| 0.2 | 5.8 | 0.2 | 3.0 | 0.2 | 2.5 |
| 0.25 | 5.8 | 0.25 | 3.0 | 0.25 | 2.5 |
| 0.3 | 5.8 | 0.3 | 3.0 | 0.3 | 2.5 |
| 0.35 | 5.8 | 0.35 | 3.0 | 0.35 | 2.5 |
| 0.4 | 5.8 | 0.4 | 3.0 | 0.4 | 2.5 |
| 0.45 | 5.8 | 0.45 | 3.0 | 0.45 | 2.5 |
| 0.5 | 5.8 | 0.5 | 3.0 | 0.5 | 2.5 |
| 0.55 | 5.8 | 0.55 | 3.0 | 0.55 | 2.5 |
| 0.6 | 5.8 | 0.6 | 3.0 | 0.6 | 2.5 |
| 0.65 | 5.8 | 0.65 | 3.0 | 0.65 | 2.5 |
| 0.7 | 5.8 | 0.7 | 3.0 | 0.7 | 2.5 |
| 0.75 | 5.8 | 0.75 | 3.0 | 0.75 | 2.5 |
| 0.8 | 5.8 | 0.8 | 2.9 | 0.8 | 2.4 |
| 0.85 | 5.8 | 0.85 | 2.7 | 0.85 | 2.3 |
| 0.9 | 5.0 | 0.9 | 2.3 | 0.9 | 2.0 |
| 0.95 | 3.5 | 0.95 | 1.9 | 0.95 | 1.7 |
| 1 | 1.2 | 1 | 1.2 | 1 | 1.2 |

| HF-HCFO-1233xf-HFO-1234yf-HFC-245cb-HFO-1234zeZ-HFO-1243zf ||||||
|---|---|---|---|---|---|
| Organics 0.2 F1233xf + 0.2 F1234yf + 0.2 F245cb 0.2 F1234zeZ + 0.2 F1243zf || Organics 0.96 F1233xf + 0.01 F1234yf + 0.01 F245cb + 0.01 F1234zeZ + 0.01 F1243zf || Organics 0.01 F1233xf + 0.96 F1234yf + 0.01 F245cb + 0.01 F1234zeZ + 0.01 F1243zf ||
| MASSFRAC HF | TOTAL PRESSURE bar | MASSFRAC HF | TOTAL PRESSURE bar | MASSFRAC HF | TOTAL PRESSURE bar |
| 0 | 4.2 | 0 | 1.7 | 0 | 6.7 |
| 0.05 | 5.3 | 0.05 | 2.8 | 0.05 | 7.6 |
| 0.1 | 5.3 | 0.1 | 2.8 | 0.1 | 7.7 |
| 0.15 | 5.3 | 0.15 | 2.8 | 0.15 | 7.6 |
| 0.2 | 5.3 | 0.2 | 2.8 | 0.2 | 7.6 |
| 0.25 | 5.3 | 0.25 | 2.8 | 0.25 | 7.6 |
| 0.3 | 5.3 | 0.3 | 2.8 | 0.3 | 7.6 |
| 0.35 | 5.3 | 0.35 | 2.8 | 0.35 | 7.6 |
| 0.4 | 5.3 | 0.4 | 2.8 | 0.4 | 7.6 |
| 0.45 | 5.3 | 0.45 | 2.8 | 0.45 | 7.6 |
| 0.5 | 5.3 | 0.5 | 2.8 | 0.5 | 7.6 |
| 0.55 | 5.3 | 0.55 | 2.8 | 0.55 | 7.6 |
| 0.6 | 5.3 | 0.6 | 2.8 | 0.6 | 7.6 |
| 0.65 | 5.3 | 0.65 | 2.8 | 0.65 | 7.6 |
| 0.7 | 5.3 | 0.7 | 2.8 | 0.7 | 7.6 |
| 0.75 | 5.3 | 0.75 | 2.8 | 0.75 | 7.5 |
| 0.8 | 5.1 | 0.8 | 2.7 | 0.8 | 7.2 |
| 0.85 | 4.7 | 0.85 | 2.5 | 0.85 | 6.6 |
| 0.9 | 4.0 | 0.9 | 2.2 | 0.9 | 5.5 |
| 0.95 | 2.9 | 0.95 | 1.8 | 0.95 | 3.8 |
| 1 | 1.2 | 1 | 1.2 | 1 | 1.2 |

| HF-HCFO-1233xf-HFO-1234yf-HFC-245cb-HFO-1234zeZ-HFO-1243zf ||||||
|---|---|---|---|---|---|
| Organics 0.01 F1233xf + 0.01 F1234yf + 0.96 F245cb + 0.01 F1234zeZ + 0.01 F1243zf || Organics 0.01 F1233xf + 0.01 F1234yf + 0.01 F245cb + 0.96 F1234zeZ + 0.01 F1243zf || Organics 0.01 F1233xf + 0.01 F1234yf + 0.01 F245cb + 0.01 F1234zeZ + 0.96 F1243zf ||
| MASSFRAC HF | TOTAL PRESSURE bar | MASSFRAC HF | TOTAL PRESSURE bar | MASSFRAC HF | TOTAL PRESSURE bar |
| 0 | 4.6 | 0 | 1.9 | 0 | 5.8 |
| 0.05 | 5.8 | 0.05 | 3.0 | 0.05 | 6.7 |
| 0.1 | 5.8 | 0.1 | 3.0 | 0.1 | 6.8 |
| 0.15 | 5.8 | 0.15 | 3.0 | 0.15 | 6.7 |
| 0.2 | 5.8 | 0.2 | 3.0 | 0.2 | 6.7 |
| 0.25 | 5.8 | 0.25 | 3.0 | 0.25 | 6.7 |
| 0.3 | 5.8 | 0.3 | 3.0 | 0.3 | 6.7 |
| 0.35 | 5.8 | 0.35 | 3.0 | 0.35 | 6.7 |
| 0.4 | 5.8 | 0.4 | 3.0 | 0.4 | 6.7 |
| 0.45 | 5.8 | 0.45 | 3.0 | 0.45 | 6.7 |
| 0.5 | 5.8 | 0.5 | 3.0 | 0.5 | 6.7 |
| 0.55 | 5.8 | 0.55 | 3.0 | 0.55 | 6.7 |
| 0.6 | 5.8 | 0.6 | 3.0 | 0.6 | 6.7 |
| 0.65 | 5.8 | 0.65 | 3.0 | 0.65 | 6.6 |
| 0.7 | 5.8 | 0.7 | 3.0 | 0.7 | 6.5 |
| 0.75 | 5.8 | 0.75 | 3.0 | 0.75 | 6.4 |
| 0.8 | 5.8 | 0.8 | 2.9 | 0.8 | 6.1 |
| 0.85 | 5.8 | 0.85 | 2.7 | 0.85 | 5.6 |
| 0.9 | 5.0 | 0.9 | 2.4 | 0.9 | 4.7 |
| 0.95 | 3.5 | 0.95 | 1.9 | 0.95 | 3.4 |
| 1 | 1.2 | 1 | 1.2 | 1 | 1.2 |

| HF - HCFO-1233xf - HFO-1234yf - HFO-1234zeE - HFO-1234zeZ - HCFO-1233zdE ||||||||||||
|---|---|---|---|---|---|---|---|---|---|---|---|
| Organics 0.2 F1233xf + 0.2 F1234yf + 0.2 F1233zdE + 0.2 F1234zeE + 0.2 F1234zeZ || Organics 0.96 F1233xf + 0.01 F1234yf + 0.01 F1233zdE + 0.01 F1234zeE + 0.01 F1234zeZ || Organics 0.01 F1233xf + 0.96 F1234yf + 0.01 F1233zdE + 0.01 F1234zeE + 0.01 F1234zeZ || Organics 0.01 F1233xf + 0.01 F1234yf + 0.96 F1233zdE + 0.01 F1234zeE + 0.01 F1234zeZ || Organics 0.01 F1233xf + 0.01 F1234yf + 0.01 F1233zdE + 0.96 F1234zeE + 0.01 F1234zeZ || Organics 0.01 F1233xf + 0.01 F1234yf + 0.01 F1233zdE + 0.01 F1234zeE + 0.96 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.4 | 0 | 1.6 | 0 | 6.6 | 0 | 1.4 | 0 | 4.8 | 0 | 1.9 |
| 0.05 | 4.4 | 0.05 | 2.8 | 0.05 | 7.6 | 0.05 | 2.5 | 0.05 | 5.8 | 0.05 | 3.0 |
| 0.1 | 4.4 | 0.1 | 2.8 | 0.1 | 7.6 | 0.1 | 2.5 | 0.1 | 5.8 | 0.1 | 3.0 |
| 0.15 | 4.4 | 0.15 | 2.8 | 0.15 | 7.6 | 0.15 | 2.5 | 0.15 | 5.8 | 0.15 | 3.0 |
| 0.2 | 4.4 | 0.2 | 2.8 | 0.2 | 7.6 | 0.2 | 2.5 | 0.2 | 5.8 | 0.2 | 3.0 |
| 0.25 | 4.4 | 0.25 | 2.8 | 0.25 | 7.6 | 0.25 | 2.5 | 0.25 | 5.8 | 0.25 | 3.0 |
| 0.3 | 4.4 | 0.3 | 2.8 | 0.3 | 7.6 | 0.3 | 2.5 | 0.3 | 5.8 | 0.3 | 3.0 |
| 0.35 | 4.4 | 0.35 | 2.8 | 0.35 | 7.6 | 0.35 | 2.5 | 0.35 | 5.8 | 0.35 | 3.0 |
| 0.4 | 4.4 | 0.4 | 2.8 | 0.4 | 7.6 | 0.4 | 2.5 | 0.4 | 5.8 | 0.4 | 3.0 |
| 0.45 | 4.4 | 0.45 | 2.7 | 0.45 | 7.6 | 0.45 | 2.5 | 0.45 | 5.7 | 0.45 | 3.0 |
| 0.5 | 4.4 | 0.5 | 2.7 | 0.5 | 7.6 | 0.5 | 2.5 | 0.5 | 5.7 | 0.5 | 3.0 |
| 0.55 | 4.4 | 0.55 | 2.7 | 0.55 | 7.6 | 0.55 | 2.5 | 0.55 | 5.7 | 0.55 | 3.0 |
| 0.6 | 4.4 | 0.6 | 2.7 | 0.6 | 7.6 | 0.6 | 2.5 | 0.6 | 5.6 | 0.6 | 3.0 |
| 0.65 | 4.4 | 0.65 | 2.7 | 0.65 | 7.6 | 0.65 | 2.5 | 0.65 | 5.5 | 0.65 | 3.0 |
| 0.7 | 4.4 | 0.7 | 2.7 | 0.7 | 7.6 | 0.7 | 2.5 | 0.7 | 5.3 | 0.7 | 3.0 |
| 0.75 | 4.2 | 0.75 | 2.7 | 0.75 | 7.4 | 0.75 | 2.5 | 0.75 | 5.1 | 0.75 | 3.0 |
| 0.8 | 4.0 | 0.8 | 2.6 | 0.8 | 7.1 | 0.8 | 2.4 | 0.8 | 4.8 | 0.8 | 2.8 |
| 0.85 | 3.6 | 0.85 | 2.4 | 0.85 | 6.5 | 0.85 | 2.2 | 0.85 | 4.3 | 0.85 | 2.6 |
| 0.9 | 3.1 | 0.9 | 2.1 | 0.9 | 5.5 | 0.9 | 2.0 | 0.9 | 3.6 | 0.9 | 2.3 |
| 0.95 | 2.3 | 0.95 | 1.7 | 0.95 | 3.8 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF - HCFO-1233xf - HFO-1234yf - HFO-1234zeE - HFO-1234zeZ - HFO-1243zf ||||||||||||
| --- | --- | --- | --- | --- | --- | --- | --- | --- | --- | --- | --- |
| Organics<br>0.2 F1233xf +<br>0.2 F1234yf +<br>0.2 F1243zf<br>0.2 F1234zeE +<br>0.2 F1234zeZ | | Organics<br>0.96 F1233xf +<br>0.01 F1234yf +<br>0.01 F1243zf +<br>0.01 F1234zeE +<br>0.01 F1234zeZ | | Organics<br>0.01 F1233xf +<br>0.96 F1234yf +<br>0.01 F1243zf +<br>0.01 F1234zeE +<br>0.01 F1234zeZ | | Organics<br>0.01 F1233xf +<br>0.01 F1234yf +<br>0.96 F1243zf +<br>0.01 F1234zeE +<br>0.01 F1234zeZ | | Organics<br>0.01 F1233xf +<br>0.01 F1234yf +<br>0.01 F1243zf +<br>0.96 F1234zeE +<br>0.01 F1234zeZ | | Organics<br>0.01 F1233xf +<br>0.01 F1234yf +<br>0.01 F1243zf +<br>0.01 F1234zeE +<br>0.96 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.3 | 0 | 1.7 | 0 | 6.7 | 0 | 5.8 | 0 | 4.8 | 0 | 1.9 |
| 0.05 | 5.3 | 0.05 | 2.8 | 0.05 | 7.6 | 0.05 | 6.7 | 0.05 | 5.8 | 0.05 | 3.0 |
| 0.1 | 5.3 | 0.1 | 2.8 | 0.1 | 7.6 | 0.1 | 6.7 | 0.1 | 5.8 | 0.1 | 3.0 |
| 0.15 | 5.3 | 0.15 | 2.8 | 0.15 | 7.6 | 0.15 | 6.7 | 0.15 | 5.8 | 0.15 | 3.0 |
| 0.2 | 5.3 | 0.2 | 2.8 | 0.2 | 7.6 | 0.2 | 6.7 | 0.2 | 5.8 | 0.2 | 3.0 |
| 0.25 | 5.3 | 0.25 | 2.8 | 0.25 | 7.6 | 0.25 | 6.7 | 0.25 | 5.8 | 0.25 | 3.0 |
| 0.3 | 5.3 | 0.3 | 2.8 | 0.3 | 7.6 | 0.3 | 6.7 | 0.3 | 5.8 | 0.3 | 3.0 |
| 0.35 | 5.3 | 0.35 | 2.8 | 0.35 | 7.6 | 0.35 | 6.7 | 0.35 | 5.8 | 0.35 | 3.0 |
| 0.4 | 5.3 | 0.4 | 2.8 | 0.4 | 7.6 | 0.4 | 6.7 | 0.4 | 5.8 | 0.4 | 3.0 |
| 0.45 | 5.3 | 0.45 | 2.8 | 0.45 | 7.6 | 0.45 | 6.7 | 0.45 | 5.8 | 0.45 | 3.0 |
| 0.5 | 5.3 | 0.5 | 2.8 | 0.5 | 7.6 | 0.5 | 6.7 | 0.5 | 5.8 | 0.5 | 3.0 |
| 0.55 | 5.3 | 0.55 | 2.8 | 0.55 | 7.6 | 0.55 | 6.7 | 0.55 | 5.7 | 0.55 | 3.0 |
| 0.6 | 5.3 | 0.6 | 2.8 | 0.6 | 7.6 | 0.6 | 6.7 | 0.6 | 5.6 | 0.6 | 3.0 |
| 0.65 | 5.3 | 0.65 | 2.8 | 0.65 | 7.6 | 0.65 | 6.6 | 0.65 | 5.5 | 0.65 | 3.0 |
| 0.7 | 5.2 | 0.7 | 2.8 | 0.7 | 7.6 | 0.7 | 6.5 | 0.7 | 5.4 | 0.7 | 3.0 |
| 0.75 | 5.0 | 0.75 | 2.8 | 0.75 | 7.5 | 0.75 | 6.3 | 0.75 | 5.1 | 0.75 | 3.0 |
| 0.8 | 4.8 | 0.8 | 2.7 | 0.8 | 7.1 | 0.8 | 6.1 | 0.8 | 4.8 | 0.8 | 2.9 |
| 0.85 | 4.3 | 0.85 | 2.5 | 0.85 | 6.5 | 0.85 | 5.6 | 0.85 | 4.3 | 0.85 | 2.7 |
| 0.9 | 3.7 | 0.9 | 2.2 | 0.9 | 5.5 | 0.9 | 4.7 | 0.9 | 3.6 | 0.9 | 2.4 |
| 0.95 | 2.7 | 0.95 | 1.8 | 0.95 | 3.8 | 0.95 | 3.4 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF - HCFO-1233xf - HFO-1234yf - HFO-1234zeE - HCFO-1233zdE - HFO-1243zf ||||||||||||
| --- | --- | --- | --- | --- | --- | --- | --- | --- | --- | --- | --- |
| Organics<br>0.2 F1233xf +<br>0.2 F1234yf +<br>0.2 F1243zf<br>0.2 F1234zeE +<br>0.2 F1233zdE | | Organics<br>0.90 F1233xf +<br>0.01 F1234yf +<br>0.01 F1243zf +<br>0.01 F1234zeE +<br>0.01 F1233zdE | | Organics<br>0.01 F1233xf +<br>0.96 F1234yf +<br>0.01 F1243zf +<br>0.01 F1234zeE +<br>0.01 F1233zdE | | Organics<br>0.01 F1233xf +<br>0.01 F1234yf +<br>0.96 F1243zf +<br>0.01 F1234zeE +<br>0.01 F1233zdE | | Organics<br>0.01 F1233xf +<br>0.01 F1234yf +<br>0.01 F1243zf +<br>0.96 F1234eE +<br>0.01 F1233zdE | | Organics<br>0.01 F1233xf +<br>0.01 F1234yf +<br>0.01 F1243zf +<br>0.81 F1234zeE +<br>0.96 F1233zdE | |
| MASSFRAG HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.3 | 0 | 1.7 | 0 | 6.7 | 0 | 5.8 | 0 | 4.8 | 0 | 1.5 |
| 0.05 | 5.3 | 0.05 | 2.8 | 0.05 | 7.6 | 0.05 | 6.7 | 0.05 | 5.8 | 0.05 | 2.6 |
| 0.1 | 5.3 | 0.1 | 2.8 | 0.1 | 7.6 | 0.1 | 6.7 | 0.1 | 5.8 | 0.1 | 2.6 |
| 0.15 | 5.3 | 0.15 | 2.8 | 0.15 | 7.6 | 0.15 | 6.7 | 0.15 | 5.8 | 0.15 | 2.6 |
| 0.2 | 5.3 | 0.2 | 2.8 | 0.2 | 7.6 | 0.2 | 6.7 | 0.2 | 5.8 | 0.2 | 2.6 |
| 0.25 | 5.3 | 0.25 | 2.8 | 0.25 | 7.6 | 0.25 | 6.7 | 0.25 | 5.8 | 0.25 | 2.6 |
| 0.3 | 5.3 | 0.3 | 2.8 | 0.3 | 7.6 | 0.3 | 5.7 | 0.3 | 5.8 | 0.3 | 2.6 |
| 0.35 | 5.3 | 0.35 | 2.8 | 0.35 | 7.6 | 0.35 | 6.7 | 0.35 | 5.8 | 0.35 | 2.6 |
| 0.4 | 5.3 | 0.4 | 2.8 | 0.4 | 7.6 | 0.4 | 5.7 | 0.4 | 5.8 | 0.4 | 2.6 |
| 0.45 | 5.3 | 0.45 | 2.8 | 0.45 | 7.6 | 0.45 | 6.7 | 0.45 | 5.8 | 0.45 | 2.6 |
| 0.5 | 5.3 | 0.5 | 2.8 | 0.5 | 7.6 | 0.5 | 6.7 | 0.5 | 5.8 | 0.5 | 2.6 |
| 0.55 | 5.3 | 0.55 | 2.8 | 0.55 | 7.6 | 0.55 | 6.7 | 0.55 | 5.7 | 0.55 | 2.6 |
| 0.6 | 5.3 | 0.6 | 2.8 | 0.6 | 7.6 | 0.6 | 6.7 | 0.6 | 5.6 | 0.6 | 2.6 |
| 0.65 | 5.2 | 0.65 | 2.8 | 0.65 | 7.6 | 0.65 | 6.6 | 0.65 | 5.5 | 0.65 | 2.6 |
| 0.7 | 5.1 | 0.7 | 2.8 | 0.7 | 7.6 | 0.7 | 6.5 | 0.7 | 5.4 | 0.7 | 2.6 |
| 0.75 | 5.0 | 0.75 | 2.8 | 0.75 | 7.5 | 0.75 | 6.3 | 0.75 | 5.1 | 0.75 | 2.6 |
| 0.8 | 4.7 | 0.8 | 2.6 | 0.8 | 7.1 | 0.8 | 6.1 | 0.8 | 4.8 | 0.8 | 2.4 |
| 0.85 | 4.3 | 0.85 | 2.5 | 0.85 | 6.5 | 0.85 | 5.6 | 0.85 | 4.3 | 0.85 | 2.3 |
| 0.9 | 3.6 | 0.9 | 2.2 | 0.9 | 5.5 | 0.9 | 4.7 | 0.9 | 3.6 | 0.9 | 2.0 |
| 0.95 | 2.6 | 0.95 | 1.8 | 0.95 | 3.8 | 0.95 | 3.4 | 0.95 | 2.6 | 0.95 | 1.7 |
| 1 | 1.2 | 1 | 1.2 | 1 | 1.2 | 1 | 1.2 | 1 | 1.2 | 1 | 1.2 |

HF - HCFO-1233xf - HFO-1234yf - HFO-1234zeZ - HCFO-1233zdE - HFO-1243zf

| Organics 0.2 F1233xf + 0.2 F1234yf + 0.2 F1243zf + 0.2 F1234zeZ + 0.2 F1233zdE | | Organics 0.96 F1233xf + 0.01 F1234yf + 0.01 F1243zf + 0.01 F1234zeZ + 0.01 F1233zdE | | Organics 0.01 F1233xf + 0.96 F1234yf + 0.01 F1243zf + 0.01 F1234zeZ + 0.01 F1233zdE | | Organics 0.01 F1233xf + 0.01 F1234yf + 0.96 F1243zf + 0.01 F1234zeZ + 0.01 F1233zdE | | Organics 0.01 F1233xf + 0.01 F1234yf + 0.01 F1243zf + 0.96 F1234zeZ + 0.01 F1233zdE | | Organics 0.01 F1233xf + 0.01 F1234yf + 0.01 F1243zf + 0.01 F1234zeZ + 0.96 F1233zdE | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.6 | 0 | 1.7 | 0 | 6.6 | 0 | 5.7 | 0 | 1.9 | 0 | 1.4 |
| 0.05 | 4.7 | 0.05 | 2.8 | 0.05 | 7.6 | 0.05 | 6.7 | 0.05 | 3.0 | 0.05 | 2.6 |
| 0.1 | 4.7 | 0.1 | 2.8 | 0.1 | 7.6 | 0.1 | 6.7 | 0.1 | 3.0 | 0.1 | 2.6 |
| 0.15 | 4.7 | 0.15 | 2.8 | 0.15 | 7.6 | 0.15 | 6.7 | 0.15 | 3.0 | 0.15 | 2.6 |
| 0.2 | 4.7 | 0.2 | 2.8 | 0.2 | 7.6 | 0.2 | 6.7 | 0.2 | 3.0 | 0.2 | 2.6 |
| 0.25 | 4.7 | 0.25 | 2.8 | 0.25 | 7.6 | 0.25 | 6.7 | 0.25 | 3.0 | 0.25 | 2.6 |
| 0.3 | 4.7 | 0.3 | 2.8 | 0.3 | 7.6 | 0.3 | 6.7 | 0.3 | 3.0 | 0.3 | 2.6 |
| 0.35 | 4.7 | 0.35 | 2.8 | 0.35 | 7.6 | 0.35 | 6.7 | 0.35 | 3.0 | 0.35 | 2.5 |
| 0.4 | 4.7 | 0.4 | 2.8 | 0.4 | 7.6 | 0.4 | 6.7 | 0.4 | 3.0 | 0.4 | 2.5 |
| 0.45 | 4.7 | 0.45 | 2.8 | 0.45 | 7.6 | 0.45 | 6.7 | 0.45 | 3.0 | 0.45 | 2.5 |
| 0.5 | 4.7 | 0.5 | 2.8 | 0.5 | 7.6 | 0.5 | 6.7 | 0.5 | 3.0 | 0.5 | 2.5 |
| 0.55 | 4.7 | 0.55 | 2.8 | 0.55 | 7.6 | 0.55 | 6.7 | 0.55 | 3.0 | 0.55 | 2.5 |
| 0.6 | 4.7 | 0.6 | 2.8 | 0.6 | 7.6 | 0.6 | 6.6 | 0.6 | 3.0 | 0.6 | 2.5 |
| 0.65 | 4.7 | 0.65 | 2.8 | 0.65 | 7.6 | 0.65 | 6.6 | 0.65 | 3.0 | 0.65 | 2.5 |
| 0.7 | 4.7 | 0.7 | 2.8 | 0.7 | 7.6 | 0.7 | 6.5 | 0.7 | 3.0 | 0.7 | 2.5 |
| 0.75 | 4.5 | 0.75 | 2.8 | 0.75 | 7.4 | 0.75 | 6.3 | 0.75 | 3.0 | 0.75 | 2.5 |
| 0.8 | 4.3 | 0.8 | 2.6 | 0.8 | 7.1 | 0.8 | 6.0 | 0.8 | 2.9 | 0.8 | 2.4 |
| 0.85 | 3.9 | 0.85 | 2.4 | 0.85 | 6.5 | 0.85 | 5.5 | 0.85 | 2.7 | 0.85 | 2.3 |
| 0.9 | 3.4 | 0.9 | 2.2 | 0.9 | 5.5 | 0.9 | 4.7 | 0.9 | 2.3 | 0.9 | 2.0 |
| 0.95 | 2.5 | 0.95 | 1.7 | 0.95 | 3.8 | 0.95 | 3.3 | 0.95 | 1.9 | 0.95 | 1.7 |
| 1 | 1.2 | 1 | 1.2 | 1 | 1.2 | 1 | 1.2 | 1 | 1.2 | 1 | 1.2 |

HF - HCFO-1233xf - HFC-245cb - HFO-1234zeE - HFO-1234zeZ - HCFO-1233zdE

| Organics 0.2 F1233xf + 0.2 F245cb + 0.2 F1233zdE + 0.2 F1234zeE + 0.2 F1234zeZ | | Organics 0.96 F1233xf + 0.01 F245cb + 0.01 F1233zdE + 0.01 F1234zeE + 0.01 F1234zeZ | | Organics 0.01 F1233xf + 0.96 F245cb + 0.01 F1233zeE + 0.01 F1234zeE + 0.01 F1234zeZ | | Organics 0.01 F1233xf + 0.01 F245cb + 0.96 F1233zdE + 0.01 F1234zeE + 0.01 F1234zeZ | | Organics 0.01 F1233xf + 0.01 F245cb + 0.01 F1233zdE + 0.96 F1234zeE + 0.01 F1234zeZ | | Organics 0.01 F1233xf + 0.01 F245cb + 0.01 F1233zdE + 0.01 F1234zeE + 0.96 F1234zeZ | |
|---|---|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.9 | 0 | 1.6 | 0 | 4.6 | 0 | 1.4 | 0 | 4.8 | 0 | 1.9 |
| 0.05 | 4.0 | 0.05 | 2.7 | 0.05 | 5.7 | 0.05 | 2.5 | 0.05 | 5.7 | 0.05 | 3.0 |
| 0.1 | 4.0 | 0.1 | 2.7 | 0.1 | 5.7 | 0.1 | 2.5 | 0.1 | 5.8 | 0.1 | 3.0 |
| 0.15 | 4.0 | 0.15 | 2.7 | 0.15 | 5.7 | 0.15 | 2.5 | 0.15 | 5.8 | 0.15 | 3.0 |
| 0.2 | 4.0 | 0.2 | 2.7 | 0.2 | 5.7 | 0.2 | 2.5 | 0.2 | 5.8 | 0.2 | 3.0 |
| 0.25 | 4.0 | 0.25 | 2.7 | 0.25 | 5.7 | 0.25 | 2.5 | 0.25 | 5.8 | 0.25 | 3.0 |
| 0.3 | 4.0 | 0.3 | 2.7 | 0.3 | 5.7 | 0.3 | 2.5 | 0.3 | 5.8 | 0.3 | 3.0 |
| 0.35 | 4.0 | 0.35 | 2.7 | 0.35 | 5.7 | 0.35 | 2.5 | 0.35 | 5.7 | 0.35 | 3.0 |
| 0.4 | 4.0 | 0.4 | 2.7 | 0.4 | 5.7 | 0.4 | 2.5 | 0.4 | 5.7 | 0.4 | 3.0 |
| 0.45 | 4.0 | 0.45 | 2.7 | 0.45 | 5.7 | 0.45 | 2.5 | 0.45 | 5.7 | 0.45 | 3.0 |
| 0.5 | 4.0 | 0.5 | 2.7 | 0.5 | 5.7 | 0.5 | 2.5 | 0.5 | 5.7 | 0.5 | 3.0 |
| 0.55 | 4.0 | 0.55 | 2.7 | 0.55 | 5.7 | 0.55 | 2.5 | 0.55 | 5.6 | 0.55 | 3.0 |
| 0.6 | 4.0 | 0.6 | 2.7 | 0.6 | 5.7 | 0.6 | 2.5 | 0.6 | 5.6 | 0.6 | 3.0 |
| 0.65 | 4.0 | 0.65 | 2.7 | 0.65 | 5.7 | 0.65 | 2.5 | 0.65 | 5.5 | 0.65 | 3.0 |
| 0.7 | 4.0 | 0.7 | 2.7 | 0.7 | 5.8 | 0.7 | 2.5 | 0.7 | 5.3 | 0.7 | 3.0 |
| 0.75 | 4.0 | 0.75 | 2.7 | 0.75 | 5.8 | 0.75 | 2.5 | 0.75 | 5.1 | 0.75 | 3.0 |
| 0.8 | 3.8 | 0.8 | 2.6 | 0.8 | 5.8 | 0.8 | 2.4 | 0.8 | 4.7 | 0.8 | 2.8 |
| 0.85 | 3.5 | 0.85 | 2.4 | 0.85 | 5.8 | 0.85 | 2.2 | 0.85 | 4.3 | 0.85 | 2.6 |
| 0.9 | 3.0 | 0.9 | 2.1 | 0.9 | 5.0 | 0.9 | 2.0 | 0.9 | 3.6 | 0.9 | 2.3 |
| 0.95 | 2.3 | 0.95 | 1.7 | 0.95 | 3.5 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF - HCFO-1233xf - HFC-245cb - HFO-1234zeE - HFO-1234zeZ - HFO-1243zf ||||||||||||
|---|---|---|---|---|---|---|---|---|---|---|---|
| Organics 0.2 F1233xf + 0.2 F245cb + 0.2 F1243zf 0.2 F1234zeE + 0.2 F1234zeZ || Organics 0.96 F1233xf + 0.01 F245cb + 0.01 F1243zf + 0.01 F1234zeE + 0.01 F1234zeZ || Organics 0.01 F1233xf + 0.96 F245cb + 0.01 F1243zf + 0.01 F1234zeE + 0.01 F1234zeZ || Organics 0.01 F1233xf + 0.01 F245cb + 0.96 F1243zf + 0.01 F1234zeE + 0.01 F1234zeZ || Organics 0.01 F1233xf + 0.01 F245cb + 0.01 F1243zf + 0.96 F1234zeE + 0.01 F1234zeZ || Organics 0.01 F1233xf + 0.01 F245cb + 0.01 F1243zf + 0.01 F1234zeE + 0.96 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.8 | 0 | 1.7 | 0 | 4.6 | 0 | 5.8 | 0 | 4.8 | 0 | 1.9 |
| 0.05 | 4.9 | 0.05 | 2.8 | 0.05 | 5.8 | 0.05 | 6.7 | 0.05 | 5.8 | 0.05 | 3.0 |
| 0.1 | 4.9 | 0.1 | 2.8 | 0.1 | 5.8 | 0.1 | 6.7 | 0.1 | 5.8 | 0.1 | 3.0 |
| 0.15 | 4.9 | 0.15 | 2.8 | 0.15 | 5.8 | 0.15 | 6.7 | 0.15 | 5.8 | 0.15 | 3.0 |
| 0.2 | 4.9 | 0.2 | 2.8 | 0.2 | 5.8 | 0.2 | 6.7 | 0.2 | 5.8 | 0.2 | 3.0 |
| 0.25 | 4.9 | 0.25 | 2.8 | 0.25 | 5.8 | 0.25 | 6.7 | 0.25 | 5.8 | 0.25 | 3.0 |
| 0.3 | 4.9 | 0.3 | 2.8 | 0.3 | 5.8 | 0.3 | 6.7 | 0.3 | 5.8 | 0.3 | 3.0 |
| 0.35 | 4.9 | 0.35 | 2.8 | 0.35 | 5.8 | 0.35 | 6.7 | 0.35 | 5.8 | 0.35 | 3.0 |
| 0.4 | 4.9 | 0.4 | 2.8 | 0.4 | 5.8 | 0.4 | 6.7 | 0.4 | 5.8 | 0.4 | 3.0 |
| 0.45 | 4.9 | 0.45 | 2.8 | 0.45 | 5.8 | 0.45 | 6.7 | 0.45 | 5.8 | 0.45 | 3.0 |
| 0.5 | 4.9 | 0.5 | 2.8 | 0.5 | 5.8 | 0.5 | 6.7 | 0.5 | 5.7 | 0.5 | 3.0 |
| 0.55 | 4.9 | 0.55 | 2.8 | 0.55 | 5.8 | 0.55 | 6.7 | 0.55 | 5.7 | 0.55 | 3.0 |
| 0.6 | 4.9 | 0.6 | 2.8 | 0.6 | 5.8 | 0.6 | 6.6 | 0.6 | 5.6 | 0.6 | 3.0 |
| 0.65 | 4.9 | 0.65 | 2.8 | 0.65 | 5.8 | 0.65 | 6.6 | 0.65 | 5.5 | 0.65 | 3.0 |
| 0.7 | 4.9 | 0.7 | 2.8 | 0.7 | 5.8 | 0.7 | 6.5 | 0.7 | 5.4 | 0.7 | 3.0 |
| 0.75 | 4.8 | 0.75 | 2.8 | 0.75 | 5.8 | 0.75 | 6.3 | 0.75 | 5.1 | 0.75 | 3.0 |
| 0.8 | 4.6 | 0.8 | 2.6 | 0.8 | 5.8 | 0.8 | 6.0 | 0.8 | 4.8 | 0.8 | 2.9 |
| 0.85 | 4.2 | 0.85 | 2.4 | 0.85 | 5.8 | 0.85 | 5.6 | 0.85 | 4.3 | 0.85 | 2.7 |
| 0.9 | 3.6 | 0.9 | 2.2 | 0.9 | 5.0 | 0.9 | 4.7 | 0.9 | 3.6 | 0.9 | 2.4 |
| 0.95 | 2.6 | 0.95 | 1.8 | 0.95 | 3.5 | 0.95 | 3.4 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF - HCFO-1233xf - HFC-245cb - HFO-1234zeE - HCFO-1233zdE - HFO-1243zf ||||||||||||
|---|---|---|---|---|---|---|---|---|---|---|---|
| Organics 0.2 F1233xf + 0.2 F245cb + 0.2F1243zf + 0.2 F1234zeE + 0.2 F1233zdE || Organics 0.96 F1233xf + 0.01 F245cb + 0.01 F1243zf + 0.01 F1234zeE + 0.01 F1233zdE || Organics 0.01 F1233xf + 0.96 F245cb + 0.01 F1243zf + 0.01 F1234zeE + 0.01 F1233zdE || Organics 0.01 F1233xf + 0.01 F245cb + 0.96 F1243zf + 0.01 F1234zeE + 0.01 F1233zdE || Organics 0.01 F1233xf + 0.01 F245cb + 0.01 F1243zf + 0.96 F1234zeE + 0.01 F1233zdE || Organics 0.01 F1233xf + 0.01 F245cb + 0.01 F1243zf + 0.01 F1234zeE + 0.96 F1233zdE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.8 | 0 | 1.7 | 0 | 4.6 | 0 | 5.8 | 0 | 4.8 | 0 | 1.5 |
| 0.05 | 4.9 | 0.05 | 2.8 | 0.05 | 5.8 | 0.05 | 6.7 | 0.05 | 5.8 | 0.05 | 2.6 |
| 0.1 | 4.9 | 0.1 | 2.8 | 0.1 | 5.8 | 0.1 | 6.7 | 0.1 | 5.8 | 0.1 | 2.6 |
| 0.15 | 4.9 | 0.15 | 2.8 | 0.15 | 5.8 | 0.15 | 6.7 | 0.15 | 5.8 | 0.15 | 2.6 |
| 0.2 | 4.9 | 0.2 | 2.8 | 0.2 | 5.8 | 0.2 | 6.7 | 0.2 | 5.8 | 0.2 | 2.6 |
| 0.25 | 4.9 | 0.25 | 2.8 | 0.25 | 5.8 | 0.25 | 6.7 | 0.25 | 5.8 | 0.25 | 2.6 |
| 0.3 | 4.9 | 0.3 | 2.8 | 0.3 | 5.8 | 0.3 | 6.7 | 0.3 | 5.8 | 0.3 | 2.6 |
| 0.35 | 4.9 | 0.35 | 2.8 | 0.35 | 5.8 | 0.35 | 6.7 | 0.35 | 5.8 | 0.35 | 2.6 |
| 0.4 | 4.9 | 0.4 | 2.8 | 0.4 | 5.8 | 0.4 | 6.7 | 0.4 | 5.8 | 0.4 | 2.6 |
| 0.45 | 4.9 | 0.45 | 2.8 | 0.45 | 5.8 | 0.45 | 6.7 | 0.45 | 5.8 | 0.45 | 2.6 |
| 0.5 | 4.9 | 0.5 | 2.8 | 0.5 | 5.8 | 0.5 | 6.7 | 0.5 | 5.7 | 0.5 | 2.6 |
| 0.55 | 4.9 | 0.55 | 2.8 | 0.55 | 5.8 | 0.55 | 6.7 | 0.55 | 5.7 | 0.55 | 2.6 |
| 0.6 | 4.9 | 0.6 | 2.8 | 0.6 | 5.8 | 0.6 | 6.6 | 0.6 | 5.6 | 0.6 | 2.6 |
| 0.65 | 4.9 | 0.65 | 2.8 | 0.65 | 5.8 | 0.65 | 6.6 | 0.65 | 5.5 | 0.65 | 2.5 |
| 0.7 | 4.9 | 0.7 | 2.8 | 0.7 | 5.8 | 0.7 | 6.5 | 0.7 | 5.4 | 0.7 | 2.5 |
| 0.75 | 4.7 | 0.75 | 2.8 | 0.75 | 5.8 | 0.75 | 6.3 | 0.75 | 5.1 | 0.75 | 2.5 |
| 0.8 | 4.5 | 0.8 | 2.6 | 0.8 | 5.8 | 0.8 | 6.0 | 0.8 | 4.8 | 0.8 | 2.4 |
| 0.85 | 4.1 | 0.85 | 2.4 | 0.85 | 5.8 | 0.85 | 5.6 | 0.85 | 4.3 | 0.85 | 2.3 |
| 0.9 | 3.5 | 0.9 | 2.2 | 0.9 | 5.0 | 0.9 | 4.7 | 0.9 | 3.6 | 0.9 | 2.0 |
| 0.95 | 2.6 | 0.95 | 1.7 | 0.95 | 3.5 | 0.95 | 3.3 | 0.95 | 2.6 | 0.95 | 1.7 |
| 1 | 1.2 | 1 | 1.2 | 1 | 1.2 | 1 | 1.2 | 1 | 1.2 | 1 | 1.2 |

| HF - HCFO-1233xf - HFC-245cb - HFO-1234zeZ - HCFO-1233zdE - HFO-1243zf ||||||||||||
| Organics 0.2 F1233xf + 0.2 F245cb + 0.2 F1243zf + 0.2 F1234zeZ + 0.2 F1233zdE || Organics 0.96 F1233xf + 0.01 F245cb + 0.01 F1243zf + 0.01 F1234zeZ + 0.01 F1233zdE || Organics 0.01 F1233xf + 0.96 F245cb + 0.01 F1243zf + 0.01 F1234zeZ + 0.01 F1233zdE || Organics 0.01 F1233xf + 0.01 F245cb + 0.96 F1243zf + 0.01 F1234zeZ + 0.01 F1233zdE || Organics 0.01 F1233xf + 0.01 F245cb + 0.01 F1243zf + 0.96 F1234zeZ + 0.01 F1233zdE || Organics 0.01 F1233xf + 0.01 F245cb + 0.01 F1243zf + 0.01 F1234zeZ + 0.96 F1233zdE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0 | 3.2 | 0 | 1.6 | 0 | 4.6 | 0 | 5.7 | 0 | 1.9 | 0 | 1.4 |
| 0.05 | 4.3 | 0.05 | 2.7 | 0.05 | 5.7 | 0.05 | 6.7 | 0.05 | 3.0 | 0.05 | 2.5 |
| 0.1 | 4.3 | 0.1 | 2.7 | 0.1 | 5.7 | 0.1 | 6.7 | 0.1 | 3.0 | 0.1 | 2.5 |
| 0.15 | 4.3 | 0.15 | 2.7 | 0.15 | 5.7 | 0.15 | 6.7 | 0.15 | 3.0 | 0.15 | 2.5 |
| 0.2 | 4.3 | 0.2 | 2.7 | 0.2 | 5.7 | 0.2 | 6.7 | 0.2 | 3.0 | 0.2 | 2.5 |
| 0.25 | 4.3 | 0.25 | 2.7 | 0.25 | 5.7 | 0.25 | 6.7 | 0.25 | 3.0 | 0.25 | 2.5 |
| 0.3 | 4.3 | 0.3 | 2.7 | 0.3 | 5.7 | 0.3 | 6.7 | 0.3 | 3.0 | 0.3 | 2.5 |
| 0.35 | 4.3 | 0.35 | 2.7 | 0.35 | 5.7 | 0.35 | 6.7 | 0.35 | 3.0 | 0.35 | 2.5 |
| 0.4 | 4.3 | 0.4 | 2.7 | 0.4 | 5.8 | 0.4 | 6.7 | 0.4 | 3.0 | 0.4 | 2.5 |
| 0.45 | 4.3 | 0.45 | 2.7 | 0.45 | 5.8 | 0.45 | 6.7 | 0.45 | 3.0 | 0.45 | 2.5 |
| 0.5 | 4.3 | 0.5 | 2.7 | 0.5 | 5.8 | 0.5 | 6.7 | 0.5 | 3.0 | 0.5 | 2.5 |
| 0.55 | 4.3 | 0.55 | 2.7 | 0.55 | 5.8 | 0.55 | 6.7 | 0.55 | 3.0 | 0.55 | 2.5 |
| 0.6 | 4.3 | 0.6 | 2.7 | 0.6 | 5.8 | 0.6 | 6.6 | 0.6 | 3.0 | 0.6 | 2.5 |
| 0.65 | 4.3 | 0.65 | 2.7 | 0.65 | 5.8 | 0.65 | 6.6 | 0.65 | 3.0 | 0.65 | 2.5 |
| 0.7 | 4.3 | 0.7 | 2.7 | 0.7 | 5.8 | 0.7 | 6.5 | 0.7 | 3.0 | 0.7 | 2.5 |
| 0.75 | 4.3 | 0.75 | 2.7 | 0.75 | 5.8 | 0.75 | 6.3 | 0.75 | 3.0 | 0.75 | 2.5 |
| 0.8 | 4.1 | 0.8 | 2.6 | 0.8 | 5.8 | 0.8 | 6.0 | 0.8 | 2.9 | 0.8 | 2.4 |
| 0.85 | 3.8 | 0.85 | 2.4 | 0.85 | 5.8 | 0.85 | 5.5 | 0.85 | 2.7 | 0.85 | 2.3 |
| 0.9 | 3.3 | 0.9 | 2.1 | 0.9 | 5.0 | 0.9 | 4.7 | 0.9 | 2.3 | 0.9 | 2.6 |
| 0.95 | 2.4 | 0.95 | 1.7 | 0.95 | 3.5 | 0.95 | 3.3 | 0.95 | 1.9 | 0.95 | 1.7 |
| 1 | 1.2 | 1 | 1.2 | 1 | 1.2 | 1 | 1.2 | 1 | 1.2 | 1 | 1.2 |

| HF - HCFO-1233xf - HFO-1234zeE- HFO-1234zeZ - HCFO-1233zdE- HFO-1243zf ||||||||||||
| Organics 0.2 F1233xf + 0.2 F1243zf + 0.2 F1233zdE + 0.2 F1234zeE + 0.2 F1234zeZ || Organics 0.96 F1233xf + 0.01 F1243zf + 0.01 F1233zdE + 0.01 F1234zeE + 0.01 F1234zeZ || Organics 0.01 F1233xf + 0.96 F1243zf + 0.01 F1233zdE + 0.01 F1234zeE + 0.01 F1234zeZ || Organics 0.01 F1233xf + 0.01 F1243zf + 0.96 F1233zdE + 0.01 F1234aeE + 0.01 F1234zeZ || Organics 0.01 F1233xf + 0.01 F1243zf + 0.01 F1233zdE + 0.96 F1234zeE + 0.01 F1234zeZ || Organics 0.01 F1233xf + 0.01 F1243zf + 0.01 F1233zdE + 0.01 F1234zeE + 0.96 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0 | 3.2 | 0 | 1.6 | 0 | 5.7 | 0 | 1.4 | 0 | 4.8 | 0 | 1.9 |
| 0.05 | 4.3 | 0.05 | 2.7 | 0.05 | 6.7 | 0.05 | 2.5 | 0.05 | 5.7 | 0.05 | 3.0 |
| 0.1 | 4.3 | 0.1 | 2.7 | 0.1 | 6.7 | 0.1 | 2.5 | 0.1 | 5.8 | 0.1 | 3.0 |
| 0.15 | 4.3 | 0.15 | 2.7 | 0.15 | 6.7 | 0.15 | 2.5 | 0.15 | 5.8 | 0.15 | 3.0 |
| 0.2 | 4.3 | 0.2 | 2.7 | 0.2 | 6.7 | 0.2 | 2.5 | 0.2 | 5.8 | 0.2 | 3.0 |
| 0.25 | 4.3 | 0.25 | 2.7 | 0.25 | 6.7 | 0.25 | 2.5 | 0.25 | 5.8 | 0.25 | 3.0 |
| 0.3 | 4.3 | 0.3 | 2.7 | 0.3 | 6.7 | 0.3 | 2.5 | 0.3 | 5.8 | 0.3 | 3.0 |
| 0.35 | 4.3 | 0.35 | 2.7 | 0.35 | 6.7 | 0.35 | 2.5 | 0.35 | 5.8 | 0.35 | 3.0 |
| 0.4 | 4.3 | 0.4 | 2.7 | 0.4 | 6.7 | 0.4 | 2.5 | 0.4 | 5.8 | 0.4 | 3.0 |
| 0.45 | 4.3 | 0.45 | 2.7 | 0.45 | 6.7 | 0.45 | 2.5 | 0.45 | 5.7 | 0.45 | 3.0 |
| 0.5 | 4.3 | 0.5 | 2.7 | 0.5 | 6.7 | 0.5 | 2.5 | 0.5 | 5.7 | 0.5 | 3.0 |
| 0.55 | 4.2 | 0.55 | 2.7 | 0.55 | 6.6 | 0.55 | 2.5 | 0.55 | 5.7 | 0.55 | 3.0 |
| 0.6 | 4.2 | 0.6 | 2.7 | 0.6 | 6.6 | 0.6 | 2.5 | 0.6 | 5.6 | 0.6 | 3.0 |
| 0.55 | 4.2 | 0.65 | 2.7 | 0.65 | 6.6 | 0.65 | 2.5 | 0.65 | 5.5 | 0.65 | 3.0 |
| 0.7 | 4.2 | 0.7 | 2.7 | 0.7 | 6.5 | 0.7 | 2.5 | 0.7 | 5.3 | 0.7 | 3.0 |
| 0.75 | 4.0 | 0.75 | 2.7 | 0.75 | 6.3 | 0.75 | 2.5 | 0.75 | 5.1 | 0.75 | 3.0 |
| 0.8 | 3.8 | 0.8 | 2.6 | 0.8 | 6.0 | 0.8 | 2.4 | 0.8 | 4.7 | 0.8 | 2.8 |
| 0.85 | 3.5 | 0.85 | 2.4 | 0.85 | 5.5 | 0.85 | 2.2 | 0.85 | 4.3 | 0.85 | 2.0 |
| 0.9 | 3.0 | 0.9 | 2.1 | 0.9 | 4.7 | 0.9 | 2.0 | 0.9 | 3.6 | 0.9 | 2.3 |
| 0.95 | 2.2 | 0.95 | 1.7 | 0.95 | 3.3 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF - HFO-1234yf - HFC-245cb - HFO-1234zeE - HFO-1234zeZ - HCFO-1233zdE |||||||||||| 
|---|---|---|---|---|---|---|---|---|---|---|---|
| Organics 0.2 F1234yf + 0.2 F245cb + 0.2 F1233zdE + 0.2 F1234zeE + 0.2 F1234zeZ | | Organics 0.96 F1234yf + 0.01 F245cb + 0.01 F1233zdE + 0.01 F1234zeE + 0.01 F1234zeZ | | Organics 0.01 F1234yf + 0.96 F245cb + 0.01 F1233zdE + 0.01 F1234zeE + 0.01 F1234zeZ | | Organics 0.01 F1234yf + 0.01 F245cb + 0.96 F1233zdE + 0.01 F1234zeE + 0.01 F1234zeZ | | Organics 0.01 F1234yf + 0.01 F245cb + 0.01 F1233zdE + 0.96 F1234zeE + 0.01 F1234zeZ | | Organics 0.01 F1234yf + 0.01 F245cb + 0.01 F1233zdE + 0.01 F1234zeE + 0.96 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.9 | 0 | 6.7 | 0 | 4.6 | 0 | 1.5 | 0 | 4.8 | 0 | 1.9 |
| 0.05 | 5.0 | 0.05 | 7.6 | 0.05 | 5.8 | 0.05 | 2.6 | 0.05 | 5.8 | 0.05 | 3.0 |
| 0.1 | 5.0 | 0.1 | 7.6 | 0.1 | 5.8 | 0.1 | 2.6 | 0.1 | 5.8 | 0.1 | 3.0 |
| 0.15 | 5.0 | 0.15 | 7.6 | 0.15 | 5.8 | 0.15 | 2.6 | 0.15 | 5.8 | 0.15 | 3.0 |
| 0.2 | 5.0 | 0.2 | 7.6 | 0.2 | 5.8 | 0.2 | 2.6 | 0.2 | 5.8 | 0.2 | 3.0 |
| 0.25 | 5.0 | 0.25 | 7.6 | 0.25 | 5.8 | 0.25 | 2.6 | 0.25 | 5.8 | 0.25 | 3.0 |
| 0.3 | 5.0 | 0.3 | 7.6 | 0.3 | 5.8 | 0.3 | 2.6 | 0.3 | 5.8 | 0.3 | 3.0 |
| 0.35 | 5.0 | 0.35 | 7.6 | 0.35 | 5.8 | 0.35 | 2.6 | 0.35 | 5.8 | 0.35 | 3.0 |
| 0.4 | 5.0 | 0.4 | 7.6 | 0.4 | 5.8 | 0.4 | 2.6 | 0.4 | 5.8 | 0.4 | 3.0 |
| 0.45 | 5.0 | 0.45 | 7.6 | 0.45 | 5.8 | 0.45 | 2.6 | 0.45 | 5.8 | 0.45 | 3.0 |
| 0.5 | 5.0 | 0.5 | 7.6 | 0.5 | 5.8 | 0.5 | 2.6 | 0.5 | 5.7 | 0.5 | 3.0 |
| 0.55 | 5.0 | 0.55 | 7.6 | 0.55 | 5.8 | 0.55 | 2.6 | 0.55 | 5.7 | 0.55 | 3.0 |
| 0.6 | 5.0 | 0.6 | 7.6 | 0.6 | 5.8 | 0.6 | 2.6 | 0.6 | 5.6 | 0.6 | 3.0 |
| 0.65 | 5.0 | 0.65 | 7.6 | 0.65 | 5.8 | 0.65 | 2.6 | 0.65 | 5.5 | 0.65 | 3.0 |
| 0.7 | 5.1 | 0.7 | 7.6 | 0.7 | 5.8 | 0.7 | 2.6 | 0.7 | 5.4 | 0.7 | 3.0 |
| 0.75 | 5.0 | 0.75 | 7.5 | 0.75 | 5.8 | 0.75 | 2.6 | 0.75 | 5.1 | 0.75 | 3.0 |
| 0.8 | 4.7 | 0.8 | 7.1 | 0.8 | 5.8 | 0.8 | 2.5 | 0.8 | 4.8 | 0.8 | 2.9 |
| 0.85 | 4.3 | 0.85 | 6.5 | 0.85 | 5.8 | 0.85 | 2.3 | 0.85 | 4.3 | 0.85 | 2.7 |
| 0.9 | 3.7 | 0.9 | 5.5 | 0.9 | 5.0 | 0.9 | 2.0 | 0.9 | 3.6 | 0.9 | 2.4 |
| 0.95 | 2.7 | 0.95 | 3.8 | 0.95 | 3.5 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF-HFO-1234yf - HFC-245cb - HFO-1234zeE - HFO-1234zeZ - HFO-1243zf |||||||||||| 
|---|---|---|---|---|---|---|---|---|---|---|---|
| Organics 0.2 F1234yf + 0.2 F245cb + 0.2 F1243zf + 0.2 F1234zeE + 0.2 F1234zeZ | | Organics 0.96 F1234yf + 0.01 F245cb + 0.01 F1243zf + 0.01 F1234zeE + 0.01 F1234zeZ | | Organics 0.01 F1234yf + 0.96 F245cb + 0.01 F1243zf + 0.01 F1234zeE + 0.01 F1234zeZ | | Organics 0.01 F1234yf + 0.01 F245cb + 0.96 F1243zf + 0.01 F1234zeE + 0.01 F1234zeZ | | Organics 0.01 F1234yf + 0.01 F245cb + 0.01 F1243zf + 0.96 F1234zeE + 0.01 F1234zeZ | | Organics 0.01 F1234yf + 0.01 F245eb + 0.01 F1243zf + 0.01 F1234zeE + 0.96 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.8 | 0 | 6.7 | 0 | 4.7 | 0 | 5.8 | 0 | 4.9 | 0 | 2.0 |
| 0.05 | 5.9 | 0.05 | 7.7 | 0.05 | 5.8 | 0.05 | 6.7 | 0.05 | 5.8 | 0.05 | 3.1 |
| 0.1 | 5.9 | 0.1 | 7.7 | 0.1 | 5.8 | 0.1 | 6.8 | 0.1 | 5.9 | 0.1 | 3.1 |
| 0.15 | 5.9 | 0.15 | 7.7 | 0.15 | 5.8 | 0.15 | 6.8 | 0.15 | 5.8 | 0.15 | 3.1 |
| 0.2 | 5.9 | 0.2 | 7.7 | 0.2 | 5.8 | 0.2 | 6.8 | 0.2 | 5.8 | 0.2 | 3.1 |
| 0.25 | 5.9 | 0.25 | 7.6 | 0.25 | 5.8 | 0.25 | 6.8 | 0.25 | 5.8 | 0.25 | 3.1 |
| 0.3 | 5.9 | 0.3 | 7.6 | 0.3 | 5.8 | 0.3 | 6.8 | 0.3 | 5.8 | 0.3 | 3.1 |
| 0.35 | 5.9 | 0.35 | 7.6 | 0.35 | 5.8 | 0.35 | 6.8 | 0.35 | 5.8 | 0.35 | 3.1 |
| 0.4 | 5.9 | 0.4 | 7.6 | 0.4 | 5.8 | 0.4 | 6.7 | 0.4 | 5.8 | 0.4 | 3.1 |
| 0.45 | 5.9 | 0.45 | 7.6 | 0.45 | 5.8 | 0.45 | 6.7 | 0.45 | 5.8 | 0.45 | 3.1 |
| 0.5 | 5.9 | 0.5 | 7.7 | 0.5 | 5.8 | 0.5 | 6.7 | 0.5 | 5.8 | 0.5 | 3.1 |
| 0.55 | 5.9 | 0.55 | 7.7 | 0.55 | 5.8 | 0.55 | 6.7 | 0.55 | 5.7 | 0.55 | 3.1 |
| 0.6 | 5.9 | 0.6 | 7.7 | 0.6 | 5.8 | 0.6 | 6.7 | 0.6 | 5.7 | 0.6 | 3.1 |
| 0.65 | 5.9 | 0.65 | 7.7 | 0.65 | 5.8 | 0.65 | 6.6 | 0.65 | 5.6 | 0.65 | 3.1 |
| 0.7 | 5.9 | 0.7 | 7.6 | 0.7 | 5.8 | 0.7 | 6.5 | 0.7 | 5.4 | 0.7 | 3.1 |
| 0.75 | 5.7 | 0.75 | 7.5 | 0.75 | 5.8 | 0.75 | 6.4 | 0.75 | 5.2 | 0.75 | 3.1 |
| 0.8 | 5.5 | 0.8 | 7.2 | 0.8 | 5.8 | 0.8 | 6.1 | 0.8 | 4.8 | 0.8 | 2.9 |
| 0.85 | 5.0 | 0.85 | 7.6 | 0.85 | 5.8 | 0.85 | 5.6 | 0.85 | 4.3 | 0.85 | 2.7 |
| 0.9 | 4.3 | 0.9 | 5.5 | 0.9 | 5.0 | 0.9 | 4.8 | 0.9 | 3.6 | 0.9 | 2.4 |
| 0.95 | 3.0 | 0.95 | 3.8 | 0.95 | 3.5 | 0.95 | 3.4 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF - HFO-1234yf- HFC-245cb - HFO-1234zeE - HCFO-1233zdE- HFO-1243zf ||||||||||||
|---|---|---|---|---|---|---|---|---|---|---|---|
| Organics<br>0.2 F1234yf +<br>0.2 F245cb +<br>0.2 F1243zf +<br>0.2 F1234zeE +<br>0.2 F1233zdE || Organics<br>0.96 F1234yf +<br>0.01 F245cb +<br>0.01 F1243zf +<br>0.01 F1234zeE +<br>0.01 F1233zdE || Organics<br>0.01 F1234yf +<br>0.96 F245cb +<br>0.01 F1243zf +<br>0.01 F1234zeE +<br>0.01 F1233zdE || Organics<br>0.01 F1234yf +<br>0.01 F245cb +<br>0.96 F1243zf +<br>0.01 F1234zeE +<br>0.01 F1233zdE || Organics<br>0.01 F1234yf +<br>0.01 F245cb +<br>0.01 F1243zf +<br>0.96 F1234zeE +<br>0.01 F1233zdE || Organics<br>0.01 F1234yf +<br>0.01 F245cb +<br>0.01 F1243zf +<br>0.01 F1234zeE +<br>0.96 F1233zdE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.8 | 0 | 6.7 | 0 | 4.7 | 0 | 5.8 | 0 | 4.9 | 0 | 1.5 |
| 0.05 | 5.9 | 0.05 | 7.7 | 0.05 | 5.8 | 0.05 | 6.7 | 0.05 | 5.8 | 0.05 | 2.6 |
| 0.1 | 5.9 | 0.1 | 7.7 | 0.1 | 5.8 | 0.1 | 6.8 | 0.1 | 5.8 | 0.1 | 2.6 |
| 0.15 | 5.9 | 0.15 | 7.7 | 0.15 | 5.8 | 0.15 | 6.8 | 0.15 | 5.8 | 0.15 | 2.6 |
| 0.2 | 5.9 | 0.2 | 7.7 | 0.2 | 5.8 | 0.2 | 6.8 | 0.2 | 5.8 | 0.2 | 2.6 |
| 0.25 | 5.9 | 0.25 | 7.6 | 0.25 | 5.8 | 0.25 | 6.8 | 0.25 | 5.8 | 0.25 | 2.6 |
| 0.3 | 5.9 | 0.3 | 7.6 | 0.3 | 5.8 | 0.3 | 6.8 | 0.3 | 5.8 | 0.3 | 2.6 |
| 0.35 | 5.9 | 0.35 | 7.6 | 0.35 | 5.8 | 0.35 | 6.8 | 0.35 | 5.8 | 0.35 | 2.6 |
| 0.4 | 5.9 | 0.4 | 7.7 | 0.4 | 5.8 | 0.4 | 6.7 | 0.4 | 5.8 | 0.4 | 2.6 |
| 0.45 | 5.9 | 0.45 | 7.7 | 0.45 | 5.8 | 0.45 | 6.7 | 0.45 | 5.8 | 0.45 | 2.6 |
| 0.5 | 5.9 | 0.5 | 7.7 | 0.5 | 5.8 | 0.5 | 6.7 | 0.5 | 5.8 | 0.5 | 2.6 |
| 0.55 | 5.9 | 0.55 | 7.7 | 0.55 | 5.8 | 0.55 | 6.7 | 0.55 | 5.7 | 0.55 | 2.6 |
| 0.6 | 5.9 | 0.6 | 7.7 | 0.6 | 5.8 | 0.6 | 6.7 | 0.6 | 5.7 | 0.6 | 2.6 |
| 0.65 | 5.9 | 0.65 | 7.7 | 0.65 | 5.8 | 0.65 | 6.6 | 0.65 | 5.6 | 0.65 | 2.6 |
| 0.7 | 5.9 | 0.7 | 7.6 | 0.7 | 5.8 | 0.7 | 6.5 | 0.7 | 5.4 | 0.7 | 2.6 |
| 0.75 | 5.7 | 0.75 | 7.5 | 0.75 | 5.8 | 0.75 | 6.4 | 0.75 | 5.2 | 0.75 | 2.6 |
| 0.8 | 5.4 | 0.8 | 7.2 | 0.8 | 5.8 | 0.8 | 6.1 | 0.8 | 4.8 | 0.8 | 2.5 |
| 0.85 | 5.0 | 0.85 | 6.6 | 0.85 | 5.8 | 0.85 | 5.6 | 0.85 | 4.3 | 0.85 | 2.3 |
| 0.9 | 4.2 | 0.9 | 5.5 | 0.9 | 5.0 | 0.9 | 4.8 | 0.9 | 3.6 | 0.9 | 2.1 |
| 0.95 | 3.6 | 0.95 | 3.8 | 0.95 | 3.5 | 0.95 | 3.4 | 0.95 | 2.6 | 0.95 | 1.7 |
| 1 | 1.2 | 1 | 1.2 | 1 | 1.2 | 1 | 1.2 | 1 | 1.2 | 1 | 1.2 |

| HF - HFO-1234yf - HFC-245cb - HFO-1234zeZ - HCFO-1233zdE- HFO-1243zf ||||||||||||
|---|---|---|---|---|---|---|---|---|---|---|---|
| Organics<br>0.2 F1234yf +<br>0.2 F245cb +<br>0.2 F1243zf +<br>0.2 F1234zeZ +<br>0.2 F1233zdE || Organics<br>0.96 F1234yf +<br>0.01 F245cb +<br>0.01 F1243zf +<br>0.01 F1234zeZ +<br>0.01 F1233zdE || Organics<br>0.01 F1234yf +<br>0.96 F245cb +<br>0.01 F1243zf +<br>0.01 F1234zeZ +<br>0.01 F1233zdE || Organics<br>0.01 F1234yf +<br>0.01 F245cb +<br>0.96 F1243zf +<br>0.01 F1234zeZ +<br>0.01 F1233zdE || Organics<br>0.01 F1234yf +<br>0.01 F245cb +<br>0.01 F1243zf +<br>0.96 F1234zeZ +<br>0.01 F1233zdE || Organics<br>0.01 F1234yf +<br>0.01 F245cb +<br>0.01 F1243zf +<br>0.01 F1234zeZ +<br>0.96 F1233zdE ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.2 | 0 | 6.7 | 0 | 4.6 | 0 | 5.8 | 0 | 1.9 | 0 | 1.5 |
| 0.05 | 5.3 | 0.05 | 7.6 | 0.05 | 5.8 | 0.05 | 6.7 | 0.05 | 3.0 | 0.05 | 2.6 |
| 0.1 | 5.3 | 0.1 | 7.6 | 0.1 | 5.8 | 0.1 | 6.7 | 0.1 | 3.0 | 0.1 | 2.6 |
| 0.15 | 5.3 | 0.15 | 7.6 | 0.15 | 5.8 | 0.15 | 6.7 | 0.15 | 3.0 | 0.15 | 2.6 |
| 0.2 | 5.3 | 0.2 | 7.6 | 0.2 | 5.8 | 0.2 | 6.7 | 0.2 | 3.0 | 0.2 | 2.6 |
| 0.25 | 5.3 | 0.25 | 7.6 | 0.25 | 5.8 | 0.25 | 6.7 | 0.25 | 3.0 | 0.25 | 2.6 |
| 0.3 | 5.3 | 0.3 | 7.6 | 0.3 | 5.8 | 0.3 | 6.7 | 0.3 | 3.0 | 0.3 | 2.6 |
| 0.35 | 5.3 | 0.35 | 7.6 | 0.35 | 5.8 | 0.35 | 6.7 | 0.35 | 3.0 | 0.35 | 2.6 |
| 0.4 | 5.3 | 0.4 | 7.6 | 0.4 | 5.8 | 0.4 | 6.7 | 0.4 | 3.0 | 0.4 | 2.6 |
| 0.45 | 5.3 | 0.45 | 7.6 | 0.45 | 5.8 | 0.45 | 6.7 | 0.45 | 3.0 | 0.45 | 2.6 |
| 0.5 | 5.3 | 0.5 | 7.6 | 0.5 | 5.8 | 0.5 | 6.7 | 0.5 | 3.0 | 0.5 | 2.6 |
| 0.55 | 5.3 | 0.55 | 7.6 | 0.55 | 5.8 | 0.55 | 6.7 | 0.55 | 3.0 | 0.55 | 2.6 |
| 0.6 | 5.3 | 0.6 | 7.6 | 0.6 | 5.8 | 0.6 | 6.7 | 0.6 | 3.0 | 0.6 | 2.6 |
| 0.65 | 5.3 | 0.65 | 7.6 | 0.65 | 5.8 | 0.65 | 6.6 | 0.65 | 3.0 | 0.65 | 2.6 |
| 0.7 | 5.3 | 0.7 | 7.6 | 0.7 | 5.8 | 0.7 | 6.5 | 0.7 | 3.0 | 0.7 | 2.6 |
| 0.75 | 5.2 | 0.75 | 7.5 | 0.75 | 5.8 | 0.75 | 6.4 | 0.75 | 3.0 | 0.75 | 2.6 |
| 0.8 | 5.6 | 0.8 | 7.2 | 0.8 | 5.8 | 0.8 | 6.1 | 0.8 | 2.9 | 0.8 | 2.5 |
| 0.85 | 4.6 | 0.85 | 6.6 | 0.85 | 5.8 | 0.85 | 5.6 | 0.85 | 2.7 | 0.85 | 2.3 |
| 0.9 | 3.9 | 0.9 | 5.5 | 0.9 | 5.0 | 0.9 | 4.7 | 0.9 | 2.4 | 0.9 | 2.0 |
| 0.95 | 2.9 | 0.95 | 3.8 | 0.95 | 3.5 | 0.95 | 3.4 | 0.95 | 1.9 | 0.95 | 1.7 |
| 1 | 1.2 | 1 | 1.2 | 1 | 1.2 | 1 | 1.2 | 1 | 1.2 | 1 | 1.2 |

| HF - HFO-1234yf- HFO-1234zeE - HFO-1234zeZ - HCFO-1233zdE- HFO-1243zf ||||||||||||
| Organics 0.2 F1234yf + 0.2 F1243zf + 0.2 F1233zdE 0.2 F1234zeE + 0.2 F1234zeZ ||  Organics 0.96 F1234yf + 0.01 F1243zf + 0.01 F1233zdE + 0.01 F1234zeE + 0.01 F1234zeZ || Organics 0.01 F1234yf + 0.96 F1243zf + 0.01 F1233zdE + 0.01 F1234zeE + 0.01 F1234zeZ || Organics 0.01 F1234yf + 0.01 F1243zf + 0.96 F1233zdE + 0.01 F1234zeE + 0.01 F1234zeZ || Organics 0.01 F1234yf + 0.01 F1243zf + 0.01 F1233zdE + 0.96 F1234zeE + 0.01 F1234zeZ || Organics 0.01 F1234yf + 0.01 F1243zf + 0.01 F1233zdE + 0.01 F1234zeE + 0.96 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0 | 4.2 | 0 | 6.7 | 0 | 5.8 | 0 | 1.5 | 0 | 4.8 | 0 | 1.9 |
| 0.05 | 5.3 | 0.05 | 7.6 | 0.05 | 6.7 | 0.05 | 2.6 | 0.05 | 5.8 | 0.05 | 3.0 |
| 0.1 | 5.3 | 0.1 | 7.6 | 0.1 | 6.7 | 0.1 | 2.6 | 0.1 | 5.8 | 0.1 | 3.0 |
| 0.15 | 5.3 | 0.15 | 7.6 | 0.15 | 6.7 | 0.15 | 2.6 | 0.15 | 5.8 | 0.15 | 3.0 |
| 0.2 | 5.3 | 0.2 | 7.6 | 0.2 | 6.7 | 0.2 | 2.6 | 0.2 | 5.8 | 0.2 | 3.0 |
| 0.25 | 5.3 | 0.25 | 7.6 | 0.25 | 6.7 | 0.25 | 2.6 | 0.25 | 5.8 | 0.25 | 3.0 |
| 0.3 | 5.3 | 0.3 | 7.6 | 0.3 | 6.7 | 0.3 | 2.6 | 0.3 | 5.8 | 0.3 | 3.0 |
| 0.35 | 5.3 | 0.35 | 7.6 | 0.35 | 6.7 | 0.35 | 2.6 | 0.35 | 5.8 | 0.35 | 3.0 |
| 0.4 | 5.3 | 0.4 | 7.6 | 0.4 | 6.7 | 0.4 | 2.6 | 0.4 | 5.8 | 0.4 | 3.0 |
| 0.45 | 5.3 | 0.45 | 7.6 | 0.45 | 6.7 | 0.45 | 2.6 | 0.45 | 5.8 | 0.45 | 3.0 |
| 0.5 | 5.3 | 0.5 | 7.6 | 0.5 | 6.7 | 0.5 | 2.6 | 0.5 | 5.8 | 0.5 | 3.0 |
| 0.55 | 5.3 | 0.55 | 7.6 | 0.55 | 6.7 | 0.55 | 2.6 | 0.55 | 5.7 | 0.55 | 3.0 |
| 0.6 | 5.2 | 0.6 | 7.6 | 0.6 | 6.7 | 0.6 | 2.6 | 0.6 | 5.6 | 0.6 | 3.0 |
| 0.65 | 5.2 | 0.65 | 7.6 | 0.65 | 6.6 | 0.65 | 2.6 | 0.65 | 5.5 | 0.65 | 3.0 |
| 0.7 | 5.2 | 0.7 | 7.6 | 0.7 | 6.5 | 0.7 | 2.6 | 0.7 | 5.4 | 0.7 | 3.0 |
| 0.75 | 5.0 | 0.75 | 7.5 | 0.75 | 6.3 | 0.75 | 2.6 | 0.75 | 5.1 | 0.75 | 3.0 |
| 0.8 | 4.7 | 0.8 | 7.1 | 0.8 | 6.1 | 0.8 | 2.5 | 0.8 | 4.8 | 0.8 | 2.9 |
| 0.85 | 4.3 | 0.85 | 6.5 | 0.85 | 5.6 | 0.85 | 2.3 | 0.85 | 4.3 | 0.85 | 2.7 |
| 0.9 | 3.7 | 0.9 | 5.5 | 0.9 | 4.7 | 0.9 | 2.0 | 0.9 | 3.6 | 0.9 | 2.4 |
| 0.95 | 2.7 | 0.95 | 3.8 | 0.95 | 3.4 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF - HFC-245cb - HFO-1234zeE - HFO-1234zeZ - HCFO-1233zdE - HFO-1243zf ||||||||||||
| Organics 0.2 F245cb + 0.2 F1243zf + 0.2 F1233zdE 0.2 F1234zeE + 0.2 F1234zeZ || Organics 0.96 F245cb + 0.01 F1243zf + 0.01 F1233zdE + 0.01 F1234zeE + 0.01 F1234zeZ || Organics 0.01 F245cb + 0.96 F1243zf + 0.01 F1233zdE + 0.01 F1234zeE + 0.01 F1234zeZ || Organics 0.01 F245cb + 0.01 F1243zf + 0.96 F1233zdE + 0.01 F1234zeE + 0.01 F1234zeZ || Organics 0.01 F245cb + 0.01 F1243zf + 0.01 F1233zdE + 0.96 F1234zeE + 0.01 F1234zeZ || Organics 0.01 F245cb + 0.01 F1243zf + 0.01 F1233zdE + 0.01 F1234zeE + 0.96 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
|---|---|---|---|---|---|---|---|---|---|---|---|
| 0 | 3.8 | 0 | 4.6 | 0 | 5.8 | 0 | 1.5 | 0 | 4.8 | 0 | 1.9 |
| 0.05 | 4.9 | 0.05 | 5.8 | 0.05 | 6.7 | 0.05 | 2.6 | 0.05 | 5.8 | 0.05 | 3.0 |
| 0.1 | 4.9 | 0.1 | 5.8 | 0.1 | 6.7 | 0.1 | 2.6 | 0.1 | 5.8 | 0.1 | 3.0 |
| 0.15 | 4.9 | 0.15 | 5.8 | 0.15 | 6.7 | 0.15 | 2.6 | 0.15 | 5.8 | 0.15 | 3.0 |
| 0.2 | 4.9 | 0.2 | 5.8 | 0.2 | 6.7 | 0.2 | 2.6 | 0.2 | 5.8 | 0.2 | 3.0 |
| 0.25 | 4.9 | 0.25 | 5.8 | 0.25 | 6.7 | 0.25 | 2.6 | 0.25 | 5.8 | 0.25 | 3.0 |
| 0.3 | 4.9 | 0.3 | 5.8 | 0.3 | 6.7 | 0.3 | 2.6 | 0.3 | 5.8 | 0.3 | 3.0 |
| 0.35 | 4.9 | 0.35 | 5.8 | 0.35 | 6.7 | 0.35 | 2.6 | 0.35 | 5.8 | 0.35 | 3.0 |
| 0.4 | 4.9 | 0.4 | 5.8 | 0.4 | 6.7 | 0.4 | 2.6 | 0.4 | 5.8 | 0.4 | 3.0 |
| 0.45 | 4.9 | 0.45 | 5.8 | 0.45 | 6.7 | 0.45 | 2.6 | 0.45 | 5.8 | 0.45 | 3.0 |
| 0.5 | 4.9 | 0.5 | 5.8 | 0.5 | 6.7 | 0.5 | 2.6 | 0.5 | 5.7 | 0.5 | 3.0 |
| 0.55 | 4.9 | 0.55 | 5.8 | 0.55 | 6.7 | 0.55 | 2.6 | 0.55 | 5.7 | 0.55 | 3.0 |
| 0.6 | 4.9 | 0.6 | 5.8 | 0.6 | 6.6 | 0.6 | 2.6 | 0.6 | 5.6 | 0.6 | 3.0 |
| 0.65 | 4.9 | 0.65 | 5.8 | 0.65 | 6.6 | 0.65 | 2.6 | 0.65 | 5.5 | 0.65 | 3.0 |
| 0.7 | 4.9 | 0.7 | 5.8 | 0.7 | 6.5 | 0.7 | 2.6 | 0.7 | 5.4 | 0.7 | 3.0 |
| 0.75 | 4.8 | 0.75 | 5.8 | 0.75 | 6.3 | 0.75 | 2.5 | 0.75 | 5.1 | 0.75 | 3.0 |
| 0.8 | 4.5 | 0.8 | 5.8 | 0.8 | 6.0 | 0.8 | 2.4 | 0.8 | 4.8 | 0.8 | 2.9 |
| 0.85 | 4.2 | 0.85 | 5.8 | 0.85 | 5.6 | 0.85 | 2.3 | 0.85 | 4.3 | 0.85 | 2.7 |
| 0.9 | 3.5 | 0.9 | 5.0 | 0.9 | 4.7 | 0.9 | 2.0 | 0.9 | 3.6 | 0.9 | 2.4 |
| 0.95 | 2.6 | 0.95 | 3.5 | 0.95 | 3.4 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

Example 11: Temperature and Pressure Range of Systems with 6 Compounds

|  | Boiling point range | |
|---|---|---|
| System with 6 compounds | Temperature ° C. | Pressure bar abs |
| HF-HCFO-1233xf-HFO-1234yf-HFC-245cb-HFO-1234zeE-HFO-1234zeZ | 0 to 40 | ~1.0~11.6 |
| HF-HCFO-1233xf-HFO-1234yf-HFC-245cb-HFO-1234zeE-HCFO-1233zdE | 0 to 40 | ~0.9 to ~11.6 |
| HF-HCFO-1233xf-HFO-1234yf-HFC-245cb-HFO-1234zeE-HFO-1243zf | 0 to 40 | ~1.0 to ~11.6 |
| HF-HCFO-1233xf-HFO-1234yf-HFC-245cb-HFO-1234zeZ-HCFO-1233zdE | 0 to 40 | ~0.9 to ~11.5 |
| HF-HCFO-1233xf-HFO-1234yf-HFC-245cb-HFO-1234zeZ-HFO-1243zf | 0 to 40 | ~1.0 to ~11.6 |
| HF-HCFO-1233xf-HFO-1234yf-HFO-1234zeE-HFO-1234zeZ-HCFO-1233zdE | 0 to 40 | ~0.9 to ~11.5 |
| HF-HCFO-1233xf-HFO-1234yf-HFO-1234zeE-HFO-1234zeZ-HFO-1243zf | 0 to 40 | ~1.0 to ~11.6 |
| HF-HCFO-1233xf-HFO-1234yf-HFO-1234zeE-HCFO-1233zdE-HFO-1243zf | 0 to 40 | ~0.9 to ~11.6 |
| HF-HCFO-1233xf-HFO-1234yf-HFO-1234zeZ-HCFO-1233zdE-HFO-1243zf | 0 to 40 | ~0.9 to ~11.6 |
| HF-HCFO-1233xf-HFC-245cb-HFO-1234zeE-HFO-1234zeZ-HCFO-1233zdE | 0 to 40 | ~0.9 to ~9.0 |
| HF-HCFO-1233xf-HFC-245cb-HFO-1234zeE-HFO-1234zeZ-HFO-1243zf | 0 to 40 | ~1.0 to ~10.3 |
| HF-HCFO-1233xf-HFC-245cb-HFO-1234zeE-HCFO-1233zdE-HFO-1243zf | 0 to 40 | ~0.9 to ~10.3 |
| HF-HCFO-1233xf-HFC-245cb-HFO-1234zeZ-HCFO-1233zdE-HFO-1243zf | 0 to 40 | ~1.0 to ~10.3 |
| HF-HCFO-1233xf-HFO-1234zeE-HFO-1234zeZ-HCFO-1233zdE-HFO-1243zf | 0 to 40 | ~0.9~10.3 |
| HF-HFO-1234yf-HFC-245cb-HFO-1234zeE-HFO-1234zeZ-HCFO-1233zdE | 0 to 40 | ~0.9~11.6 |
| HF-HFO-1234yf-HFC-245cb-HFO-1234zeE-HFO-1234zeZ-HFO-1243zf | 0 to 40 | ~1.2 to ~11.6 |
| HF-HFO-1234yf-HFC-245cb-HFO-1234zeE-HCFO-1233zdE-HFO-1243zf | 0 to 40 | ~1.0 to ~11.7 |
| HF-HFO-1234yf-HFC-245cb-HFO-1234zeZ-HCFO-1233zdE-HFO-1243zf | 0 to 40 | ~0.9 to ~11.6 |
| HF-HFO-1234yf-HFO-1234zeE-HFO-1234zeZ-HCFO-1233zdE-HFO-1243zf | 0 to 40 | ~0.9 to ~11.6 |
| HF-HFC-245cb-HFO-1234zeE-HFO-1234zeZ-HCFO-1233zdE-HFO-1243zf | 0 to 40 | ~0.9 to ~10.3 |

Example 12: Decantation Range of Systems with 6 Compounds

|  | Decantation ranges Mass percentage of HF Isotherm | | |
|---|---|---|---|
| System with 6 compounds | 0° C. | 25° C. | 40° C. |
| HF-HCFO-1233xf-HFO-1234yf-HFC-245cb-HFO-1234zeE-HFO-1234zeZ | 5-75 | 5-70 | 15-55 |
| HF-HCFO-1233xf-HFO-1234yf-HFC-245cb-HFO-1234zeE-HCFO-1233zdE | 5-75 | 5-70 | 15-55 |
| HF-HCFO-1233xf-HFO-1234yf-HFC-245cb-HFO-1234zeE-HFO-1243zf | 5-75 | 10-65 | * |
| HF-HCFO-1233xf-HFO-1234yf-HFC-245cb-HFO-1234zeZ-HCFO-1233zdE | 5-75 | 5-75 | 10-65 |
| HF-HCFO-1233xf-HFO-1234yf-HFC-245cb-HFO-1234zeZ-HFO-1243zf | 5-75 | 10-70 | 15-50 |
| HF-HCFO-1233xf-HFO-1234yf-HFO-1234zeE-HFO-1234zeZ-HCFO-1233zdE | 5-75 | 5-65 | 10-55 |
| HF-HCFO-1233xf-HFO-1234yf-HFO-1234zeE-HFO-1234zeZ-HFO-1243zf | 5-70 | 10-65 | * |
| HF-HCFO-1233xf-HFO-1234yf-HFO-1234zeE-HCFO-1233zdE-HFO-1243zf | 5-70 | 10-75 | * |
| HF-HCFO-1233xf-HFO-1234yf-HFO-1234zeZ-HCFO-1233zdE-HFO-1243zf | 5-75 | 5-70 | 10-55 |
| HF-HCFO-1233xf-HFC-245cb-HFO-1234zeE-HFO-1234zeZ-HCFO-1233zdE | 5-75 | 5-70 | 10-65 |
| HF-HCFO-1233xf-HFC-245cb-HFO-1234zeE-HFO-1234zeZ-HFO-1243zf | 5-75 | 10-70 | 15-45 |
| HF-HCFO-1233xf-HFC-245cb-HFO-1234zeE-HCFO-1233zdE-HFO-1243zf | 5-75 | 5-70 | 15-50 |
| HF-HCFO-1233xf-HFC-245cb-HFO-1234zeZ-HCFO-1233zdE-HFO-1243zf | 5-75 | 5-70 | 10-65 |
| HF-HCFO-1233xf-HFO-1234zeE-HFO-1234zeZ-HCFO-1233zdE-HFO-1243zf | 5-75 | 5-65 | 10-55 |
| HF-HFO-1234yf-HFC-245cb-HFO-1234zeE-HFO-1234zeZ-HCFO-1233zdE | 5-75 | 5-70 | 15-55 |
| HF-HFO-1234yf-HFC-245cb-HFO-1234zeE-HFO-1234zeZ-HFO-1243zf | 5-75 | 10-65 | * |
| HF-HFO-1234yf-HFC-245cb-HFO-1234zeE-HCFO-1233zdE-HFO-1243zf | 5-75 | 10-65 | * |
| HF-HFO-1234yf-HFC-245cb-HFO-1234zeZ-HCFO-1233zdE-HFO-1243zf | 5-75 | 10-70 | 15-55 |
| HF-HFO-1234yf-HFO-1234zeE-HFO-1234zeZ-HCFO-1233zdE-HFO-1243zf | 5-70 | 10-65 | * |
| HF-HFC-245cb-HFO-1234zeE-HFO-1234zeZ-HCFO-1233zdE-HFO-1243zf | 5-75 | 5-70 | 15-50 |

Example 13: Systems with Seven Compounds, Isotherm at 25° C.

| HF-HCFO-1233xf-HFC-245cb-HCFO-1233zdE-HFO-1234zeE-HFO-1234zeZ-HFO-1243zf ||||||||
|---|---|---|---|---|---|---|---|
| Organics 0.15 F1233xf + 0.17 F245cb + 0.17 F1233zdE + 0.17 F1234zeE + 0.17 F1234zeZ + 0.17 F1243zf |  | Organics 0.95 F1233xf + 0.01 F245cb + 0.01 F1233zdE + 0.01 F1234zeE + 0.01 F1234zeZ + 0.01 F1243zf |  | Organics 0.01 F1233xf + 0.95 F24cb + 0.01 F1233zdE + 0.01 F1234zeE + 0.01 F1234zeZ + 0.01 F1243zf |  | Organics 0.01 F1233xf + 0.01 F245cb + 0.95 F1233zdE + 0.01 F1234zeE + 0.01 F1234zeZ + 0.01 F1243zf |  |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.5 | 0 | 1.7 | 0 | 4.6 | 0 | 1.5 |
| 0.05 | 4.6 | 0.05 | 2.8 | 0.05 | 5.7 | 0.05 | 2.6 |
| 0.1 | 4.6 | 0.1 | 2.8 | 0.1 | 5.7 | 0.1 | 2.6 |
| 0.15 | 4.6 | 0.15 | 2.8 | 0.15 | 5.7 | 0.15 | 2.6 |
| 0.2 | 4.6 | 0.2 | 2.8 | 0.2 | 5.7 | 0.2 | 2.6 |
| 0.25 | 4.6 | 0.25 | 2.8 | 0.25 | 5.8 | 0.25 | 2.6 |
| 0.3 | 4.6 | 0.3 | 2.8 | 0.3 | 5.8 | 0.3 | 2.6 |
| 0.35 | 4.6 | 0.35 | 2.8 | 0.35 | 5.8 | 0.35 | 2.6 |
| 0.4 | 4.6 | 0.4 | 2.8 | 0.4 | 5.8 | 0.4 | 2.6 |
| 0.45 | 4.6 | 0.45 | 2.8 | 0.45 | 5.8 | 0.45 | 2.6 |
| 0.5 | 4.6 | 0.5 | 2.8 | 0.5 | 5.8 | 0.5 | 2.6 |
| 0.55 | 4.6 | 0.55 | 2.8 | 0.55 | 5.8 | 0.55 | 2.6 |
| 0.6 | 4.6 | 0.6 | 2.8 | 0.6 | 5.8 | 0.6 | 2.6 |
| 0.65 | 4.6 | 0.65 | 2.8 | 0.65 | 5.8 | 0.65 | 2.6 |
| 0.7 | 4.6 | 0.7 | 2.8 | 0.7 | 5.8 | 0.7 | 2.6 |
| 0.75 | 4.5 | 0.75 | 2.8 | 0.75 | 5.8 | 0.75 | 2.6 |
| 0.8 | 4.2 | 0.8 | 2.6 | 0.8 | 5.8 | 0.8 | 2.4 |
| 0.85 | 3.9 | 0.85 | 2.4 | 0.85 | 5.8 | 0.85 | 2.3 |
| 0.9 | 3.3 | 0.9 | 2.2 | 0.9 | 4.9 | 0.9 | 2.0 |
| 0.95 | 2.5 | 0.95 | 1.8 | 0.95 | 3.5 | 0.95 | 1.7 |
| 1 | 1.2 | 1 | 1.2 | 1 | 1.2 | 1 | 1.2 |
|  |  | Organics 0.01 F1233xf + 0.01 F245cb + 0.01 F1233zdE + 0.95 F1234zeE + 0.01 F1234zeZ + 0.01 F1243zf |  | Organics 0.01 F1233xf + 0.01 F245cb + 0.01 F1233zdE + 0.01 F1234zeE + 0.95 F1234zeZ + 0.01 F1243zf |  | Organics 0.01 F1233xf + 0.01 F245cb + 0.01 F1233zdE + 0.01 F1234zeE + 0.01 F1234zeZ + 0.95 F1243zf |  |
|  |  | MASSFRAC HF | TOTAL PRESSURE bar | MASSFRAC HF | TOTAL PRESSURE bar | MASSFRAC HF | TOTAL PRESSURE bar |
|  |  | 0 | 4.8 | 0 | 5.7 | 0 | 1.9 |
|  |  | 0.05 | 5.7 | 0.05 | 6.7 | 0.05 | 3.0 |
|  |  | 0.1 | 5.8 | 0.1 | 6.7 | 0.1 | 3.0 |
|  |  | 0.15 | 5.8 | 0.15 | 6.7 | 0.15 | 3.0 |
|  |  | 0.2 | 5.8 | 0.2 | 6.7 | 0.2 | 3.0 |
|  |  | 0.25 | 5.8 | 0.25 | 6.7 | 0.25 | 3.0 |
|  |  | 0.3 | 5.8 | 0.3 | 6.7 | 0.3 | 3.0 |
|  |  | 0.35 | 5.8 | 0.35 | 6.7 | 0.35 | 3.0 |
|  |  | 0.4 | 5.8 | 0.4 | 6.7 | 0.4 | 3.0 |
|  |  | 0.45 | 5.7 | 0.45 | 6.7 | 0.45 | 3.0 |
|  |  | 0.5 | 5.7 | 0.5 | 6.7 | 0.5 | 3.0 |
|  |  | 0.55 | 5.7 | 0.55 | 6.6 | 0.55 | 3.0 |
|  |  | 0.6 | 5.6 | 0.6 | 6.6 | 0.6 | 3.0 |
|  |  | 0.65 | 5.5 | 0.65 | 6.6 | 0.65 | 3.0 |
|  |  | 0.7 | 5.3 | 0.7 | 6.5 | 0.7 | 3.0 |
|  |  | 0.75 | 5.1 | 0.75 | 6.3 | 0.75 | 3.0 |
|  |  | 0.8 | 4.8 | 0.8 | 6.0 | 0.8 | 2.9 |
|  |  | 0.85 | 4.3 | 0.85 | 5.5 | 0.85 | 2.7 |
|  |  | 0.9 | 3.6 | 0.9 | 4.7 | 0.9 | 2.4 |
|  |  | 0.95 | 2.6 | 0.95 | 3.3 | 0.95 | 1.9 |
|  |  | 1 | 1.2 | 1 | 1.2 | 1 | 1.2 |

HF-HCFO-1233xf-HFO-1234yf-HFC-245cb-HCFO-1233zdE-HFO-1234zeE-HFO-1234zeZ

| Organics 0.15 F1233xf + 0.17 F1234yf + 0.17 F245cb + 0.17 F1233zdE + 0.17 F1234zeE + 0.17 F1234zeZ | | Organics 0.01 F1233xf + 0.95 F1234yf + 0.01 F245cb + 0.01 F1233zdE + 0.01 F1234zeE + 0.01 F1234zeZ | | Organics 0.01 F1233xf + 0.01 F1234yf + 0.95 F245cb + 0.01 F1233zdE + 0.01 F1234zeE + 0.01 F1234zeZ | | Organics 0.01 F1233xf + 0.01 F1234yf + 0.01 F245cb + 0.95 F1233zdE + 0.01 F1234zeE + 0.01 F1234zeZ | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.6 | 0 | 6.6 | 0 | 4.6 | 0 | 1.5 |
| 0.05 | 4.7 | 0.05 | 7.6 | 0.05 | 5.8 | 0.05 | 2.6 |
| 0.1 | 4.7 | 0.1 | 7.6 | 0.1 | 5.8 | 0.1 | 2.6 |
| 0.15 | 4.7 | 0.15 | 7.6 | 0.15 | 5.8 | 0.15 | 2.6 |
| 0.2 | 4.7 | 0.2 | 7.6 | 0.2 | 5.8 | 0.2 | 2.6 |
| 0.25 | 4.7 | 0.25 | 7.6 | 0.25 | 5.8 | 0.25 | 2.6 |
| 0.3 | 4.7 | 0.3 | 7.6 | 0.3 | 5.8 | 0.3 | 2.6 |
| 0.35 | 4.7 | 0.35 | 7.6 | 0.35 | 5.8 | 0.35 | 2.6 |
| 0.4 | 4.7 | 0.4 | 7.6 | 0.4 | 5.8 | 0.4 | 2.6 |
| 0.45 | 4.7 | 0.45 | 7.6 | 0.45 | 5.8 | 0.45 | 2.6 |
| 0.5 | 4.7 | 0.5 | 7.6 | 0.5 | 5.8 | 0.5 | 2.6 |
| 0.55 | 4.7 | 0.55 | 7.6 | 0.55 | 5.8 | 0.55 | 2.6 |
| 0.6 | 4.7 | 0.6 | 7.6 | 0.6 | 5.8 | 0.6 | 2.6 |
| 0.65 | 4.7 | 0.65 | 7.6 | 0.65 | 5.8 | 0.65 | 2.6 |
| 0.7 | 4.7 | 0.7 | 7.6 | 0.7 | 5.8 | 0.7 | 2.6 |
| 0.75 | 4.6 | 0.75 | 7.4 | 0.75 | 5.8 | 0.75 | 2.6 |
| 0.8 | 4.4 | 0.8 | 7.1 | 0.8 | 5.8 | 0.8 | 2.5 |
| 0.85 | 4.1 | 0.85 | 6.5 | 0.85 | 5.8 | 0.85 | 2.3 |
| 0.9 | 3.5 | 0.9 | 5.5 | 0.9 | 5.0 | 0.9 | 2.0 |
| 0.95 | 2.5 | 0.95 | 3.8 | 0.95 | 3.5 | 0.95 | 1.7 |
| 1 | 1.2 | 1 | 1.2 | 1 | 1.2 | 1 | 1.2 |

| | | Organics 0.01 F1233xf + 0.01 F1234yf + 0.01 F245cb + 0.01 F1233zdE + 0.95 F1234zeE + 0.01 F1234zeZ | | Organics 0.01 F1233xf + 0.01 F1234yf + 0.01 F245cb + 0.01 F1233zdE + 0.01 F1234zeE + 0.95 F1234zeZ | | Organics 0.95 F1233xf + 0.01 F1234yf + 0.01 F245cb + 0.01 F1233zdE + 0.01 F1234zeE + 0.01 F1234zeZ | |
|---|---|---|---|---|---|---|---|
| | | MASSFRAC HF | TOTAL PRESSURE bar | MASSFRAC HF | TOTAL PRESSURE bar | MASSFRAC HF | TOTAL PRESSURE bar |
| | | 0 | 4.8 | 0 | 1.9 | 0 | 1.7 |
| | | 0.05 | 5.8 | 0.05 | 3.0 | 0.05 | 2.8 |
| | | 0.1 | 5.8 | 0.1 | 3.0 | 0.1 | 2.8 |
| | | 0.15 | 5.8 | 0.15 | 3.0 | 0.15 | 2.8 |
| | | 0.2 | 5.8 | 0.2 | 3.0 | 0.2 | 2.8 |
| | | 0.25 | 5.8 | 0.25 | 3.0 | 0.25 | 2.8 |
| | | 0.3 | 5.8 | 0.3 | 3.0 | 0.3 | 2.8 |
| | | 0.35 | 5.8 | 0.35 | 3.0 | 0.35 | 2.8 |
| | | 0.4 | 5.8 | 0.4 | 3.0 | 0.4 | 2.8 |
| | | 0.45 | 5.7 | 0.45 | 3.0 | 0.45 | 2.8 |
| | | 0.5 | 5.7 | 0.5 | 3.0 | 0.5 | 2.8 |
| | | 0.55 | 5.7 | 0.55 | 3.0 | 0.55 | 2.8 |
| | | 0.6 | 5.6 | 0.6 | 3.0 | 0.6 | 2.8 |
| | | 0.65 | 5.5 | 0.65 | 3.0 | 0.65 | 2.8 |
| | | 0.7 | 5.3 | 0.7 | 3.0 | 0.7 | 2.8 |
| | | 0.75 | 5.1 | 0.75 | 3.0 | 0.75 | 2.8 |
| | | 0.8 | 4.8 | 0.8 | 2.9 | 0.8 | 2.6 |
| | | 0.85 | 4.3 | 0.85 | 2.7 | 0.85 | 2.5 |
| | | 0.9 | 3.6 | 0.9 | 2.4 | 0.9 | 2.2 |
| | | 0.95 | 2.6 | 0.95 | 1.9 | 0.95 | 1.8 |
| | | 1 | 1.2 | 1 | 1.2 | 1 | 1.2 |

| HF-HCFO-1233xf-HFO-1234yf-HFC-245cb-HCFO-1233zdE-HFO-1234zeE-HFO-1243zf ||||||||
|---|---|---|---|---|---|---|---|
| Organics 0.15 F1233xf + 0.17 F1234yf + 0.17 F245cb + 0.17 F1233zdE + 0.17 F1234zeE + 0.17 F1243zf || Organics 0.01 F1233xf + 0.95 F1234yf + 0.01 F245cb + 0.01 F1233zdE + 0.01 F1234zeE + 0.01 F1243zf || Organics 0.01 F1233xf + 0.01 F1234yf + 0.95 F245cb + 0.01 F1233zdE + 0.01 F1234zeE + 0.01 F1243zf || Organics 0.01 F1233xf + 0.01 F1234yf + 0.01 F245cb + 0.95 F1233zdE + 0.01 F1234zeE + 0.01 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 6.6 | 0 | 4.6 | 0 | 1.5 |
| 0.05 | 5.4 | 0.05 | 7.6 | 0.05 | 5.8 | 0.05 | 2.6 |
| 0.1 | 5.4 | 0.1 | 7.6 | 0.1 | 5.8 | 0.1 | 2.6 |
| 0.15 | 5.4 | 0.15 | 7.6 | 0.15 | 5.8 | 0.15 | 2.6 |
| 0.2 | 5.4 | 0.2 | 7.6 | 0.2 | 5.8 | 0.2 | 2.6 |
| 0.25 | 5.4 | 0.25 | 7.6 | 0.25 | 5.8 | 0.25 | 2.6 |
| 0.3 | 5.4 | 0.3 | 7.6 | 0.3 | 5.8 | 0.3 | 2.6 |
| 0.35 | 5.4 | 0.35 | 7.6 | 0.35 | 5.8 | 0.35 | 2.6 |
| 0.4 | 5.4 | 0.4 | 7.6 | 0.4 | 5.8 | 0.4 | 2.6 |
| 0.45 | 5.4 | 0.45 | 7.6 | 0.45 | 5.8 | 0.45 | 2.6 |
| 0.5 | 5.4 | 0.5 | 7.6 | 0.5 | 5.8 | 0.5 | 2.6 |
| 0.55 | 5.4 | 0.55 | 7.6 | 0.55 | 5.8 | 0.55 | 2.6 |
| 0.6 | 5.4 | 0.6 | 7.6 | 0.6 | 5.8 | 0.6 | 2.6 |
| 0.65 | 5.4 | 0.65 | 7.6 | 0.65 | 5.8 | 0.65 | 2.6 |
| 0.7 | 5.4 | 0.7 | 7.6 | 0.7 | 5.8 | 0.7 | 2.6 |
| 0.75 | 5.3 | 0.75 | 7.4 | 0.75 | 5.8 | 0.75 | 2.6 |
| 0.8 | 5.0 | 0.8 | 7.1 | 0.8 | 5.8 | 0.8 | 2.5 |
| 0.85 | 4.6 | 0.85 | 6.5 | 0.85 | 5.8 | 0.85 | 2.3 |
| 0.9 | 3.9 | 0.9 | 5.5 | 0.9 | 5.0 | 0.9 | 2.1 |
| 0.95 | 2.8 | 0.95 | 3.8 | 0.95 | 3.5 | 0.95 | 1.7 |
| 1 | 1.2 | 1 | 1.2 | 1 | 1.2 | 1 | 1.2 |

| Organics 0.01 F1233xf + 0.01 F1234yf + 0.01 F245cb + 0.01 F1233zdE + 0.95 F1234zeE + 0.01 F1243zf || Organics 0.01 F1233xf + 0.01 F1234yf + 0.01 F245cb + 0.01 F1233zdE + 0.01 F1234zeE + 0.95 F1243zf || Organics 0.95 F1233xf + 0.01 F1234yf + 0.01 F245cb + 0.01 F1233zdE + 0.01 F1234zeE + 0.01 F1243zf ||
|---|---|---|---|---|---|
| MASSFRAC HF | TOTAL PRESSURE bar | MASSFRAC HF | TOTAL PRESSURE bar | MASSFRAC HF | TOTAL PRESSURE bar |
| 0 | 4.8 | 0 | 5.8 | 0 | 1.7 |
| 0.05 | 5.8 | 0.05 | 6.7 | 0.05 | 2.8 |
| 0.1 | 5.8 | 0.1 | 6.7 | 0.1 | 2.8 |
| 0.15 | 5.8 | 0.15 | 6.7 | 0.15 | 2.8 |
| 0.2 | 5.8 | 0.2 | 6.7 | 0.2 | 2.8 |
| 0.25 | 5.8 | 0.25 | 6.7 | 0.25 | 2.8 |
| 0.3 | 5.8 | 0.3 | 6.7 | 0.3 | 2.8 |
| 0.35 | 5.8 | 0.35 | 6.7 | 0.35 | 2.8 |
| 0.4 | 5.8 | 0.4 | 6.7 | 0.4 | 2.8 |
| 0.45 | 5.8 | 0.45 | 6.7 | 0.45 | 2.8 |
| 0.5 | 5.8 | 0.5 | 6.7 | 0.5 | 2.8 |
| 0.55 | 5.7 | 0.55 | 6.7 | 0.55 | 2.8 |
| 0.6 | 5.6 | 0.6 | 6.7 | 0.6 | 2.8 |
| 0.65 | 5.5 | 0.65 | 6.6 | 0.65 | 2.8 |
| 0.7 | 5.4 | 0.7 | 6.5 | 0.7 | 2.8 |
| 0.75 | 5.1 | 0.75 | 6.3 | 0.75 | 2.8 |
| 0.8 | 4.8 | 0.8 | 6.1 | 0.8 | 2.7 |
| 0.85 | 4.3 | 0.85 | 5.6 | 0.85 | 2.5 |
| 0.9 | 3.6 | 0.9 | 4.7 | 0.9 | 2.2 |
| 0.95 | 2.6 | 0.95 | 3.4 | 0.95 | 1.8 |
| 1 | 1.2 | 1 | 1.2 | 1 | 1.2 |

| HF-HCFO-1233xf-HFO-1234yf-HFC-245cb-HCFO-1233zdE-HFO-1234zeZ-HFO-1234zeZ ||||||||
|---|---|---|---|---|---|---|---|
| Organics 0.15 F1233xf + 0.17 F1234yf + 0.17 F245cb + 0.17 F1243zf + 0.17 F1233zdE + 0.17 F1234zeZ || Organics 0.01 F1233xf + 0.95 F1234yf + 0.01 F245cb + 0.01 F1243zf + 0.01 F1233zdE + 0.01 F1234zeZ || Organics 0.01 F1233xf + 0.01 F1234yf + 0.95 F245cb + 0.01 F1243zf + 0.01 F1233zdE + 0.01 F1234zeZ || Organics 0.01 F1233xf + 0.01 F1234yf + 0.01 F245cb + 0.95 F1243zf + 0.01 F1233zdE + 0.01 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.8 | 0 | 6.6 | 0 | 4.6 | 0 | 5.7 |
| 0.05 | 4.9 | 0.05 | 7.6 | 0.05 | 5.8 | 0.05 | 6.7 |
| 0.1 | 4.9 | 0.1 | 7.6 | 0.1 | 5.8 | 0.1 | 6.7 |
| 0.15 | 4.9 | 0.15 | 7.6 | 0.15 | 5.8 | 0.15 | 6.7 |
| 0.2 | 4.9 | 0.2 | 7.6 | 0.2 | 5.8 | 0.2 | 6.7 |
| 0.25 | 4.9 | 0.25 | 7.6 | 0.25 | 5.8 | 0.25 | 6.7 |
| 0.3 | 4.9 | 0.3 | 7.6 | 0.3 | 5.8 | 0.3 | 6.7 |
| 0.35 | 4.9 | 0.35 | 7.6 | 0.35 | 5.8 | 0.35 | 6.7 |
| 0.4 | 4.9 | 0.4 | 7.6 | 0.4 | 5.8 | 0.4 | 6.7 |
| 0.45 | 4.9 | 0.45 | 7.6 | 0.45 | 5.8 | 0.45 | 6.7 |
| 0.5 | 4.9 | 0.5 | 7.6 | 0.5 | 5.8 | 0.5 | 6.7 |
| 0.55 | 4.9 | 0.55 | 7.6 | 0.55 | 5.8 | 0.55 | 6.7 |
| 0.6 | 4.9 | 0.6 | 7.6 | 0.6 | 5.8 | 0.6 | 6.6 |
| 0.65 | 4.9 | 0.65 | 7.6 | 0.65 | 5.8 | 0.65 | 6.6 |
| 0.7 | 4.9 | 0.7 | 7.6 | 0.7 | 5.8 | 0.7 | 6.5 |
| 0.75 | 4.9 | 0.75 | 7.4 | 0.75 | 5.8 | 0.75 | 6.3 |
| 0.8 | 4.7 | 0.8 | 7.1 | 0.8 | 5.8 | 0.8 | 6.0 |
| 0.85 | 4.3 | 0.85 | 6.5 | 0.85 | 5.8 | 0.85 | 5.5 |
| 0.9 | 3.7 | 0.9 | 5.5 | 0.9 | 5.0 | 0.9 | 4.7 |
| 0.95 | 2.7 | 0.95 | 3.8 | 0.95 | 3.5 | 0.95 | 3.3 |
| 1 | 1.2 | 1 | 1.2 | 1 | 1.2 | 1 | 1.2 |
| || Organics 0.01 F1233xf + 0.01 F1234yf + 0.01 F245cb + 0.01 F1243zf + 0.95 F1233zdE + 0.01 F1234zeZ || Organics 0.01 F1233xf + 0.01 F1234yf + 0.01 F245cb + 0.01 F1243zf + 0.01 F1233zdE + 0.95 F1234zeZ || Organics 0.95 F1233xf + 0.01 F1234yf + 0.01 F245cb + 0.01 F1243zf + 0.01 F1233zdE + 0.01 F1234zeZ ||
| || MASSFRAC HF | TOTAL PRESSURE bar | MASSFRAC HF | TOTAL PRESSURE bar | MASSFRAC HF | TOTAL PRESSURE bar |
| || 0 | 1.5 | 0 | 1.9 | 0 | 1.7 |
| || 0.05 | 2.6 | 0.05 | 3.0 | 0.05 | 2.8 |
| || 0.1 | 2.6 | 0.1 | 3.0 | 0.1 | 2.8 |
| || 0.15 | 2.6 | 0.15 | 3.0 | 0.15 | 2.8 |
| || 0.2 | 2.6 | 0.2 | 3.0 | 0.2 | 2.8 |
| || 0.25 | 2.6 | 0.25 | 3.0 | 0.25 | 2.8 |
| || 0.3 | 2.6 | 0.3 | 3.0 | 0.3 | 2.8 |
| || 0.35 | 2.6 | 0.35 | 3.0 | 0.35 | 2.8 |
| || 0.4 | 2.6 | 0.4 | 3.0 | 0.4 | 2.8 |
| || 0.45 | 2.6 | 0.45 | 3.0 | 0.45 | 2.8 |
| || 0.5 | 2.6 | 0.5 | 3.0 | 0.5 | 2.8 |
| || 0.55 | 2.6 | 0.55 | 3.0 | 0.55 | 2.8 |
| || 0.6 | 2.6 | 0.6 | 3.0 | 0.6 | 2.8 |
| || 0.65 | 2.6 | 0.65 | 3.0 | 0.65 | 2.8 |
| || 0.7 | 2.6 | 0.7 | 3.0 | 0.7 | 2.8 |
| || 0.75 | 2.6 | 0.75 | 3.0 | 0.75 | 2.8 |
| || 0.8 | 2.5 | 0.8 | 2.9 | 0.8 | 2.7 |
| || 0.85 | 2.3 | 0.85 | 2.7 | 0.85 | 2.5 |
| || 0.9 | 2.0 | 0.9 | 2.4 | 0.9 | 2.2 |
| || 0.95 | 1.7 | 0.95 | 1.9 | 0.95 | 1.8 |
| || 1 | 1.2 | 1 | 1.2 | 1 | 1.2 |

| HF-HCFO-1233xf-HFO-1234yf-HFC-245cb-HFO-1234zeE-HFO-1234zeZ-HFO-12437zf ||||||||
|---|---|---|---|---|---|---|---|
| Organics<br>0.15 F1233xf + 0.17 F1234yf + 0.17 F245cb + 0.17 F1243zf + 0.17 F1234zeE + 0.17 F1234zeZ || Organics<br>0.01 F1233xf + 0.95 F1234yf + 0.01 F245cb + 0.01 F1243zf + 0.01 F1234zeE + 0.01 F1234zeZ || Organics<br>0.01 F1233xf + 0.01 F1234yf + 0.95 F245cb + 0.01 F1243zf + 0.01 F1234zeE + 0.01 F1234zeZ || Organics<br>0.01 F1233xf + 0.01 F1234yf + 0.01 F245cb + 0.95 F1243zf + 0.01 F1234zeE + 0.01 F1234zeZ ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 6.6 | 0 | 4.6 | 0 | 5.8 |
| 0.05 | 5.5 | 0.05 | 7.6 | 0.05 | 5.8 | 0.05 | 6.7 |
| 0.1 | 5.5 | 0.1 | 7.6 | 0.1 | 5.8 | 0.1 | 6.7 |
| 0.15 | 5.5 | 0.15 | 7.6 | 0.15 | 5.8 | 0.15 | 6.7 |
| 0.2 | 5.5 | 0.2 | 7.6 | 0.2 | 5.8 | 0.2 | 6.7 |
| 0.25 | 5.5 | 0.25 | 7.6 | 0.25 | 5.8 | 0.25 | 6.7 |
| 0.3 | 5.5 | 0.3 | 7.6 | 0.3 | 5.8 | 0.3 | 6.7 |
| 0.35 | 5.5 | 0.35 | 7.6 | 0.35 | 5.8 | 0.35 | 6.7 |
| 0.4 | 5.5 | 0.4 | 7.6 | 0.4 | 5.8 | 0.4 | 6.7 |
| 0.45 | 5.5 | 0.45 | 7.6 | 0.45 | 5.8 | 0.45 | 6.7 |
| 0.5 | 5.5 | 0.5 | 7.6 | 0.5 | 5.8 | 0.5 | 6.7 |
| 0.55 | 5.5 | 0.55 | 7.6 | 0.55 | 5.8 | 0.55 | 6.7 |
| 0.6 | 5.5 | 0.6 | 7.6 | 0.6 | 5.8 | 0.6 | 6.7 |
| 0.65 | 5.5 | 0.65 | 7.6 | 0.65 | 5.8 | 0.65 | 6.6 |
| 0.7 | 5.5 | 0.7 | 7.6 | 0.7 | 5.8 | 0.7 | 6.5 |
| 0.75 | 5.3 | 0.75 | 7.4 | 0.75 | 5.8 | 0.75 | 6.3 |
| 0.8 | 5.1 | 0.8 | 7.1 | 0.8 | 5.8 | 0.8 | 6.1 |
| 0.85 | 4.6 | 0.85 | 6.5 | 0.85 | 5.8 | 0.85 | 5.6 |
| 0.9 | 3.9 | 0.9 | 5.5 | 0.9 | 5.0 | 0.9 | 4.7 |
| 0.95 | 2.8 | 0.95 | 3.8 | 0.95 | 3.5 | 0.95 | 3.4 |
| 1 | 1.2 | 1 | 1.2 | 1 | 1.2 | 1 | 1.2 |
|  |  | Organics<br>0.01 F1233xf + 0.01 F1234yf + 0.01 F245cb + 0.01 F1243zf + 0.95 F1234zeE + 0.01 F1234zeZ || Organics<br>0.01 F1233xf + 0.01 F1234yf + 0.01 F245cb + 0.01 F1243zf + 0.01 F1234zeE + 0.95 F1234zeZ || Organics<br>0.95 F1233xf + 0.01 F1234yf + 0.01 F245cb + 0.01 F1243zf + 0.01 F1234zeE + 0.01 F1234zeZ ||
|  |  | MASSFRAC HF | TOTAL PRESSURE bar | MASSFRAC HF | TOTAL PRESSURE bar | MASSFRAC HF | TOTAL PRESSURE bar |
|  |  | 0 | 4.8 | 0 | 2.0 | 0 | 1.7 |
|  |  | 0.05 | 5.8 | 0.05 | 3.1 | 0.05 | 2.8 |
|  |  | 0.1 | 5.8 | 0.1 | 3.1 | 0.1 | 2.8 |
|  |  | 0.15 | 5.8 | 0.15 | 3.1 | 0.15 | 2.8 |
|  |  | 0.2 | 5.8 | 0.2 | 3.1 | 0.2 | 2.8 |
|  |  | 0.25 | 5.8 | 0.25 | 3.1 | 0.25 | 2.8 |
|  |  | 0.3 | 5.8 | 0.3 | 3.1 | 0.3 | 2.8 |
|  |  | 0.35 | 5.8 | 0.35 | 3.1 | 0.35 | 2.8 |
|  |  | 0.4 | 5.8 | 0.4 | 3.1 | 0.4 | 2.8 |
|  |  | 0.45 | 5.8 | 0.45 | 3.1 | 0.45 | 2.8 |
|  |  | 0.5 | 5.8 | 0.5 | 3.1 | 0.5 | 2.8 |
|  |  | 0.55 | 5.7 | 0.55 | 3.1 | 0.55 | 2.8 |
|  |  | 0.6 | 5.5 | 0.6 | 3.1 | 0.6 | 2.8 |
|  |  | 0.65 | 5.5 | 0.65 | 3.1 | 0.65 | 2.8 |
|  |  | 0.7 | 5.4 | 0.7 | 3.1 | 0.7 | 2.8 |
|  |  | 0.75 | 5.1 | 0.75 | 3.1 | 0.75 | 2.8 |
|  |  | 0.8 | 4.8 | 0.8 | 2.9 | 0.8 | 2.7 |
|  |  | 0.85 | 4.3 | 0.85 | 2.7 | 0.85 | 2.5 |
|  |  | 0.9 | 3.6 | 0.9 | 2.4 | 0.9 | 2.2 |
|  |  | 0.95 | 2.6 | 0.95 | 1.9 | 0.95 | 1.8 |
|  |  | 1 | 1.2 | 1 | 1.2 | 1 | 1.2 |

| HF-HCFO-1233xf-HFO-1234yf-HCFO-1233zdE-HFO-1234zeE-HFO-1234zeZ-HFO-1243zf | | | | | | | |
|---|---|---|---|---|---|---|---|
| Organics 0.15 F1233xf + 0.17 F1234yf + 0.17 F1233zdE + 0.17 F1243zf + 0.17 F1234zeE + 0.17 F1234zeZ | | Organics 0.01 F1233xf + 0.95 F1234yf + 0.01 F1233zdE + 0.01 F1243zf + 0.01 F1234zeE + 0.01 F1234zeZ | | Organics 0.01 F1233xf + 0.01 F1234yf + 0.95 F1233zdE + 0.01 F1243zf + 0.01 F1234zeE + 0.01 F1234zeZ | | Organics 0.01 F1233xf + 0.01 F1234yf + 0.01 F1233zdE + 0.95 F1243zf + 0.01 F1234zeE + 0.01 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 3.9 | 0 | 6.6 | 0 | 1.5 | 0 | 5.7 |
| 0.05 | 5.0 | 0.05 | 7.6 | 0.05 | 2.6 | 0.05 | 6.7 |
| 0.1 | 4.9 | 0.1 | 7.6 | 0.1 | 2.6 | 0.1 | 6.7 |
| 0.15 | 4.9 | 0.15 | 7.6 | 0.15 | 2.6 | 0.15 | 6.7 |
| 0.2 | 4.9 | 0.2 | 7.6 | 0.2 | 2.6 | 0.2 | 6.7 |
| 0.25 | 4.9 | 0.25 | 7.6 | 0.25 | 2.6 | 0.25 | 6.7 |
| 0.3 | 4.9 | 0.3 | 7.6 | 0.3 | 2.6 | 0.3 | 6.7 |
| 0.35 | 4.9 | 0.35 | 7.6 | 0.35 | 2.6 | 0.35 | 6.7 |
| 4 | 4.9 | 0.4 | 7.6 | 0.4 | 2.6 | 0.4 | 6.7 |
| 0.45 | 4.9 | 0.45 | 7.6 | 0.45 | 2.6 | 0.45 | 6.7 |
| 0.5 | 4.9 | 0.5 | 7.6 | 0.5 | 2.6 | 0.5 | 6.7 |
| 0.55 | 4.9 | 0.55 | 7.6 | 0.55 | 2.6 | 0.55 | 6.7 |
| 0.6 | 4.9 | 0.6 | 7.6 | 0.6 | 2.6 | 0.6 | 6.6 |
| 0.65 | 4.9 | 0.65 | 7.6 | 0.65 | 2.6 | 0.65 | 6.6 |
| 0.7 | 4.8 | 0.7 | 7.6 | 0.7 | 2.6 | 0.7 | 6.5 |
| 0.75 | 4.7 | 0.75 | 7.4 | 0.75 | 2.6 | 0.75 | 6.3 |
| 0.8 | 4.4 | 0.8 | 7.1 | 0.8 | 2.5 | 0.8 | 6.0 |
| 0.85 | 4.0 | 0.85 | 6.5 | 0.85 | 2.3 | 0.85 | 5.5 |
| 0.9 | 3.4 | 0.9 | 5.5 | 0.9 | 2.0 | 0.9 | 4.7 |
| 0.95 | 2.5 | 0.95 | 3.8 | 0.95 | 1.7 | 0.95 | 3.3 |
| 1 | 1.2 | 1 | 1.2 | 1 | 1.2 | 1 | 1.2 |

| | | | | | | |
|---|---|---|---|---|---|---|
| Organics 0.01 F1233xf + 0.01 F1234yf + 0.01 F1233zdE + 0.01 F1243zf + 0.95 F1234zeE + 0.01 F1234zeZ | | Organics 0.01 F1233xf + 0.01 F1234yf + 0.01 F1233zdE + 0.01 F1243zf + 0.01 F1234zeE + 0.95 F1234zeZ | | Organics 0.95 F1233xf + 0.01 F1234yf + 0.01 F1233zdE + 0.01 F1243zf + 0.01 F1234zeE + 0.01 F1234zeZ | | |
| MASSFRAC HF | TOTAL PRESSURE bar | MASSFRAC HF | TOTAL PRESSURE bar | MASSFRAC HF | TOTAL PRESSURE bar | |
| 0 | 4.8 | 0 | 1.9 | 0 | 1.7 | |
| 0.05 | 5.8 | 0.05 | 3.0 | 0.05 | 2.8 | |
| 0.1 | 5.8 | 0.1 | 3.0 | 0.1 | 2.8 | |
| 0.15 | 5.8 | 0.15 | 3.0 | 0.15 | 2.8 | |
| 0.2 | 5.8 | 0.2 | 3.0 | 0.2 | 2.8 | |
| 0.25 | 5.8 | 0.25 | 3.0 | 0.25 | 2.8 | |
| 0.3 | 5.8 | 0.3 | 3.0 | 0.3 | 2.8 | |
| 0.35 | 5.8 | 0.35 | 3.0 | 0.35 | 2.8 | |
| 0.4 | 5.8 | 0.4 | 3.0 | 0.4 | 2.3 | |
| 0.45 | 5.8 | 0.45 | 3.0 | 0.45 | 2.8 | |
| 0.5 | 5.7 | 0.5 | 3.0 | 0.5 | 2.8 | |
| 0.55 | 5.7 | 0.55 | 3.0 | 0.55 | 2.8 | |
| 0.6 | 5.6 | 0.6 | 3.0 | 0.6 | 2.8 | |
| 0.65 | 5.5 | 0.65 | 3.0 | 0.65 | 2.8 | |
| 0.7 | 5.3 | 0.7 | 3.0 | 0.7 | 2.8 | |
| 0.75 | 5.1 | 0.75 | 3.0 | 0.75 | 2.8 | |
| 0.8 | 4.8 | 0.8 | 2.9 | 0.8 | 2.6 | |
| 0.85 | 4.3 | 0.85 | 2.7 | 0.85 | 2.5 | |
| 0.9 | 3.6 | 0.9 | 2.4 | 0.9 | 2.2 | |
| 0.95 | 2.6 | 0.95 | 1.9 | 0.95 | 1.8 | |
| 1 | 1.2 | 1 | 1.2 | 1 | 1.2 | |

| HF-HFO-1234yf-HFC-245cb-HCFO-1233zdE-HFO-1234zeE-HFO-1234zeZ-HFO-1243zf ||||||||
|---|---|---|---|---|---|---|---|
| Organics<br>0.15 F1234yf + 0.17 F245cb + 0.17 F1233zdE + 0.17 F1234zeE + 0.17 F1234zeZ + 0.17 F1243zf || Organics<br>0.95 F1234yf + 0.01 F245cb + 0.01 F1233zdE + 0.01 F1234zeE + 0.01 F1234zeZ + 0.01 F1243zf || Organics<br>0.01 F1234yf + 0.95 F245cb + 0.01 F1233zdE + 0.01 F1234zeE + 0.01 F1234zeZ + 0.01 F1243zf || Organics<br>0.01 F1234yf + 0.01 F245cb + 0.95 F1233zdE + 0.01 F1234zeE + 0.01 F1234zeZ + 0.01 F1243zf ||
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.3 | 0 | 6.6 | 0 | 4.6 | 0 | 1.5 |
| 0.05 | 5.3 | 0.05 | 7.6 | 0.05 | 5.8 | 0.05 | 2.6 |
| 0.1 | 5.3 | 0.1 | 7.6 | 0.1 | 5.8 | 0.1 | 2.6 |
| 0.15 | 5.3 | 0.15 | 7.6 | 0.15 | 5.8 | 0.15 | 2.6 |
| 0.2 | 5.3 | 0.2 | 7.6 | 0.2 | 5.8 | 0.2 | 2.6 |
| 0.25 | 5.3 | 0.25 | 7.6 | 0.25 | 5.8 | 0.25 | 2.6 |
| 0.3 | 5.3 | 0.3 | 7.6 | 0.3 | 5.8 | 0.3 | 2.6 |
| 0.35 | 5.3 | 0.35 | 7.6 | 0.35 | 5.8 | 0.35 | 2.6 |
| 0.4 | 5.3 | 0.4 | 7.6 | 0.4 | 5.8 | 0.4 | 2.6 |
| 0.45 | 5.3 | 0.45 | 7.6 | 0.45 | 5.8 | 0.45 | 2.6 |
| 0.5 | 5.3 | 0.5 | 7.6 | 0.5 | 5.8 | 0.5 | 2.6 |
| 0.55 | 5.3 | 0.55 | 7.6 | 0.55 | 5.8 | 0.55 | 2.6 |
| 0.6 | 5.3 | 0.6 | 7.6 | 0.6 | 5.8 | 0.6 | 2.6 |
| 0.65 | 5.3 | 0.65 | 7.6 | 0.65 | 5.8 | 0.65 | 2.6 |
| 0.7 | 5.3 | 0.7 | 7.6 | 0.7 | 5.8 | 0.7 | 2.6 |
| 0.75 | 5.2 | 0.75 | 7.4 | 0.75 | 5.8 | 0.75 | 2.6 |
| 0.8 | 4.9 | 0.8 | 7.1 | 0.8 | 5.8 | 0.8 | 2.5 |
| 0.85 | 4.5 | 0.85 | 6.5 | 0.85 | 5.8 | 0.85 | 2.3 |
| 0.9 | 3.9 | 0.9 | 5.5 | 0.9 | 5.0 | 0.9 | 2.1 |
| 0.95 | 2.8 | 0.95 | 3.8 | 0.95 | 3.5 | 0.95 | 1.7 |
| 1 | 1.2 | 1 | 1.2 | 1 | 1.2 | 1 | 1.2 |

| | | Organics<br>0.01 F1234yf + 0.01 F245cb + 0.01 F1233zdE + 0.95 F1234zeE + 0.01 F1234zeZ + 0.01 F1243zf || Organics<br>0.01 F1234yf + 0.01 F245cb + 0.01 F1233zdE + 0.01 F1234zeE + 0.95 F1234zeZ + 0.01 F1243zf || Organics<br>0.01 F1234yf + 0.01 F245cb + 0.01 F1233zdE + 0.01 F1234zeE + 0.01 F1234zeZ + 0.95 F1243zf ||
|---|---|---|---|---|---|---|---|
| | | MASSFRAC HF | TOTAL PRESSURE bar | MASSFRAC HF | TOTAL PRESSURE bar | MASSFRAC HF | TOTAL PRESSURE bar |
| | | 0 | 4.8 | 0 | 5.8 | 0 | 2.0 |
| | | 0.05 | 5.8 | 0.05 | 6.7 | 0.05 | 3.1 |
| | | 0.1 | 5.8 | 0.1 | 6.7 | 0.1 | 3.1 |
| | | 0.15 | 5.8 | 0.15 | 6.7 | 0.15 | 3.1 |
| | | 0.2 | 5.8 | 0.2 | 6.7 | 0.2 | 3.1 |
| | | 0.25 | 5.8 | 0.25 | 6.7 | 0.25 | 3.1 |
| | | 0.3 | 5.8 | 0.3 | 6.7 | 0.3 | 3.1 |
| | | 0.35 | 5.8 | 0.35 | 6.7 | 0.35 | 3.1 |
| | | 0.4 | 5.8 | 0.4 | 6.7 | 0.4 | 3.1 |
| | | 0.45 | 5.8 | 0.45 | 6.7 | 0.45 | 3.1 |
| | | 0.5 | 5.8 | 0.5 | 6.7 | 0.5 | 3.1 |
| | | 0.55 | 5.7 | 0.55 | 6.7 | 0.55 | 3.1 |
| | | 0.6 | 5.6 | 0.6 | 6.7 | 0.6 | 3.1 |
| | | 0.65 | 5.5 | 0.65 | 6.6 | 0.65 | 3.1 |
| | | 0.7 | 5.4 | 0.7 | 6.5 | 0.7 | 3.1 |
| | | 0.75 | 5.1 | 0.75 | 6.3 | 0.75 | 3.1 |
| | | 0.8 | 4.8 | 0.8 | 6.1 | 0.8 | 2.9 |
| | | 0.85 | 4.3 | 0.85 | 5.6 | 0.85 | 2.7 |
| | | 0.9 | 3.6 | 0.9 | 4.7 | 0.9 | 2.4 |
| | | 0.95 | 2.6 | 0.95 | 3.4 | 0.95 | 1.9 |
| | | 1 | 1.2 | 1 | 1.2 | 1 | 1.2 |

| MASSFRAC HF | Organics 0.15 F1234zeE + 0.17 F244bb + 0.17 F245fa + 0.17TFP + 0.17 F1225yeZ + 0.17 F1225zc TOTAL PRESSURE bar | Organics 0.95 F1234zeE + 0.01 F244bb + 0.01 F245fa + 0.01 TFP + 0.01 F1225yeZ + 0.01 F1225zc TOTAL PRESSURE bar | Organics 0.01 F1234zeE + 0.9 F244bb + 0.01 F245fa + 0.01 TFP + 0.01 F1225yeZ + 0.01 F1225zc TOTAL PRESSURE bar | Organics 0.01 F1234zeE + 0.01 F244bb + 0.01 F245fa + 0.01 TFP + 0.95 F1225yeZ + 0.01 F1225zc TOTAL PRESSURE bar | Organics 0.01 F1234zeE + 0.01 F244bb + 0.01 F245fa + 0.95 TFP + 0.01 F1225yeZ + 0.01 F1225zc TOTAL PRESSURE bar | Organics 0.01 F1234zeE + 0.01 F244bb + 0.01 F245fa + 0.01 TFP + 0.95 F1225yeZ + 0.01 F1225zc TOTAL PRESSURE bar | Organics 0.01 F1234zeE + 0.01 F244bb + 0.01 F245fa + 0.01 TFP + 0.01 F1225yeZ + 0.95 F1225zc TOTAL PRESSURE bar |
|---|---|---|---|---|---|---|---|
| 0 | 5.3 | 4.9 | 1.0 | 1.8 | 11.3 | 5.2 | 5.3 |
| 0.05 | 6.3 | 5.8 | 2.1 | 2.9 | 12.1 | 6.2 | 6.3 |
| 0.1 | 6.3 | 5.9 | 2.1 | 2.9 | 12.0 | 6.2 | 6.3 |
| 0.15 | 6.3 | 5.9 | 2.1 | 2.9 | 11.9 | 6.2 | 6.3 |
| 0.2 | 6.3 | 5.9 | 2.1 | 2.9 | 11.8 | 6.2 | 6.3 |
| 0.25 | 6.3 | 5.9 | 2.1 | 2.9 | 11.7 | 6.2 | 6.3 |
| 0.3 | 6.3 | 5.9 | 2.1 | 2.9 | 11.6 | 6.2 | 6.3 |
| 0.35 | 6.3 | 5.9 | 2.1 | 2.9 | 11.5 | 6.2 | 6.3 |
| 0.4 | 6.2 | 5.9 | 2.1 | 2.9 | 11.5 | 6.2 | 6.3 |
| 0.45 | 6.2 | 5.8 | 2.1 | 2.9 | 11.5 | 6.2 | 6.3 |
| 0.5 | 6.2 | 5.8 | 2.1 | 2.9 | 11.5 | 6.2 | 6.2 |
| 0.55 | 6.2 | 5.8 | 2.1 | 2.9 | 11.5 | 6.2 | 6.2 |
| 0.6 | 6.1 | 5.7 | 2.1 | 2.8 | 11.6 | 6.2 | 6.1 |
| 0.65 | 6.1 | 5.6 | 2.1 | 2.8 | 11.6 | 6.2 | 6.0 |
| 0.7 | 6.0 | 5.4 | 2.0 | 2.8 | 11.7 | 6.1 | 5.9 |
| 0.75 | 5.8 | 5.2 | 2.0 | 2.8 | 11.6 | 5.9 | 5.6 |
| 0.8 | 5.5 | 4.8 | 2.0 | 2.7 | 11.3 | 5.6 | 5.2 |
| 0.85 | 5.0 | 4.3 | 2.0 | 2.5 | 10.5 | 5.1 | 4.7 |
| 0.9 | 4.2 | 3.6 | 1.9 | 2.2 | 8.9 | 4.2 | 3.8 |
| 0.95 | 3.0 | 2.6 | 1.6 | 1.8 | 6.0 | 3.0 | 2.7 |
| 1 | 1.2 | 1.2 | 1.2 | 1.2 | 1.2 | 1.2 | 1.2 |

HF-HFO-1234zeE-HCFC-244bb-HFC-245fa-Trifluoropropyne-HFO-1225yeZ-HFO-1225zc

| MASSFRAC HF | Organics 0.15 F1234zeZ + 0.17 F244bb + 0.17 F245fa + 0.17TFP + 0.17 F1225yeZ + 0.17 F1225zc TOTAL PRESSURE bar | Organics 0.95 F1234zeZ + 0.01 F244bb + 0.01 F245fa + 0.01 TFP + 0.01 F1225yeZ + 0.01 F1225zc TOTAL PRESSURE bar | Oranics 0.01 F1234zeZ + 0.95 F244bb + 0.01 F246fa + 0.01 TFP + 0.01 F1225yeZ + 0.01 F1225zc TOTAL PRESSURE bar | Organics 0.01 F1234zeZ + 0.01 F244bb + 0.01 F245fa + 0.01 TFP + 0.95 F1225yeZ + 0.01 F1225zc TOTAL PRESSURE bar | Organics 0.01 F1234zeZ + 0.01 F244bb + 0.01 F245fa + 0.95 TFP + 0.01 F1225yeZ + 0.01 F1225zc TOTAL PRESSURE bar | Organics 0.01 F1234zeZ + 0.01 F244bb + 0.01 F245fa + 0.01 TFP + 0.95 F1225yeZ + 0.01 F1225zc TOTAL PRESSURE bar | Organics 0.01 F1234zeZ + 0.01 F244bb + 0.01 F245fa + 0.01 TFP + 0.01 F1225yeZ + 0.95 F1225zc TOTAL PRESSURE bar |
|---|---|---|---|---|---|---|---|
| 0 | 4.8 | 2.0 | 0.9 | 1.7 | 11.3 | 5.1 | 5.3 |
| 0.05 | 5.9 | 3.1 | 2.1 | 2.8 | 12.0 | 6.2 | 6.2 |
| 0.1 | 5.9 | 3.1 | 2.1 | 2.8 | 12.0 | 6.2 | 6.3 |
| 0.15 | 5.9 | 3.1 | 2.1 | 2.8 | 11.9 | 6.2 | 6.3 |
| 0.2 | 5.8 | 3.1 | 2.1 | 2.8 | 11.8 | 6.2 | 6.3 |
| 0.25 | 5.8 | 3.1 | 2.1 | 2.8 | 11.7 | 6.2 | 6.2 |
| 0.3 | 5.8 | 3.1 | 2.1 | 2.8 | 11.6 | 6.2 | 6.2 |
| 0.35 | 5.8 | 3.1 | 2.1 | 2.8 | 11.5 | 6.2 | 6.2 |
| 0.4 | 5.8 | 3.1 | 2.1 | 2.8 | 11.4 | 6.2 | 6.2 |
| 0.45 | 5.8 | 3.1 | 2.1 | 2.8 | 11.4 | 6.2 | 6.2 |
| 0.5 | 5.8 | 3.1 | 2.0 | 2.8 | 11.5 | 6.2 | 6.2 |
| 0.55 | 5.7 | 3.1 | 2.0 | 2.8 | 11.5 | 6.2 | 6.2 |
| 0.6 | 5.7 | 3.1 | 2.0 | 2.8 | 11.5 | 6.2 | 6.1 |
| 0.65 | 5.6 | 3.1 | 2.0 | 2.8 | 11.5 | 6.2 | 6.0 |
| 0.7 | 5.6 | 3.1 | 2.0 | 2.8 | 11.5 | 6.1 | 5.8 |
| 0.75 | 5.5 | 3.1 | 2.0 | 2.8 | 11.5 | 5.9 | 5.6 |
| 0.8 | 5.2 | 2.9 | 2.0 | 2.7 | 11.3 | 5.6 | 5.2 |
| 0.85 | 4.7 | 2.7 | 2.0 | 2.5 | 10.5 | 5.0 | 4.6 |
| 0.9 | 4.0 | 2.4 | 1.9 | 2.2 | 8.9 | 4.2 | 3.8 |
| 0.95 | 2.8 | 1.9 | 1.6 | 1.8 | 6.0 | 3.0 | 2.7 |
| 1 | 1.2 | 1.2 | 1.2 | 1.2 | 1.2 | 1.2 | 1.2 |

HF-HFO-1234zeZ-HCFC-244bb-HFC-245fa-Trifluoropropyne-HFO-1225yeZ-HFO-1225zc

Example 14: Temperature and Pressure Range of System with 7 Compounds

|  | Boiling point range | |
|---|---|---|
| System with 7 compounds | Temp. | Pressure bar abs |
| HF-HCFO-1233xf-HFO-1234yf-HFC-245cb-HCFO-1233zdE-HFO-1234zeE-HFO-1234zeZ | 0 to 40 | ~0.9~11.5 |
| HF-HCFO-1233xf-HFO-1234yf-HFC-245cb-HCFO-1233zdE-HFO-1234zeE-HFO-1243zf | 0 to 40 | ~1.0 to ~11.6 |
| HF-HCFO-1233xf-HFO-1234yf-HFC-245cb-HCFO-1233zdE-HFO-1234zeZ-HFO-1243zf | 0 to 40 | ~0.9 to ~11.5 |
| HF-HCFO-1233xf-HFO-1234yf-HFC-245cb-HFO-1234zeE-HFO-1234zeZ-HFO-1243zf | 0 to 40 | ~1.1 to ~11.6 |
| HF-HCFO-1233xf-HFO-1234yf-HCFO-1233zdE-HFO-1234zeE-HFO-1234zeZ-HFO-1243zf | 0 to 40 | ~0.9 to ~11.5 |
| HF-HCFO-1233xf-HFC-245cb-HCFO-1233zdE-HFO-1234zeE-HFO-1234zeZ-HFO-1243zf | 0 to 40 | ~0.9 to ~10.3 |
| HF-HFO-1234yf-HFC-245cb-HCFO-1233zdE-HFO-1234zeE-HFO-1234zeZ-HFO-1243zf | 0 to 40 | ~1.0 to ~11.6 |
| HF - HFO-1234zeE - HCFC-244bb- HFC-245fa -Trifluoropropyne- HFO-1225yeZ- HFO-1225zc | 0 to 40 | ~0.7 to ~17.5 |
| HF - HFO-1234zeZ - HCFC-244bb- HFC-245fa -Trifluoropropyne- HFO-1225yeZ- HFO-1225zc | 0 to 40 | ~0.7 to ~17.5 |

Example 15: Decantation Range of System with 7 Compounds

|  | Decantation ranges Mass percentage of HF | | |
|---|---|---|---|
| System with 7 compounds | Temp 0° C. | Temp 25° C. | Temp 40° C. |
| HF-HCFO-1233xf-HFO-1234yf-HFC-245cb-HCFO-1233zdE-HFO-1234zeE-HFO-1234zeZ | 5-75 | 5-70 | 10-60 |
| HF-HCFO-1233xf-HFO-1234yf-HFC-245cb-HCFO-1233zdE-HFO-1234zeE-HFO-1243zf | 5-75 | 10-65 | 20 |
| HF-HCFO-1233xf-HFO-1234yf-HFC-245cb-HCFO-1233zdE-HFO-1234zeZ-HFO-1243zf | 5-70 | 5-70 | 10-60 |
| HF-HCFO-1233xf-HFO-1234yf-HFC-245cb-HFO-1234zeE-HFO-1234zeZ-HFO-1243zf | 5-75 | 10-65 | * |
| HF-HCFO-1233xf-HFO-1234yf-HCFO-1233zdE-HFO-1234zeE-HFO-1234zeZ-HFO-1243zf | 5-75 | 10-65 | 15-45 |
| HF-HCFO-1233xf-HFC-245cb-HCFO-1233zdE-HFO-1234zeE-HFO-1234zeZ-HFO-1243zf | 5-75 | 5-70 | 10-55 |
| HF-HFO-1234yf-HFC-245cb-HCFO-1233zdE-HFO-1234zeE-HFO-1234zeZ-HFO-1243zf | 5-75 | 10-65 | * |
| HF - HFO-1234zeE - HCFC-244bb- HFC-245fa - Trifluoropropyne- HFO-1225yeZ- HFO-1225zc | 5-75 | 10-70 | * |
| HF - HFO-1234zeZ - HCFC-244bb- HFC-245fa - Trifluoropropyne- HFO-1225yeZ- HFO-1225zc | 5-75 | 5-70 | 10-60 |

Example 16: Systems with 8 Compounds

| HF-HCFO-1233xf-HFO-1234yf-HFC-245cb-HCFO-1233zdE-HFO-1234zeE-HFO-1234zeZ-HFO-1243zf | | | | | | | |
|---|---|---|---|---|---|---|---|
| Organics 0.01 F1233xf + 0.94 F1234yf + 0.01 F245cb + 0.01 F1233zdE + 0.01 F1234zeE + 0.01 F1234zeZ + 0.01 F1243zf | | Organics 0.01 F1233xf + 0.01 F1234yf + 0.94 F245cb + 0.01 F1233zdE + 0.01 F1234zeE + 0.01 F1234zeZ + 0.01 F1243zf | | Organics 0.01 F1233xf + 0.01 F1234yf + 0.01 F245cb + 0.94 F1233zdE + 0.01 F1234zeE + 0.01 F1234zeZ + 0.01 F1243zf | | Organics 0.01 F1233xf + 0.01 F1234yf + 0.01 F245cb + 0.01 F1233zdE + 0.94 F1234zeE + 0.01 F1234zeZ + 0.01 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.6 | 0 | 4.6 | 0 | 1.5 | 0 | 4.8 |
| 0.05 | 7.6 | 0.05 | 5.8 | 0.05 | 2.6 | 0.05 | 5.8 |
| 0.1 | 7.6 | 0.1 | 5.8 | 0.1 | 2.6 | 0.1 | 5.8 |
| 0.15 | 7.6 | 0.15 | 5.8 | 0.15 | 2.6 | 0.15 | 5.8 |
| 0.2 | 7.6 | 0.2 | 5.8 | 0.2 | 2.6 | 0.2 | 5.8 |
| 0.25 | 7.6 | 0.25 | 5.8 | 0.25 | 2.6 | 0.25 | 5.8 |
| 0.3 | 7.6 | 0.3 | 5.8 | 0.3 | 2.6 | 0.3 | 5.8 |
| 0.35 | 7.6 | 0.35 | 5.8 | 0.35 | 2.6 | 0.35 | 5.8 |
| 0.4 | 7.6 | 0.4 | 5.8 | 0.4 | 2.6 | 0.4 | 5.8 |
| 0.45 | 7.6 | 0.45 | 5.8 | 0.45 | 2.6 | 0.45 | 5.8 |
| 0.5 | 7.6 | 0.5 | 5.8 | 0.5 | 2.6 | 0.5 | 5.7 |
| 0.55 | 7.6 | 0.55 | 5.8 | 0.55 | 2.6 | 0.55 | 5.7 |
| 0.6 | 7.6 | 0.6 | 5.8 | 0.6 | 2.6 | 0.6 | 5.6 |
| 0.65 | 7.6 | 0.65 | 5.8 | 0.65 | 2.6 | 0.65 | 5.5 |
| 0.7 | 7.5 | 0.7 | 5.8 | 0.7 | 2.6 | 0.7 | 5.4 |
| 0.75 | 7.4 | 0.75 | 5.8 | 0.75 | 2.6 | 0.75 | 5.1 |
| 0.8 | 7.1 | 0.3 | 5.8 | 0.8 | 2.5 | 0.8 | 4.8 |
| 0.85 | 6.5 | 0.35 | 5.8 | 0.85 | 2.3 | 0.85 | 4.3 |
| 0.9 | 5.5 | 0.9 | 5.0 | 0.9 | 2.1 | 0.9 | 3.6 |
| 0.95 | 3.8 | 0.95 | 3.5 | 0.95 | 1.7 | 0.95 | 9.6 |
| 1 | 1.2 | 1 | 1.2 | 1 | 1.2 | 1 | 1.2 |

HF-HCFO-1233xf-HFO-1234yf-HFC-245cb-HCFO-1233zdE-HFO-1234zeE-HFO-1234zeZ-HFO-1243zf

| | Organics 0.01 F1233xf + 0.01 F1234yf + 0.01 F245cb + 0.01 F1233zdE + 0.01 F1234zeE + 0.94 F1234zeZ + 0.01 F1243zf | | Organics 0.01 F1233xf + 0.01 F1234yf + 0.01 F245cb + 0.01 F1233zdE + 0.01 F1234zeE + 0.01 F1234zeZ + 0.94 F1243zf | | Organics 0.16 F1233xf + 0.14 F1234yf + 0.14 F245cb + 0.14 F1233zdE + 0.14 F1234zeE + 0.14 F1234zeZ + 0.14 F1243zf | |
|---|---|---|---|---|---|---|
| | MASSFRAC HF | TOTAL PRESSURE bar | MASSFRAC HF | TOTAL PRESSURE bar | MASSFRAC HF | TOTAL PRESSURE bar |
| | 0 | 2.0 | 0 | 5.7 | 0 | 3.9 |
| | 0.05 | 3.1 | 0.05 | 6.7 | 0.05 | 5.0 |
| | 0.1 | 3.1 | 0.1 | 6.7 | 0.1 | 5.0 |
| | 0.15 | 3.1 | 0.15 | 6.7 | 0.15 | 5.0 |
| | 0.2 | 3.1 | 0.2 | 6.7 | 0.2 | 5.0 |
| | 0.25 | 3.1 | 0.25 | 6.7 | 0.25 | 5.0 |
| | 0.3 | 3.1 | 0.3 | 6.7 | 0.3 | 5.0 |
| | 0.35 | 3.1 | 0.35 | 6.7 | 0.35 | 5.0 |
| | 0.4 | 3.1 | 0.4 | 6.7 | 0.4 | 5.0 |
| | 0.45 | 3.1 | 0.45 | 6.7 | 0.45 | 5.0 |
| | 0.5 | 3.1 | 0.5 | 6.7 | 0.5 | 5.0 |
| | 0.55 | 3.1 | 0.55 | 6.7 | 0.55 | 5.0 |
| | 0.6 | 3.1 | 0.6 | 6.6 | 0.6 | 5.0 |
| | 0.65 | 3.1 | 0.65 | 6.6 | 0.65 | 5.0 |
| | 0.7 | 3.1 | 0.7 | 6.5 | 0.7 | 5.0 |
| | 0.75 | 3.1 | 0.75 | 6.3 | 0.75 | 4.9 |
| | 0.8 | 2.9 | 0.8 | 6.0 | 0.8 | 4.6 |
| | 0.85 | 2.7 | 0.85 | 5.5 | 0.85 | 4.2 |
| | 0.9 | 2.4 | 0.9 | 4.7 | 0.9 | 3.6 |
| | 0.95 | 1.9 | 0.95 | 3.3 | 0.95 | 2.6 |
| | 1 | 1.2 | 1 | 1.2 | 1 | 1.2 |

HF-HFO-1234yf-HFC-245cb-HCFO-1233xf-HFO-1234zeE-HFO-1234zeZ-HCFO-1233zdE-HCFC-244bb

| MASSFRAC HF | Organics 0.94 F1233xf + 0.01 F1234yf + 0.01 F245cb + 0.01 F1233zdE + 0.01 F1234zeE + 0.01 F1234zeZ + 0.01 F244bb TOTAL PRESSURE bar | Organics 0.01 F1233xf + 0.94 F1234yf + 0.01 F245cb + 0.01 F1233zdE + 0.01 F1234zeE + 0.01 F1234zeZ + 0.01 F244bb TOTAL PRESSURE bar | Organics 0.01 F1233xf + 0.01 F1234yf + 0.94 F245cb + 0.01 F1233zdE + 0.01 F1234zeE + 0.01 F1234zeZ + 0.01 F244bb TOTAL PRESSURE bar | Organics 0.01 F1233xf + 0.01 F1234yf + 0.01 F245cb + 0.94 F1233zdE + 0.01 F1234zeE + 0.01 F1234zeZ + 0.01 F244bb TOTAL PRESSURE bar |
|---|---|---|---|---|
| 0 | 1.7 | 6.6 | 4.5 | 1.5 |
| 0.05 | 2.8 | 7.5 | 5.7 | 2.6 |
| 0.1 | 2.8 | 7.5 | 5.7 | 2.6 |
| 0.15 | 2.8 | 7.5 | 5.7 | 2.6 |
| 0.2 | 2.8 | 7.5 | 5.7 | 2.6 |
| 0.25 | 2.8 | 7.5 | 5.7 | 2.6 |
| 0.3 | 2.8 | 7.5 | 5.7 | 2.6 |
| 0.35 | 2.8 | 7.5 | 5.7 | 2.6 |
| 0.4 | 2.8 | 7.5 | 5.7 | 2.6 |
| 0.45 | 2.8 | 7.5 | 5.7 | 2.6 |
| 0.5 | 2.8 | 7.5 | 5.7 | 2.6 |
| 0.55 | 2.8 | 7.5 | 5.7 | 2.6 |
| 0.6 | 2.8 | 7.5 | 5.7 | 2.6 |
| 0.65 | 2.8 | 7.5 | 5.7 | 2.6 |
| 0.7 | 2.8 | 7.5 | 5.7 | 2.6 |
| 0.75 | 2.8 | 7.4 | 5.7 | 2.6 |
| 0.8 | 2.6 | 7.0 | 5.7 | 2.4 |
| 0.85 | 2.4 | 6.5 | 5.7 | 2.3 |
| 0.9 | 2.2 | 5.4 | 4.9 | 2.0 |
| 0.95 | 1.8 | 3.8 | 3.5 | 1.7 |
| 1 | 1.2 | 1.2 | 1.2 | 1.2 |

HF-HFO-1234yf-HFC-245cb-HCFO-1233xf-HFO-1234zeE-HFO-1234zeZ-HCFO-1233zdE-HCFC-244bb

| MASSFRAC HF | Organics 0.01 F1233xf + 0.01 F1234yf + 0.01 F245cb + 0.01 F1233zdE + 0.94 F1234zeE + 0.01 F1234zeZ + 0.01 F244bb TOTAL PRESSURE bar | Organics 0.01 F1233xf + 0.01 F1234yf + 0.01 F245cb + 0.01 F1233zdE + 0.01 F1234zeE + 0.94 F1234zeZ + 0.01 F244bb TOTAL PRESSURE bar | Organics 0.01 F1233xf 0.01 F1234yf + 0.01 F245cb + 0.01 F1233zdE + 0.01 F1234zeE + 0.01 F1234zeZ + 0.94 F244bb TOTAL PRESSURE bar | Organics 0.16 F1233xf + 0.14 F1234yf + 0.14 F245cb + 0.14 F1233zdE + 0.14 F1234zeE + 0.14 F1234zeZ + 0.14 F244bb TOTAL PRESSURE bar |
|---|---|---|---|---|
| 0 | 4.8 | 1.9 | 0.8 | 3.2 |
| 0.05 | 5.7 | 3.0 | 2.0 | 4.3 |
| 0.1 | 5.7 | 3.0 | 2.0 | 4.3 |
| 0.15 | 5.7 | 3.0 | 2.0 | 4.3 |
| 0.2 | 5.7 | 3.0 | 2.0 | 4.3 |
| 0.25 | 5.7 | 3.0 | 2.0 | 4.3 |
| 0.3 | 5.7 | 3.0 | 2.0 | 4.3 |
| 0.35 | 5.7 | 3.0 | 2.0 | 4.3 |
| 0.4 | 5.7 | 3.0 | 2.0 | 4.3 |
| 0.45 | 5.7 | 3.0 | 2.0 | 4.3 |
| 0.5 | 5.7 | 3.0 | 2.0 | 4.3 |
| 0.55 | 5.6 | 3.0 | 2.0 | 4.2 |
| 0.6 | 5.6 | 3.0 | 2.0 | 4.2 |
| 0.65 | 5.5 | 3.0 | 2.0 | 4.2 |
| 0.7 | 5.3 | 3.0 | 2.0 | 4.2 |
| 0.75 | 5.1 | 3.0 | 1.9 | 4.2 |
| 0.8 | 4.7 | 2.9 | 1.9 | 4.0 |
| 0.85 | 4.3 | 2.7 | 1.9 | 3.7 |
| 0.9 | 3.6 | 2.4 | 1.8 | 3.2 |
| 0.95 | 2.6 | 1.9 | 1.6 | 2.4 |
| 1 | 1.2 | 1.2 | 1.2 | 1.2 |

HF-HFO-1234yf-HFC-245cb-HCFO-1233xf-HFO-1234zeE-HFO-1234zeZ-HCFO-1233zdE-Trifluoropropyne

| MASSFRAC HF | Organics 0.16 F1234yf + 0.14 F245cb + 0.14 F1233xf + 0.14 F1234zeE + 0.14 F1234zeZ + 0.14 F1233zdE + 0.14 TPF TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 TPF TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 TPF TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 TPF TOTAL PRESSURE bar |
|---|---|---|---|---|
| 0 | 5.0 | 6.7 | 4.7 | 1.8 |
| 0.05 | 6.0 | 7.6 | 5.8 | 2.9 |
| 0.1 | 6.0 | 7.6 | 5.8 | 2.9 |
| 0.15 | 6.0 | 7.6 | 5.8 | 2.9 |
| 0.2 | 6.0 | 7.6 | 5.8 | 2.9 |
| 0.25 | 6.0 | 7.6 | 5.8 | 2.9 |
| 0.3 | 6.0 | 7.6 | 5.8 | 2.9 |
| 0.35 | 6.0 | 7.6 | 5.8 | 2.9 |
| 0.4 | 6.0 | 7.6 | 5.8 | 2.9 |
| 0.45 | 6.0 | 7.6 | 5.8 | 2.9 |
| 0.5 | 6.0 | 7.6 | 5.8 | 2.9 |
| 0.55 | 6.0 | 7.6 | 5.8 | 2.9 |
| 0.6 | 6.0 | 7.6 | 5.8 | 2.9 |
| 0.65 | 6.0 | 7.6 | 5.8 | 2.9 |
| 0.7 | 6.0 | 7.6 | 5.8 | 2.9 |
| 0.75 | 5.9 | 7.5 | 5.8 | 2.9 |
| 0.8 | 5.6 | 7.1 | 5.8 | 2.8 |
| 0.85 | 5.1 | 6.6 | 5.8 | 2.6 |
| 0.9 | 4.3 | 5.5 | 5.0 | 2.2 |
| 0.95 | 3.1 | 3.8 | 3.5 | 1.8 |
| 1 | 1.2 | 1.2 | 1.2 | 1.2 |

HF-HFO-1234yf-HFC-245cb-HCFO-1233xf-HFO-1234zeE-HFO-1234zeZ-HCFO-1233zdE-Trifluoropropyne

| MASSFRAC HF | Organics 0.01 F1234yf + 0.01 F245cb + 0.01 F1233xf + 0.94 F1234zeE + 0.01 F1234zeZ + 0.01 F1233zdE + 0.01 TPF TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 TPF TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 TPF TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 TPF TOTAL PRESSURE bar |
|---|---|---|---|---|
| 0 | 4.9 | 2.0 | 1.6 | 11.2 |
| 0.05 | 5.8 | 3.1 | 2.7 | 12.0 |
| 0.1 | 5.9 | 3.1 | 2.7 | 11.9 |
| 0.15 | 5.9 | 3.1 | 2.7 | 11.8 |
| 0.2 | 5.9 | 3.1 | 2.7 | 11.7 |
| 0.25 | 5.8 | 3.1 | 2.7 | 11.6 |
| 0.3 | 5.8 | 3.1 | 2.7 | 11.5 |
| 0.35 | 5.8 | 3.1 | 2.7 | 11.5 |
| 0.4 | 5.8 | 3.1 | 2.7 | 11.4 |
| 0.45 | 5.8 | 3.1 | 2.7 | 11.4 |
| 0.5 | 5.8 | 3.1 | 2.7 | 11.4 |
| 0.55 | 5.8 | 3.1 | 2.7 | 11.5 |
| 0.6 | 5.7 | 3.1 | 2.7 | 11.5 |
| 0.65 | 5.6 | 3.1 | 2.7 | 11.5 |
| 0.7 | 5.4 | 3.1 | 2.7 | 11.5 |
| 0.75 | 5.2 | 3.1 | 2.7 | 11.5 |
| 0.8 | 4.9 | 3.0 | 2.6 | 11.2 |
| 0.85 | 4.4 | 2.8 | 2.4 | 10.4 |
| 0.9 | 3.6 | 2.4 | 2.1 | 8.8 |
| 0.95 | 2.6 | 1.9 | 1.7 | 5.9 |
| 1 | 1.2 | 1.2 | 1.2 | 1.2 |

HF-HFO-1234yf-HFC-245cb-HCFO-1233xf-HFO-1234zeE-HFO-1234zeZ-HCFO-1233zdE-HFC-245fa

| MASSFRAC HF | Organics 0.16 F1234yf + 0.14 F245cb + 0.14 F1233xf + 0.14 F1234zeE + 0.14 F1234zeZ + 0.14 F1233zdE + 0.14 F245fa TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F245fa TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F245fa TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F245fa TOTAL PRESSURE bar |
|---|---|---|---|---|
| 0 | 3.4 | 6.6 | 4.5 | 1.7 |
| 0.05 | 4.5 | 7.5 | 5.7 | 2.8 |
| 0.1 | 4.5 | 7.5 | 5.7 | 2.8 |
| 0.15 | 4.5 | 7.5 | 5.7 | 2.8 |
| 0.2 | 4.5 | 7.5 | 5.7 | 2.8 |
| 0.25 | 4.5 | 7.5 | 5.7 | 2.8 |
| 0.3 | 4.5 | 7.5 | 5.7 | 2.8 |
| 0.35 | 4.5 | 7.5 | 5.7 | 2.8 |
| 0.4 | 4.5 | 7.5 | 5.7 | 2.8 |
| 0.45 | 4.5 | 7.5 | 5.7 | 2.8 |
| 0.5 | 4.5 | 7.5 | 5.7 | 2.8 |
| 0.55 | 4.5 | 7.5 | 5.7 | 2.8 |
| 0.6 | 4.5 | 7.5 | 5.7 | 2.8 |
| 0.65 | 4.5 | 7.5 | 5.7 | 2.8 |
| 0.7 | 4.5 | 7.5 | 5.7 | 2.8 |
| 0.75 | 4.4 | 7.4 | 5.7 | 2.8 |
| 0.8 | 4.2 | 7.1 | 5.8 | 2.6 |
| 0.85 | 3.9 | 6.5 | 5.7 | 2.5 |
| 0.9 | 3.3 | 5.4 | 4.9 | 2.2 |
| 0.95 | 2.4 | 3.8 | 3.5 | 1.8 |
| 1 | 1.2 | 1.2 | 1.2 | 1.2 |

-continued

| | HF-HFO-1234yf-HFC-245cb-HCFO-1233xf-HFO-1234zeE-HFO-1234zeZ-HCFO-1233zdE-HFC-245fa | | | |
|---|---|---|---|---|
| MASSFRAC HF | Organics 0.01 F1234yf + 0.01 F245cb + 0.01 F1233xf + 0.94 F1234zeE + 0.01 F1234zeZ + 0.01 F1233zdE + 0.01 F245fa TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F245fa TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F245fa TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F245fa TOTAL PRESSURE bar |
| 0 | 4.8 | 1.9 | 1.5 | 1.6 |
| 0.05 | 5.7 | 3.0 | 2.6 | 2.8 |
| 0.1 | 5.7 | 3.0 | 2.6 | 2.8 |
| 0.15 | 5.7 | 3.0 | 2.6 | 2.8 |
| 0.2 | 5.7 | 3.0 | 2.6 | 2.8 |
| 0.25 | 5.7 | 3.0 | 2.6 | 2.8 |
| 0.3 | 5.7 | 3.0 | 2.6 | 2.8 |
| 0.35 | 5.7 | 3.0 | 2.6 | 2.8 |
| 0.4 | 5.7 | 3.0 | 2.6 | 2.8 |
| 0.45 | 5.7 | 3.0 | 2.6 | 2.8 |
| 0.5 | 5.7 | 3.0 | 2.6 | 2.8 |
| 0.55 | 5.6 | 3.0 | 2.6 | 2.8 |
| 0.6 | 5.6 | 3.0 | 2.6 | 2.8 |
| 0.65 | 5.5 | 3.0 | 2.6 | 2.8 |
| 0.7 | 5.3 | 3.0 | 2.6 | 2.8 |
| 0.75 | 5.1 | 3.0 | 2.6 | 2.8 |
| 0.8 | 4.7 | 2.9 | 2.5 | 2.7 |
| 0.85 | 4.3 | 2.7 | 2.3 | 2.5 |
| 0.9 | 3.6 | 2.4 | 2.0 | 2.2 |
| 0.95 | 2.6 | 1.9 | 1.7 | 1.8 |
| 1 | 1.2 | 1.2 | 1.2 | 1.2 |

| | HF-HFO-1234yf-HFC-245cb-HCFO-1233xf-HFO-1234zeE-HFO-1234zeZ-HCFO-1233zdE-HFO-1225yeZ | | | |
|---|---|---|---|---|
| MASSFRAC HF | Organics 0.16 F1234yf + 0.14 F245cb + 0.14 F1233xf + 0.14 F1234zeE + 0.14 F1234zeZ + 0.14 F1233zdE + 0.14 F1225yeZ TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F1225yeZ TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F1225yeZ TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F1225yeZ TOTAL PRESSURE bar |
| 0 | 3.8 | 6.6 | 4.6 | 1.7 |
| 0.05 | 4.9 | 7.6 | 5.8 | 2.8 |
| 0.1 | 4.9 | 7.6 | 5.8 | 2.8 |
| 0.15 | 4.9 | 7.6 | 5.8 | 2.8 |
| 0.2 | 4.9 | 7.6 | 5.8 | 2.8 |
| 0.25 | 4.9 | 7.6 | 5.8 | 2.8 |
| 0.3 | 4.9 | 7.6 | 5.8 | 2.8 |
| 0.35 | 4.9 | 7.6 | 5.8 | 2.8 |
| 0.4 | 4.9 | 7.6 | 5.8 | 2.8 |
| 0.45 | 4.9 | 7.6 | 5.8 | 2.8 |
| 0.5 | 4.9 | 7.6 | 5.8 | 2.8 |
| 0.55 | 4.9 | 7.6 | 5.8 | 2.8 |
| 0.6 | 4.9 | 7.6 | 5.8 | 2.8 |
| 0.65 | 4.9 | 7.6 | 5.8 | 2.8 |
| 0.7 | 5.0 | 7.5 | 5.8 | 2.8 |
| 0.75 | 4.8 | 7.4 | 5.8 | 2.8 |
| 0.8 | 4.6 | 7.1 | 5.8 | 2.7 |
| 0.85 | 4.2 | 6.5 | 5.8 | 2.5 |
| 0.9 | 3.6 | 5.5 | 4.9 | 2.2 |
| 0.95 | 2.6 | 3.8 | 3.5 | 1.8 |
| 1 | 1.2 | 1.2 | 1.2 | 1.2 |

HF-HFO-1234yf-HFC-245cb-HCFO-1233xf-HFO-1234zeE-HFO-1234zeZ-HCFO-1233zdE-HFO-1225yeZ

| MASSFRAC HF | Organics 0.01 F1234yf + 0.01 F245cb + 0.01 F1233xf + 0.94 F1234zeE + 0.01 F1234zeZ + 0.01 F1233zdE + 0.01 F1225yeZ TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F1225yeZ TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F1225yeZ TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F1225yeZ TOTAL PRESSURE bar |
|---|---|---|---|---|
| 0 | 4.8 | 1.9 | 1.5 | 5.1 |
| 0.05 | 5.8 | 3.0 | 2.6 | 6.1 |
| 0.1 | 5.8 | 3.0 | 2.6 | 6.1 |
| 0.15 | 5.8 | 3.0 | 2.6 | 6.1 |
| 0.2 | 5.8 | 3.0 | 2.6 | 6.1 |
| 0.25 | 5.8 | 3.0 | 2.6 | 6.1 |
| 0.3 | 5.8 | 3.0 | 2.6 | 6.1 |
| 0.35 | 5.8 | 3.0 | 2.6 | 6.1 |
| 0.4 | 5.8 | 3.0 | 2.6 | 6.1 |
| 0.45 | 5.8 | 3.0 | 2.6 | 6.1 |
| 0.5 | 5.7 | 3.0 | 2.6 | 6.1 |
| 0.55 | 5.7 | 3.0 | 2.6 | 6.1 |
| 0.6 | 5.6 | 3.0 | 2.6 | 6.1 |
| 0.65 | 5.5 | 3.0 | 2.6 | 6.1 |
| 0.7 | 5.3 | 3.0 | 2.6 | 6.0 |
| 0.75 | 5.1 | 3.0 | 2.6 | 5.8 |
| 0.8 | 4.8 | 2.9 | 2.5 | 5.5 |
| 0.85 | 4.3 | 2.7 | 2.3 | 5.0 |
| 0.9 | 3.6 | 2.4 | 2.1 | 4.2 |
| 0.95 | 2.6 | 1.9 | 1.7 | 2.9 |
| 1 | 1.2 | 1.2 | 1.2 | 1.2 |

HF-HFO-1234yf-HFC-245cb-HCFO-1233xf-HFO-1234zeE-HFO-1234zeZ-HCFC-1233zdE-HFO-1225zc

| MASSFRAC HF | Organics 0.16 F1234yf + 0.14 F245cb + 0.14 F1233xf + 0.14 F1234zeE + 0.14 F1234zeZ + 0.14 F1233zdE + 0.14 F1225zc TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F1225zc TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F1225zc TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F1225zc TOTAL PRESSURE bar |
|---|---|---|---|---|
| 0 | 3.9 | 6.6 | 4.6 | 1.7 |
| 0.05 | 4.9 | 7.6 | 5.8 | 2.8 |
| 0.1 | 4.9 | 7.6 | 5.8 | 2.8 |
| 0.15 | 4.9 | 7.6 | 5.8 | 2.8 |
| 0.2 | 4.9 | 7.6 | 5.8 | 2.8 |
| 0.25 | 4.9 | 7.6 | 5.8 | 2.8 |
| 0.3 | 4.9 | 7.6 | 5.8 | 2.8 |
| 0.35 | 4.9 | 7.6 | 5.8 | 2.8 |
| 0.4 | 4.9 | 7.6 | 5.8 | 2.8 |
| 0.45 | 4.9 | 7.6 | 5.8 | 2.8 |
| 0.5 | 4.9 | 7.6 | 5.8 | 2.8 |
| 0.55 | 4.9 | 7.6 | 5.8 | 2.8 |
| 0.6 | 4.9 | 7.6 | 5.8 | 2.8 |
| 0.65 | 4.9 | 7.6 | 5.8 | 2.8 |
| 0.7 | 4.9 | 7.5 | 5.8 | 2.8 |
| 0.75 | 4.8 | 7.4 | 5.8 | 2.8 |
| 0.8 | 4.6 | 7.1 | 5.8 | 2.7 |
| 0.85 | 4.2 | 6.5 | 5.8 | 2.5 |
| 0.9 | 3.5 | 5.5 | 4.9 | 2.2 |
| 0.95 | 2.6 | 3.8 | 3.5 | 1.8 |
| 1 | 1.2 | 1.2 | 1.2 | 1.2 |

-continued

| | HF-HFO-1234yf-HFC-245cb-HCFO-1233xf-HFO-1234zeE-HFO-1234zeZ-HCFC-1233zdE-HFO-1225zc | | | |
|---|---|---|---|---|
| MASSFRAC HF | Organics 0.01 F1234yf + 0.01 F245cb + 0.01 F1233xf + 0.94 F1234zeE + 0.01 F1234zeZ + 0.01 F1233zdE + 0.01 F1225zc TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F1225zc TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F1225zc TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F1225zc TOTAL PRESSURE bar |
| 0 | 4.8 | 1.9 | 1.5 | 5.2 |
| 0.05 | 5.8 | 3.0 | 2.6 | 6.2 |
| 0.1 | 5.8 | 3.0 | 2.6 | 6.2 |
| 0.15 | 5.8 | 3.0 | 2.6 | 6.2 |
| 0.2 | 5.8 | 3.0 | 2.6 | 6.2 |
| 0.25 | 5.8 | 3.0 | 2.6 | 6.2 |
| 0.3 | 5.8 | 3.0 | 2.6 | 6.2 |
| 0.35 | 5.8 | 3.0 | 2.6 | 6.2 |
| 0.4 | 5.8 | 3.0 | 2.6 | 6.2 |
| 0.45 | 5.8 | 3.0 | 2.6 | 6.2 |
| 0.5 | 5.7 | 3.0 | 2.6 | 6.1 |
| 0.55 | 5.7 | 3.0 | 2.6 | 6.1 |
| 0.6 | 5.6 | 3.0 | 2.6 | 6.0 |
| 0.65 | 5.5 | 3.0 | 2.6 | 5.9 |
| 0.7 | 5.3 | 3.0 | 2.6 | 5.8 |
| 0.75 | 5.1 | 3.0 | 2.6 | 5.5 |
| 0.8 | 4.8 | 2.9 | 2.5 | 5.1 |
| 0.85 | 4.3 | 2.7 | 2.3 | 4.6 |
| 0.9 | 3.6 | 2.4 | 2.1 | 3.8 |
| 0.95 | 2.6 | 1.9 | 1.7 | 2.7 |
| 1 | 1.2 | 1.2 | 1.2 | 1.2 |

Example 17: Temperature and Pressure Range of System with 8 Compounds

| | Boiling point range | |
|---|---|---|
| System with 8 compounds | Temperature ° C. | Pressure bar abs |
| HF-HCFO-1233xf-HFO-1234yf-HFC-245cb-HCFO-1233zdE-HFO-1234zeE-HFO-1234zeZ-HFO-1243zf | 0 to 40 | ~1.0~11.5 |
| HF-HFO-1234yf-HFC-245cb-HCFO-1233xf-HFO-1234zeE-HFO-1234zeZ-HCFO-1233zdE-HCFC-244bb | 0 to 40 | ~0.7 to ~11.5 |
| HF-HFO-1234yf-HFC-245cb-HCFO-1233xf-HFO-1234zeE-HFO-1234zeZ-HCFO-1233zdE-Trifluoropropyne | 0 to 40 | ~1.0 to ~17.4 |
| HF-HFO-1234yf-HFC-245cb-HCFO-1233xf-HFO-1234zeE-HFO-1234zeZ-HCFO-1233zdE-HFC-245fa | 0 to 40 | ~0.9 to ~11.5 |
| HF-HFO-1234yf-HFC-245cb-HCFO-1233xf-HFO-1234zeE-HFQ-1234zeZ-HCFO-1233zdE-HFQ-1225yeZ | 0 to 40 | ~1.0 to ~11.5 |
| HF-HFO-1234yf-HFC-245cb-HCFO-1233xf-HFO-1234zeE-HFO-1234zeZ-HCFC-1233zdE-HFO-1225zc | 0 to 40 | ~1.0 to ~11.5 |

Example 18: Decantation Ranges of System with 8 Compounds

| | Decantation ranges Mass percentage of HF Temperature | | |
|---|---|---|---|
| System with 8 compounds | 0° C. | 25° C. | 40° C. |
| HF-HCFO-1233xf-HFO-1234yf-HFC-245cb-HCFO-1233zdE-HFO-1234zeE-HFO-1234zeZ-HFO-1243zf | 5-75% | 5-70% | 15-50% |
| HF-HFO-1234yf-HFC-245cb-HCFO-1233xf-HFO-1234zeE-HFO-1234zeZ-HCFO-1233zdE-HCFC-244bb | 5-80 | 5-75 | 5-70 |
| HF-HFO-1234yf-HFC-245cb-HCFO-1233xf-HFO-1234zeE-HFO-1234zeZ-HCFO-1233zdE-Trifluoropropyne | 5-75 | 10-65 | * |
| HF-HFO-1234yf-HFC-245cb-HCFO-1233xf-HFO-1234zeE-HFO-1234zeZ-HCFO-1233zdE-HFC-245fa | 5-75 | 5-70 | 10-60 |
| HF-HFO-1234yf-HFC-245cb-HCFO-1233xf-HFO-1234zeE-HFO-1234zeZ-HCFO-1233zdE-HFO-1225yeZ | 5-75 | 5-70 | 15-55 |
| HF-HFO-1234yf-HFC-245cb-HCFO-1233xf-HFO-1234zeE-HFO-1234zeZ-HCFC-1233zdE-HFO-1225zc | 5-75 | 5-65 | 15-50 |

Example 19: Systems with 13 Compounds

HF - HFO-1234yf - HFC-245cb - HCFO-1233xf - HCFO-1233zdE - HFO-1234zeE - HFO-1234zeZ - HFC-1243zf - HCFC-244bb - TFP - HFC-245fa - HFO-1225yeZ - HFO-1225zc

| MASSFRAC HF | Organics 0.087 F1234yf + 0.083 F245cb + 0.083 F1233xf + 0.083 F1233zdE + 0.083 F1234zeE + 0.083 F1234zeZ + 0.083 F1243zf + 0.083 F244bb + 0.083 F245fa + 0.083 TFP + 0.083 F1225yeZ + 0.83 F1225zc TOTAL PRESSURE bar | Organics 0.89 F1234yf + 0.01 F245cb + 0.01 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.89 F1233xf + 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.89 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.89 F1233zdE + 0.01 F1234zeE + 0.01 F1234zeZ + 0.01 F1243z7 + 0.01 F244bb + 0.01 F245fa + 0.01 TFP + 0.01 F1225yeZ + 0.1 F1225zc TOTAL PRESSURE bar |
|---|---|---|---|---|---|
| 0 | 4.5 | 6.5 | 1.9 | 4.8 | 1.7 |
| 0.05 | 5.6 | 7.5 | 3.0 | 5.8 | 2.9 |
| 0.1 | 5.6 | 7.5 | 3.0 | 5.8 | 2.9 |
| 0.15 | 5.6 | 7.5 | 3.0 | 5.8 | 2.8 |
| 0.2 | 5.6 | 7.5 | 3.0 | 5.8 | 2.8 |
| 0.25 | 5.6 | 7.5 | 3.0 | 5.8 | 2.8 |
| 0.3 | 5.6 | 7.5 | 3.0 | 5.8 | 2.8 |
| 0.35 | 5.6 | 7.5 | 3.0 | 5.8 | 2.8 |
| 0.4 | 5.6 | 7.5 | 3.0 | 5.8 | 2.8 |
| 0.45 | 5.5 | 7.5 | 3.0 | 5.8 | 2.8 |
| 0.5 | 5.5 | 7.5 | 3.0 | 5.8 | 2.8 |
| 0.55 | 5.5 | 7.5 | 3.0 | 5.7 | 2.8 |
| 0.6 | 5.5 | 7.5 | 3.0 | 5.6 | 2.8 |
| 0.65 | 5.5 | 7.5 | 3.0 | 5.5 | 2.8 |
| 0.7 | 5.4 | 7.5 | 3.0 | 5.4 | 2.8 |
| 0.75 | 5.3 | 7.3 | 3.0 | 5.2 | 2.8 |
| 0.8 | 5.1 | 7.0 | 2.8 | 4.8 | 2.7 |
| 0.85 | 4.6 | 6.4 | 2.6 | 4.3 | 2.5 |
| 0.9 | 3.9 | 5.4 | 2.3 | 3.6 | 2.2 |
| 0.95 | 2.8 | 3.7 | 1.8 | 2.6 | 1.8 |
| 1 | 1.2 | 1.2 | 1.2 | 1.2 | 1.2 |

Example 20: Temperature and Pressure Range of System with 13 Compounds

| | Boiling point range | |
|---|---|---|
| System with 13 compounds | Temperature °C. | Pressure bar abs |
| HF - HFO-1234yf - HFC-245cb - HCFO-1233xf - HCFO-1233zdE - HFO-1234zeE - HFO-1234zeZ - HFC-1243zf - HCFC-244bb - TFP - HFC-245fa - HFO-1225yeZ - HFO-1225zc | 0 to 40 | ~0.7~18.0 |

Example 21: Decantation Ranges of System with 13 Compounds

| | Decantation ranges Mass percentage of HF Temperature | | |
|---|---|---|---|
| System with 13 compounds | 0° C. | 25° C. | 40° C. |
| HF - HFO-1234yf - HFC-245cb - HCFO-1233xf - HCFO-1233zdE - HFO-1234zeE - HFO-1234zeZ - HFC-1243zf - HCFC-244bb - TFP - HFC-245fa - HFO-1225yeZ - HFO-1225zc | 5-75% | 10-70% | 15-60% |

The invention claimed is:

1. An azeotropic or quasi-azeotropic composition consisting essentially of from 75% to 95% by weight of hydrogen fluoride and from 25% to 5% by weight E-1,3,3,3-tetrafluoropropene.

2. The composition as claimed in claim 1, wherein the composition consists of hydrogen fluoride and E-1,3,3,3-tetrafluoropropene.

3. The composition as claimed in claim 1, in which the composition consists essentially of from 75% to 85% by weight of hydrogen fluoride and from 25% to 15% by weight of the E-1,3,3,3-tetrafluoropropene.

4. The composition as claimed in claim 1, in which the composition consists essentially of from 75% to 80% by weight of hydrogen fluoride and from 25% to 20% by weight of the E-1,3,3,3-tetrafluoropropene.

5. The composition as claimed in claim 1, in which the boiling point of said composition is between −20° C. and 80° C. and at a pressure of between 0.1 and 44 bar absolute.

6. The composition as claimed in claim 1, in which the boiling point of said composition is between 0° C. and 40° C. and at a pressure of between 0.7 and 18 bar absolute.

7. The composition as claimed in claim 1, in which the boiling point of said composition is between 0° C. and 40° C. and at a pressure of between 0.9 and 12.5 bar absolute.

8. The composition as claimed in claim 2, in which the composition consists of from 75% to 85% by weight of hydrogen fluoride and from 25% to 15% by weight of the E-1,3,3,3-tetrafluoropropene.

9. The composition as claimed in claim 2, in which the composition consists essentially of from 75% to 80% by weight of hydrogen fluoride and from 25% to 20% by weight of the E-1,3,3,3-tetrafluoropropene.

10. The composition as claimed in claim 2, in which the boiling point of said composition is between −20° C. and 80° C. and at a pressure of between 0.1 and 44 bar absolute.

11. The composition as claimed in claim 2, in which the boiling point of said composition is between 0° C. and 40° C. and at a pressure of between 0.7 and 18 bar absolute.

12. The composition as claimed in claim 2, in which the boiling point of said composition is between 0° C. and 40° C. and at a pressure of between 0.9 and 12.5 bar absolute.

13. An azeotropic or quasi-azeotropic composition comprising from 75% to 95% by weight of hydrogen fluoride and from 25% to 5% by weight E-1,3,3,3-tetrafluoropropene, in which the boiling point of said composition is between 0° C. and 40° C. and at a pressure of between 0.7 and 18 bar absolute.

* * * * *